(12) United States Patent
Dahl et al.

(10) Patent No.: US 12,371,506 B2
(45) Date of Patent: Jul. 29, 2025

(54) SUBCUTANEOUS ADMINISTRATION OF ANTI-CD38 ANTIBODIES

(71) Applicants: Takeda Pharmaceutical Company Limited, Osaka (JP); Martin Dahl, San Diego, CA (US); Eric Fedyk, San Deigo, CA (US); Robert Evans, San Diego, CA (US); Lin Zhao, San Diego, CA (US)

(72) Inventors: Martin Dahl, San Diego, CA (US); Eric Fedyk, San Deigo, CA (US); Robert Evans, San Diego, CA (US); Lin Zhao, San Diego, CA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 129 days.

(21) Appl. No.: 16/961,346

(22) PCT Filed: Jan. 14, 2019

(86) PCT No.: PCT/US2019/013547
§ 371 (c)(1),
(2) Date: Jul. 10, 2020

(87) PCT Pub. No.: WO2019/140410
PCT Pub. Date: Jul. 18, 2019

(65) Prior Publication Data
US 2021/0388103 A1 Dec. 16, 2021

Related U.S. Application Data

(60) Provisional application No. 62/617,146, filed on Jan. 12, 2018.

(51) Int. Cl.
*C07K 16/28* (2006.01)
*A61K 39/00* (2006.01)
*A61P 35/00* (2006.01)

(52) U.S. Cl.
CPC .......... *C07K 16/2896* (2013.01); *A61P 35/00* (2018.01); *A61K 2039/505* (2013.01); *A61K 2039/545* (2013.01); *C07K 2317/565* (2013.01)

(58) Field of Classification Search
CPC .......... C07K 16/2896; C07K 2317/565; C07K 2317/33; C07K 2317/94; A61P 35/00; A61P 19/02; A61K 2039/505; A61K 2039/545; A61K 2039/54
See application file for complete search history.

(56) References Cited

U.S. PATENT DOCUMENTS

| 6,086,875 A | 7/2000 | Blumberg et al. |
|---|---|---|
| 6,737,056 B1 | 5/2004 | Presta |
| 7,317,091 B2 | 1/2008 | Lazar et al. |
| 7,670,600 B2 | 3/2010 | Dall'Acqua et al. |
| 7,829,673 B2 | 11/2010 | De Weers et al. |
| 8,084,582 B2 | 12/2011 | Dahiyat et al. |
| 8,088,896 B2 | 1/2012 | Tesar et al. |
| 8,188,231 B2 | 5/2012 | Lazar et al. |
| 8,362,211 B2 * | 1/2013 | Elias .................. A61P 1/04 530/387.3 |
| 8,367,805 B2 | 2/2013 | Chamberlain et al. |
| 8,877,899 B2 | 11/2014 | Rojkjaer et al. |
| 8,926,969 B2 | 1/2015 | Elias et al. |
| 8,937,158 B2 | 1/2015 | Lazar et al. |
| 9,040,041 B2 | 5/2015 | Desjarlais et al. |
| 9,040,050 B2 | 5/2015 | van de Winkel et al. |
| 9,102,744 B2 * | 8/2015 | Elias .................. C07K 16/40 |
| 9,289,490 B2 | 3/2016 | Rojkjaer et al. |
| 9,676,869 B2 | 6/2017 | Elias et al. |
| 9,790,285 B2 | 10/2017 | Elias et al. |
| 9,944,711 B2 | 4/2018 | De Weers et al. |
| 10,232,041 B2 | 3/2019 | Pogue et al. |
| 10,336,833 B2 | 7/2019 | Elias et al. |
| 10,494,444 B2 | 12/2019 | Elias et al. |
| 2004/0013210 A1 | 1/2004 | Bollano et al. |
| 2005/0054832 A1 | 3/2005 | Lazar et al. |
| 2005/0261480 A1 | 11/2005 | Foote |
| 2006/0024298 A1 | 2/2006 | Lazar et al. |
| 2006/0121032 A1 | 6/2006 | Dahiyat et al. |
| 2006/0235208 A1 | 10/2006 | Lazar et al. |
| 2007/0003554 A1 | 1/2007 | Miller |
| 2007/0148170 A1 | 6/2007 | Desjarlais et al. |

(Continued)

FOREIGN PATENT DOCUMENTS

| CN | 103282383 A | 9/2013 |
|---|---|---|
| CN | 107365385 A | 11/2017 |

(Continued)

OTHER PUBLICATIONS

Jørgensen JT, Rømsing J, Rasmussen M, Møller-Sonnergaard J, Vang L, Musaeus L. Pain assessment of subcutaneous injections. Ann Pharmacother. Jul.-Aug. 1996;30(7-8):729-32. doi: 10.1177/106002809603000703. PMID: 8826549. (Year: 1996).*

Benfaremo D, Gabrielli A. Is There a Future for Anti-CD38 Antibody Therapy in Systemic Autoimmune Diseases? Cells. Dec. 27, 2019;9(1):77. doi: 10.3390/cells9010077. PMID: 31892266; PMCID: PMC7016693. (Year: 2019).*

Raab et al. Phase I/IIa Study of the Human Anti-CD38 Antibody MOR202 (MOR03087) in Relapsed or Refractory Multiple Myeloma Blood 2015 126: 3035 (Year: 2015).*

Doyle GR et al. Chapter 7.3 Intradermal and Subcutaneous Injections. Clinical Procedures for Safer Patient Care (publication date Nov. 23, 2015) (https://opentextbc.ca/clinicalskills/chapter/6-7-intradermal-subcutaneous-and-intramuscular-injections/). (Year: 2015).*

(Continued)

*Primary Examiner* — Karen A. Canella
*Assistant Examiner* — John J Skoko, III
(74) *Attorney, Agent, or Firm* — Morgan, Lewis & Bockius LLP

(57) ABSTRACT

Methods of administering isolated anti-CD38 antibodies at low dosages subcutaneously are disclosed. The methods provide an effective treatment for autoimmune diseases and cancers, including hematologic diseases. Also disclosed are unit dosage forms for the anti-CD38 antibodies.

27 Claims, 62 Drawing Sheets
Specification includes a Sequence Listing.

(56) References Cited

U.S. PATENT DOCUMENTS

| | | |
|---|---|---|
| 2009/0076249 A1 | 3/2009 | De Weers et al. |
| 2009/0148449 A1 | 6/2009 | De Weers et al. |
| 2009/0203538 A1 | 8/2009 | Sugioka et al. |
| 2010/0028346 A1 | 2/2010 | Lutz et al. |
| 2010/0092489 A1 | 4/2010 | van de Winkel et al. |
| 2011/0099647 A1 | 4/2011 | De Weers et al. |
| 2011/0262454 A1 | 10/2011 | Park et al. |
| 2013/0209355 A1 | 8/2013 | De Weers et al. |
| 2013/0302318 A1 | 11/2013 | Rojkjaer et al. |
| 2014/0154247 A1 | 6/2014 | Behrens et al. |
| 2014/0161819 A1 | 6/2014 | Hann et al. |
| 2015/0231235 A1 | 8/2015 | van de Winkel et al. |
| 2016/0067205 A1 | 3/2016 | Lokhorst et al. |
| 2016/0075766 A1 | 3/2016 | Ritter et al. |
| 2016/0130362 A1 | 5/2016 | De Weers et al. |
| 2016/0139117 A1 | 5/2016 | Yamamura et al. |
| 2016/0168266 A1 | 6/2016 | Yamazaki et al. |
| 2017/0008966 A1 | 1/2017 | Chaulagain et al. |
| 2017/0107295 A1 | 4/2017 | Lokhorst et al. |
| 2017/0121417 A1 | 5/2017 | Jansson et al. |
| 2017/0224817 A1 | 8/2017 | Venstrom |
| 2018/0022823 A1 | 1/2018 | Rojkjaer et al. |
| 2018/0117150 A1 | 5/2018 | O'Dwyer et al. |
| 2018/0235986 A1 | 8/2018 | Labotka et al. |
| 2019/0127479 A1 | 5/2019 | Ahmadi et al. |
| 2021/0171650 A1 | 6/2021 | Audat et al. |
| 2021/0388103 A1 | 12/2021 | Smithson et al. |

FOREIGN PATENT DOCUMENTS

| | | | |
|---|---|---|---|
| EP | 1914242 | | 4/2008 |
| EP | 2658871 B1 | | 5/2018 |
| JP | 2001-509817 A | | 7/2001 |
| JP | 2014-502491 A | | 2/2014 |
| JP | 2014-509837 A | | 4/2014 |
| JP | 2014-514345 A | | 6/2014 |
| JP | 2015-511008 A | | 4/2015 |
| JP | 2015-522822 A | | 8/2015 |
| JP | 2016-536314 A | | 11/2016 |
| KR | 10-2014- 0032963 A | | 3/2014 |
| TW | 201919699 A | | 6/2019 |
| WO | WO 1994/013804 A1 | | 6/1994 |
| WO | WO 1998/045331 | | 10/1998 |
| WO | WO 2003/011161 A1 | | 2/2003 |
| WO | WO 2006/099875 | | 9/2006 |
| WO | WO 2006/125640 | | 11/2006 |
| WO | WO 2008/037257 | | 4/2008 |
| WO | WO 2008/047242 A2 | | 4/2008 |
| WO | WO 2009/077993 | | 6/2009 |
| WO | WO 2010/021874 | | 2/2010 |
| WO | WO 2010/061357 A1 | | 6/2010 |
| WO | WO 2010/061358 A1 | | 6/2010 |
| WO | WO 2010/061359 A1 | | 6/2010 |
| WO | WO 2010/061360 A1 | | 6/2010 |
| WO | WO 2012/076663 A1 | | 6/2012 |
| WO | WO 2012/080721 A1 | | 6/2012 |
| WO | WO 2012/080721 A2 | | 6/2012 |
| WO | WO 2012/092616 | | 7/2012 |
| WO | WO-2012092612 A1 * | 7/2012 | ......... A61K 47/6871 |
| WO | WO 2012/118750 A2 | | 9/2012 |
| WO | WO 2012/151199 A1 | | 11/2012 |
| WO | WO 2013/132245 A1 | | 9/2013 |
| WO | WO 2014/013225 A1 | | 1/2014 |
| WO | WO 2014/089416 A1 | | 6/2014 |
| WO | WO 2015/066450 A1 | | 5/2015 |
| WO | WO 2016/180958 A1 | | 11/2016 |
| WO | WO 2017/079150 A1 | | 5/2017 |
| WO | WO 2018/013917 A1 | | 1/2018 |
| WO | WO 2019/089832 A1 | | 5/2019 |

OTHER PUBLICATIONS

Davda JP et al. A model-based meta-analysis of monoclonal antibody pharmacokinetics to guide optimal first-in-human study design (mAbs, 2015 6:4, 1094-1102) (Year: 2015).*

Alexander, Tobias et al. "The proteasome inhibitior bortezomib depletes plasma cells and ameliorates clinical manifestations of refractory systemic lupus erythematosus." Annals of the rheumatic diseases vol. 74,7 (2015): 1474-8.

Alvarez-Rodriguez, Lorena et al. "Peripheral B-Cell Subset Distribution in Primary Antiphospholipid Syndrome." International journal of molecular sciences vol. 19,2 589. Feb. 16, 2018.

Antonelli, A et al. "Anti-CD38 autoimmunity in patients with chronic autoimmune thyroiditis or Graves' disease." Clinical and experimental immunology vol. 126,3 (2001): 426-31.

Antonelli, A, and E Ferrannini. "CD38 autoimmunity: recent advances and relevance to human diabetes." Journal of endocrinological investigation vol. 27,7 (2004): 695-707.

Banchereau, Romain et al. "Personalized Immunomonitoring Uncovers Molecular Networks that Stratify Lupus Patients." Cell vol. 165,3 (2016): 551-65.

Barbas, C F 3rd et al. "In vitro evolution of a neutralizing human antibody to human immunodeficiency virus type 1 to enhance affinity and broaden strain cross-reactivity." Proceedings of the National Academy of Sciences of the United States of America vol. 91,9 (1994): 3809-13.

Behzad, Masumeh Maleki et al. "Cellular expression of CD markers in immune thrombocytopenia purpura: implications for prognosis." APMIS : acta pathologica, microbiologica, et immunologica Scandinavica vol. 126,6 (2018): 523-532.

Bird, R E et al. "Single-chain antigen-binding proteins." Science (New York, N.Y.) vol. 242,4877 (1988): 423-6.

Casneuf, Tineke et al. "Effects of daratumumab on natural killer cells and impact on clinical outcomes in relapsed or refractory multiple myeloma." Blood advances vol. 1,23 2105-2114. Oct. 24, 2017.

Chiba, Asako et al. "The involvement of V(alpha)14 natural killer T cells in the pathogenesis of arthritis in murine models." Arthritis and rheumatism vol. 52,6 (2005): 1941-8.

Chihara, Norio et al. "Interleukin 6 signaling promotes anti-aquaporin 4 autoantibody production from plasmablasts in neuromyelitis optica." Proceedings of the National Academy of Sciences of the United States of America vol. 108,9 (2011): 3701-6.

Chothia, C, and A M Lesk. "Canonical structures for the hypervariable regions of immunoglobulins." Journal of molecular biology vol. 196,4 (1987): 901-17.

Clemens, Pamela L et al. "Pharmacokinetics of Daratumumab Following Intravenous Infusion in Relapsed or Refractory Multiple Myeloma After Prior Proteasome Inhibitor and Immunomodulatory Drug Treatment." Clinical pharmacokinetics vol. 56,8 (2017): 915-924.

Cole, Suzanne et al. "Integrative analysis reveals CD38 as a therapeutic target for plasma cell-rich pre-disease and established rheumatoid arthritis and systemic lupus erythematosus." Arthritis research & therapy vol. 20,1 85. May 2, 2018.

Costello, Caitlin. "An update on the role of daratumumab in the treatment of multiple myeloma." Therapeutic advances in hematology vol. 8,1 (2017): 28-37.

De Weers, Michel et al. "Daratumumab, a novel therapeutic human CD38 monoclonal antibody, induces killing of multiple myeloma and other hematological tumors." Journal of immunology (Baltimore, MD. : 1950) vol. 186,3 (2011): 1840-8.

Dürig, J et al. "CD38 expression is an important prognostic marker in chronic lymphocytic leukaemia." Leukemia vol. 16,1 (2002): 30-5.

Fedyk et al. (2018) Blood 132:3249.

Friberg, Lena E et al. "Model of chemotherapy-induced myelosuppression with parameter consistency across drugs." Journal of clinical oncology : official journal of the American Society of Clinical Oncology vol. 20,24 (2002): 4713-21.

Gibiansky, Leonid, and Ekaterina Gibiansky. "Target-mediated drug disposition model: approximations, identifiability of model param-

(56) References Cited

OTHER PUBLICATIONS eters and applications to the population pharmacokinetic-pharmacodynamic modeling of biologics." Expert opinion on drug metabolism & toxicology vol. 5,7 (2009): 803-12.

Glassman, Patrick M, and Joseph P Balthasar. "Mechanistic considerations for the use of monoclonal antibodies for cancer therapy." Cancer biology & medicine vol. 11,1 (2014): 20-33.

Grammer, Amrie C et al. "Abnormal germinal center reactions in systemic lupus erythematosus demonstrated by blockade of CD154-CD40 interactions." The Journal of clinical investigation vol. 112,10 (2003): 1506-20.

Hamblin, Terry J et al. "CD38 expression and immunoglobulin variable region mutations are independent prognostic variables in chronic lymphocytic leukemia, but CD38 expression may vary during the course of the disease." Blood vol. 99,3 (2002): 1023-9.

Han, Chao, and Honghui Zhou. "Monoclonal antibodies: interspecies scaling with minimal preclinical information." Therapeutic delivery vol. 2,3 (2011): 359-68.

Hawkins, R E et al. "Selection of phage antibodies by binding affinity. Mimicking affinity maturation." Journal of molecular biology vol. 226,3 (1992): 889-96.

Holliger, P et al. ""Diabodies": small bivalent and bispecific antibody fragments." Proceedings of the National Academy of Sciences of the United States of America vol. 90,14 (1993): 6444-8.

Huston, J S et al. "Protein engineering of antibody binding sites: recovery of specific activity in an anti-digoxin single-chain Fv analogue produced in *Escherichia coli*." Proceedings of the National Academy of Sciences of the United States of America vol. 85,16 (1988): 5879-83.

International Myeloma Working Group. "Criteria for the classification of monoclonal gammopathies, multiple myeloma and related disorders: a report of the International Myeloma Working Group." British journal of haematology vol. 121,5 (2003): 749-57.

Ishizawa, Kenichi et al. "Safety, efficacy and pharmacokinetics of humanized anti-CD52 monoclonal antibody alemtuzumab in Japanese patients with relapsed or refractory B-cell chronic lymphocytic leukemia." Japanese journal of clinical oncology vol. 47,1 (2017): 54-60.

Jackson, J R et al. "In vitro antibody maturation. Improvement of a high affinity, neutralizing antibody against IL-1 beta." Journal of immunology (Baltimore, MD. : 1950) vol. 154,7 (1995): 3310-9.

Jackson, N et al. "An analysis of myeloma plasma cell phenotype using antibodies defined at the IIIrd International Workshop on Human Leucocyte Differentiation Antigens." Clinical and experimental immunology vol. 72,3 (1988): 351-6.

Jelinek, D F et al. "Analysis of clonal B-cell CD38 and immunoglobulin variable region sequence status in relation to clinical outcome for B-chronic lymphocytic leukaemia." British journal of haematology vol. 115,4 (2001): 854-61.

Kabat et al. (1991) Sequences of Proteins of Immunological Interest, 5th Ed. Public Health Service, National Institutes of Health, Bethesda, MD.

Kamath, Amrita V. "Translational pharmacokinetics and pharmacodynamics of monoclonal antibodies." Drug discovery today. Technologies vol. 21-22 (2016): 75-83.

Kato, Atsuhiko et al. "Early effects of tocilizumab on bone and bone marrow lesions in a collagen-induced arthritis monkey model." Experimental and molecular pathology vol. 84,3 (2008): 262-70.

Keyhani, A et al. "Increased CD38 expression is associated with favorable prognosis in adult acute leukemia." Leukemia research vol. 24,2 (2000): 153-9.

Kosmas, C et al. "Anti-CD20-based therapy of B cell lymphoma: state of the art." Leukemia vol. 16,10 (2002): 2004-15.

Kraan, M C et al. "Immunohistological analysis of synovial tissue for differential diagnosis in early arthritis." Rheumatology (Oxford, England) vol. 38,11 (1999): 1074-80.

Krejcik, Jakub et al. "Daratumumab depletes CD38+ immune regulatory cells, promotes T-cell expansion, and skews T-cell repertoire in multiple myeloma." Blood vol. 128,3 (2016): 384-94.

Kyle, Robert A et al. "Clinical course and prognosis of smoldering (asymptomatic) multiple myeloma." The New England journal of medicine vol. 356,25 (2007): 2582-90.

Mager, Donald E et al. "Diversity of mechanism-based pharmacodynamic models." Drug metabolism and disposition: the biological fate of chemicals vol. 31,5 (2003): 510-8.

Mallone, R et al. "Autoantibody response to CD38 in Caucasian patients with type 1 and type 2 diabetes: immunological and genetic characterization." Diabetes vol. 50,4 (2001): 752-62.

Marinov, J et al. "Immunophenotypic significance of the "lymphoid" CD38 antigen in myeloid blood malignancies." Neoplasma vol. 40,6 (1993): 355-8.

Marks, J., Griffiths, A., Malmqvist, M. et al. By-Passing Immunization: Building High Affinity Human Antibodies by Chain Shuffling. Nat Biotechnol 10, 779-783 (1992).

Mihara, M et al. "Humanized antibody to human interleukin-6 receptor inhibits the development of collagen arthritis in cynomolgus monkeys." Clinical immunology (Orlando, FLA.) vol. 98,3 (2001): 319-26.

Morabito, F et al. "Peripheral blood CD38 expression predicts survival in B-cell chronic lymphocytic leukemia." Leukemia research vol. 25,11 (2001): 927-32.

Mustafa, Nurulhuda et al., "Daratumumab Efficiently Targets NK/T Cell Lymphoma with High CD38 Expression." Blood 2017; 130 (Supplement 1): 2814.

Nijhof, Inger S et al. "CD38 expression and complement inhibitors affect response and resistance to daratumumab therapy in myeloma." Blood vol. 128,7 (2016): 959-70.

Nilsson and Koke (2001) Drug Inform. J. 35: 1289-1299.

Reiter, Y et al. "Engineering antibody Fv fragments for cancer detection and therapy: disulfide-stabilized Fv fragments." Nature biotechnology vol. 14, 10 (1996): 1239-45.

Richter et al. (2016) J. Clin. Oncol. 34 (suppl): abstr 8005.

Roepcke, Stefan et al. "Pharmacokinetics and pharmacodynamics of the cytolytic anti-CD38 human monoclonal antibody TAK-079 in monkey—model assisted preparation for the first in human trial." Pharmacology research & perspectives vol. 6,3 (2018): e00402.

Shier et al. (1995) Gene 169: 147-155.

Smithson, G. et al. "TAK-079 is a high affinity monoclonal antibody that effectively mediates CD38+ cell depletion." J. Immunol. 198 (1 Supplement) (2017) 224.20.

Sonneveld, Pieter, and Annemiek Broijl. "Treatment of relapsed and refractory multiple myeloma." Haematologica vol. 101,4 (2016): 396-406.

Stebbings, Richard et al. ""Cytokine storm" in the phase I trial of monoclonal antibody TGN1412: better understanding the causes to improve preclinical testing of immunotherapeutics." Journal of immunology (Baltimore, MD. : 1950) vol. 179,5 (2007): 3325-31.

Sullivan, Harold C et al. "Daratumumab (anti-CD38) induces loss of CD38 on red blood cells." Blood vol. 129,22 (2017): 3033-3037.

Tomlinson, I, and P Holliger. "Methods for generating multivalent and bispecific antibody fragments." Methods in enzymology vol. 326 (2000): 461-79.

Uchiyama, Yasushi et al. "Anemia in monkey collagen-induced arthritis is correlated with serum IL-6, but not TNFalpha." Rheumatology international vol. 28,9 (2008): 879-83.

Uchiyama, Yasushi et al. "Tocilizumab, a humanized anti-interleukin-6 receptor antibody, ameliorates joint swelling in established monkey collagen-induced arthritis." Biological & pharmaceutical bulletin vol. 31,6 (2008): 1159-63.

Van de Donk, Niels W C J et al. "Monoclonal antibodies targeting CD38 in hematological malignancies and beyond." Immunological reviews vol. 270,1 (2016): 95-112.

Vital, Edward M et al. "B cell biomarkers of rituximab responses in systemic lupus erythematosus." Arthritis and rheumatism vol. 63,10 (2011): 3038-47.

Voorhees, Peter M., et al. "Management of Infusion-Related Reactions Following Daratumumab Monotherapy in Patients with at Least 3 Lines of Prior Therapy or Double Refractory Multiple Myeloma (MM): 54767414MMY2002" (Sirius). Blood 2015; 126 (23): 1829.

Wang et al. (2016) Arthritis Rheumatol. 68(suppl 10). 2016 ACR/ARHP Annual Meeting, 1085.

(56) References Cited

OTHER PUBLICATIONS

Ward, E S et al. "Binding activities of a repertoire of single immunoglobulin variable domains secreted from *Escherichia coli*." Nature vol. 341,6242 (1989): 544-6.

Witzig, T E et al. "Quantitation of circulating peripheral blood plasma cells and their relationship to disease activity in patients with multiple myeloma." Cancer vol. 72,1 (1993): 108-13.

Xu, X S et al. "Clinical Implications of Complex Pharmacokinetics for Daratumumab Dose Regimen in Patients With Relapsed/Refractory Multiple Myeloma." Clinical pharmacology and therapeutics vol. 101,6 (2017): 721-724.

Yelton, D E et al. "Affinity maturation of the BR96 anti-carcinoma antibody by codon-based mutagenesis." Journal of immunology (Baltimore, MD. : 1950) vol. 155,4 (1995): 1994-2004.

Yilmaz, Vuslat et al. "Regulatory B cells in myasthenia gravis are differentially affected by therapies." Annals of clinical and translational neurology vol. 5,11 1408-1414. Sep. 22, 2018.

Yoshiga, Y et al. "Invariant NKT cells produce IL-17 through IL-23-dependent and -independent pathways with potential modulation of Th17 response in collagen-induced arthritis." International journal of molecular medicine vol. 22,3 (2008): 369-74.

Belousov, Y. B., Gurevich, K. G., Clinical pharmacokinetics. Drug dosing practice: Spec. release of the series "Rational pharmacotherapy", 2005. p. 1-288.

Ptitsyna Y. S. et al., Differences in serum forms of CD38 antigen in immune disorders of various etiology, Medical Immunology, 1999, vol. 1, No. 3-4, p. 82.

Smithson G. et al., CD38+ cell depletion with TAK-079 reduces arthritis in a cynomolgus collagen-induced arthritis (CIA) model, J Immunol, 2017, 198 (1 Supplement) 127.17.

Aggarwal, Rohit et al. "Serum free light chains as biomarkers for systemic lupus erythematosus disease activity." Arthritis care & research vol. 63,6 (2011): 891-8. doi:10.1002/acr.20446.

Atanackovic, Djordje et al. "Immunotherapies targeting CD38 in Multiple Myeloma." Oncoimmunology vol. 5,11 e1217374. Aug. 5, 2016, doi:10.1080/2162402X.2016.1217374.

Ausiello et al., Functional topography of discrete domains of human CD38., Tissue Antigens. Dec. 2000;56(6):539-47.

Cohen, Adam D, and Raymond L Comenzo. "Systemic light-chain amyloidosis: advances in diagnosis, prognosis, and therapy." Hematology. American Society of Hematology. Education Program vol. 2010 (2010): 287-94.

Cole, S., et al. "Integrative analysis reveals CD38 as a therapeutic target for plasma cell-rich pre-disease and established rheumatoid arthritis and systemic lupus erythematosus." *Arthritis research & therapy* vol. 20,1 85. May 2, 2018.

Cooper, L J et al. "Role of heavy chain constant domains in antibody-antigen interaction. Apparent specificity differences among streptococcal IgG antibodies expressing identical variable domains." Journal of immunology (Baltimore, MD. : 1950) vol. 150,6 (1993): 2231-42.

Daratumumab (Darzalex) I FDA, May 17, 2017, retrieved from the Internet: URL:https://www.fda.gov/drugs/resources-information-approved-drugs/daratumumab-darzalex.

Dimopoulos et al. (2018) Blood 132 (suppl. 1): ASH abstract 155/oral presentation.

Draborg, A.H., Lydolph MC, Westergaard M, et al., PLoS One (2015) 10(9):e0138753. doi: 10.1371/journal.pone.0138753. eCollection 2015.

Duebel "Handbook of Therapeutic Antibodies Chapter 6" Handbook of Therapeutic Antibodies, pp. 119-144 (2007).

Edwards, Bryan M et al. "The remarkable flexibility of the human antibody repertoire; isolation of over one thousand different antibodies to a single protein, BLyS." Journal of molecular biology vol. 334,1 (2003): 103-18. doi:10.1016/j.jmb.2003.09.054.

Ellis et al., "Engineered Anti-CD38 Monoclonal Antibodies for Immunotherapy of Multiple Myeloma", J Immunology, 1995, 155: 925-9237.

Fassbinder, T., Saunders U, Mickholz E, et al., Arthritis Res Ther (2015).

Ferrero et al., Characterization and phylogenetic epitope mapping of CD38 ADPR cyclase in the cynomolgus macaque., BMC Immunol. Sep. 21, 2004;5:21.

Foote, J., et al. "Antibody framework residues affecting the conformation of the hypervariable loops." Journal of molecular biology, vol. 224,2 (1992): 487-99.

Gertz, Morie A et al. "Amyloidosis and Waldenstrom's macroglobulinemia." Hematology. American Society of Hematology. Education Program (2004): 257-82.

Goldmacher et al., "Anti-CD38-blocked-ricin; An immunotoxin for the treatment of multiple myeloma", Blood 84(9); 3017-25, Nov. 1, 1994.

Groen, Richard W. et al., "In Vitro and In Vivo Efficacy of CD38 Directed Therapy with Daratumumab in the Treatment of Multiple Myeloma", Blood, vol. 116, No. 21, Nov. 2010, pp. 1261-1262, XP009157537.

Hutchinson, A., "Cell membrane associated free kappa light chains are found on a subset of tonsil and in vitro-derived plasmablasts" Human Immunology, vol. 75, Issue 9 (2014) pp. 986-990.

IOTest&αχιρχ; CD38-PE // A07779CE_C Feb. 6, 2006 //[online], [found on Nov. 3, 2020]. found on: https://www.bc-cytometry.com/PDF/DataSheet/A07779_D.S.pdf.

Keizer, R J et al. "Modeling and Simulation Workbench for NONMEM: Tutorial on Pirana, PsN, and Xpose." CPT: pharmacometrics & systems pharmacology vol. 2,6 e50. Jun. 26, 2013.

Kiyoshi MA, et al: "Affinity improvement of a therapeutic antibody by structure-based computational design: generation of electrostatic interactions in the transition states stabilized the antibody-antigen complex". PLoS One. Jan. 27, 2014;9(1).

Kong, Sun-Young et al., "Daratumumab Directly Induces Human Multiple Myeloma Cell Death and Acts Synergistically with Conventional and Novel Anti-Myeloma Drugs", Blood, vol. 116, No. 21, Nov. 2010, pp. 1241-1242, XP009157536.

Kormelink, T. G. et al. "Decrease in immunoglobulin free light chains in patients with rheumatoid arthritis upon rituximab (anti-CD20) treatment correlates with decrease in disease activity." Annals of the rheumatic diseases vol. 69, 12 (2010): 2137-44.

Kuerten et al., MP4- and MOG:35-55-induced EAE in C57BL/6 mice differentially targets brain, spinal cord and cerebellum., J Neuroimmunol. Sep. 2007;189(1-2):31-40. Epub Jul. 25, 2007.

Laubach, Jacob P, and Paul G Richardson. "CD38-Targeted Immunochemotherapy in Refractory Multiple Myeloma: A New Horizon." Clinical cancer research : an official journal of the American Association for Cancer Research vol. 21, 12 (2015): 2660-2. doi:10.1158/1078-0432.CCR-14-3190.

Little, M. et al., "Of mice and men: hybridoma and recombinant antibodies", Immunology Today, El Sevier Publications, Cambridge, GB, vol. 21, No. 8, Aug. 2000, pp. 364-370, XP004215163.

Lloyd, C et al. "Modelling the human immune response: performance of a 1011 human antibody repertoire against a broad panel of therapeutically relevant antigens." Protein engineering, design & selection : PEDS vol. 22,3 (2009): 159-68. doi:10.1093/protein/gzn058.

Lugar, Patricia L et al. "Molecular characterization of circulating plasma cells in patients with active systemic lupus erythematosus." PloS one vol. 7,9 (2012): e44362. doi:10.1371/journal.pone.0044362.

Malavasi, F., Deaglio S, Funaro A, et al., Physiol Rev (2008) 88(3):841-86.

Martin, W. et al., "Serum-free light chain—a new biomarker for patients with B-cell non-Hodgkin lymphoma and chronic lymphocytic leukemia", Translational Research, vol. 149, Issue 4, 2007, pp. 231-235, https://doi.org/10.1016/j.trsl.2006.11.001.

Mei, H. et al. "Rationale of anti-CD19 immunotherapy: an option to target autoreactive plasma cells in autoimmunity." Arthritis research & therapy vol. 14 Suppl 5, Suppl 5 (2012): S1. doi:10.1186/ar3909.

Merlini, Giampaolo, and Vittorio Bellotti. "Molecular mechanisms of amyloidosis." The New England journal of medicine vol. 349,6 (2003): 583-96.

Murray et al. (2010) Blood (ASH Annual Meeting Abstracts) 116 (21): abstr 1909.

(56) References Cited

OTHER PUBLICATIONS

Odendahl, M., "Disturbed peripheral B lymphocyte homeostasis in systemic lupus erythematosus.", J Immunol. Nov. 15, 2000;165(10):5970-9.

Odendahl, M., "Perturbations of peripheral B lymphocyte homeostasis in children with systemic lupus erythematosus.", Ann Rheum Dis. Sep. 2003;62(9):851-8.

Owczarczyk, K., "A plasmablast biomarker for nonresponse to antibody therapy to CD20 in rheumatoid arthritis.", Sci Transl Med. Sep. 21, 2011;3(101):101ra92.

Palumbo, Antonio et al. "International Myeloma Working Group consensus statement for the management, treatment, and supportive care of patients with myeloma not eligible for standard autologous stem-cell transplantation." Journal of clinical oncology : official journal of the American Society of Clinical Oncology vol. 32,6 (2014): 587-600. doi:10.1200/JCO.2013.48.7934.

Park, Peter U. et al., "SAR650984: A Potent Anti-CD38 Therapeutic Antibody with Three Mechanisms of Action (Apoptosis, ADCC, CDC) for Hematological Malignancies.", Blood, vol. 112, No. 11, Nov. 2008, p. 951, XP009157535.

Pavon, E.J., "Increased association of CD38 with lipid rafts in T cells from patients with systemic lupus erythematosus and in activated normal T cells.", Mol Immunol. Mar. 2006;43(7):1029-39. Epub Jun. 16, 2005.

Pinto, L. et al. "Fixation and cryopreservation of whole blood and isolated mononuclear cells: Influence of different procedures on lymphocyte subset analysis by flow cytometry." Cytometry. Part B, Clinical cytometry vol. 63,1 (2005): 47-55. doi:10.1002/cyto.b.20038.

Rajkumar, S Vincent et al. "Consensus recommendations for the uniform reporting of clinical trials: report of the International Myeloma Workshop Consensus Panel 1." Blood vol. 117,18 (2011): 4691-5. doi:10.1182/blood-2010-10-299487.

Rich RL et al: "A global benchmark study using affinity-based biosensors" Analytical Biochemistry, Mar. 15, 2009;386(2): 194-216.

Shaul, Merav E et al. "Tumor-associated neutrophils display a distinct N1 profile following TGFβ modulation: A transcriptomics analysis of pro- vs. antitumor TANs." Oncoimmunology vol. 5,11 e1232221. Sep. 13, 2016, doi:10.1080/2162402X.2016.1232221.

Stevenson et al., "Preliminary studies for an immunotherapeutic approach to the treatment of human myeloma using chimeric anti-CD38 antibody", Blood, 1991, 77: 1071-1079.

Study NCT02219256. A Phase 1 Study to Assess the Safety, Tolerability, and Pharmacokinetics of TAK-079 in Healthy Participants, clinicaltrials.gov, Mar. 22, 2017, pp. 1-13; found on the Internet Dec. 15, 2021, URL: https://clinicaltrials.gov/ct2/history/NCT02219256?V_8=View#StudyPageTop.

Usmani S.Z. et al., Open-Label, Multicenter, Dose Escalation Phase 1b Study to Assess the Subcutaneous Delivery of Daratumumab in Patients(pts) with Relapsed or Refractory Multiple Myeloma (PAVO), Blood, 2016, vol. 128 (22) : 1149.

Van Bueren, J. et al. "Direct in Vitro Comparison of Daratumumab with Surrogate Analogs of CD38 Antibodies MOR03087, SAR650984 and Ab79" Blood 2014; 124 (21): 3474. doi: https://doi.org/10.1182/blood.V124.21.3474.3474.

Van de Donk, Niels W C J et al. "CD38 antibodies in multiple myeloma: back to the future." Blood vol. 131,1 (2018): 13-29. doi:10.1182/blood-2017-06-740944.

Van Noort et al., Cell biology of autoimmune diseases., Int Rev Cytol. 1998;178:127-206.

Vital, E.M., "Management of nonresponse to rituximab in rheumatoid arthritis: predictors and outcome of re-treatment.", Arthritis Rheum. May 2010;62(5):1273-9.

Walpole, Sarah Catherine et al. "The weight of nations: an estimation of adult human biomass." BMC public health vol. 12 439. Jun. 18, 2012, doi: 10.1186/1471-2458-12-439.

Winter, G., et al. "Humanized antibodies." Immunology today, vol. 14,6 (1993): 243-6.

Yu. B. Belousov, K. G. Gurevich. Clinical pharmacokinetics. The practice of dosing drugs. Moscow, Litterra Publishing House, 2005, 288 p., see p. 18, last paragraph,—p. 20 (Russian).

Zhang, Tiantian et al. "Systematic review and meta-analysis of the efficacy and safety of novel monoclonal antibodies for treatment of relapsed/refractory multiple myeloma." Oncotarget vol. 8,20 (2017): 34001-34017. doi:10.18632/oncotarget.16987.

International Preliminary Report on Patentability mailed Sep. 29, 2020, for PCT/IB19/00314, 6 pages.

International Search Report and Written Opinion for International Patent Application No. PCT/US19/13547 mailed Apr. 4, 2029, 12 pages.

Perez-Ramirez: "Approaches in subcutaneous delivery of monoclonal antibodies", European Pharmaceutical Review, Aug. 24, 2016 (Aug. 24, 2016), pp. 1-22, XP055573387.

Stevenson, G. T., "CD38 as a Therapeutic Target", Molecular Medicine, 2006, vol. 12, pp. 345-346.

Pivot, X et al. "Efficacy and safety of subcutaneous trastuzumab and intravenous trastuzumab as part of adjuvant therapy for HER2-positive early breast cancer: Final analysis of the randomised, two-cohort PrefHer study." European journal of cancer (Oxford, England : 1990) vol. 86 (2017): 82-90. doi:10.1016/j.ejca.2017.08.019.

* cited by examiner

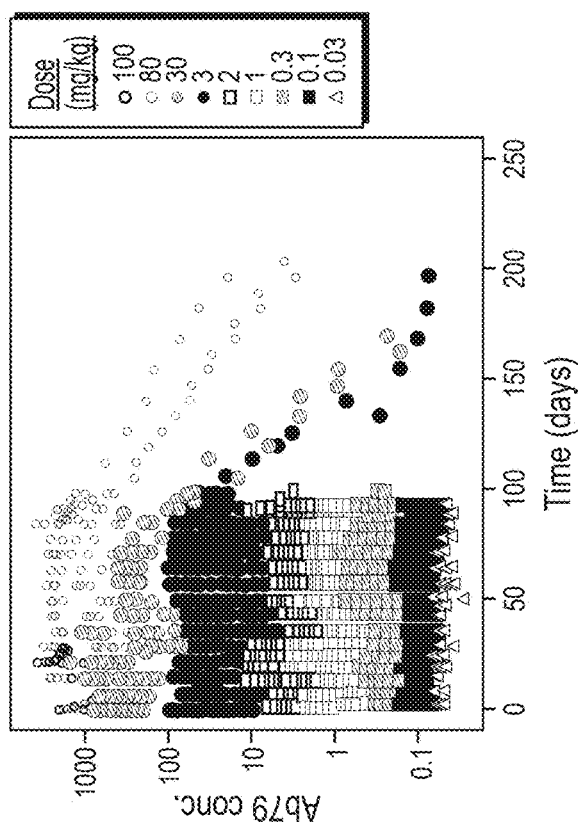
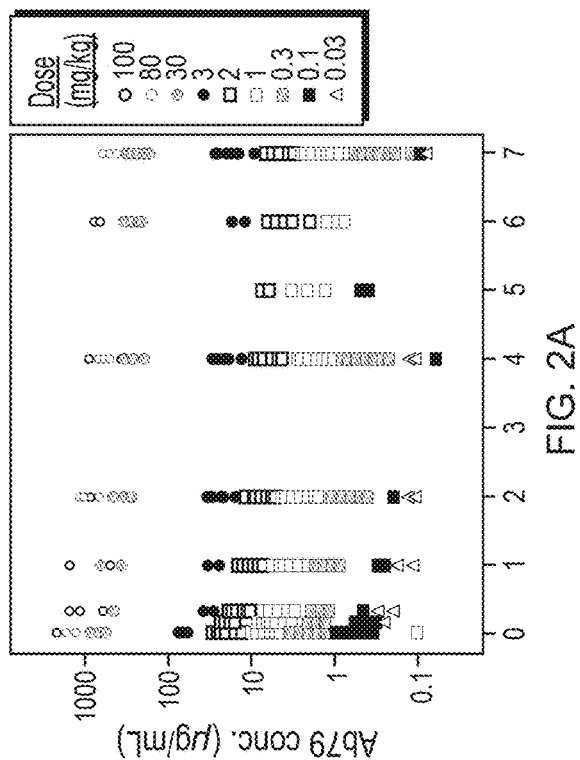
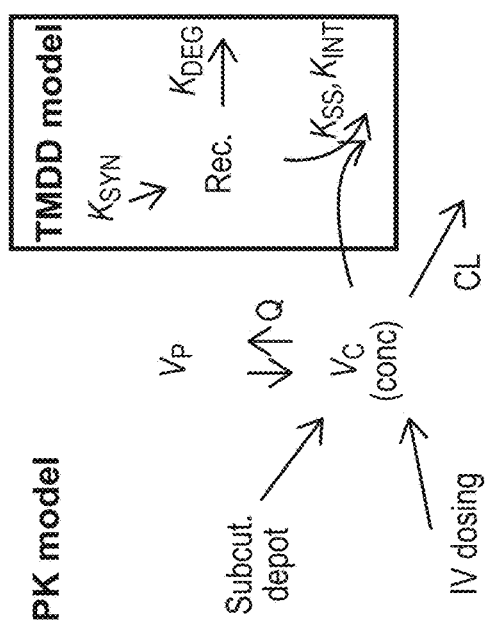
FIG. 2A
FIG. 2B
FIG. 2C

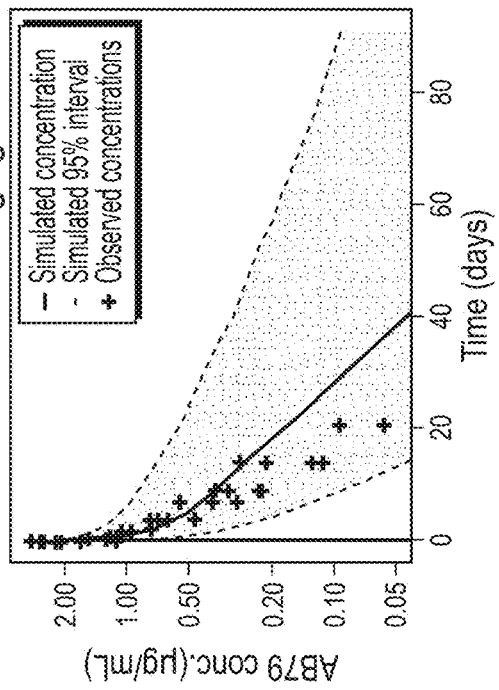
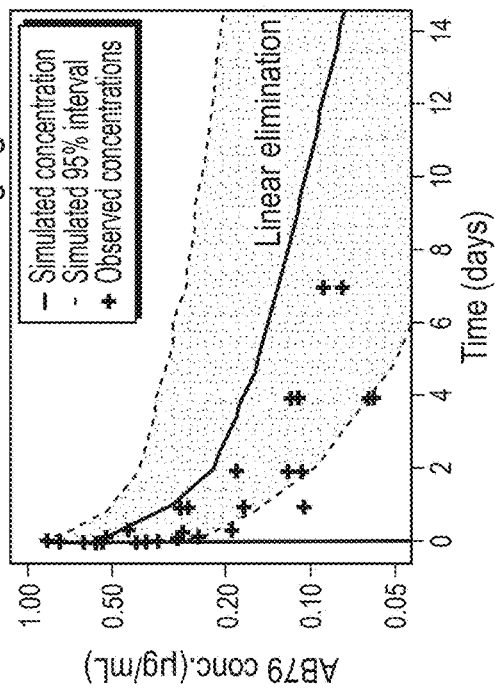
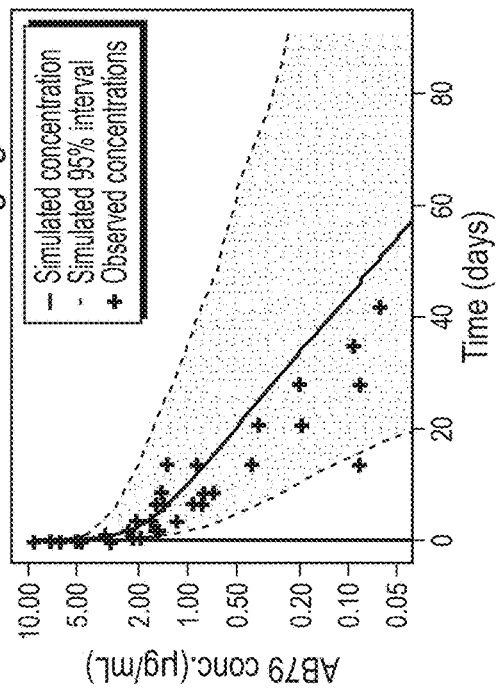

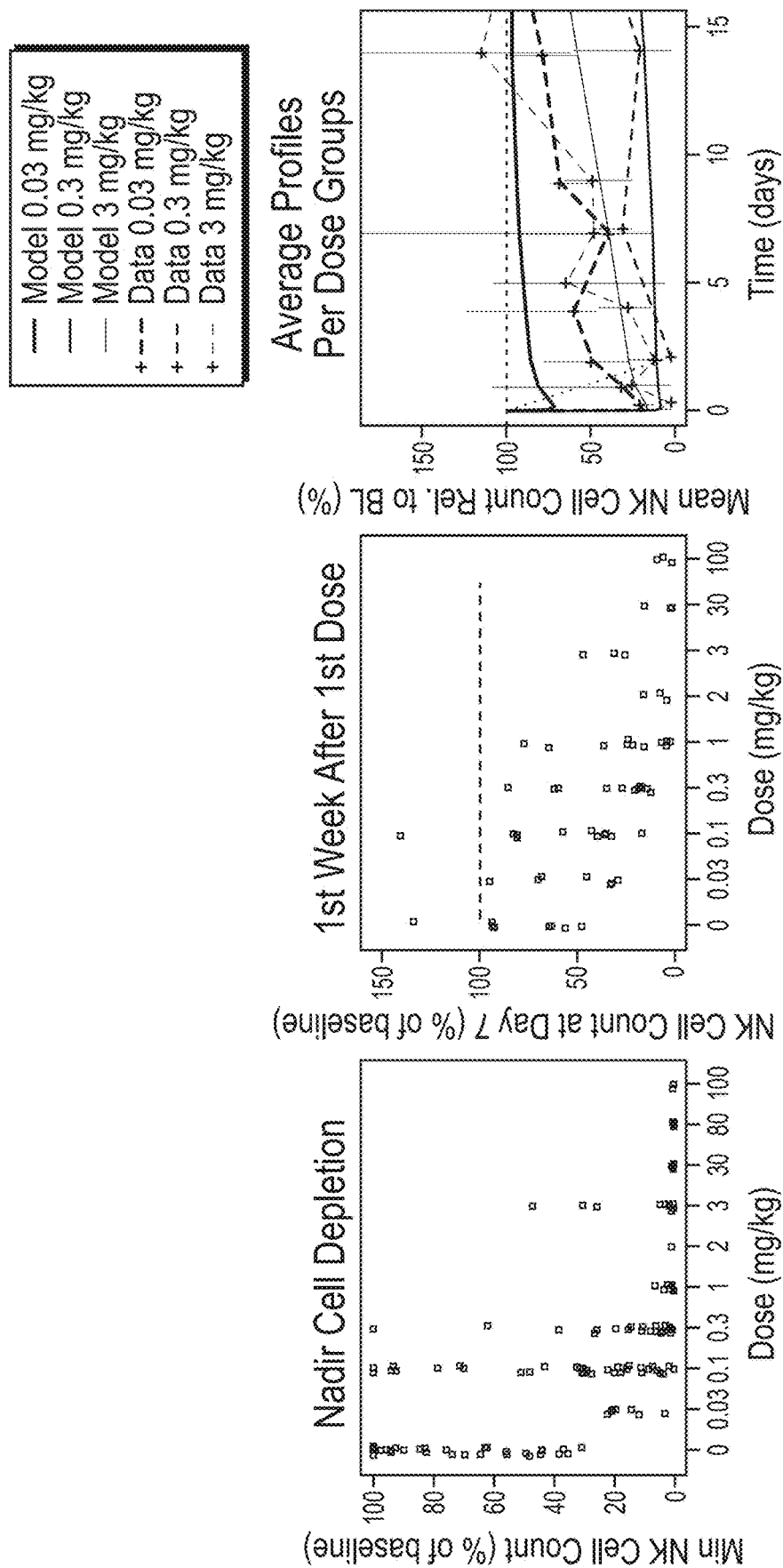

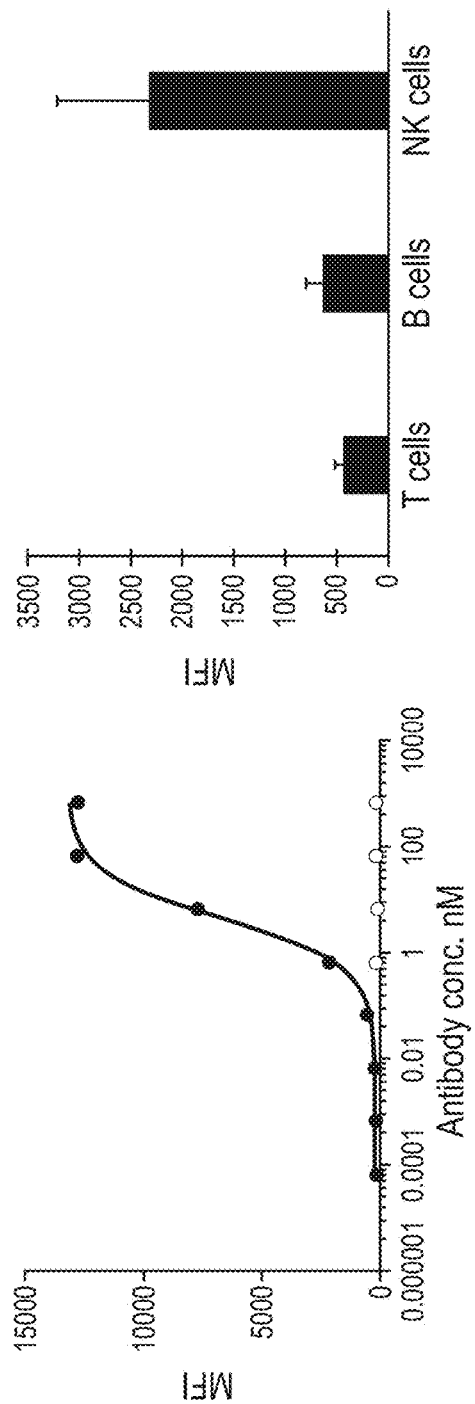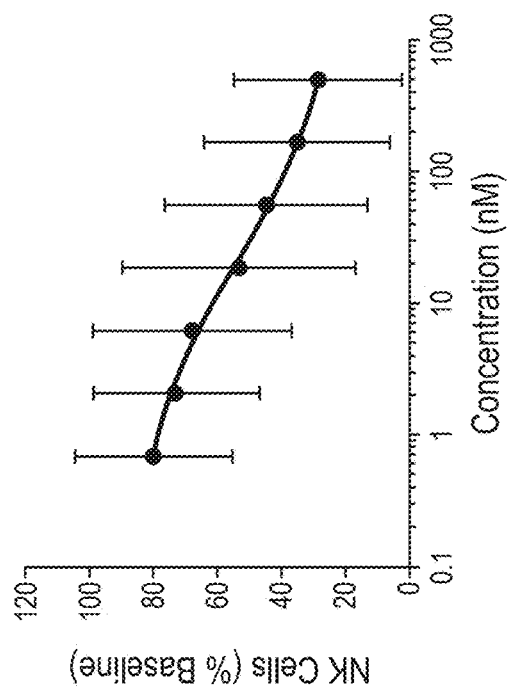
FIG. 32A
FIG. 32B
FIG. 32C

SEQUENCE LISTING

```
<160> NUMBER OF SEQ ID NOS: 13

<210> SEQ ID NO 1
<211> LENGTH: 300
<212> TYPE: PRT
<213> ORGANISM: Artificial Sequence
<220> FEATURE:
<223> OTHER INFORMATION: Human CD38

<400> SEQUENCE: 1

Met Ala Asn Cys Glu Phe Ser Pro Val Ser Gly Asp Lys Pro Cys Cys
1               5                   10                  15

Arg Leu Ser Arg Arg Ala Gln Leu Cys Leu Gly Val Ser Ile Leu Val
            20                  25                  30

Leu Ile Leu Val Val Val Leu Ala Val Val Val Pro Arg Trp Arg Gln
        35                  40                  45

Gln Trp Ser Gly Pro Gly Thr Thr Lys Arg Phe Pro Glu Thr Val Leu
    50                  55                  60

Ala Arg Cys Val Lys Tyr Thr Glu Ile His Pro Glu Met Arg His Val
65                  70                  75                  80

Asp Cys Gln Ser Val Trp Asp Ala Phe Lys Gly Ala Phe Ile Ser Lys
                85                  90                  95

His Pro Cys Asn Ile Thr Glu Glu Asp Tyr Gln Pro Leu Met Lys Leu
            100                 105                 110

Gly Thr Gln Thr Val Pro Cys Asn Lys Ile Leu Leu Trp Ser Arg Ile
        115                 120                 125

Lys Asp Leu Ala His Gln Phe Thr Gln Val Gln Arg Asp Met Phe Thr
    130                 135                 140

Leu Glu Asp Thr Leu Leu Gly Tyr Leu Ala Asp Asp Leu Thr Trp Cys
145                 150                 155                 160

Gly Glu Phe Asn Thr Ser Lys Ile Asn Tyr Gln Ser Cys Pro Asp Trp
                165                 170                 175

Arg Lys Asp Cys Ser Asn Asn Pro Val Ser Val Phe Trp Lys Thr Val
            180                 185                 190

Ser Arg Arg Phe Ala Glu Ala Ala Cys Asp Val Val His Val Met Leu
        195                 200                 205

Asn Gly Ser Arg Ser Lys Ile Phe Asp Lys Asn Ser Thr Phe Gly Ser
    210                 215                 220

Val Glu Val His Asn Leu Gln Pro Glu Lys Val Gln Thr Leu Glu Ala
225                 230                 235                 240

Trp Val Ile His Gly Gly Arg Glu Asp Ser Arg Asp Leu Cys Gln Asp
                245                 250                 255
```

```
Pro Thr Ile Lys Glu Leu Glu Ser Ile Ile Ser Lys Arg Asn Ile Gln
            260                 265                 270

Phe Ser Cys Lys Asn Ile Tyr Arg Pro Asp Lys Phe Leu Gln Cys Val
            275                 280                 285

Lys Asn Pro Glu Asp Ser Ser Cys Thr Ser Glu Ile
            290                 295                 300

<210> SEQ ID NO 2
<211> LENGTH: 301
<212> TYPE: PRT
<213> ORGANISM: Artificial Sequence
<220> FEATURE:
<223> OTHER INFORMATION: Cyno CD38

<400> SEQUENCE: 2

Met Ala Asn Cys Glu Phe Ser Pro Val Ser Gly Asp Lys Pro Cys Cys
 1               5                  10                  15

Arg Leu Ser Arg Arg Ala Gln Val Cys Leu Gly Val Cys Leu Leu Val
            20                  25                  30

Leu Leu Ile Leu Val Val Val Ala Val Val Leu Pro Arg Trp Arg
            35                  40                  45

Gln Gln Trp Ser Gly Ser Gly Thr Thr Ser Arg Phe Pro Glu Thr Val
        50                  55                  60

Leu Ala Arg Cys Val Lys Tyr Thr Glu Val His Pro Glu Met Arg His
65                  70                  75                  80

Val Asp Cys Gln Ser Val Trp Asp Ala Phe Lys Gly Ala Phe Ile Ser
            85                  90                  95

Lys Tyr Pro Cys Asn Ile Thr Glu Glu Asp Tyr Gln Pro Leu Val Lys
            100                 105                 110

Leu Gly Thr Gln Thr Val Pro Cys Asn Lys Thr Leu Leu Trp Ser Arg
            115                 120                 125

Ile Lys Asp Leu Ala His Gln Phe Thr Gln Val Gln Arg Asp Met Phe
130                 135                 140

Thr Leu Glu Asp Met Leu Leu Gly Tyr Leu Ala Asp Asp Leu Thr Trp
145                 150                 155                 160

Cys Gly Glu Phe Asn Thr Phe Glu Ile Asn Tyr Gln Ser Cys Pro Asp
            165                 170                 175

Trp Arg Lys Asp Cys Ser Asn Asn Pro Val Ser Val Phe Trp Lys Thr
            180                 185                 190

Val Ser Arg Arg Phe Ala Glu Thr Ala Cys Gly Val Val His Val Met
            195                 200                 205

Leu Asn Gly Ser Arg Ser Lys Ile Phe Asp Lys Asn Ser Thr Phe Gly
            210                 215                 220

Ser Val Glu Val His Asn Leu Gln Pro Glu Lys Val Gln Ala Leu Glu
225                 230                 235                 240

Ala Trp Val Ile His Gly Gly Arg Glu Asp Ser Arg Asp Leu Cys Gln
            245                 250                 255

Asp Pro Thr Ile Lys Glu Leu Glu Ser Ile Ile Ser Lys Arg Asn Ile
            260                 265                 270

Arg Phe Phe Cys Lys Asn Ile Tyr Arg Pro Asp Lys Phe Leu Gln Cys
            275                 280                 285

Val Lys Asn Pro Glu Asp Ser Ser Cys Leu Ser Gly Ile
            290                 295                 300

<210> SEQ ID NO 3
<211> LENGTH: 8
```

```
<212> TYPE: PRT
<213> ORGANISM: Artificial Sequence
<220> FEATURE:
<223> OTHER INFORMATION: HCDR1 AB79

<400> SEQUENCE: 3

Gly Phe Thr Phe Asp Asp Tyr Gly
1               5

<210> SEQ ID NO 4
<211> LENGTH: 8
<212> TYPE: PRT
<213> ORGANISM: Artificial Sequence
<220> FEATURE:
<223> OTHER INFORMATION: HCDR2 AB79

<400> SEQUENCE: 4

Ile Ser Trp Asn Gly Gly Lys Thr
1               5

<210> SEQ ID NO 5
<211> LENGTH: 16
<212> TYPE: PRT
<213> ORGANISM: Artificial Sequence
<220> FEATURE:
<223> OTHER INFORMATION: HCDR3 AB79

<400> SEQUENCE: 5

Ala Arg Gly Ser Leu Phe His Asp Ser Ser Gly Phe Tyr Phe Gly His
1               5                   10                  15

<210> SEQ ID NO 6
<211> LENGTH: 8
<212> TYPE: PRT
<213> ORGANISM: Artificial Sequence
<220> FEATURE:
<223> OTHER INFORMATION: LCDR1 AB79

<400> SEQUENCE: 6

Ser Ser Asn Ile Gly Asp Asn Tyr
1               5

<210> SEQ ID NO 7
<211> LENGTH: 3
<212> TYPE: PRT
<213> ORGANISM: Artificial Sequence
<220> FEATURE:
<223> OTHER INFORMATION: LCDR2 AB79

<400> SEQUENCE: 7

Arg Asp Ser
1

<210> SEQ ID NO 8
<211> LENGTH: 10
<212> TYPE: PRT
<213> ORGANISM: Artificial Sequence
<220> FEATURE:
<223> OTHER INFORMATION: LCDR3 AB79

<400> SEQUENCE: 8

Gln Ser Tyr Asp Ser Ser Leu Ser Gly Ser
1               5                   10

<210> SEQ ID NO 9
<211> LENGTH: 135
<212> TYPE: PRT
```

<213> ORGANISM: Artificial Sequence
<220> FEATURE:
<223> OTHER INFORMATION: (VH) chain amino acid sequence

<400> SEQUENCE: 9

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Asp Ile Ser Trp Asn Gly Gly Lys Thr His Tyr Val Asp Ser Val
    50                  55                  60

Lys Gly Gln Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Leu Phe His Asp Ser Ser Gly Phe Tyr Phe Gly His
            100                 105                 110

Trp Gly Gln Gly Thr Leu Val Thr Val Ser Ser Ala Ser Thr Lys Gly
        115                 120                 125

Pro Ser Val Phe Pro Leu Ala
        130                 135
```

<210> SEQ ID NO 10
<211> LENGTH: 129
<212> TYPE: PRT
<213> ORGANISM: Artificial Sequence
<220> FEATURE:
<223> OTHER INFORMATION: (VL) chain amino acid sequence

<400> SEQUENCE: 10

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asp Asn
            20                  25                  30

Tyr Val Ser Trp Tyr Gln Gln Leu Pro Gly Thr Ala Pro Lys Leu Leu
        35                  40                  45

Ile Tyr Arg Asp Ser Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Ser Ser Leu
                85                  90                  95

Ser Gly Ser Val Phe Gly Gly Gly Thr Lys Leu Thr Val Leu Gly Gln
            100                 105                 110

Pro Lys Ala Asn Pro Thr Val Thr Leu Phe Pro Pro Ser Ser Glu Glu
        115                 120                 125

Leu
```

<210> SEQ ID NO 11
<211> LENGTH: 453
<212> TYPE: PRT
<213> ORGANISM: Artificial Sequence
<220> FEATURE:
<223> OTHER INFORMATION: (HC) amino acid sequence

<400> SEQUENCE: 11

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Asp Ile Ser Trp Asn Gly Gly Lys Thr His Tyr Val Asp Ser Val
    50                  55                  60

Lys Gly Gln Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Leu Phe His Asp Ser Ser Gly Phe Tyr Phe Gly His
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
```

```
                    420                 425                 430
Val Met His Glu Ala Leu His Asn His Tyr Thr Gln Lys Ser Leu Ser
            435                 440                 445

Leu Ser Pro Gly Lys
        450

<210> SEQ ID NO 12
<211> LENGTH: 216
<212> TYPE: PRT
<213> ORGANISM: Artificial Sequence
<220> FEATURE:
<223> OTHER INFORMATION: (LC) amino acid sequence

<400> SEQUENCE: 12

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asp Asn
            20                  25                  30

Tyr Val Ser Trp Tyr Gln Gln Leu Pro Gly Thr Ala Pro Lys Leu Leu
        35                  40                  45

Ile Tyr Arg Asp Ser Gln Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Ser Ser Leu
                85                  90                  95

Ser Gly Ser Val Phe Gly Gly Gly Thr Lys Leu Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
210                 215

<210> SEQ ID NO 13
<211> LENGTH: 318
<212> TYPE: PRT
<213> ORGANISM: Artificial Sequence
<220> FEATURE:
<223> OTHER INFORMATION: Human CD157

<400> SEQUENCE: 13

Met Ala Ala Gln Gly Cys Ala Ala Ser Arg Leu Leu Gln Leu Leu Leu
1               5                   10                  15

Gln Leu Leu Leu Leu Leu Leu Leu Ala Ala Gly Gly Ala Arg Ala
            20                  25                  30

Arg Trp Arg Gly Glu Gly Thr Ser Ala His Leu Arg Asp Ile Phe Leu
        35                  40                  45
```

-continued

```
Gly Arg Cys Ala Glu Tyr Arg Ala Leu Leu Ser Pro Glu Gln Arg Asn
    50              55                  60

Lys Asn Cys Thr Ala Ile Trp Glu Ala Phe Lys Val Ala Leu Asp Lys
65              70                  75                      80

Asp Pro Cys Ser Val Leu Pro Ser Asp Tyr Asp Leu Phe Ile Asn Leu
                85                  90                  95

Ser Arg His Ser Ile Pro Arg Asp Lys Ser Leu Phe Trp Glu Asn Ser
                100                 105                 110

His Leu Leu Val Asn Ser Phe Ala Asp Asn Thr Arg Arg Phe Met Pro
        115                 120                 125

Leu Ser Asp Val Leu Tyr Gly Arg Val Ala Asp Phe Leu Ser Trp Cys
    130                 135                 140

Arg Gln Lys Asn Asp Ser Gly Leu Asp Tyr Gln Ser Cys Pro Thr Ser
145                 150                 155                 160

Glu Asp Cys Glu Asn Asn Pro Val Asp Ser Phe Trp Lys Arg Ala Ser
                165                 170                 175

Ile Gln Tyr Ser Lys Asp Ser Ser Gly Val Ile His Val Met Leu Asn
            180                 185                 190

Gly Ser Glu Pro Thr Gly Ala Tyr Pro Ile Lys Gly Phe Phe Ala Asp
        195                 200                 205

Tyr Glu Ile Pro Asn Leu Gln Lys Glu Lys Ile Thr Arg Ile Glu Ile
        210                 215                 220

Trp Val Met His Glu Ile Gly Gly Pro Asn Val Glu Ser Cys Gly Glu
225                 230                 235                 240

Gly Ser Met Lys Val Leu Glu Lys Arg Leu Lys Asp Met Gly Phe Gln
                245                 250                 255

Tyr Ser Cys Ile Asn Asp Tyr Arg Pro Val Lys Leu Leu Gln Cys Val
                260                 265                 270

Asp His Ser Thr His Pro Asp Cys Ala Leu Lys Ser Ala Ala Ala Ala
            275                 280                 285

Thr Gln Arg Lys Ala Pro Ser Leu Tyr Thr Glu Gln Arg Ala Gly Leu
        290                 295                 300

Ile Ile Pro Leu Phe Leu Val Leu Ala Ser Arg Thr Gln Leu
305                 310                 315
```

SUBCUTANEOUS ADMINISTRATION OF ANTI-CD38 ANTIBODIES

CROSS REFERENCE TO RELATED APPLICATIONS

This application claims priority under 35 U.S.C. § 119(e) to U.S. Provisional Application Ser. No. 62/617,146 filed on Jan. 12, 2018, the entire disclosure of which is incorporated herein by reference.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 17.6 kilobytes ASCII (text) file named "101588-5009-US_Sequence_Listing.txt," created on Jul. 9, 2020.

FIELD OF THE INVENTION

Methods of administering isolated anti-CD38 antibodies at low dosages and in low volumes via subcutaneous (SC) administration are disclosed.

BACKGROUND OF THE INVENTION

CD38, also known as cyclic ADP ribose hydrolase, is a type II transmembrane glycoprotein with a long C-terminal extracellular domain and a short N-terminal cytoplasmic domain. CD38 is a member of a group of related membrane bound or soluble enzymes that comprises CD157 and Aplysia ADPR cyclase. This family of enzymes has the unique capacity to convert NAD to cyclic ADP ribose or nicotinic acid-adenine dinucleotide phosphate. CD38 is involved in $Ca^{2+}$ mobilization and in signal transduction through tyrosine phosphorylation of numerous signaling molecules, including phospholipase Cy, ZAP-70, syk, and c-cb1. Based on these observations, CD38 is an important signaling molecule in the maturation and activation of lymphoid cells during their normal development. Among hematopoietic cells, an assortment of functional effects have been ascribed to CD38-mediated signalling, including lymphocyte proliferation, cytokine release, regulation of B and myeloid cell development and survival, and induction of dendritic cell (DC) maturation.

CD38 is expressed in immature hematopoietic cells, down regulated in mature hematopoietic cells, and re-expressed at high levels in activated lymphocytes and plasma cells. For example, high CD38 expression is seen in activated B cells, plasma cells, activated CD4+ T cells, activated CD8+ T cells, NK cells, NKT cells, mature DCs and activated monocytes (U.S. Pat. No. 8,362,211). CD38 deficiency in mice has been associated with decreased levels of peripheral T regulatory and invariant NKT cells, defects in humoral B-cell responses and DC trafficking, and an attenualted form of collagen-induced arthritis (CIA) (Chiba et al. (2005) Arthrit. Rheum. 52:1941-48).

The presence of autoantibodies to CD38 has been associated with a number of diseases, including diabetes, chronic autoimmune thyroiditis and Graves' disease (Antonelli et al. (2001) Clin. Exp. Immunol. 126: 426-431; Mallone et al. (2001) Diabetes 50: 752 and Antonelli et al. (2004) J. Endocrinol. Invest. 27: 695-707).

Increased expression of CD38 has been documented in a variety of diseases, including autoimmune diseases and cancers. Such diseases include systemic lupus erythematosus (SLE), rheumatoid arthritis (RA), inflammatory bowel disease (IBD), ulcerative colitis (UC), myasthenia gravis (MG) (Yilmaz et al. (2018) Ann. Clin. Transl. Neurol. 5(11):1408-1414), neuromyelitis optica (NMO) (Chihara et al. (2011) Proc. Natl. Acad. Sci. USA 108(9):3701-6), immune thrombocytopenic purpura (ITP), thrombotic thrombocytopenic purpura (TTP) (Behzad et al. (2018) APMIS 126(6):523-532), anti-phospholipid syndrome (APS) (Alvarez-Rodriguez et al. (2018) Int. J. Mol. Sci. 19(2): pii), pemphigus vulgaris (PV), pemphigus foliaceus (PF), anti-NMDAR encephalitis (NMDR), autoimmune hemolytic anemia (AIHA), Grave's disease, membranous nephropathy, Sjogren's syndrome (SS), ANCA vasculitis, epidermolysis bullosa acquisita (EBA), bullous pemphigoid (BP), Hashimoto's thyroiditis, scleroderma, and $IgG_4$-related disease. In patients with RA, plasma cells are increased in the joint tissue compared to controls. In patients with SLE, plasmablasts are increased in the peripheral blood in patients with more active disease. However, current CD20-based B cell depleting therapies such as rituximab effectively deplete CD20+ B cells, but cannot directly and effectively deplete plasma cells or plasmablasts because they do not express CD20. Thus, patients with RA or SLE with high levels of plasma cells or plasmablasts are unlikely to gain substantial clinical benefit from CD20-based therapies.

Therapeutics that target CD38, which is highly expressed on plasma cells, plasmablasts, NK cells, activated B lymphocytes, plasmacytoid dendritic cells, and activated T cells, may provide an effective treatment for RA and SLE as well as other diseases characterized by CD38 expression. The level of CD38-expressing plasmablasts in peripheral blood of adult SLE patients treated with rituximab and oral steroids was the best predictor of time of relapse. Moreover, circulating immunoglobulin (Ig)-secreting cells which express high levels of CD38 were identified in peripheral blood of SLE patients with active disease and the level of this subset was associated with treatment-induced decreases in anti-double-stranded DNA (anti-dsDNA) antibody levels, proteinuria, and disease activity (Grammer et al. (2003) J. Clin. Invest. 112: 1506-1520). In addition, plasma cells are sensitive to proteasome inhibition and are reduced in peripheral blood of highly refractory SLE patients exposed to bortezomib (Alexander et al. (2015) Ann. Rheum. Dis. 74(7): 1474-1478). This reduction corresponded with a decrease in anti-dsDNA antibodies and a corresponding improvement in disease activity in each patient. Unfortunately, therapy was associated with treatment-emergent adverse events (TEAEs; e.g., neuropathy, diarrehea) which may have resulted from proteasome inhibition in non-lymphoid cells (e.g., neurons, epithelium). Collectively, these data indicate that specifically reducing CD38-expressing plasma cells could yield an improved benefit to risk profile for refractory SLE patients. As current therapies for both RA and SLE produce major clinical responses and sustained remission in only a minority of patients there is an urgent need to explore additional treatment mechanisms.

Increased expression of CD38 has been documented in a variety of diseases of hematopoietic origin, as well as cell lines derived therefrom, and has been described as a negative prognostic marker in hematologic cancers. Such diseases include, but are not limited to, multiple myeloma (MM), chronic lymphoblastic leukemia, B-cell chronic lymphocytic leukemia (B-CLL), including B-cell acute lymphocytic leukemia, B and T acute lymphocytic leukemia (ALL), acute lymphoblastic leukemia, Waldenstrom macroglobulinemia, mantle-cell lymphoma, pro-lymphocytic/myelocytic leukemia, acute myeloid leukemia (AML), chronic myeloid leukemia (CML), follicular lymphoma, NK-cell leukemia, plasma-cell leukemia, non-Hodgkin lymphoma (NHL), Burkitt lymphoma (BL), T cell lymphoma (TCL), hairy cell leukemia (HCL), and Hodgkin lymphoma (HL). Furthermore, CD38 expression is a prognostic indicator for patients with conditions such as, for example, B-CLL (Dirig et al. (2002) Leukemia 16: 30-35; and Morabito et al. (2001) Leukemia Res. 25: 927-932) and acute myelogenous leukemia (Keyhani et al. (1999) Leukemia Res. 24: 153-159). CD38 therefore provides a useful target for the treatment of diseases of the hematopoietic system.

Several anti-CD38 antibodies are in clinical trials for the treatment of CD38-associated cancers. However, these prior art therapeutic anti-CD38 antibodies bind to red blood cells (RBCs) and platelets, which may explain why a higher required dosing is needed to overcome such the sink created by binding to RBCs. For example, treatment with daratumumab (anti-CD38 IgG1 mAb Darzalex®, which is FDA approved and commercially available from Janssen Oncology) requires a very high dose (≥16 mg/kg) and an intensive regime (weekly 8×, bi-weekly 8×, then monthly) for optimal anti-tumor activity (Xu et al. (2017) Clin. Pharmacol. Ther. 101(6): 721-724). Daratumumab's binding to CD38 on RBCs and platelets results in a positive antiglobulin test (indirect Coombs test), which may persist for up to 6 months after the last daratumumab infusion (Sullivan et al. (2017) Blood 129(22): 3033-3037). This is a significant property of daratumumab and other antibodies that bind RBCs. Although CD38 is expressed on RBCs at a level that is approximately 1000-fold lower than that on myeloma cells (deWeers et al. (2011) J. Immunol. 186(3):1840-1848), there are approximately 36,000 RBCs for each myeloma cell in the blood of an MM patient with active disease (Witzig et al. (1993) Cancer 72(1): 108-113). As such, there are 36-fold more CD38 molecules expressed by the RBC population compared to a tumor cell population. Thus, it has been hypothesized that RBCs bind a significant amount of any anti-CD38 antibody that is administered, resulting in the need to administer large dosages in order to have sufficient levels of anti-CD38 antibody to achieve a therapeutic effect on the tumor cells.

Accordingly, treatments using anti-CD38 antibodies are currently focused on intravenous (IV) administration because of the high volume of antibody required to achieve therapeutic efficacy, as such large volumes are not suitable for subcutaneous administration and there is a limit to how concentrated Abs can be formulated. For example, a 1200 mg dose of daratumumab administered IV over at least 2 hours is approved for treating relapsed and refractory multiple myeloma (RRMM) and newly diagnosed multiple myeloma (NDMM). A subcutaneous (SC) formulation of daratumumab consisting of 1800 mg in 15 mL that must be a co-formulation with Enhance™ (Halozyme-containing, in order to speed up absorption) and administered weekly 8×, biweekly 8× and then once monthly, is currently in Ph3 trials for RRMM.

Another anti-CD38 antibody, isatuximab (commercially available from Sanofi Genzyme and currently in Phase 3 clinical trials), is administered at 10 mg/kg and 20 mg/kg, which corresponds to 700-1400 mg per 70 kg patient, with a projected injection volume of 3.5-14 mL.

The higher doses and volumes required of the prior art anti-CD38 antibodies presently in the clinic may also cause serious side effects such as, for example, hemolytic anemia, a condition in which RBCs are destroyed more quickly than they can be replaced. In an open-label, single-arm study, isatuximab was administered intravenously to 97 total patients at 3 mg/kg every 2 weeks (Q2W; n=23), 10 mg/kg Q2W for 2 cycles followed by Q4W (n=25), 10 mg/kg Q2W (n=24), and 20 mg/kg every week for 4 doses (1 cycle) followed by Q2W (n=25). The most common severe (grade 3/4) adverse event was anemia, which affected 24% of patients (see the 2016 ASCO Annual Meeting; Richter et al. (2016) J. Clin. Oncol. 34 (suppl): abstr 8005). In one daratumumab study, 45% of all patients experienced anemia (19% of which were grade 3) and 48% of patients experienced thrombocytopenia (10% of which were grade 3 and 8% of which were grade 4) (see, for example, https://www.rxlist.com/darzalex-side-effects-drug-center.htm; Costello (2017) Ther. Adv. Hematol. 8(1): 28-37). Thus, patients being treated with isatuximab or daratumumab must be carefully monitored for these life threatening and other serious side effects The physical challenges in administering large amounts of anti-CD38 mAbs to patients subcutaneously illustrates the need in the art for more potent anti-CD38 antibodies because a more potent antibody could achieve the desired pharmacologic effects in a smaller amount/volume and thereby enable more effective forms of administration. A more potent antibody could result in formulating lower volumes which would be administered SC more effectively than daratumumab (Darzalex) to patients in which depletion of CD38-expressing cells is warranted, such as for the treatment of autoimmune diseases and hematologic forms of cancer. The advantages of administering a lower amount of drug would include administration that took seconds compared to minutes for daratumumab administered SC and hours for daratumumab, isatuximab, or MOR202 administered IV as well as fewer infusion reactions (as has been seen for daratumumab SC administration. Reducing the time that a patient needs to spend in an infusion center would allow the option of in-home therapy, increased efficiency of administration and productivity of infusion centers; lower healthcare expenditures per patient as a result of increased institutional efficiency; and wider utility if the drug could be used by patients without access to an infusion center.

AB79 is a fully human immunoglobulin IgG1 monoclonal antibody that binds specifically to CD38 with high affinity (Kd=3.5 nM) (U.S. Pat. No. 8,362,211, the contents of which is hereby incorporated by reference in its entirety). AB79 inhibits the growth of tumor cells expressing CD38 by cell depletion via antibody dependent cellular cytotoxicity (ADCC) and complement dependent cytotoxicity (CDC). AB79 also reduces the level of plasma cells and plasmablasts in blood isolated from healthy subjects and systemic lupus erythematosus (SLE) patients. In the case of SLE, 80% of the plasma cell population including short- and long-lived plasma cells, is reduced. Additionally, the number of cells producing pathogenic autoantibodies was also reduced, including VH4-34 9G4+ antibodies (70% reduction), anti-Ro antibody (70% reduction), and anti-dsDNA antibody (80% reduction). The anti-human CD38 mAb daratumumab also depletes CD38-expressing plasmablasts and plasma cells in samples from patients with SLE and RA in a dose-dependent manner in vitro. In contrast to daratumumab, AB79 cross-reacts with CD38 expressed by cynomolgus monkeys providing a unique opportunity to determine if reducing the level of cells expressing CD38 would affect inflammation and tissue damage in a non-human primate model of autoimmune disease. In healthy cynomolgus monkeys, the efficiency of depletion for lymphocytes, and B, T and NK cells correlated positively with level of CD38 expression and AB79 dose level (PCT Application No. PCT/US2017/042128; U.S. Pat. No. 8,362,211).

Given that many CD38 antibodies in the clinic are not suitable for low-dosage or low volume subcutaneous administration and possess dangerous side effects, there remains a need in the art for antibody formulations that are safer, more convenient, and more effective for treating diseases in which binding to CD38 is indicated, such as autoimmune diseases and hematologic forms of cancer.

SUMMARY OF THE INVENTION

Provided herein are methods for treating diseases in which binding to CD38 is indicated such as, for example, autoimmune diseases and hematological cancers comprising subcutaneously administering isolated anti-CD38 antibodies at unexpectedly low dosages and/or small volumes.

In one aspect, the invention provides a method for treating a disease in which binding to CD38 is indicated in a subject, the method comprising the step of subcutaneously administering to a subject having a disease in which binding to CD38 is indicated a therapeutically effective amount of an isolated human anti-CD38 antibody sufficient to treat the disease, wherein the anti-CD38 antibody comprises a variable heavy (VH) chain region comprising a CDR1 having the amino acid sequence of SEQ ID NO:3, a CDR2 having the amino acid sequence of SEQ ID NO:4, and a CDR3 having the amino acid sequence of SEQ ID NO:5; and a variable light (VL) chain region comprising a CDR1 having the amino acid sequence of SEQ ID NO:6, a CDR2 having the amino acid sequence of SEQ ID NO:7 and a CDR3 having the amino acid sequence of SEQ ID NO:8.

In another aspect, the invention provides a method for treating a disease in which binding to CD38 is indicated in a subject, the method comprising the step of subcutaneously administering to a subject having a disease in which binding to CD38 is indicated a therapeutically effective amount of an isolated human anti-CD38 antibody sufficient to treat the disease, wherein the anti-CD38 antibody comprises a VH chain region comprising a CDR1 having the amino acid sequence of SEQ ID NO:3, a CDR2 having the amino acid sequence of SEQ ID NO:4, and a CDR3 having the amino acid sequence of SEQ ID NO:5; and a VL chain region comprising a CDR1 having the amino acid sequence of SEQ ID NO:6, a CDR2 having the amino acid sequence of SEQ ID NO:7 and a CDR3 having the amino acid sequence of SEQ ID NO:8, wherein the anti-CD38 antibody is administered in a volume of 3 milliliter or less.

In another aspect, the invention provides a method for treating a disease in which binding to CD38 is indicated in a subject, the method comprising the step of subcutaneously administering to a subject having a disease in which binding to CD38 is indicated a therapeutically effective amount of an isolated human anti-CD38 antibody sufficient to treat the disease, wherein the anti-CD38 antibody comprises a VH chain region comprising a CDR1 having the amino acid sequence of SEQ ID NO:3, a CDR2 having the amino acid sequence of SEQ ID NO:4, and a CDR3 having the amino acid sequence of SEQ ID NO:5; and a VL chain region comprising a CDR1 having the amino acid sequence of SEQ ID NO:6, a CDR2 having the amino acid sequence of SEQ ID NO:7 and a CDR3 having the amino acid sequence of SEQ ID NO:8, wherein the anti-CD38 antibody is administered at a dosage of from 0.03 to 0.6 milligram per kilogram body weight.

In one aspect, the anti-CD38 antibody does not cause hemolytic anemia or thrombocytopenia.

In one aspect, administering the anti-CD38 antibody results in less than 60%, less than 50%, less than 40%, less than 30%, less than 25%, less than 20%, less than 15%, less than 10%, or less than 5% incidence of grade 3 or 4 of one or more treatment-emergent adverse events (TEAEs) selected from the group consisting of anemia, hemolytic anemia, thrombocytopenia, fatigue, infusion-related reactions (IRRs), leukopenia, and lymphopenia.

In one aspect, the anti-CD38 antibody results in less than 10%, less than 20%, less than 30%, less than 40%, less than 50% depletion of RBCs.

In one aspect, the anti-CD38 antibody results in less than 10%, less than 20%, less than 30%, less than 40%, less than 50% depletion of platelets.

In one aspect, the disease is selected from the group consisting of an autoimmune disease and a cancer.

In one aspect, the autoimmune disease is selected from the group consisting of systemic lupus erythematosus (SLE), rheumatoid arthritis (RA), inflammatory bowel disease (IBD), ulcerative colitis, myasthenia gravis (MG), neuromyelitis optica (NMO), immune thrombocytopenic purpura (ITP), thrombotic thrombocytopenic purpura (TTP), antiphospholipid syndrome (APS), pemphigus vulgaris (PV), pemphigus foliaceus (PF), anti-NMDAR encephalitis (NMDR), autoimmune hemolytic anemia (AIHA), Grave's disease, membranous nephropathy, Sjogren's syndrome (SS), ANCA vasculitis, epidermolysis bullosa acquisita (EBA), bullous pemphigoid (BP), Hashimoto's thyroiditis, scleroderma, $IgG_4$-related disease, and graft-v-host disease. (Yilmaz V, et. al., Ann Clin Transl Neurol. 2018 Sep. 22; 5(11):1408-1414; Chihara N, Aranami T, Sato W, Miyazaki Y, Miyake S, Okamoto T, Ogawa M, Toda T, Yamamura T. Proc Natl Acad Sci USA. 2011 Mar. 1; 108(9):3701-6; Behzad MM, et al., APMIS. 2018 June;126(6):523-532; or Alvarez-Rodriguez L., et al., Int J Mol Sci. 2018 Feb. 16; 19(2).

In one aspect, the hematological cancer is selected from the group consisting of multiple myeloma, NK/T cell lymphoma, chronic lymphoblastic leukemia, chronic lymphocytic leukemia, plasma cell leukemia, acute myeloid leukemia, chronic myeloid leukemia, B-cell lymphoma, and Burkitt lymphoma.

In one aspect, the hematological cancer is multiple myeloma. In certain embodiments, the multiple myeloma is selected from the group consisting of RRMM and EDMM.

In one aspect, wherein the VH chain region has the amino acid sequence of SEQ ID NO:9 and the VL chain region has the amino acid sequence of SEQ ID NO:10.

In one aspect, the anti-CD38 antibody comprises a heavy chain amino acid sequence of SEQ ID NO: 11 and a light chain amino acid sequence of SEQ ID NO:12.

In one aspect, the therapeutically effective amount is a dosage of from 0.03 to 0.6 milligram per kilogram body weight.

In one aspect, the therapeutically effective amount is in a volume of 3 milliliter or less.

In one aspect, the therapeutically effective amount is in a volume of 2 milliliter or less.

In one aspect, the therapeutically effective amount is in a volume of 1 milliliter or less.

In one aspect, the human anti-CD38 antibody is administered in the form of a pharmaceutically acceptable composition.

In another aspect, the invention provides a method for treating a hematological cancer in a subject, the method comprising the step of subcutaneously administering to a subject having a hematological cancer a therapeutically effective amount of an isolated human anti-CD38 antibody sufficient to treat the hematological cancer, wherein the anti-CD38 antibody comprises a VH chain region comprising a CDR1 having the amino acid sequence of SEQ ID NO:3, a CDR2 having the amino acid sequence of SEQ ID NO:4, and a CDR3 having the amino acid sequence of SEQ ID NO:5; and a variablVL chain region comprising a CDR1 having the amino acid sequence of SEQ ID NO:6, a CDR2 having the amino acid sequence of SEQ ID NO:7 and a CDR3 having the amino acid sequence of SEQ ID NO:8.

In another aspect, the invention provides a method for treating a hematological cancer in a subject, the method comprising the step of subcutaneously administering to a subject having a hematological cancer a therapeutically effective amount of an isolated human anti-CD38 antibody sufficient to treat the hematological cancer, wherein the anti-CD38 antibody comprises a VH chain region comprising a CDR1 having the amino acid sequence of SEQ ID NO:3, a CDR2 having the amino acid sequence of SEQ ID NO:4, and a CDR3 having the amino acid sequence of SEQ ID NO:5; and a VL chain region comprising a CDR1 having the amino acid sequence of SEQ ID NO:6, a CDR2 having the amino acid sequence of SEQ ID NO:7 and a CDR3 having the amino acid sequence of SEQ ID NO:8 wherein the anti-CD38 antibody is administered in a volume of 3 mL or less, 2 mL or less, or 1 mL or less.

In another aspect, the invention provides a method for treating a hematological cancer in a subject, the method comprising the step of subcutaneously administering to a subject having a hematological cancer a therapeutically effective amount of an isolated human anti-CD38 antibody sufficient to treat the hematological cancer, wherein the anti-CD38 antibody comprises a VH chain region comprising a CDR1 having the amino acid sequence of SEQ ID NO:3, a CDR2 having the amino acid sequence of SEQ ID NO:4, and a CDR3 having the amino acid sequence of SEQ ID NO:5; and a VL chain region comprising a CDR1 having the amino acid sequence of SEQ ID NO:6, a CDR2 having the amino acid sequence of SEQ ID NO:7 and a CDR3 having the amino acid sequence of SEQ ID NO:8 wherein the anti-CD38 antibody is administered at a dosage of from 0.03 to 0.6 milligram per kilogram body weight.

In one aspect, the anti-CD38 antibody does not cause hemolytic anemia or thrombocytopenia.

In one aspect, administering the anti-CD38 antibody results in less than 60%, less than 50%, less than 40%, less than 30%, less than 25%, less than 20%, less than 15%, less than 10%, or less than 5% incidence of grade 3 or 4 of one or more TEAEs selected from the group consisting of anemia, including hemolytic anemia, thrombocytopenia, fatigue, infusion-related reactions (IRRs), leukopenia, and lymphopenia.

In one aspect, the anti-CD38 antibody results in less than 10%, less than 20%, less than 30%, less than 40%, or less than 50% depletion of RBCs.

In one aspect, the anti-CD38 antibody results in less than 10%, less than 20%, less than 30%, less than 40%, or less than 50% depletion of platelets.

In one aspect, the hematological cancer is selected from the group consisting of multiple myeloma, chronic lymphoblastic leukemia, chronic lymphocytic leukemia, plasma cell leukemia, acute myeloid leukemia, chronic myeloid leukemia, B-cell lymphoma, NK/T cell lymphoma, and Burkitt lymphoma.

In one aspect, the hematological cancer is multiple myeloma. In certain embodiments, the multiple myeloma is selected from the group consisting of RRMM and EDMM.

In one aspect, the VH chain region has the amino acid sequence of SEQ ID NO:9 and the VL chain region of has the amino acid sequence of SEQ ID NO:10.

In one aspect, the anti-CD38 antibody comprises a heavy chain amino acid sequence of SEQ ID NO: 11 and a light chain amino acid sequence of SEQ ID NO:12.

In one aspect, the therapeutically effective amount is a dosage of from 0.03 to 0.6 milligram per kilogram body weight.

In one aspect, the therapeutically effective amount is in a volume of 3 milliliter or less.

In one aspect, the therapeutically effective amount is in a volume of 2 milliliter or less.

In one aspect, the therapeutically effective amount is in a volume of 1 milliliter or less.

In one aspect, the human anti-CD38 antibody is administered in the form of a pharmaceutically acceptable composition.

In another aspect, the invention provides a unit dosage form comprising an isolated antibody that comprises a heavy chain variable region amino acid sequence of SEQ ID NO:9 and a light chain variable region amino acid sequence of SEQ ID NO:10, wherein the isolated antibody binds to CD38, wherein the unit dosage form is formulated for subcutaneous administration of the antibody at a dosage of from 0.03 to 0.6 milligram per kilogram body weight.

In one aspect, the heavy chain comprises the amino acid sequence of SEQ ID NO:11 and the light chain comprises the amino acid sequence of SEQ ID NO:12.

In one aspect, the unit dosage form is in a volume of 3 milliliter or less.

In one aspect, the unit dosage form is in a volume of 2 milliliter or less.

In one aspect, the unit dosage form is in a volume of 1 milliliter or less.

In one aspect, the unit dosage form is formulated for subcutaneous administration of the antibody in the treatment of a hematological cancer selected from the group consisting of multiple myeloma, chronic lymphoblastic leukemia, chronic lymphocytic leukemia, plasma cell leukemia, acute myeloid leukemia, chronic myeloid leukemia, B-cell lymphoma, and Burkitt lymphoma.

In one aspect, the hematological cancer is multiple myeloma. In certain embodiments, the multiple myeloma is selected from the group consisting of RRMM and EDMM.

In one aspect, the anti-CD38 antibody does not cause hemolytic anemia or thrombocytopenia.

In one aspect, the anti-CD38 antibody results in less than 10%, less than 20%, less than 30%, less than 40%, or less than 50% depletion of RBCs.

In one aspect, the anti-CD38 antibody results in less than 10%, less than 20%, less than 30%, less than 40%, or less than 50% depletion of platelets.

These and other embodiments, features and potential advantages will become apparent with reference to the following description and drawings.

BRIEF DESCRIPTION OF THE DRAWINGS

The objects and features of the invention may be better understood by reference to the drawings described below in which.

FIG. 2 shows cyno PK data and PK models for AB79. Panels A and B show the raw PK data of the IV data from the 8 monkey studies; panel A, the first 7 days after the first dose and panel B the entire observation period. The SC data was omitted (see FIG. 1 for SC data). Panel C depicts the final PK model structure including target mediated drug disposition (TMDD) marked with a blue box. $V_C$ designates the volume of the central compartment where the AB79 concentrations are observed (marked with Conc). $V_P$ designates the volume of the peripheral compartment. $R_{total}$ represents the compartment of the antibody bound and unbound receptor CD38. $K_{SYN}$ and $K_{DEG}$ designate the production and degradation rate constants of the receptor and $K_{INT}$ the internalization rate constant (complex elimination rate constant). $K_{SS}$ is the steady state constant, defined as $K_{SS}=(K_{OFF}+K_{INT})/K_{ON}$, where $K_{OFF}$ is the dissociation and $K_{ON}$ the binding rate constant. Panels D-F show the overlays of the linear 2-compartment model predictions (median, 95% prediction interval) without a TMDD component and the observed data of the lowest 3 doses (Study 8). Please note the different time scales between panels D, E and F.

FIG. 4 shows GOF plots for the final population PK model stratified by dose and route of administration (IV—crosses, SC—triangles).

FIG. 6 shows inter- and intra-individual variability in the T cell, B cell and NK cell count data of the placebo treated animals from the study depicted in FIG. 5. FIG. 6C—T cells.

FIG. 7 shows predose NK, B, and T cell counts (cells per μL) stratified by study (upper row) or sex (lower row). FIG. 7C—T cells by study; FIG. 7E—B cells by male/female; and FIG. 7F—T cells by male/female.

FIG. 8 shows AB79 dependent NK cell, B cell, and T cell depletion. The graphs focus on changes that occurred within the first 7 days after treatment with the first dose of AB79. It was possible to pool data from single and multi-dose studies with weekly or every other week dosing schedule. FIG. 8A—Nadir cell depletion for NK cells; FIG. 8B—1 week after $1^{st}$ dose for NK cells; FIG. 8C—mean profile per dose group for NK cells; FIG. 8D—Nadir cell depletion for B cells; FIG. 8E—1 week after $1^{st}$ dose for B cells; FIG. 8F—mean profile per dose group for B cells; FIG. 8G—Nadir cell depletion for T cells; FIG. 8H—1 week after $1^{st}$ dose for T cells; and FIG. 8I—mean profile per dose group for T cells. Graphs A-C show the individual minimal cell counts (i.e., the maximal PD effect), the individual cell counts 7 days after the first dose, and the average per dose cell depletion profiles and PK-PD model structure of the NK cells, respectively. Graphs D-F show the same information for the B cells and graphs G-I show the same information for the T cells.

FIG. 9 shows the effect of AB79 treatment on RBCs two days post dose (FIG. 9A) and total lymphocyte count on the first day post dose in Study 7 (Table 2) (FIG. 9B).

FIG. 9C—via IV in NK cells; FIG. 9D—via SC in NK cells; FIG. 9E—via IV in B cells; FIG. 9F—via SC in B cells; FIG. 9G—via IV in T cells; and FIG. 9H—via SC in T cells.

FIG. 13 shows that AB79 mediates depletion of monkey lymphocytes. AB79 dose-dependently depleted blood NK cells>B cells>T cells in female cynomolgus monkeys (n=4/dose group) after a single IV dose of AB79 as quantified with Flow-Count™ fluorospheres (Beckman-Coulter) using flow cytometry. Samples were collected at pretreatment (Week-1), Day 1: predose, postdose at 15, 30 minutes, 1, 4, 8, 24, 48, 96, and 168 hours, on Days 10, 15, 22, 29, 36, 43, 50, and 57. Only 2-weeks of data are shown for clarity. The mean cell number values were calculated at each time point and were used to calculate % of baseline counts. FIG. 13A—T cells.

FIG. 32 shows the concentration-dependent binding of AB79 (A) to CHO cells expressing recombinant cynomolgus monkey CD38; and (B) to endogenous cynomolgus monkey CD38 expressed on CD3+T lymphocytes, CD3-CD20+B lymphocytes and CD3-/CD20-/CD16+NK cells. Levels of NK cells in whole blood from cynomolgus monkeys (n=3) after incubation with AB79 for 48 hours in culture are depicted in FIG. 32C.

DETAILED DESCRIPTION OF THE INVENTION

Figure 1:
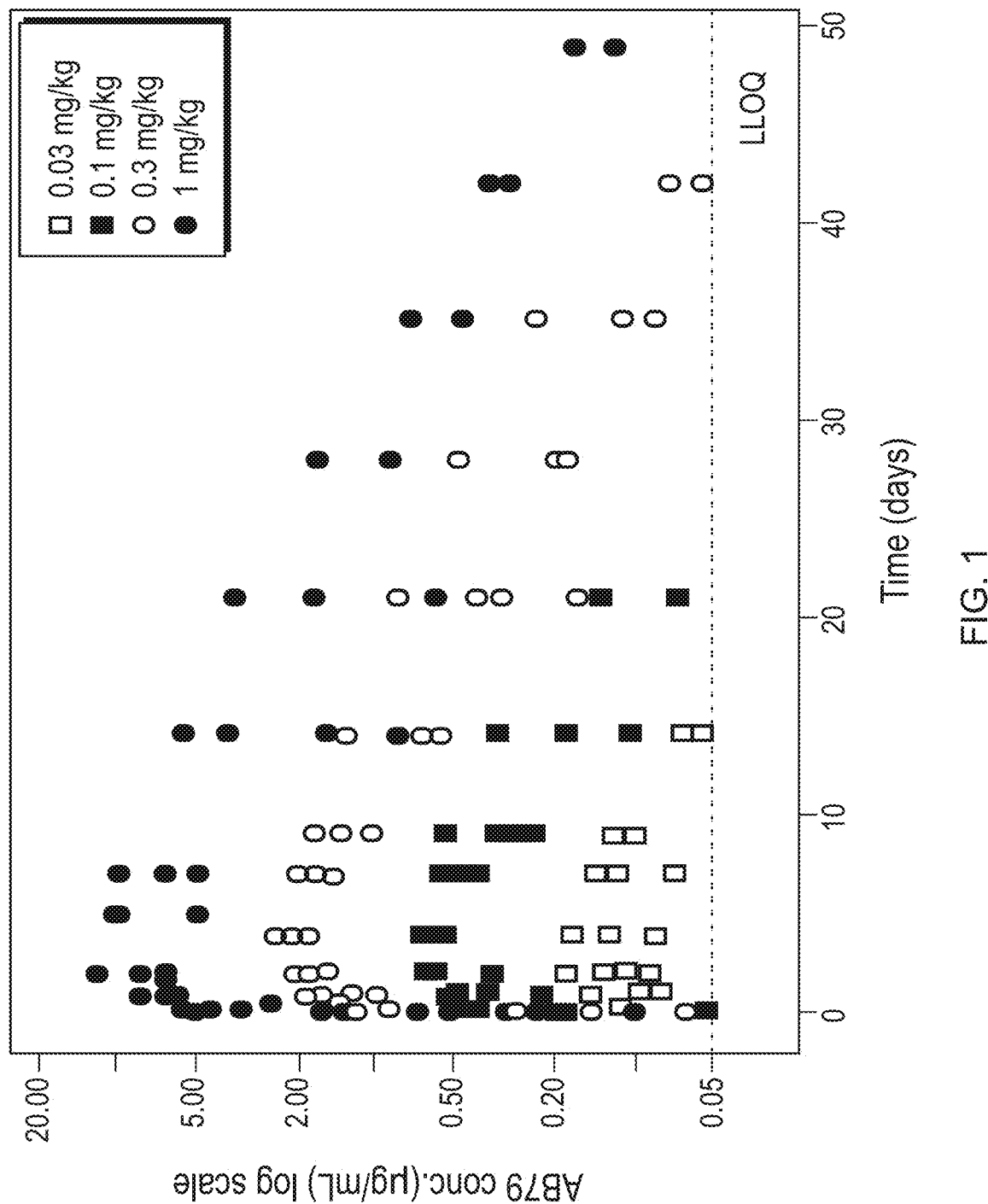
FIG. 1 shows cynomolgus monkey (cyno) PK data of SC dose groups described in Table 2. Anti-drug antibodies (ADA) were detected with a validated qualitative electrochemiluminescent (ECL) assay. The incidence increased over time and affected PK when it reached a specific threshold titer of about 1000 (~log(7)).

The present invention relates to methods for treating CD38 related diseases by the subcutaneous administration of low doses (≤600 mg) and volumes (≤3 mL) of anti-CD38 antibodies.

AB79, daratumumab, isatuximab, and MOR202 are IgG1s that primarily kill tumors by antibody-dependent cellular cytotoxicity (ADCC). This mechanism requires effector cells, such as NK cells, to bind antibodies on target cells and form a lytic synapse to secrete cytotoxic agents in a focused manner. The frequency of these effector cells in blood is orders of magnitude lower than that of RBCs and platelets. For example, the ratio of RBCs to NK cells in blood is 20,000:1. Further, there are approximately 36-fold more CD38 molecules expressed on RBCs than on myeloma cells of patients with active disease. It has been postulated that effector activity for daratumumab, isatuximab and MOR202 is diverted from tumors because the effector cells are primarily bound by those anti-CD38 antibodies bound to RBCs and platelets, preventing the formation of a lytic synapse with tumors, which results in a low efficiency of ADCC. In contrast, the decreased or more transient RBC and platelet binding by AB79 relative to daratumumab may allow effector cells to focus on the tumor, which results in more efficient ADCC, higher tumoricidal activity, and lower effective dose.

Treatment of patients with anti-CD38 antibodies that bind to RBCs and platelets may also result in life threatening side effects. For example, treatment of RRMM with MOR202 resulted in several serious treatment-emergent adverse events (TEAEs) (see, e.g., Raab et al. (2015) Blood 126: 3035). The most common TEAEs at any grade were anemia (15 patients, 34%), fatigue (14 patients, 32%), infusion-related reactions (IRRs) and leukopenia (13 patients, 30% each), lymphopenia and nausea (11 patients, 25% each). Grade ≥3 TEAEs were reported for 28 patients (64%); the most common included lymphopenia (8 patients, 18%), leukopenia (5 patients, 11%) and hypertension (4 patients, 9%). IRRs arose mainly during the first infusion; all were grade 1-2 except for one patient (grade 3). Infections were commonly reported (26 patients, 59%) but in the majority of the cases were not considered to be treatment-related. MOR202 has only been used clinically via IV infusion. This is in contrast to the present invention which allows for subcutaneous administration of AB79 at low doses and at low volumes, as described herein.

Other Morphosys antibodies targeting CD38 are known (see, e.g., WO 2006/125640, which discloses four human antibodies: MOR03077, MOR03079, MOR03080, and MOR03100 and two murine antibodies: OKT10 and 1B4). These prior art antibodies are inferior to AB79 for a variety of reasons. MOR03080 binds to human CD38 and cynomolgus CD38 but with a low affinity to human CD38 (Biacore $K_D$=27.5 nm). OKT10 binds to human CD38 and cynomolgus CD38 but with a low/moderate affinity to human CD38 (Biacore $K_D$=8.28 nm). MOR03079 binds to human CD38 with a high affinity (Biacore $K_D$=2.4 nm) but does not bind to cynomolgus CD38. MOR03100 and MOR03077 bind to human CD38 with moderate or low affinity (Biacore $K_D$=10 nm and 56 nm, respectively). By comparison, AB79 binds to human and cynomolgus CD38 with a high affinity (to human CD38 with Biacore $K_D$=5.4 nm). Moreover, the prior art antibodies have poor ADCC as well as CDC activity.

An advantage of more efficient ADCC is the ability to deliver an anti-CD38 therapeutic as a low volume injection. If AB79 is formulated at a concentration of 135 mg/mL, an efficacious dose for an 80 kg myeloma patient could be administered as a single SC injection of <2.5 mL. In contrast, the SC dose of daratumumab being tested in Ph3 clinical trials is 1800 mg suspended in a 15 mL co-formulation of Enhance™ (Halozyme).

The safety, tolerability, pharmacokinetics, and pharmacodynamics of AB79 administered IV and SC was initially characterized in monkeys. AB79 was administered as a single dose by IV bolus or SC injection to cynomolgus monkeys in sterile saline (IV) or SC dilution solution at 0.03, 0.1, and 0.3 mg/kg (4 females/group). For the IV route, Cmax was approximately dose proportional from 0.03 to 0.3 mg/kg AB79, and the AUC(0-t) was greater than dose proportional from 0.03 to 0.1 mg/kg AB79, but was approximately dose-proportional from 0.1 to 0.3 mg/kg AB79. For the SC route, the Cmax and AUC(0-t) increased with dose, but AUC(0-t) increased greater than dose proportionally after SC dosing over the range of 0.03 to 0.3 mg/kg. The $T_{1/2}$ was estimated to be between 120 and 144 hours. The mean bioavailability for the SC route was approximately 100% (120%, 73%, and 120% for 0.03, 0.1, and 0.3 mg/kg, respectively). Administration of AB79 at 0.03, 0.1, or 0.3 mg/kg via a single intravenous or subcutaneous injection to female cynomolgus monkeys was well-tolerated. Anticipated pharmacological effects of mild to moderate decreases in lymphocytes (T-lymphocytes, B-lymphocytes) and dose-dependent decreases in NK cell populations were observed at all dose levels and via both routes; the maximal cell depletion effects after SC dosing were similar to or slightly less than that observed after IV dosing at the same dose level (Roepcke et al. (2018) Pharmacol. Res. Perspect. 6(3): e00402). On the basis of the results of this study, the no-observed-adverse-effect-level (NOAEL) was considered to be 0.3 mg/kg via both IV and SC routes. Changes in lymphocytes and NK cells were resolved after a 56-day AB79-free period. The serum AUC and Cmax associated with the NOAEL were 574 hr*μg/mL and 7.94 g/mL for IV and 698 hr*μg/mL and 2.15 g/mL for SC, respectively.

The safety, tolerability, pharmacokinetics, and pharmacodynamics of AB79 was then characterized clinically in a randomised, double-blind, placebo-controlled study of a single intravenous (IV) infusion or 1 mL subcutaneous (SC) injection in escalating dose cohorts of healthy human subjects. AB79 was well tolerated, all adverse events (AEs) were mild or moderate and there were no withdrawals due to AEs or infusion reactions (Fedyk et al. (2018) Blood 132:3249). In higher dose cohorts, transient, mild to moderate increases in cytokine levels coincided with reductions in CD38-expressing cells; clinical symptoms primarily included pyrexia, headache, and postural hypotension. No remarkable findings for laboratory tests, electrocardiograms, vital signs, or physical examinations were reported related to AB79 treatment. AB79 reduced levels of plasmablasts and natural killer (NK) cells at similar doses, with a 50% of maximum effective dose ($ED_{50}$) of 0.003 mg/kg IV and 0.1 mg/kg SC. Reductions in total immunoglobulins (Ig) M and A occurred without comparable changes in IgG. Total white blood cell, granulocyte, lymphocyte, red blood cell, and platelet counts remained within normal ranges for all dose levels. In sum, AB79 selectively reduced the level of plasmablasts and NK cells in peripheral blood of healthy subjects when administered IV or SC and was overall safe and well tolerated. This plasmacytolytic profile could be useful for treating disorders caused by plasma or NK cells, malignant counterparts (e.g., multiple myeloma and NK cell leukemia), and pathogenic antibodies or Igs.

AB79 may induce a therapeutic response (e.g., disease remission) in Ig or antibody-mediated diseases relatively quickly because it targets plasma cells directly, unlike therapeutics that target the B cell progenitors of plasma cells (e.g., anti-BAFF mAbs (e.g., belimumab), anti-CD20 mAbs (e.g., rituximab), and BTK inhibitors (e.g., baricitinib)). These latter strategies target plasma cells indirectly, essentially eliminating the de novo generation of plasma cells by inhibiting the differentiation of predecessors. The pre-existing pools of plasma cells remain relatively unaffected and continue producing pathogenic antibodies/Igs throughout their lifespan. Thus, the lifespan of pre-existing plasma cells, some of which survive for decades, would drive a potential decrease in pathogenic antibody/Ig, which is why indirect strategies may exhibit a slower onset of activity and efficacy than AB79. The only other therapeutics demonstrated to reduce plasma cells directly are proteasome inhibitors (e.g., bortezomib) and this class of agents is relatively poorly tolerated and include dose-limiting adverse events (e.g., neuropathy, diarrhea) which are attributed to proteasome inhibition in non-plasma cells (e.g., neurons, epithelial cells) because the proteasome is ubiquitously expressed in these tissues. Thus, the specificity of AB79 for CD38 combined with the restricted expression profile of CD38, creates a mechanism of action that directly targets plasma cells, while minimizing non-plasma cell effects and has the potential to provide rapid efficacy in diseases caused by plasma cells, transformed counterparts and/or pathogenic antibodies/Igs.

The anti-CD38 methods and unit dosages of the disclosure provide, for the first time, subcutaneous administration of therapeutically effective low doses and volumes of anti-CD38 antibodies, thereby providing unexpected benefits and preventing the side effects, inconvenience, and expense of administering high dose, systemic anti-CD38 antibody therapies.

The present invention provides methods and unit dosage forms for subcutaneous administration of a therapeutically effective amount of an isolated anti-CD38 antibody to a patient in need thereof to treat diseases in which binding to CD38 is indicated, including hematological cancers. In some embodiments, the antibody for subcutaneous administration comprises a heavy chain variable region comprising SEQ ID NO:9 and a light chain variable region comprising SEQ ID NO:10. The anti-CD38 antibody provided herein is capable of being therapeutically effective when administered at unexpectedly low dosages and as such can be administered in a surprisingly small volume, facilitating subcutaneous administration.

Another advantage of the anti-CD38 antibodies of the invention is that, unlike some other anti-CD38 antibodies in the clinic, the anti-CD38 antibodies of the present invention (e.g., AB79) are able to bind to cynomolgus monkey (cyno) CD38, providing a useful animal model for preclinical evaluation of dosing tolerability, toxicity, and efficacy, etc.

Another advantage of the anti-CD38 antibodies of the invention is that they can be used to screen for other antibodies that compete for binding to CD38 at the same epitope and can be useful in the methods and unit dosages of the invention.

Another advantage of the anti-CD38 antibodies of the invention is that they can be used to screen for other antibodies with decreased or alternative (e.g., more transient) binding to RBCs and/or platelets relative to daratumumab and can be useful in the methods and unit dosages of the invention, e.g., an antibody that competes for or that binds the same epitope as AB79.

Unless otherwise defined herein, scientific and technical terms used in connection with the present invention shall have the meanings that are commonly understood by those of ordinary skill in the art. The meaning and scope of the terms should be clear. However, in the event of any latent ambiguity, definitions provided herein take precedence over any dictionary or extrinsic definition. Further, unless otherwise required by context, singular terms shall include pluralities and plural terms shall include the singular. The term "or" includes "and/or" unless stated otherwise. Furthermore, the use of the term "including," "includes," or "included" is not limiting. Terms such as "element" and "component" encompass both elements and components comprising one unit and elements and components that comprise more than one subunit unless specifically stated otherwise.

The methods and techniques of the present invention are generally performed according to conventional methods well known in the art and as described in various general and more specific references that are cited and discussed throughout the present specification unless otherwise indicated The nomenclatures used in connection with, and the laboratory procedures and techniques of, cell and tissue culture, molecular biology, immunology, microbiology, genetics, protein and nucleic acid chemistry and hybridization, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, delivery, and treatment of patients. Commercial enzymatic reactions and purification techniques are performed according to manufacturer's specifications, as commonly accomplished in the art or as described herein.

All headings and section designations are used for clarity and reference purposes only and are not to be considered limiting in any way. For example, those of skill in the art will appreciate the usefulness of combining various aspects of the disclosure from different headings and sections as appropriate according to the spirit and scope of the invention described herein.

Select terms are defined below in order for the present invention to be more readily understood.

The terms "human CD38" and "human CD38 antigen" refer to the amino acid sequence of SEQ ID NO:1, or a functional fraction thereof, such as an epitope, as defined herein (Table 1). In general, CD38 possesses a short intracytoplasmic tail, a transmembrane domain, and an extracellular domain. The terms "cynomolgus CD38" and "cynomolgus CD38 antigen" refer to the amino acid sequence of SEQ ID NO:2, which is 92% identical to the amino acid sequence of human CD38 (Table 1). Synonyms for CD38 include cyclic ADP ribose hydrolase; cyclic ADP ribose-hydrolase 1; ADP ribosyl cyclase; ADP-ribosyl cyclase 1; cADPr hydrolase 1; CD38-rs1; I-19; NIM-R5 antigen; 2'-phospho-cyclic-ADP-ribose transferase; 2'-phospho-ADP-ribosyl cyclase; 2'-phospho-cyclic-ADP-ribose transferase; 2'-phospho-ADP-ribosyl cyclase; and T10.

TABLE 1

Amino Acid Sequence of Human and Cynomolgus Monkey CD38

| Species | Amino Acid Sequence<br>123456789012345678901234567890123456789 0 | SEQ<br>ID<br>NO |
|---|---|---|
| Human<br>CD38 | MANCEFSPVSGDKPCCRLSRRAQLCLGVSILVLILVVVLA<br>VVVPRWRQQWSGPGITKREPETVLARCVKYTEIHPEMRHV<br>DCQSVWDAFKGAFISKHPCNITEEDYQPLMKLGTQTVPCN<br>KILLWSRIKDLAHQFTQVQRDMFTLEDTLLGYLADDLTWC<br>GEENTSKINYQSCPDWRKDCSNNPVSVFMKTVSRRFAEAA<br>CDVVHVMLNGSRSKIFDKNSTFGSVEVHNLQPEKVQTLEA<br>WVIHGGREDSRDLCQDPTIKELESIISKRNIQFSCKNIYR<br>PDKFLQCVKNPEDSSCTSEI | 1 |
| Cyno<br>CD38 | MANCEFSPVSGDKPCCRLSRRAQVCLGVCLLVLLILVVVV<br>AVVLPRWRQQWSGSGTTSRFPETVLARCVKYTEVHPEMRH<br>VDCQSVWDAFKGAFISKYPCNITEEDYQPLVKLGTQTVPC<br>NKTLLWSRIKDLAHQFTQVQRDMFTLEDMLLGYLADDLTW<br>CGEENTFEINYQSCPDWRKDCSNNPVSVFMKTVSRRFAET<br>ACGVVHVMLNGSRSKIFDKNSTFGSVEVHNLQPEKVQALE<br>AWVIHGGREDSRDLCQDPTIKELESIISKRNIRFFCKNIY<br>RPDKFLQCVKNPEDSSCLSGI | 2 |
| Human<br>CD157 | MAAQGCAASRLLQLLLQLLLLLLLLAAGGARARWRGEGTS<br>AHLRDIFLGRCAEYRALLSPEQRNKNCTAIWEAFKVALDK<br>DPCSVLPSDYDLFINLSRHSIPRDKSLFWENSHLLVNSFA<br>DNTRREMPLSDVLYGRVADELSWCRQKNDSGLDYQSCPTS<br>EDCENNPVDSFWKRASIQYSKDSSGVIHVMLNGSEPTGAY<br>PIKGFEADYEIPNLQKEKITRIEIWVMHEIGGPNVESCGE<br>GSMKVLEKRLKDMGFQYSCINDYRPVKLLQCVDHSTHPDC<br>ALKSAAAATQRKAPSLYTEQRAGLIIPLFLVLASRTQL | 13 |

The terms "therapeutically effective amount" and "therapeutically effective dosage" refer to an amount of a therapy that is sufficient to reduce or ameliorate the severity and/or duration of a disorder or one or more symptoms thereof; prevent the advancement of a disorder; cause regression of a disorder; prevent the recurrence, development, onset, or progression of one or more symptoms associated with a disorder; or enhance or improve the prophylactic or therapeutic effect(s) of another therapy (e.g., prophylactic or therapeutic agent), at dosages and for periods of time necessary to achieve a desired therapeutic result. A therapeutically effective amount may vary according to factors such as the disease state, age, sex, and weight of the individual, and the ability of the medicaments to elicit a desired response in the individual. A therapeutically effective amount of an antibody is one in which any toxic or detrimental effects of the antibody or antibody portion are outweighed by the therapeutically beneficial effects. A therapeutically effective amount of an antibody for tumor therapy may be measured by its ability to stabilize the progression of disease. The ability of a compound to inhibit cancer may be evaluated in an animal model system predictive of efficacy in human cancer.

The terms "patient" and "subject" include both humans and other animals. Thus the compositions, dosages, and methods disclosed herein are applicable to both human and veterinary therapies. In one embodiment, the patient is a mammal, for example, a human.

The term "disease in which binding to CD38 is indicated" means a disease in which binding of a binding partner (e.g., an anti-CD38 antibody of the disclosure) to CD38 provides a prophylactic or curative effect, including the amelioration of one or more symptoms of the disease. Such binding could result in the blocking of other factors or binding partners for CD38, neutralization of CD38, ADCC, CDC, complement activation, or some other mechanism by which the disease is prevented or treated. Factors and binding partners for CD38 include autoantibodies to CD38, which are blocked by the anti-CD38 antibodies of the invention. Such binding may be indicated as a consequence of expression of CD38 by cells or a subset of cells, e.g., MM cells, by which providing a binding partner of CD38 to the subject results in the removal, e.g., lysis, of those cells, e.g., via hemolysis or apoptosis. Such expression of CD38 may be, e.g., normal, overexpressed, inappropriately expressed, or a consequence of activation of CD38, relative to normal cells or relative to other cells types either during a non-disease state or a disease state.

The term "hematologic cancer" refers to malignant neoplasms of blood-forming tissues and encompasses leukemias, lymphomas and multiple myelomas. Non-limiting examples of conditions associated with aberrant CD38 expression include, but are not limited to, multiple myeloma (MM) (Jackson et al. (1988) Clin. Exp. Immunol. 72: 351-356) including relapsing refractory MM (RRMM) or newly diagnosed MM (NDMM); B-cell chronic lymphocytic leukemia (B-CLL) (Drig et al. (2002) Leukemia 16: 30-35; Morabito et al. (2001) Leukemia Res. 25: 927-932; Marinov et al. (1993) Neoplasma 40(6): 355-358; and Jelinek et al. (2001) Br. J. Haematol. 115: 854-861); acute lymphoblastic leukemia (Keyhani et al. (1999) Leukemia Res. 24: 153-159; and Marinov et al. (1993) Neoplasma 40(6): 355-358; chronic myeloid leukemia (Marinov et al. (1993) Neoplasma 40(6): 355-358); acute myeloid leukemia (Keyhani et al. (1999) Leukemia Res. 24: 153-159); chronic lymphocytic leukemia (CLL); chronic myelogenous leukemia or chronic myeloid leukemia (CML); acute myelogenous leukemia or acute myeloid leukemia (AML); acute lymphocytic leukemia (ALL); hairy cell leukemia (HCL); NK/T cell lymphoma, myelodysplastic syndromes (MDS) (Nurulhuda et al. (2017) Blood 130:2814); and all subtypes and stages (e.g., CML blastic phase (BP), chronic phase (CP), or accelerated phase (AP)) of these leukemias and other hematologic diseases, which are defined by morphological, histochemical and immunological techniques that are well known to those of skill in the art.

The terms "neoplasm" and "neoplastic condition" refer to a condition associated with proliferation of cells characterized by a loss of normal controls that results in one or more symptoms including unregulated growth, lack of differentiation, dedifferentiation, local tissue invasion, and metastasis.

The term "isolated antibody" refers to an antibody that is substantially free of other antibodies having different antigenic specificities. For instance, an isolated antibody that specifically binds to CD38 is substantially free of antibodies that specifically bind antigens other than CD38. An isolated antibody that specifically binds to an epitope, isoform or variant of human CD38 or cynomolgus CD38 may, however, have cross-reactivity to other related antigens, for instance from other species, such as CD38 species homologs. Moreover, an isolated antibody may be substantially free of other cellular material and/or chemicals.

The terms "red blood cells," "RBCs," and "erythrocytes" refer to bone marrow derived hemoglobin-containing blood cells that carry oxygen to cells and tissues and carry carbon dioxide back to respiratory organs. RBCs are also referred to as red cells, red blood corpuscles, haematids, and erythroid cells.

The terms "specific binding," "specifically binds to," and "is specific for" in reference to the interaction of a particular antibody, protein, or peptide with an antigen, epitope, or other chemical species means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target. The anti-CD38 antibodies of the present invention specifically bind CD38 ligands. The terms "specific binding," "specifically binds to," and "is specific for" also mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody. Specific binding for a particular antigen or an epitope can be exhibited, for example, by an antibody having a KD for an antigen or epitope of at least about $10^{-4}$ M, at least about $10^{-5}$ M, at least about $10^{-6}$ M, at least about $10^{-7}$ M, at least about $10^{-8}$ M, at least about $10^{-9}$ M, at least about $10^{-10}$ M, at least about $10^{-11}$ M, at least about $10^{-12}$ M, or greater, where KD refers to a dissociation rate of a particular antibody-antigen interaction. Typically, an antibody that specifically binds an antigen will have a KD that is 20-, 50-, 100-, 500-, 1000-, 5,000-, 10,000- or more times greater for a control molecule relative to the antigen or epitope. Also, specific binding for a particular antigen or an epitope can be exhibited, for example, by an antibody having a KA or Ka for an antigen or epitope of at least 20-, 50-, 100-, 500-, 1000-, 5,000-, 10,000- or more times greater for the epitope relative to a control, where KA or Ka refers to an association rate of a particular antibody-antigen interaction.

The term "over a period of time" refers to any period of time, e.g., minutes, hours, days, months, or years. For example, over a period of time can refer to at least 10 minutes, at least 15 minutes, at least 30 minutes, at least 60 minutes, at least 75 minutes, at least 90 minutes, at least 105 minutes, at least 120 minutes, at least 3 hours, at least 4 hours, at least 5 hours, at least 6 hours, at least 7 hours, at least 8 hours, at least 9 hours, at least 10 hours, at least 12 hours, at least 14 hours, at least 16, hours, at least 18 hours, at least 20 hours, at least 22 hours, at least one day, at least two days, at least three days, at least 4 days, at least 5 days, at least 6 days, at least a week, at least on month, at least one year, or any interval of time in between. In other words, the antibody from the composition can be absorbed by the individual to whom it is administered over a period of at least 10 minutes, at least 15 minutes, at least 30 minutes, at least 60 minutes, at least 75 minutes, at least 90 minutes, at least 105 minutes, at least 120 minutes, at least 3 hours, at least 4 hours, at least 5 hours, at least 6 hours, at least 7 hours, at least 8 hours, at least 9 hours, at least 10 hours, at least 12 hours, at least 14 hours, at least 16, hours, at least 18 hours, at least 20 hours, at least 22 hours, at least one day, at least two days, at least three days, at least 4 days, at least 5 days, at least 6 days, at least a week, at least on month, at least one year, or any interval of time in between.

A composition that "substantially" comprises a component means that the composition contains more than about 80% by weight, in some embodiments more than about 90% by weight, in some embodiments more than about 95% by weight, in some embodiments more than about 97% by weight, in some embodiments more than about 98% by weight, in some embodiments more than about 99% by weight of the component.

The term "about" refers to an extent near in number, degree, volume, time, etc., with only minor variations in dimension of up to 10%.

The term "pharmaceutically acceptable carrier" refers to a pharmaceutically acceptable material, composition or vehicle, suitable for administering compounds of the present invention to mammals. The carriers include liquid or solid filler, diluent, excipient, solvent or encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. In one embodiment, the pharmaceutically acceptable carrier is suitable for intravenous administration. In another embodiment, the pharmaceutically acceptable carrier is suitable for locoregional injection. In another embodiment, the pharmaceutically acceptable carrier is suitable for subcutaneous administration. In another embodiment, the pharmaceutically acceptable carrier is suitable for subcutaneous injection.

The term "pharmaceutical composition" refers to preparations suitable for administration to a subject and treatment of disease. When the anti-CD38 antibodies of the present invention are administered as pharmaceuticals to mammals, e.g., humans, they can be administered "as is" or as a pharmaceutical composition containing the anti-CD38 antibody in combination with a pharmaceutically acceptable carrier and/or other excipients. The pharmaceutical composition can be in the form of a unit dosage form for administration of a particular dosage of the anti-CD38 antibody at a particular concentration, a particular amount, or a particular volume. Pharmaceutical compositions comprising the anti-CD38 antibodies, either alone or in combination with prophylactic agents, therapeutic agents, and/or pharmaceutically acceptable carriers are provided.

Traditional antibody structural units typically comprise a tetramer. Each tetramer is typically composed of two identical pairs of polypeptide chains, each pair having one "light" chain (typically having a molecular weight of about 25 kDa) and one "heavy" chain (typically having a molecular weight of about 50-70 kDa). Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4. IgM has subclasses, including, but not limited to, IgM1 and IgM2. Thus, "isotype" refers to any of the subclasses of immunoglobulins defined by the chemical and antigenic characteristics of their constant regions. The known human immunoglobulin isotypes are IgG1, IgG2, IgG3, IgG4, IgA1, IgA2, IgM1, IgM2, IgD, and IgE. Therapeutic antibodies can also comprise hybrids of isotypes and/or subclasses.

Each variable heavy (VH) and variable light (VL) region (about 100 to 110 amino acids in length) is composed of three hypervariable regions called "complementarity determining regions" (CDRs) and four framework regions (FRs) (about 15-30 amino acids in length), arranged from amino-terminus to carboxy-terminus in the following order: FR1-CDR1-FR2-CDR2-FR3-CDR3-FR4. "Variable" refers to the fact that the CDRs differ extensively in sequence among antibodies and thereby determines a unique antigen binding site.

The hypervariable region generally encompasses amino acid residues from about amino acid residues 24-34 (LCDR1; "L" denotes light chain), 50-56 (LCDR2) and 89-97 (LCDR3) in the light chain variable region and around about 31-35B (HCDR1; "H" denotes heavy chain), 50-65 (HCDR2), and 95-102 (HCDR3) in the heavy chain variable region (Kabat et al. (1991) Sequences Of Proteins Of Immunological Interest, 5th Ed. Public Health Service, National Institutes of Health, Bethesda, MD) and/or those residues forming a hypervariable loop (e.g., residues 26-32 (LCDR1), 50-52 (LCDR2) and 91-96 (LCDR3) in the light chain variable region and 26-32 (HCDR1), 53-55 (HCDR2) and 96-101 (HCDR3) in the heavy chain variable region (Chothia and Lesk (1987) J. Mol. Biol. 196: 901-917.

The Kabat numbering system is generally used when referring to a residue in the variable domain (approximately, residues 1-107 of the light chain variable region and residues 1-113 of the heavy chain variable region) (e.g., Kabat et al. (1991) Sequences Of Proteins Of Immunological Interest, 5th Ed. Public Health Service, National Institutes of Health, Bethesda, MD), with the EU number system used for the Fc region.

The term "immunoglobulin (Ig) domain" refers to a region of an immunoglobulin having a distinct tertiary structure. In addition to the variable domains, each heavy and light chain has constant domains: constant heavy (CH) domains; constant light (CL) domains and hinge domains. In the context of IgG antibodies, the IgG isotypes each have three CH regions. The carboxy-terminal portion of each HC and LC defines a constant region primarily responsible for effector function. Accordingly, "CH" domains in the context of IgG are as follows: "CH1" refers to positions 118-220 according to the EU index as in Kabat. "CH2" refers to positions 237-340 according to the EU index as in Kabat, and "CH3" refers to positions 341-447 according to the EU index as in Kabat.

Another type of Ig domain of the heavy chain is the hinge region. The term "hinge region" refers to the flexible polypeptide comprising the amino acids between the first and second constant domains of an antibody. Structurally, the IgG CH1 domain ends at EU position 220, and the IgG CH2 domain begins at residue EU position 237. Thus, for IgG the antibody hinge is herein defined to include positions 221 (D221 in IgG1) to 236 (G236 in IgG1), wherein the numbering is according to the EU index as in Kabat. In some embodiments, for example in the context of an Fc region, the lower hinge is included, with the "lower hinge" generally referring to positions 226 or 230.

The term "Fc region" refers to the polypeptide comprising the constant region of an antibody excluding the first constant region immunoglobulin domain and in some cases, part of the hinge. Thus, Fc refers to the last two constant region immunoglobulin domains of IgA, IgD, and IgG, the last three constant region immunoglobulin domains of IgE and IgM, and the flexible hinge N-terminal to these domains. For IgA and IgM, Fc may include the J chain. For IgG, the Fc domain comprises immunoglobulin domains Cγ2 and Cγ3 (Cγ2 and Cγ3) and the lower hinge region between Cγ1 (Cγ1) and Cγ2 (Cγ2). Although the boundaries of the Fc region may vary, the human IgG heavy chain Fc region is usually defined to include residues C226 or P230 to its carboxyl-terminus, wherein the numbering is according to the EU index as in Kabat. In some embodiments, as is more fully described below, amino acid modifications are made to the Fc region, for example to alter binding to one or more FcγR receptors or to the FcRn receptor.

CD38 Antibodies

Accordingly, the present invention provides isolated anti-CD38 antibodies that specifically bind human and primate CD38 protein and which have decreased or less than 10%, less than 20%, less than 30%, less than 40%, less than 50% binding to human RBCs as compared to daratumumab and thereby find use in subcutaneous administration methods and unit dosage forms. Of particular use in the present invention are antibodies that bind to both the human and primate CD38 proteins, particularly primates used in clinical testing, such as cynomolgus monkeys (Macacafascicularis, Crab eating macaque, also referred to herein as "cyno").

In some embodiments, the anti-CD38 antibodies of the invention interact with CD38 at a number of amino acid residues including K121, F135, Q139, D141, M142, D202, V203, H205, Q236, E239, W241, S274, C275, K276, F284, C287, V288, K289, N290, P291, E292, and D293, the epitope of AB79. Any antibody that interacts with these residues also finds use in therapeutic methods and unit dosages of the invention.

In some embodiments, the anti-CD38 antibodies of the invention interact with CD38 at a number of amino acid residues including K121, F135, Q139, D141, M142, E239, W241, S274, C275, K276, F284, V288, K289, N290, P291, E292 and D293. It should be noted that these residues are identical in both human and cynomolgus monkeys, with the exception that S274 is actually F274 in cynomolgus monkeys. These residues may represent the immunodominant epitope and/or residues within the footprint of the specific antigen binding peptide.

In some embodiments, the anti-CD38 antibody comprises a heavy chain comprising the following CDR amino acid sequences: GFTFDDYG (SEQ ID NO:3; HCDR1 AB79), ISWNGGKT (SEQ ID NO:4; HCDR2 AB79), and ARGSLFHDSSGFYFGH (SEQ ID NO:5; HCDR3 AB79). In some embodiments, the antibody comprises a light chain comprising the following CDR amino acid sequences: SSNIGDNY (SEQ ID NO:6; LCDR1 AB79), RDS (SEQ ID NO:7; LCDR2 AB79), and QSYDSSLSGS (SEQ ID NO:8; LCDR3 AB79). In some embodiments, the antibody comprises a heavy chain comprising the following CDR amino acid sequences: GFTFDDYG (SEQ ID NO:3; HCDR1 AB79), ISWNGGKT (SEQ ID NO:4; HCDR2 AB79), ARGSLFHDSSGFYFGH (SEQ ID NO:5; HCDR3 AB79) and a light chain comprising the following CDR amino acid sequences: SSNIGDNY (SEQ ID NO:6; LCDR1 AB79), RDS (SEQ ID NO:7; LCDR2 AB79), and QSYDSSLSGS (SEQ ID NO:8; LCDR3 AB79). In some embodiments, the antibody comprises a heavy chain comprising the variable heavy (VH) chain amino acid sequence of SEQ ID NO:9.

```
                                                (SEQ ID NO: 9)
EVQLLESGGGLVQPGGSLRLSCAASGFTFDDYGMSWVRQAPGKGLEWVSD

ISWNGGKTHYVDSVKGQFTISRDNSKNTLYLQMNSLRAEDTAVYYCARGS

LFHDSSGFYFGHWGQGTLVTVSSASTKGPSVFPLA.
```

In some embodiments, the antibody comprises a light chain comprising the variable light (VL) chain amino acid sequence of SEQ ID NO:10.

```
                                               (SEQ ID NO: 10)
QSVLTQPPSASGTPGQRVTISCSGSSSNIGDNYVSWYQQLPGTAPKLLIY

RDSQRPSGVPDRFSGSKSGTSASLAISGLRSEDEADYYCQSYDSSLSGSV

FGGGTKLTVLGQPKANPTVTLFPPSSEEL.
```

In some embodiments, the antibody comprises a heavy chain comprising the VH chain amino acid sequence of SEQ ID NO:9 and a light chain comprising the VL chain amino acid sequence of SEQ ID NO:10.

As will be appreciated by those in the art, the variable heavy and light chains can be joined to human IgG constant domain sequences, generally IgG1, IgG2 or IgG4.

In some embodiments, the antibody comprises the heavy chain (HC) amino acid sequence of SEQ ID NO:11.

(SEQ ID NO: 11)
EVQLLESGGGLVQPGGSLRLSCAASGFTFDDYGMSWVRQAPGKGLEWVSD

ISWNGGKTHYVDSVKGQFTISRDNSKNTLYLQMNSLRAEDTAVYYCARGS

LFHDSSGFYFGHWGQGTLVTVSSASTKGPSVFPLAPSSKSTSGGTAALGC

LVKDYFPEPVTVSWNSGALTSGVHTFPAVLQSSGLYSLSSVVTVPSSSLG

TQTYICNVNHKPSNTKVDKRVEPKSCDKTHTCPPCPAPELLGGPSVFLFP

PKPKDTLMISRTPEVTCVVVDVSHEDPEVKFNWYVDGVEVHNAKTKPREE

QYNSTYRVVSVLTVLHQDWLNGKEYKCKVSNKALPAPIEKTISKAKGQPR

EPQVYTLPPSREEMTKNQVSLTCLVKGFYPSDIAVEWESNGQPENNYKTT

PPVLDSDGSFFLYSKLTVDKSRWQQGNVFSCSVMHEALHNHYTQKSLSLS

PGK.

In some embodiments, the antibody comprises the light chain (LC) amino acid sequence of SEQ ID NO:12.

(SEQ ID NO: 12)
QSVLTQPPSASGTPGQRVTISCSGSSSNIGDNYVSWYQQLPGTAPKLLIY

RDSQRPSGVPDRFSGSKSGTSASLAISGLRSEDEADYYCQSYDSSLSGSV

FGGGTKLTVLGQPKANPTVTLFPPSSEELQANKATLVCLISDFYPGAVTV

AWKADGSPVKAGVETTKPSKQSNNKYAASSYLSLTPEQWKSHRSYSCQVT

HEGSTVEKTVAPTECS.

In some embodiments, the antibody comprises the HC amino acid sequence of SEQ ID NO:11 and the LC amino acid sequence of SEQ ID NO: 12.

The present invention encompasses antibodies that bind to both human and cyno CD38 and interact with at least 80%, 85%, 90%, 91%, 92%, 93%, 94%, 95%, 96%, 97%, 98% or 99% of these amino acid residues.

In some embodiments, the antibodies are full length. By "full length antibody" herein is meant the structure that constitutes the natural biological form of an antibody, including variable and constant regions, including one or more modifications as outlined herein.

Alternatively, the antibodies can be a variety of structures, including, but not limited to, antibody fragments, monoclonal antibodies, bispecific antibodies, minibodies, domain antibodies, synthetic antibodies (sometimes referred to herein as "antibody mimetics"), chimeric antibodies, humanized antibodies, antibody fusions (sometimes referred to as "antibody conjugates"), and fragments of each, respectively. Specific antibody fragments include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment (Ward et al. (1989) Nature 341: 544-546) which consists of a single variable, (v) isolated CDR regions, (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al. (1988) Science 242: 423-426, Huston et al. (1988) Proc. Natl. Acad. Sci. USA 85: 5879-5883), (viii) bispecific single chain Fv (WO 03/11161) and (ix) "diabodies" or "triabodies", multivalent or multi-specific fragments constructed by gene fusion (Tomlinson et al. (2000) Methods Enzymol. 326: 461-479; WO94/13804; Holliger et al. (1993) Proc. Natl. Acad. Sci. USA 90: 6444-6448).

Antibody Modifications

The present invention further provides variant anti-CD38 antibodies. That is, there are a number of modifications that can be made to the antibodies of the disclosure, including, but not limited to, amino acid modifications in the CDRs (affinity maturation), amino acid modifications in the Fc region, glycosylation variants, covalent modifications of other types, etc.

The term "variant" means a polypeptide that differs from that of a parent polypeptide. Amino acid variants can include substitutions, insertions and deletions of amino acids. In general, variants can include any number of modifications, as long as the function of the protein is still present, as described herein. That is, in the case of amino acid variants generated with the CDRs of either AB79, for example, the antibody should still specifically bind to both human and cynomolgus CD38 and not bind to RBCs or have decreased or less than 10%, less than 20%, less than 30%, less than 40%, less than 50% binding to RBCs as compared to daratumumab. The term "variant Fc region" means an Fc sequence that differs from that of a wild-type or parental Fc sequence by virtue of at least one amino acid modification. Fc variant may refer to the Fc polypeptide itself, compositions comprising the Fc variant polypeptide, or the amino acid sequence. If amino acid variants are generated with the Fc region, for example, the variant antibodies should maintain the required functions for the particular application or indication of the antibody. For example, 1, 2, 3, 4, 5, 6, 7, 8, 9 or 10 amino acid substitutions can be utilized, for example, 1-10, 1-5, 1-4, 1-3, and 1-2 substitutions. Suitable modifications can be made at one or more positions as is generally outlined, for example in U.S. Pat. Nos. 6,086,875; 6,737,056; 7,317,091; 7,670,600; 8,084,582; 8,188,231; 8,367,805; 8,937,158; and 9,040,041; all of which are expressly incorporated by reference in their entirety, and in particular for specific amino acid substitutions that increase binding to Fc receptors.

It may be desirable to have from 1-5 modifications in the Fc region of wild-type or engineered proteins, as well as from 1 to 5 modifications in the Fv region, for example. A variant polypeptide sequence will preferably possess at least about 80%, 85%, 90%, 91%, 92%, 93%, 94%, 95%, 96%, 97%, 98% or 99% identity to the parent sequences (e.g., the variable regions, the constant regions, and/or the heavy and light chain sequences for AB79).

The term "amino acid substitution" means the replacement of an amino acid at a particular position in a parent polypeptide sequence with another amino acid. For example, the substitution S100A refers to a variant polypeptide in which the serine at position 100 is replaced with alanine. The term "amino acid insertion" means the addition of an amino acid at a particular position in a parent polypeptide sequence. The term "amino acid deletion" means the removal of an amino acid at a particular position in a parent polypeptide sequence.

The terms "parent antibody" and "precursor antibody" mean an unmodified antibody that is subsequently modified to generate a variant. In an embodiment, the parent antibody herein is AB79. Parent antibody may refer to the polypeptide itself, compositions that comprise the parent antibody, or the amino acid sequence that encodes it. Accordingly, the term "parent Fc polypeptide" means an Fc polypeptide that is modified to generate a variant.

The terms "wild type," "WT," and "native" mean an amino acid sequence or a nucleotide sequence that is found in nature, including allelic variations. A WT protein, polypeptide, antibody, immunoglobulin, IgG, etc., has an amino acid sequence or a nucleotide sequence that has not been intentionally modified.

In some embodiments, one or more amino acid modifications are made in one or more of the CDRs of the anti-CD38 antibody. In general, only 1, 2, or 3 amino acids are substituted in any single CDR, and generally no more than from 4, 5, 6, 7, 8 9 or 10 changes are made within a set of CDRs. However, it should be appreciated that any combination of no substitutions, 1, 2 or 3 substitutions in any CDR can be independently and optionally combined with any other substitution.

In some cases, amino acid modifications in the CDRs are referred to as "affinity maturation". An "affinity matured" antibody is one having one or more alteration(s) in one or more CDRs which results in an improvement in the affinity of the antibody for antigen, compared to a parent antibody which does not possess those alteration(s). In some cases, it may be desirable to decrease the affinity of an antibody to its antigen.

Affinity maturation can be done to increase the binding affinity of the antibody for the antigen by at least about 10% to 50%, 100%, 150% or more, or from 1 to 5 fold as compared to the "parent" antibody. Preferred affinity matured antibodies will have nanomolar or even picomolar affinities for the target antigen. Affinity matured antibodies are produced by known procedures (e.g., Marks et al. (1992) Biotechnol. 10: 779-783; Barbas et al. (1994) Proc. Nat. Acad. Sci. USA 91: 3809-3813; Shier et al. (1995) Gene 169: 147-155; Yelton et al. (1995) J. Immunol. 155: 1994-2004; Jackson et al. (1995) J. Immunol. 154(7): 3310-9; and Hawkins et al. (1992) J. Mol. Biol. 226: 889-896).

Alternatively, amino acid modifications can be made in one or more of the CDRs of the antibodies of the invention that are "silent", e.g., that do not significantly alter the affinity of the antibody for the antigen. These can be made for a number of reasons, including optimizing expression (as can be done for the nucleic acids encoding the antibodies of the invention).

Thus, included within the definition of the CDRs and antibodies of the invention are variant CDRs and antibodies; that is, the antibodies of the invention can include amino acid modifications in one or more of the CDRs of AB79. In addition, as outlined below, amino acid modifications can also independently and optionally be made in any region outside the CDRs, including framework and constant regions.

In some embodiments, variant antibodies of AB79 that are specific for human CD38 (SEQ ID NO:1) and cynomolgus CD38 (SEQ ID NO:2) is described. This antibody is composed of six CDRs, wherein each CDR of this antibody can differ from SEQ ID NO:3, SEQ ID NO:4, SEQ ID NO:5, SEQ ID NO:6, SEQ ID NO:7, and/or SEQ ID NO:8 by 0, 1, 2 or more amino acid substitutions without significantly altering or inhibiting function.

In addition to the modifications outlined above, other modifications can be made. For example, the molecules may be stabilized by the incorporation of disulphide bridges linking the VH and VL domains (Reiter et al. (1996) Nature Biotech. 14: 1239-1245). In addition, there are a variety of covalent modifications of antibodies that can be made as outlined below.

Covalent modifications of antibodies are included within the scope of this invention, and are generally, but not always, done post-translationally. For example, several types of covalent modifications of the antibody are introduced into the molecule by reacting specific amino acid residues of the antibody with an organic derivatizing agent that is capable of reacting with selected side chains or the N- or C-terminal residues.

In some embodiments, the anti-CD38 antibody of the present invention specifically binds to one or more residues or regions in CD38 but also does not cross-react with other proteins with homology to CD38, such as BST-1 (bone marrow stromal cell antigen-1) and Mo5, also called CD157.

Typically, a lack of cross-reactivity means less than about 5% relative competitive inhibition between the molecules when assessed by ELISA and/or FACS analysis using sufficient amounts of the molecules under suitable assay conditions.

Inhibition Of CD38 Activity And Side Effect Reduction

The disclosed antibodies may find use in blocking a ligand-receptor interaction or inhibiting receptor component interaction. The anti-CD38 antibodies of the invention may be "blocking" or "neutralizing." The term "neutralizing antibody" refers to an antibody whose binding to CD38 results in inhibition of the biological activity of CD38, for example its capacity to interact with ligands, enzymatic activity, signaling capacity and, in particular, it's ability to cause activated lymphocytes. Inhibition of the biological activity of CD38 can be assessed by one or more of several standard in vitro or in vivo assays known in the art.

The terms "inhibits binding" and "blocks binding" (e.g., when referring to inhibition/blocking of binding of a CD38 antibody to CD38) encompass both partial and complete inhibition/blocking. The inhibition/blocking of binding of a CD38 antibody to CD38 may reduce or alter the normal level or type of cell signaling that occurs when a CD38 antibody binds to CD38 without inhibition or blocking. Inhibition and blocking are also intended to include any measurable decrease in the binding affinity of a CD38 antibody to CD38 when in contact with an anti-CD38 antibody, as compared to the ligand not in contact with an anti-CD38 antibody, for instance a blocking of binding of a CD38 antibody to CD38 by at least about 10%, 20%, 30%, 40%, 50%, 60%, 70%, 80%, 90%, 99%, or 100%.

The disclosed anti-CD38 antibodies may also inhibit cell growth. The term "inhibits growth" refers to any measurable decrease in cell growth when contacted with an anti-CD38 antibody, as compared to the growth of the same cells not in contact with an anti-CD38 antibody, e.g., an inhibition of growth of a cell culture by at least about 10%, 20%, 30%, 40%, 50%, 60%, 70%, 80%, 90%, 99%, or 100%.

In some embodiments, the disclosed anti-CD38 antibodies are able to deplete activated lymphocytes and plasma cells. The term "depletion" in this context means a measurable decrease in serum levels of activated lymphocytes and/or plasma cells in a subject as compared to untreated subjects. In general, depletions of at least about 10%, 20%, 30%, 40%, 50%, 60%, 70%, 80%, 90%, 99%, or 100% are seen. As shown below in the Examples, one particular advantage that the antibodies of the present invention exhibit is the recoverability of these cells after dosing; that is, as is known for some treatments (for example with anti-CD20 antibodies for example), cell depletion can last for long periods of time, causing unwanted side effects. As shown herein, the effects on the activated lymphocytes and/or plasma cells are recoverable.

The anti-CD38 antibodies of the present invention allow for reduced side effects compared to prior art anti-CD38 antibodies. In some embodiments, AB79 does not induce TEAEs. In some embodiments, AB79 allows for a reduction of TEAEs as compared to other anti-CD38 antibodies, such as MOR202. TEAEs are typically referred to by grades 1, 2, 3, 4, and 5, grade 1 being the least severe and grade 5 being the most severe TEAE. Based on FDA and other guidelines for Common Terminology Criteria for Adverse Events (CT-CAE) standards for oncology drugs (see, e.g., U.S. Department of Health and Human Services, Common Terminology Criteria for Adverse Events (CTCAE), Version 4.0, 2009; Nilsson and Koke (2001) Drug Inform. J. 35: 1289-1299) the following is how such grades are generally determined. Grade 1 is mild: asymptomatic or mild symptoms; clinical or diagnostic observations only; no intervention indicated. Grade 2 is moderate: minimal, local or noninvasive intervention indicated; limiting age-appropriate instrumental ADL. Grade 3 is severe or medically significant but not immediately life-threatening: hospitalization or prolongation of hospitalization indicated; disabling; limiting self care ADL. Grade 4 is life-threatening consequence: urgent intervention indicated. Grade 5 is death related to AE.

In some embodiments, AB79 allows for a reduction in the grade of the TEAEs as compared to other anti-CD38 antibodies, such as MOR202. In some embodiments, AB79 allows for a reduction in the grade of the TEAEs as compared to other anti-CD38 antibodies from grade 5 to grade 4. In some embodiments, AB79 allows for a reduction in the grade of the TEAEs as compared to other anti-CD38 antibodies from grade 4 to grade 3. In some embodiments, AB79 allows for a reduction in the grade of the TEAEs as compared to other anti-CD38 antibodies from grade 3 to grade 2. In some embodiments, AB79 allows for a reduction in the grade of the TEAEs as compared to other anti-CD38 antibodies from grade 2 to grade 1.

In some embodiments, AB79 allows for a reduction in grade of one or more TEAEs selected from the group consisting of anemia (including hemolytic anemia), thrombocytopenia, fatigue, infusion-related reactions (IRRs), leukopenia, lymphopenia, and nausea. In some embodiments, AB79 allows for a reduction in the occurrence of one or more TEAEs selected from the group consisting of anemia (including hemolytic anemia), thrombocytopenia, fatigue, infusion-related reactions (IRRs), leukopenia, lymphopenia, and nausea.

In some embodiments, a diagnostic test is used for determining the presence and/or grade of anemia, including hemolytic anemia. Diagnostic tests for anemia, including hemolytic anemia including measuring the hemoglobin level. Generally, hemoglobin levels are interpreted as follows: (i) very mild/absent anemia: ≥12.0 g/dL, (ii) mild: 10-12 g/dL, (iii) moderate: 8-10 g/dL, (iv) severe: 6-8 g/dL, and (v) very severe: ≤6 g/dL. Other diagnostic tests for anemia, including hemolytic anemia, include measuring the haptoglobin level. Generally, a haptoglobin level ≤25 mg/dL is indicative of the presence of anemia, including hemolytic anemia. Other diagnostic tests include the direct antiglobulin test (DAT) (also referred to as the direct Coombs Test), which is used to determine whether RBCs have been coated in vivo with immunoglobulin, complement, or both.

In some embodiments, a diagnostic test is used for determining the presence and/or grade of thrombocytopenia. Generally, the diagnostic test of thrombocytopenia includes measuring the number of platelets per microliter (µL) blood. Normally, there are $150 \times 10^3$-$450 \times 10^3$ platelets per µL blood. Generally, thrombocytopenia is diagnosed when there is $<150 \times 10^3$ platelets per µL blood. Mild thrombocytopenia is generally diagnosed if there is $70$-$150 \times 10^3$ per L blood. Moderate thrombocytopenia is generally diagnosed if there is $20$-$70 \times 10^3$ per µL. Severe thrombocytopenia is generally diagnosed if there is $<20 \times 10^3$ per 4 blood.

Disease Indications

The antibodies, methods, and dosage units of the invention find use in a variety of applications, including treatment or amelioration of CD38-related diseases.

CD38 is expressed in immature hematopoietic cells, down regulated in mature cells, and re-expressed at high levels in activated lymphocytes and plasma cells. For example, high CD38 expression is seen in activated B cells, plasma cells, activated CD4+ T cells, activated CD8+ T cells, NK cells, NKT cells, mature dendritic cells (DCs) and activated monocytes. Certain conditions are associated with cells that express CD38 and certain conditions are associated with the overexpression, high-density expression, or upregulated expression of CD38 on the surfaces of cells. Whether a cell population expresses CD38 or not can be determined by methods known in the art, for example, flow cytometric determination of the percentage of cells in a given population that are labeled by an antibody that specifically binds CD38 or immunohistochemical assays, as are generally described below for diagnostic applications. For example, a population of cells in which CD38 expression is detected in about 10-30% of the cells can be regarded as having weak positivity for CD38; and a population of cells in which CD38 expression is detected in greater than about 30% of the cells can be regarded as definite positivity for CD38 (as in Jackson et al. (1988) Clin. Exp. Immunol. 72: 351-356), though other criteria can be used to determine whether a population of cells expresses CD38. Density of expression on the surface of cells can be determined using methods known in the art, such as, for example, flow cytometric measurement of the mean fluorescence intensity of cells that have been fluorescently labeled using antibodies that specifically bind CD38.

The therapeutic anti-CD38 antibodies of the present invention bind to CD38 positive cells, resulting in depletion of these cells through multiple mechanisms of action, including both CDC and ADCC pathways.

It is known in the art that certain conditions are associated with cells that express CD38, and that certain conditions are associated with the overexpression, high-density expression, or upregulated expression of CD38 on the surfaces of cells. Whether a cell population expresses CD38 or not can be determined by methods known in the art, for example flow cytometric determination of the percentage of cells in a given population that are labeled by an antibody that specifically binds CD38 or immunohistochemical assays, as are generally described below for diagnostic applications. For example, a population of cells in which CD38 expression is detected in about 10-30% of the cells can be regarded as having weak positivity for CD38; and a population of cells in which CD38 expression is detected in greater than about 30% of the cells can be regarded as definite positivity for CD38 (Jackson et al. (1988) Clin. Exp. Immunol. 72: 351-356), though other criteria can be used to determine whether a population of cells expresses CD38. Density of expression on the surfaces of cells can be determined using methods known in the art, such as, for example, flow cytometric measurement of the mean fluorescence intensity of cells that have been fluorescently labeled using antibodies that specifically bind CD38.

In one aspect, the invention provides methods of treating a condition associated with proliferation of cells expressing CD38, comprising administering to a patient a pharmaceutically effective amount of a disclosed antibody. In some embodiments, the condition is cancer, and in particular embodiments, the cancer is a hematological cancer. In some embodiments, the condition is multiple myeloma, chronic lymphoblastic leukemia, chronic lymphocytic leukemia, acute lymphocytic leukemia, chronic myelogenous leukemia, acute myelogenous leukemia, and plasma cell leukemia, acute myeloid leukemia, chronic myeloid leukemia, B-cell lymphoma, or Burkitt lymphoma In some embodiments, the condition is multiple myeloma and the therapeutic anti-CD38 antibody does not bind to or has decreased binding to human RBCs as compared to daratumumab. In some embodiments, the condition is multiple myeloma and the therapeutic anti-CD38 antibody does not bind to or has decreased binding to cynomolgus RBCs as compared to daratumumab. In some embodiments, the condition is multiple myeloma and the therapeutic anti-CD38 antibody does not bind to or has decreased binding to human or cynomolgus RBCs.

CLL is the most common leukemia of adults in the Western world. CLL involves clonal expansion of mature-appearing lymphocytes involving lymph nodes and other lymphoid tissues with progressive infiltration of bone marrow and presence in the peripheral blood. The B-cell form (B-CLL) represents most cases.

B Cell Form Of Chronic Lymphocytic Leukemia (B-CLL)

B-CLL is an incurable disease characterized by a progressive increase of anergic monoclonal B lineage cells that accumulate in the bone marrow and peripheral blood in a protracted fashion over many years. The expression of CD38 is regarded as an independent poor prognostic factor for B-CLL (Hamblin et al. (2002) Blood 99: 1023-9).

B-CLL is characterized by two subtypes, indolent and aggressive. These clinical phenotypes correlate with the presence or absence of somatic mutations in the immunoglobulin heavy-chain variable region (IgVH) gene. As used herein, indolent B-CLL refers to a disorder in a subject having a mutated IgVH gene and/or presenting with one or more clinical phenotypes associated with indolent B-CLL. As used herein, the phrase aggressive B-CLL refers to a disorder in a subject having an unmutated IgVH gene and/or presenting with one or more clinical phenotypes associated with aggressive B-CLL.

Today's standard therapy of B-CLL is palliative and is mainly carried out with the cytostatic agent chlorambucil or fludarabine. When relapses occur, a combination therapy using fludarabine, cyclophosphamide in combination with rituximab (monoclonal antibody against CD20) or alemtuzumab (monoclonal antibody against CD52) is often initiated. In one study, thirty-five patients with relapsed or refractory aggressive B cell NHL underwent high dose chemotherapy (HCT) followed by rituximab 375 mg/m$^2$ weekly for 4 doses starting on day 40 and repeated for four more doses starting on day 180. Rituximab infusions were well tolerated with only one grade 3/4 infusion-related toxicity. The unexpected adverse event noted in this trial was delayed neutropenia in more than half the patients (19/35 patients with 46 episodes of grade 3 or 4 neutropenia; Kosmas et al. (2002) Leukemia 16: 2004-2015, which can be found online at https://www.nature.com/articles/2402639). In another study, six patients received alemtuzumab by intravenous infusion every other day three times a week for 12 weeks. The dose was gradually escalated on daily basis (3, 10 and then 30 mg) until the patient tolerated. The major TEAEs were anemia, neutropenia (6/6 patients each) and thrombocytopenia (5/6 patients) in hematologic adverse events (Ishizawa et al. (2017) Jpn. J. Clin. Oncol. 47(1): 54-60). Thus, there is a critical unmet medical need for the treatment of B-CLL with decreased hematological adverse events. In some embodiments, methods for treating B-CLL using the disclosed anti-CD38 antibodies are provided and, as outlined below, this may be done using combination therapies including optionally and independently any of the above drugs.

Multiple Myeloma (MM)

Multiple myeloma is a malignant disorder of the B cell lineage characterized by neoplastic proliferation of plasma cells in the bone marrow and/or extramedullary sites. Proliferation of myeloma cells causes a variety of effects, including lytic bone lesions (holes), organ damage, anemia (decreased red blood cell number), production of abnormal proteins (with attendant damage to the kidney, nerves, and other organs), reduced immune system function, renal impairment, and elevated blood calcium levels (hypercalcemia). Currently treatment options include chemotherapy, preferably associated when possible with autologous stem cell transplantation (ASCT). These treatment regimens exhibit moderate response rates. However, only marginal changes in overall survival are observed and the median survival is approximately 3 years. Thus, there is a critical unmet medical need for the treatment of multiple myeloma. In some embodiments, methods for treating multiple myeloma using the disclosed antibodies are provided.

Newly diagnosed MM (NDMM) is distinguished from relapsed MM or relapsed and refractory MM (RRMM). Relapsed MM is regarded as a recurrence of the disease after prior response, and has been defined based on objective laboratory and radiological criteria: ≥25% increase of the serum or urine monoclonal protein (M-protein) or ≥25% difference between involved and uninvolved serum free light chains from its nadir, respectively, or the development of new plasmacytomas or hypercalcemia. In patients with non-secretory disease, relapse is defined as an increase of the bone marrow plasma cells. In general, an indication for relapse treatment has been defined as either the appearance or reappearance of one or more MM symptoms described above or a rapid and consistent biochemical relapse. Relapsed/refractory MM (RRMM) is defined as a disease which becomes non-responsive or progressive on therapy or within 60 days of the last treatment in patients who had achieved a minimal response (MR) or better on prior therapy (Sonneveld and Broijl (2016) Haematologica 101(4):396-406).

Monoclonal Gammopathy Of Undetermined Significance (MGUS) And Smoldering Multiple Myeloma (SMM)

Monoclonal gammopathy of undetermined significance (MGUS) and smoldering multiple myeloma (SMM) are asymptomatic, pre-malignant disorders characterized by monoclonal plasma cell proliferation in the bone marrow and absence of end-organ damage.

Smoldering multiple myeloma (SMM) is an asymptomatic proliferative disorder of plasma cells with a high risk of progression to symptomatic, or active multiple myeloma (Kyle et al. (2007) N. Engl. J. Med. 356(25): 2582-2590). International consensus criteria defining SMM were adopted in 2003 and require that a patient have a M-protein level of >30 g/L and/or bone marrow clonal plasma cells >10% (Internat. Myeloma Working Group (2003) Br. J. Haematol.

121: 749-757). The patients must have no organ or related tissue impairment, such as bone lesions or symptoms. Recent studies have identified two subsets of SMM: i) patients with evolving disease and ii) patients with non-evolving disease (Internat. Myeloma Working Group (2003) Br. J. Haematol. 121: 749-757).

SMM resembles monoclonal gammopathy of undetermined significance (MGUS) as end-organ damage is absent (Kyle et al. (2007) N. Engl. J. Med. 356(25): 2582-2590). Clinically, however, SMM is far more likely to progress to active multiple myeloma or amyloidosis at 20 years (78% probability for SMM vs. 21% for MGUS) (Kyle et al. (2007) N. Engl. J. Med. 356(25): 2582-2590).

International consensus criteria defining MGUS require that a patient have a M-protein level of <30 g/L, bone marrow plasma cells <10% and the absence of organ or related tissue impairment, including bone lesions or symptoms (Internat. Myeloma Working Group (2003) Br. J. Haematol. 121: 749-757).

CD38 Related Conditions

The antibodies, methods, and dosage units of the invention find use in a variety of applications, including treatment or amelioration of CD38-related diseases, such as diseases and conditions associated with inflammation and immune diseases, particularly diseases associated with activated lymphocytes. The anti-CD38 antibodies of the present invention bind to CD38 positive cells, resulting in depletion of these cells, such as activated lymphocytes, through multiple mechanisms of action, including both CDC and ADCC pathways.

Thus, any autoimmune disease that exhibits either increased expression of CD38 or increased numbers of CD38 expressing cells as a component of the disease may be treated using the antibodies of the invention. These include, but are not limited to, allogenic islet graft rejection, alopecia areata, ankylosing spondylitis, antiphospholipid syndrome, autoimmune Addison's disease, antineutrophil cytoplasmic autoantibodies (ANCA), autoimmune diseases of the adrenal gland, autoimmune hemolytic anemia, autoimmune hepatitis, autoimmune myocarditis, autoimmune neutropenia, autoimmune oophoritis and orchitis, autoimmune thrombocytopenia, autoimmune urticaria, Behcet's disease, bullous pemphigoid, cardiomyopathy, Castleman's syndrome, celiac spruce-dermatitis, chronic fatigue immune disfunction syndrome, chronic inflammatory demyelinating polyneuropathy, Churg-Strauss syndrome, cicatrical pemphigoid, CREST syndrome, cold agglutinin disease, Crohn's disease, dermatomyositis, discoid lupus, essential mixed cryoglobulinemia, factor VIII deficiency, fibromyalgia-fibromyositis, glomerulonephritis, Grave's disease, Guillain-Barre, Goodpasture's syndrome, graft-versus-host disease (GVHD), Hashimoto's thyroiditis, hemophilia A, idiopathic pulmonary fibrosis, idiopathic thrombocytopenia purpura (ITP), IgA neuropathy, IgM polyneuropathies, immune mediated thrombocytopenia, juvenile arthritis, Kawasaki's disease, lichen plantus, lupus erthematosis, Meniere's disease, mixed connective tissue disease, multiple sclerosis, type 1 diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobinuremia, primary biliary cirrhosis, psoriasis, psoriatic arthritis, Reynauld's phenomenon, Reiter's syndrome, rheumatoid arthritis, sarcoidosis, scleroderma, Sjorgen's syndrome, solid organ transplant rejection, stiff-man syndrome, systemic lupus erythematosus, takayasu arteritis, temporal arteristis/giant cell arteritis, thrombotic thrombocytopenia purpura, ulcerative colitis, uveitis, vasculitides such as dermatitis herpetiformis vasculitis, vitiligo, and Wegner's granulomatosis.

Of particular use in some embodiments are the use of the present antibodies for the use in the diagnosis and/or treatment of a number of diseases, including, but not limited to autoimmune diseases, including but not limited to systemic lupus erythematosus (SLE), rheumatoid arthritis (RA), inflammatory bowel disease (IBD), ulcerative colitis, and graft-v-host disease.

Thus, for example, patients with high plasma cell content can be treated, such as SLE patients who exhibit high plasma cell levels, as well as RA patients shown to be unresponsive to CD20 based therapies.

Antibody Compositions for In Vivo Administration

Formulations of the antibodies used in accordance with the present invention are prepared for storage by mixing an antibody having the desired degree of purity with optional pharmaceutically acceptable carriers, excipients or stabilizers (Remington's Pharmaceutical Sciences 16th edition (1980) Osol, A. Ed.), in the form of lyophilized formulations or aqueous solutions.

The formulations herein may also contain more than one active compound as necessary for the particular indication being treated, preferably those with complementary activities that do not adversely affect each other. For example, it may be desirable to provide antibodies with other specificities. Alternatively, or in addition, the composition may comprise a cytotoxic agent, cytokine, growth inhibitory agent and/or small molecule antagonist. Such molecules are suitably present in combination in amounts that are effective for the purpose intended.

Subcutaneous Administration

The present invention is based on the unexpected discovery that the anti-CD38 antibodies described herein, such as AB79, can be administered at sufficiently low dosages that are therapeutically effective, thereby allowing for subcutaneously administering low volumes of liquid formulations. Subcutaneous administration is a minimally invasive mode of administration and is considered the most versatile and therefore desirable mode of administration that can be used for short term and long term therapies. In some embodiments, subcutaneous administration can be performed by injection. In some embodiments, the site of the injection or device can be rotated when multiple injections or devices are needed.

Accordingly, subcutaneous formulations are much easier for a patient to self administer, especially since the formulation may have to be taken regularly during the patient's entire life (e.g., starting as early as a child's first year of life). Furthermore, the ease and speed of subcutaneous delivery allows increased patient compliance and quicker access to medication when needed. Thus, the subcutaneous formulations of the anti-CD38 antibodies provided herein provide a substantial benefit over the prior art and solve certain unmet needs.

In some embodiments, the antibodies of the invention are administered to a subject in accordance with known methods via a subcutaneous route. In some embodiments, antibodies of the present invention can be administered by subcutaneous injection. In specific embodiments, the subcutaneous formulation is subcutaneously injected into the same site of a patient (e.g., administered to the upper arm, anterior surface of the thigh, lower portion of the abdomen, or upper back) for repeat or continuous injections. In other embodiments, the subcutaneous formulation is subcutaneously injected into a different or rotating site of a patient. Single or multiple administrations of the formulations may be employed.

In some embodiments, the subcutaneous unit dosage forms described herein can be used for the treatment of cancer. In some embodiments, the subcutaneous unit dosage forms described herein can be used for the treatment of a hematological cancer. In some embodiments, the subcutaneous unit dosage forms described herein can be used for the treatment of multiple myeloma.

In some embodiments, the antibodies of the invention that bind human RBCs transiently have increased bioavailability. In some embodiments, the bioavailability of the antibodies of the present invention that bind RBCs transiently is increased 10%, 20%, 30%, 40%, 50%, 60%, 70%, 80%, 90%, or 100% or more. In some embodiments, the bioavailability of the antibodies of the present invention that bind human RBCs transiently is 110%, 120%, 130%, 140%, 150%, 160%, 170%, 180%, 190%, 200%, 250%, or 300% or more.

In some embodiments, the increase in bioavailability allows for subcutaneous administration. In some embodiments, the increase in bioavailability is due to the fact that the antibodies of the invention bind to RBCs transiently. In some embodiments, the increase in human bioavailability is due to the fact that the antibodies of the invention bind to human RBCs differently.

In some embodiments, the antibodies of the invention lead to depletion of NK cells, B cells and/or T cells. In some embodiments, the antibodies of the invention allow for increased depletion of NK cells as compared to the depletion of B cells or T cells. In some embodiments, the antibodies of the invention allow for increased depletion of NK cells as compared to B cells, as well as increased depletion of NK cells as compared to T cells. In some embodiments, the antibodies of the invention allow for increased depletion of NK cells as compared to B cells, as well as increased depletion of B cells as compared to T cells. In some embodiments, the antibodies of the invention allow for increased depletion of NK cells as compared to B cells and increased depletion of B cells as compared to T cells.

In certain embodiments, the bioavailability of the anti-CD38 antibodies described herein after subcutaneous administration is between at least 50% and at least 80% as compared to intravenous administration normalized for the same dose. In certain embodiments, the bioavailability of the anti-CD38 antibodies described herein after subcutaneous administration is between at least 60% and at least 80% as compared to intravenous administration normalized for the same dose. In certain embodiments, the bioavailability of the anti-CD38 antibodies described herein after subcutaneous administration is between at least 50% and 70% as compared to intravenous administration normalized for the same dose. In certain embodiments, the bioavailability of the anti-CD38 antibodies described herein after subcutaneous administration is between at least 55% and 65% as compared to intravenous administration normalized for the same dose. In certain embodiments, the bioavailability of the anti-CD38 antibodies described herein after subcutaneous administration is between at least 55% and 70% as compared to intravenous administration normalized for the same dose.

In certain embodiments, the bioavailability of the anti-CD38 antibodies described herein after subcutaneous administration is at least 40%, at least 45%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, or at least 85% as compared to intravenous administration normalized for the same dose.

In some embodiments, the present disclosure provides a method wherein the bioavailability of the antibodies of the invention that bind human RBCs transiently after subcutaneous administration is 50%-80% as compared to intravenous administration normalized for the same dose.

In some embodiments, the present disclosure provides a method wherein the bioavailability of the antibodies of the invention that bind human RBCs transiently after subcutaneous administration is at least 50% as compared to intravenous administration normalized for the same dose.

In some embodiments, the present disclosure provides a method wherein the bioavailability of the antibodies of the invention that bind human RBCs transiently after subcutaneous administration is at least 55% as compared to intravenous administration normalized for the same dose.

In some embodiments, the present disclosure provides a method wherein the bioavailability of the antibodies of the invention that bind human RBCs transiently after subcutaneous administration is at least 60% as compared to intravenous administration normalized for the same dose.

In some embodiments, the present disclosure provides a method wherein the bioavailability of the antibodies of the invention that bind human RBCs transiently after subcutaneous administration is at least 65% as compared to intravenous administration normalized for the same dose.

In some embodiments, the present disclosure provides a method wherein the bioavailability of the antibodies of the invention that bind human RBCs transiently after subcutaneous administration is at least 70% as compared to intravenous administration normalized for the same dose.

In some embodiments, the present disclosure provides a method wherein the bioavailability of the antibodies of the invention that bind human RBCs transiently after subcutaneous administration is at least 75% as compared to intravenous administration normalized for the same dose.

In some embodiments, the present disclosure provides a method wherein the bioavailability of the antibodies of the invention that bind human RBCs transiently after subcutaneous administration is at least 80% as compared to intravenous administration normalized for the same dose.

In certain embodiments, the anti-CD38 antibodies described herein are subcutaneously administered in a single bolus injection. In certain embodiments, the anti-CD38 antibodies described herein are subcutaneously administered monthly. In certain embodiments, the anti-CD38 antibodies described herein are subcutaneously administered once every three weeks. In certain embodiments, the anti-CD38 antibodies described herein are subcutaneously administered every two weeks. In certain embodiments, the anti-CD38 antibodies described herein are subcutaneously administered weekly. In certain embodiments, the anti-CD38 antibodies described herein are subcutaneously administered twice a week. In certain embodiments, the anti-CD38 antibodies described herein are subcutaneously administered daily. In certain embodiments, the anti-CD38 antibodies described herein are subcutaneously administered every 12 hours. In certain embodiments, the anti-CD38 antibodies described herein are subcutaneously administered every 8 hours. In certain embodiments, the anti-CD38 antibodies described herein are subcutaneously administered every six hours. In certain embodiments, the anti-CD38 antibodies described herein are subcutaneously administered every four hours. In certain embodiments, the anti-CD38 antibodies described herein are subcutaneously administered every two hours.

In some embodiments, the subcutaneous unit dosage forms are administered at a dosage of about 0.01 mg per kilogram body weight to about 0.8 milligram per kilogram body weight. In some embodiments, the subcutaneous unit dosage forms comprise an amount sufficient to administer a dosage of about 0.02 mg per kilogram body weight to about 0.75 milligram per kilogram body weight. In some embodiments, the subcutaneous unit dosage forms comprises an amount sufficient to administer a dosage of about 0.02 mg per kilogram body weight to about 0.7 milligram per kilogram body weight. In some embodiments, the subcutaneous unit dosage forms comprises an amount sufficient to administer a dosage of about 0.03 mg per kilogram body weight to about 0.6 milligram per kilogram body weight. In some embodiments, the amount is formulated in a volume of between about 0.25 milliliter (mL) and about 3.5 milliliter (mL). In some embodiments, the amount is formulated in a volume of between about 0.5 mL and about 3 mL. In some embodiments, the amount is formulated in a volume of between about 0.5 mL and about 2.5 mL. In some embodiments, the amount is formulated in a volume of between about 0.5 mL and about 2 mL. In some embodiments, the amount is formulated in a volume of between about 1 mL and about 2 mL. In some embodiments, the amount is formulated in a volume of between about 0.25 mL and about 1.25 mL. In some embodiments, the amount is formulated in a volume of between about 0.5 mL and about 1.25 mL. In some embodiments, the amount is formulated in a volume of between about 0.75 mL and about 1.25 mL. In some embodiments, the amount is formulated in a volume of between about 0.75 mL and about 1 mL. In some embodiments, the amount is formulated in a volume of between about 0.9 mL and about 1.5 mL. In some embodiments, the amount is formulated in a volume of between about 0.9 mL and about 1.1 mL. In some embodiments, the amount is formulated in a volume of between about 1 mL and about 1.0 mL. In some embodiments, the amount is formulated in a volume of between about 0.95 mL and about 1.05 mL. In some embodiments, the amount is formulated in a volume of about 3.5 mL. In some embodiments, the amount is formulated in a volume of about 3 mL. In some embodiments, the amount is formulated in a volume of about 2.5 mL. In some embodiments, the amount is formulated in a volume of about 2 mL. In some embodiments, the amount is formulated in a volume of about 1.5 mL. In some embodiments, the amount is formulated in a volume of about 1 mL. In some embodiments, the amount is formulated in a volume of about 0.5 mL. In some embodiments, the amount is formulated in a volume of about 0.25 mL.

Unit Dosage Forms

In some embodiments, the therapeutic anti-CD38 antibodies are formulated as part of a unit dosage form. In some embodiments, the antibody comprises a heavy chain comprising the following CDR amino acid sequences: GFTFDDYG (SEQ ID NO:3; HCDR1 AB79), ISWNGGKT (SEQ ID NO:4; HCDR2 AB79), and ARGSLFHDSSGFYFGH (SEQ ID NO:5; HCDR3 AB79). In some embodiments, the antibody comprises a light chain comprising the following CDR amino acid sequences: SSNIGDNY (SEQ ID NO:6; LCDR1 AB79), RDS (SEQ ID NO:7; LCDR2 AB79), and QSYDSSLSGS (SEQ ID NO:8; LCDR3 AB79). In some embodiments, the antibody comprises a heavy chain comprising the following CDR amino acid sequences: GFTFD-DYG (SEQ ID NO:3; HCDR1 AB79), ISWNGGKT (SEQ ID NO:4; HCDR2 AB79), ARGSLFHDSSGFYFGH (SEQ ID NO:5; HCDR3 AB79) and a light chain comprising the following CDR amino acid sequences: SSNIGDNY (SEQ ID NO:6; LCDR1 AB79), RDS (SEQ ID NO:7; LCDR2 AB79), and QSYDSSLSGS (SEQ ID NO:8; LCDR3 AB79). In some embodiments, the antibody comprises a heavy chain comprising the variable heavy (VH) chain amino acid sequence of SEQ ID NO:9.

```
                                              (SEQ ID NO: 9)
EVQLLESGGGLVQPGGSLRLSCAASGFTFDDYGMSWVRQAPGKGLEWVSD

ISWNGGKTHYVDSVKGQFTISRDNSKNTLYLQMNSLRAEDTAVYYCARGS

LFHDSSGFYFGHWGQGTLVTVSSASTKGPSVFPLA.
```

In some embodiments, the antibody comprises a light chain comprising the variable light (VL) chain amino acid sequence of SEQ ID NO:10.

```
                                             (SEQ ID NO: 10)
QSVLTQPPSASGTPGQRVTISCSGSSSNIGDNYVSWYQQLPGTAPKLLIY

RDSQRPSGVPDRFSGSKSGTSASLAISGLRSEDEADYYCQSYDSSLSGSV

FGGGTKLTVLGQPKANPTVTLFPPSSEEL.
```

In some embodiments, the antibody comprises a heavy chain comprising the VH chain amino acid sequence of SEQ ID NO:9 and a light chain comprising the VL chain amino acid sequence of SEQ ID NO:10.

As will be appreciated by those in the art, the variable heavy and light chains can be joined to human IgG constant domain sequences, generally IgG1, IgG2 or IgG4.

In some embodiments, the antibody comprises the heavy chain (HC) amino acid sequence of SEQ ID NO:11.

```
                                             (SEQ ID NO: 11)
EVQLLESGGGLVQPGGSLRLSCAASGFTFDDYGMSWVRQAPGKGLEWVSD

ISWNGGKTHYVDSVKGQFTISRDNSKNTLYLQMNSLRAEDTAVYYCARGS

LFHDSSGFYFGHWGQGTLVTVSSASTKGPSVFPLAPSSKSTSGGTAALGC

LVKDYFPEPVTVSWNSGALTSGVHTFPAVLQSSGLYSLSSVVTVPSSSLG

TQTYICNVNHKPSNTKVDKRVEPKSCDKTHTCPPCPAPELLGGPSVFLFP

PKPKDTLMISRTPEVTCVVVDVSHEDPEVKFNWYVDGVEVHNAKTKPREE

QYNSTYRVVSVLTVLHQDWLNGKEYKCKVSNKALPAPIEKTISKAKGQPR

EPQVYTLPPSREEMTKNQVSLTCLVKGFYPSDIAVEWESNGQPENNYKTT

PPVLDSDGSFFLYSKLTVDKSRWQQGNVFSCSVMHEALHNHYTQKSLSLS

PGK.
```

In some embodiments, the antibody comprises the light chain (LC) amino acid sequence of SEQ ID NO: 12.

```
                                             (SEQ ID NO: 12)
QSVLTQPPSASGTPGQRVTISCSGSSSNIGDNYVSWYQQLPGTAPKLLIY

RDSQRPSGVPDRFSGSKSGTSASLAISGLRSEDEADYYCQSYDSSLSGSV

FGGGTKLTVLGQPKANPTVTLFPPSSEELQANKATLVCLISDFYPGAVTV

AWKADGSPVKAGVETTKPSKQSNNKYAASSYLSLTPEQWKSHRSYSCQVT

HEGSTVEKTVAPTECS.
```

In some embodiments, the antibody comprises the HC amino acid sequence of SEQ ID NO:11 and the LC amino acid sequence of SEQ ID NO:12.

In some embodiments, the formulation comprising the anti-CD38 antibody is a unit dosage form. In some embodiments, the unit dosage form comprises an amount sufficient to administer a dosage of about 0.01 mg per kilogram body weight to about 0.8 milligram per kilogram body weight. In some embodiments, the unit dosage form comprises an amount sufficient to administer a dosage of about 0.02 mg per kilogram body weight to about 0.75 milligram per kilogram body weight. In some embodiments, the unit dosage form comprises an amount sufficient to administer a dosage of about 0.02 mg per kilogram body weight to about 0.7 milligram per kilogram body weight. In some embodiments, the unit dosage form comprises an amount sufficient to administer a dosage of about 0.03 mg per kilogram body weight to about 0.6 milligram per kilogram body weight. In some embodiments, the amount is formulated in a volume of between about 0.25 milliliter (mL) and about 3.5 milliliter (mL). In some embodiments, the amount is formulated in a volume of between about 0.5 mL and about 3 mL. In some embodiments, the amount is formulated in a volume of between about 0.5 mL and about 2.5 mL. In some embodiments, the amount is formulated in a volume of between about 0.5 mL and about 2 mL. In some embodiments, the amount is formulated in a volume of between about 1 mL and about 2 mL. In some embodiments, the amount is formulated in a volume of between about 0.25 mL and about 1.25 mL. In some embodiments, the amount is formulated in a volume of between about 0.5 mL and about 1.25 mL. In some embodiments, the amount is formulated in a volume of between about 0.75 mL and about 1.25 mL. In some embodiments, the amount is formulated in a volume of between about 0.75 mL and about 1 mL. In some embodiments, the amount is formulated in a volume of between about 0.9 mL and about 1.5 mL. In some embodiments, the amount is formulated in a volume of between about 0.9 mL and about 1.1 mL. In some embodiments, the amount is formulated in a volume of between about 1 mL and about 1.1 mL. In some embodiments, the amount is formulated in a volume of between about 0.95 mL and about 1.05 mL. In some embodiments, the amount is formulated in a volume of about 3.5 mL. In some embodiments, the amount is formulated in a volume of about 3 mL. In some embodiments, the amount is formulated in a volume of about 2.5 mL. In some embodiments, the amount is formulated in a volume of about 2 mL. In some embodiments, the amount is formulated in a volume of about 1.5 mL. In some embodiments, the amount is formulated in a volume of about 1 mL. In some embodiments, the amount is formulated in a volume of about 0.5 mL. In some embodiments, the amount is formulated in a volume of about 0.25 mL.

In some embodiments, the anti-CD38 antibody unit dosage forms provided herein may further comprise one or more pharmaceutically acceptable excipients, carriers, and/or diluents.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. Compositions may be formulated in dosage unit form for ease of administration and uniformity of dosage. Dosage unit forms as used herein can, in some embodiments, refer to physically discrete units suited as unitary dosages for the subjects to be treated, each unit containing a predetermined quantity of active compound calculated to produce the desired therapeutic effect in association with the required pharmaceutical carrier.

The specification for the dosage unit forms of the present invention are dictated by and are directly dependent on (a) the unique characteristics of the active compound and the particular therapeutic effect to be achieved, and (b) the limitations inherent in the art of compounding such an active compound for the treatment of an individual.

The efficient dosages and the dosage regimens for the anti-CD38 antibodies used in the present invention depend on the type and severity of the disease or condition to be treated and may be determined by persons skilled in the art.

The dosage forms provided herein are based on a subcutaneous administration that is achieved at least in part based upon a lower ability to bind to or stay bound to RBCs as compared to daratumumab. Not to be bound to any particular theory but such binding activity may be due to the transient nature of AB79 binding to RBCs. In some embodiments, the therapeutic antibodies bind human RBCs transiently. In some embodiments, the therapeutic anti-CD38 antibodies bind cynomolgus RBCs transiently. In some embodiments, the therapeutic anti-CD38 antibodies bind human or cynomolgus RBCs transiently. In some embodiments, the therapeutic anti-CD38 antibodies bind human and cynomolgus RBCs transiently.

In one embodiment, the anti-CD38 antibody is administered by subcutaneous administration in a weekly dosage of about 0.01 to about 1 mg/kg, such as of about 0.02 to about 0.8 mg/kg. Such administration may be repeated, e.g., 1 to 14 times, such as 3 to 5 times. An exemplary, non-limiting range for a therapeutically effective amount of an anti-CD38 antibody used in the present invention is about 0.01-1 mg/kg, such as about 0.01-0.8 mg/kg, about 0.02-0.75 mg/kg, about 0.02-0.7 mg/kg, or about 0.03-0.6 mg/kg.

As non-limiting examples, treatment according to the present invention may be provided as a daily dosage of an antibody in an amount of about 0.01 to about 1 mg/kg, such as 0.009, 0.01, 0.03, 0.05, 0.07, 0.09, 0.11, 0.13, 0.15, 0.17, 0.19, 0.21, 0.23, 0.25, 0.27, 0.29, 0.31, 0.33, 0.35, 0.37, 0.39, 0.41, 0.43, 0.45, 0.47, 0.49, 0.51, 0.53, 0.55, 0.57, 0.59, 0.61, 0.63, 0.65, 0.67, 0.69, 0.71, 0.72, 0.73, 0.75, 0.77, 0.79, 0.81, 0.83, 0.85, 0.87, 0.89, 0.91, 0.93, 0.95, 0.97 or 0.99, 1.0, or 1.1 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, on at least one of week 1, 2, 3, 4, 5, 6, 7, 8, 9, 10, 11, 12, 13, 14, 15, 16, 17, 18, 19 or 20 after initiation of treatment, or any combination thereof, using single or divided doses of every 24, 18, 12, 8, 6, 4, or 2 hours, or any combination thereof.

In one embodiment the anti-CD38 antibody is administered in a weekly dosage of about 0.01 to about 1 mg/kg, such as about 0.02 to about 0.8 mg/kg. Such administration may be repeated, e.g., 1 to 14 times, such as 3 to 5 times. The administration may be performed by continuous infusion over a period of 2 to 24 hours, such as of 2 to 12 hours. Such regimen may be repeated one or more times as necessary, for example, after 6 months or 12 months. The dosage may be determined or adjusted by measuring the amount of compound of the present invention in the blood upon administration, for instance, by taking a biological sample and using anti-idiotypic antibodies that target the antigen binding region of the anti-CD38 antibody.

In a further embodiment, the anti-CD38 antibody is administered once weekly for 2 to 12 weeks, such as for 3 to 10 weeks, such as for 4 to 8 weeks.

In one embodiment, the anti-CD38 antibody is administered by maintenance therapy, such as, e.g., once a week for a period of 6 months or more.

In one embodiment, the anti-CD38 antibody is administered by a regimen including one infusion of an anti-CD38 antibody followed by an infusion of an anti-CD38 antibody conjugated to a radioisotope. The regimen may be repeated, e.g., 7 to 9 days later.

In some embodiments, the anti-CD38 antibody of the invention is used in combination with one or more additional therapeutic agents, e.g., a chemotherapeutic agent. Non-limiting examples of DNA damaging chemotherapeutic agents include topoisomerase I inhibitors (e.g., irinotecan, topotecan, camptothecin and analogs or metabolites thereof, and doxorubicin); topoisomerase II inhibitors (e.g., etoposide, teniposide, and daunorubicin); alkylating agents (e.g., melphalan, chlorambucil, busulfan, thiotepa, ifosfamide, carmustine, lomustine, semustine, streptozocin, decarbazine, methotrexate, mitomycin C, and cyclophosphamide); DNA intercalators (e.g., cisplatin, oxaliplatin, and carboplatin); DNA intercalators and free radical generators such as bleomycin; and nucleoside mimetics (e.g., 5-fluorouracil, capecitibine, gemcitabine, fludarabine, cytarabine, mercaptopurine, thioguanine, pentostatin, and hydroxyurea).

Chemotherapeutic agents that disrupt cell replication include: paclitaxel, docetaxel, and related analogs; vincristine, vinblastin, and related analogs; thalidomide, lenalidomide, and related analogs (e.g., CC-5013 and CC-4047); protein tyrosine kinase inhibitors (e.g., imatinib mesylate and gefitinib); proteasome inhibitors (e.g., bortezomib); NF-κB inhibitors, including inhibitors of IxB kinase; antibodies which bind to proteins overexpressed, inappropriately expressed, or activated in cancers and thereby downregulate cell replication (e.g., trastuzumab, rituximab, cetuximab, and bevacizumab); and other inhibitors of proteins or enzymes known to be upregulated, overexpressed, inappropriately expressed, or activated in cancers, the inhibition of which downregulates cell replication.

In some embodiments, the antibodies of the invention can be used prior to, concurrent with, or after treatment with Velcade® (bortezomib).

Treatment Modalities

In the methods of the invention, therapy is used to provide a positive therapeutic response with respect to a disease or condition. The term "positive therapeutic response" refers to an improvement in a disease or condition, and/or an improvement in the symptoms associated with the disease or condition. For example, a positive therapeutic response would refer to one or more of the following improvements in the disease: (1) a reduction in the number of neoplastic cells; (2) an increase in neoplastic cell death; (3) inhibition of neoplastic cell survival; (5) inhibition (i.e., slowing to some extent, preferably halting) of tumor growth; (6) an increased patient survival rate; and (7) some relief from one or more symptoms associated with the disease or condition.

Positive therapeutic responses in any given disease or condition can be determined by standardized response criteria specific to that disease or condition. Tumor response can be assessed for changes in tumor morphology (i.e., overall tumor burden, tumor size, and the like) using screening techniques such as magnetic resonance imaging (MRI) scan, x-radiographic imaging, computed tomographic (CT) scan, bone scan imaging, endoscopy, and tumor biopsy sampling including bone marrow aspiration (BMA) and counting of tumor cells in the circulation.

In addition to these positive therapeutic responses, the subject undergoing therapy may experience the beneficial effect of an improvement in the symptoms associated with the disease. For B cell tumors, the subject may experience a decrease in the so-called B symptoms, e.g., night sweats, fever, weight loss, and/or urticaria. For pre-malignant conditions, therapy with an anti-CD38 therapeutic antibody may block and/or prolong the time before development of a related malignant condition, for example, development of multiple myeloma in subjects suffering from monoclonal gammopathy of undetermined significance (MGUS).

An improvement in the disease may be characterized as a complete response. The term "complete response" refers to the absence of clinically detectable disease with normalization of any previously abnormal radiographic studies, bone marrow, and cerebrospinal fluid (CSF) or abnormal monoclonal protein in the case of myeloma.

Such a response may persist for at least 4 to 8 weeks, or at least 6 to 8 weeks, following treatment according to the methods of the invention. Alternatively, an improvement in the disease may be categorized as being a partial response. The term "partial response" refers to at least about a 50% decrease in all measurable tumor burden (i.e., the number of malignant cells present in the subject, or the measured bulk of tumor masses or the quantity of abnormal monoclonal protein) in the absence of new lesions, which may persist for 4 to 8 weeks, or 6 to 8 weeks.

Treatment according to the present invention includes a "therapeutically effective amount" of the medicaments used. A "therapeutically effective amount" refers to an amount effective, at dosages and for periods of time necessary, to achieve a desired therapeutic result.

The terms "therapeutically effective amount" and "therapeutically effective dosage" refer to an amount of a therapy that is sufficient to reduce or ameliorate the severity and/or duration of a disorder or one or more symptoms thereof; prevent the advancement of a disorder; cause regression of a disorder; prevent the recurrence, development, onset, or progression of one or more symptoms associated with a disorder; or enhance or improve the prophylactic or therapeutic effect(s) of another therapy (e.g., prophylactic or therapeutic agent), at dosages and for periods of time necessary to achieve a desired therapeutic result. A therapeutically effective amount may vary according to factors such as the disease state, age, sex, and weight of the individual, and the ability of the medicaments to elicit a desired response in the individual. A therapeutically effective amount is also one in which any toxic or detrimental effects of the antibody or antibody portion are outweighed by the therapeutically beneficial effects. A "therapeutically effective amount" of an antibody for tumor therapy may be measured by its ability to stabilize the progression of disease. The ability of a compound to inhibit cancer may be evaluated in an animal model system predictive of efficacy in human tumors.

Alternatively, this property of a composition may be evaluated by examining the ability of the compound to inhibit cell growth or to induce apoptosis by in vitro assays known to the skilled practitioner. A therapeutically effective amount of a therapeutic compound may decrease tumor size, or otherwise ameliorate symptoms in a subject. One of ordinary skill in the art would be able to determine such amounts based on such factors as the subject's size, the severity of the subject's symptoms, and the particular composition or route of administration selected.

Anti-CD38 Antibody Kits

In another aspect of the invention, kits are provided for the treatment of a disease or condition associated with hematological cancers. In one embodiment, the kit comprises a dose of an anti-CD38 antibody described herein, such as AB79. In some embodiments, the kits provided herein may contain one or more dose of a liquid or lyophilized formulation as provided herein. When the kits comprise a lyophilized formulation of an anti-CD38 antibody described herein such as AB79, generally the kits will also contain a suitable liquid for reconstitution of the liquid formulation, for example, sterile water or a pharmaceutically acceptable buffer. In some embodiments, the kits may comprise an anti-CD38 antibody formulation described herein prepackaged in a syringe for subcutaneous administration by a health care professional or for home use.

In certain embodiments, the kit will be for a single administration or dose of an anti-CD38 antibody described herein such as AB79. In other embodiments, the kit may contain multiple doses of an anti-CD38 antibody described herein such as AB79 for subcutaneous administration. In one embodiment, the kit may comprise an anti-CD38 antibody formulation described herein prepackaged in a syringe for subcutaneous administration by a health care professional or for home use.

Articles Of Manufacture

In other embodiments, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is the antibody. The label on, or associated with, the container indicates that the composition is used for treating the condition of choice. The article of manufacture may further comprise a second container comprising a pharmaceutically-acceptable buffer, such as phosphate-buffered saline, Ringer's solution or dextrose solution. It may further include other materials desirable from a commercial and user standpoint, including other buffers, diluents, filters, needles, syringes, and package inserts with instructions for use.

EXAMPLES

Example 1: Model-Based Characterization Of Anti-CD38 Antibody In Cynomolgus Monkey Anti-CD38 antibody AB79 binds cynomolgus monkey (cyno) CD38, distinguishing it from daratumumab (Darzalex™), a cytolytic CD38 monoclonal antibody recently approved for the treatment of multiple myeloma. This unique function supported the use of cyno for preclinical studies to characterize AB79 pharmacokinetics (PK), pharmacodynamics (PD) and safety. To this end, assays were developed to measure drug concentrations, immunogenicity, and to quantify T, B, and NK lymphocytes in the blood of cyno monkeys. We assessed these parameters in 8 pharmacological and toxicological preclinical studies. Of the tested cell populations, CD38 is most highly expressed on NK cells; therefore, we assume that the drug effect on NK cells comes closest to the effect on the considered target cells, the plasmablasts, plasma cells and other activated lymphocytes.

Data was pooled from 8 studies in healthy monkeys using a dose range of 0.03-100 mg/kg and mathematical models that describe the pharmacokinetics and the exposure-effect relationship for each of the cell types was developed. NK cell depletion was identified as the most sensitive pharmacodynamic effect of AB79. This depletion was described with a turnover model ($EC50=34.8$ µg/mL on depletion rate) and complete depletion was achieved with an IV dose of 0.3 mg/kg. Also observed were intermediate effects on T cell counts using a direct response model ($EC50=9.43$ µg/mL) and on B cell counts using a 4-transit-compartment model ($EC50=19.3$ µg/mL on depletion rate). These analyses substantiated the observation that each of the measured lymphocyte subsets was cleared by AB79 at different rates and required different time spans to deplete the blood compartment.

Mathematical models that describe the PK and PD data are useful tools to gain mechanistic and quantitative insights into the relationships between drug exposure and effect (Friberg et al. (2002) J. Clin. Oncol. 20: 4713-4721; Mager et al. (2003) Drug Metab. Dispos. 31: 510-518; Han and Zhou (2011) Ther. Deliv. 2: 359-368). Typical PK features of IgG antibodies including distribution and elimination, physiological and genetic similarities between monkey and human can be leveraged to explain the pharmacology of AB79 (Glassman and Balthasar (2014) Cancer Biol. Med. 11: 20-33; Kamath (2016) Drug Discov. Today Technol. 21-22: 75-83). In addition, those models have been successfully applied to predict PK concentrations and PD effects in healthy human subjects (Han and Zhou (2011) Ther. Deliv. 2:359-368).

Materials And Methods

A summary of the monkey studies is shown in Table 2 in chronological order. The single dose studies 2, 7, and 8 were primarily conducted to evaluate PK and PD of intravenously (IV) and subcutaneously (SC) administered AB79 (FIG. 1). The repeated dose studies were performed to evaluate safety, PK and PD including two 4-week studies (studies 1 and 3) and three 13-week studies under GLP conditions (studies 4, 5, and 6). In the 13-week study 5 a dosing error occurred. Animals of the lowest dose group received 0.01 mg/kg instead of the intended 0.1 mg/kg at one occasion (the second dose) and then continued with 0.1 mg/kg. These data were added to the data set with the correct information of the actually administered dosing amounts. Study 6 repeated the low dose of 0.1 mg/kg QW group of Study 5. All animal studies were carried out in accordance with the Guide for the Care and Use of Laboratory Animals as adopted and promulgated by the U.S. National Institutes of Health.

TABLE 2

AB79 Monkey Studies In Chronological Order

| Study No. | Study Description | Number of animals (female, male) | Doses (mg/kg) | Number of samples per animal (PK/PD) |
|---|---|---|---|---|
| 1 | Day 1 (1 mg/kg) +Day 28 (2 mg/kg), IV, PK, PD | 6 (0, 6) | plc, 1, 2 | 19/10 |
| 2 | Single dose, IV, PK, PD | 9 (0, 9) | plc, 0.3, 3 | 14/9 |
| 3 | 4 weeks tox, once weekly, IV, PK, PD | 12 (4, 8) | plc, 1, 30, 100 | 15/8 |

TABLE 2-continued

AB79 Monkey Studies In Chronological Order

| Study No. | Study Description | Number of animals (female, male) | Doses (mg/kg) | Number of samples per animal (PK/PD) |
|---|---|---|---|---|
| 4 | 13 weeks tox, q2 wk, IV, PK, PD | 40 (20, 20) | plc, 3, 30, 80 | 47/29 |
| 5 | 13 weeks tox, once weekly, IV, PK, PD | 52 (26, 26) | plc, 0.1, 0.3, 1 | 31/9 |
| 6 | 13 weeks tox, once weekly, IV, PK, PD | 20 (20, 0) | plc, 0.1 | 31/10 |
| 7 | Single dose, IV/SC, PK, PD | 12 (12, 0) | 0.1, 0.3, 1 | 16/16 |
| 8 | Single dose, IV/SC, PK, PD | 24 (24, 0) | 0.03, 0.1, 0.3 | 19/19 |

IV: intravenous 30 minute infusion (studies 1-4) or bolus (studies 5-8),
SC: subcutaneous injection (group 4 of study 7 and 3 groups of study 8),
PK: dense PK sampling,
PD: dense sampling of whole blood for flow cytometry analyses yielding cell count data of T, B, and NK cells.
plc-placebo, "4 weeks" or "13 weeks" describe the duration of the treatment period, tox: toxicology study,
q2wk: every other week dosing schedule.

Bioanalytics

PK was analyzed using a validated method developed and performed by Charles River Laboratories (Reno, NV). Briefly, the concentration of AB79 was measured in monkey serum using an indirect enzyme linked immunosorbent assay (ELISA). A 96-well microtiter format was coated with an anti-idiotypic antibody against AB79. Blanks, standards, and quality control (QC) samples containing AB79 at various concentrations were added to the plate, and incubated for 55-65 minutes at room temperature (RT). After washing the microtiter plate, a peroxidase conjugated affinipure mouse anti-human IgG (Peroxidase AffiniPure Mouse Anti-Human IgG, Fcγ Fragment Specific; Jackson ImmunoResearch) was added, and incubated on the plate for an additional 55-65 minutes. The plate was washed again, and tetramethylbenzidine (TMB) was added to the wells to generate a chromophore, and the development of color was stopped by the addition of a stopping solution (2N sulfuric acid). The absorbance at 450 nm was measured using a SPECTRAmax® 190 microplate reader (Molecular Devices) and AB79 concentrations were calculated using a 4-parameter logistic weighted ($1/y^2$) standard calibration curve. In study 1 (Table 2) the lower limit of quantification (LLOQ) of AB79 in serum was 0.061 µg/mL and in all other studies it was 0.05 µg/mL.

Determination of Anti-AB79 Antibodies (Immunogenicity)

Anti-drug antibodies (ADA) screening of monkey serum was analyzed using a qualitative electrochemiluminescent (ECL) method, validated and performed by Charles River Laboratories (Reno, NV). Briefly, undiluted serum samples were incubated with 300 mM acetic acid. Acid-dissociated samples were incubated in a mixture of biotinylated AB79, AB79 labeled with SULFO-TAG (Meso Scale Diagnostics, labeled at Charles River Laboratories) and 1.5 M Trizma base to neutralize the acid and form an immune complex. This complex was then added to a streptavidin-coated MSD plate (Meso Scale Diagnostics) and allowed to bind. After washing, the complex was detected by the addition of MSD read buffer T (Meso Scale Diagnostics) to the plate and subsequent excitation of the SULFO-TAG™ via an electrochemical reaction of Ru(bpy)3 to generate luminescence (light), which was read using the MSD Sector 6000 (Meso Scale Diagnostics). The quantity of luminescence correlated with the level of monkey anti-AB79 antibodies present in the serum of individual samples.

Characterization of Blood Cells

To evaluate and compare the level of AB79 binding between humans and monkeys, blood samples from each were collected into sodium heparin tubes. An aliquot of blood (100 µL) was mixed with appropriate volume of a characterizing antibody (Table 3) and incubated for 15-20 minutes at RT in the dark. After incubation, 1 mL of BD FACS lyse (1×; BD Biosciences; San Jose, CA) was added to lyse red blood cells and the cells incubated for 10 minutes at RT in the dark, then centrifuged, decanted and resuspended in 1 mL of staining buffer with bovine serum albumin (BD Biosciences). The cells were centrifuged a second time, decanted and 250 µL of Flow Fix (1% paraformaldehyde in calcium and magnesium free Dulbecco's-PBS (Life Technologies, Carlsbad, CA) and fluorescence measured by flow cytometric analyses using a FACSCanto™ II Flow Cytometer (BD Biosciences). Monkey NK cells (CD3−, CD159a+), B cells (CD3−, CD20+) and T cells (CD3+) and human NK cells (CD3−, CD16/CD56+), B cells (CD3−, CD19+) and T cells (CD3+) were measured. The mean fluorescence intensity for AB79 staining for each cell population was converted into units of molecules of equivalent soluble fluorescence (MOEF) using a standard curve generated using Rainbow Beads (Spherotech; Lake Forest, IL).

TABLE 3

Antibodies Used to Characterise Blood Cells

| Antibody | Antibody volume per sample (µl/100 µl sample) | Vendor |
|---|---|---|
| CD3-APCH7 (SK7)* | 5 | BD Biosciences |
| CD3-APC Cy7 (SP34-2) | 1.25 | BD Biosciences |
| CD3-PerCp Cy 5.5 (SP34-2) | 5 | BD Biosciences |
| AB19-AF647 | 1 | Prepared at Takeda |
| AB79-AF488 | 2 | Prepared at Takeda |
| AB19-AF488 | 0.42 | Prepared at Takeda |
| CD19-PerCp Cy 5.5 (HIB19)* | 5 | BD Biosciences |
| CD20-PE (2H7) | 10 | BD Biosciences |
| CD20-APCH7 (2H7) | 2.5 | BD Biosciences |
| CD16-PE (B73.1)* | 5 | BD Biosciences |
| CD16-PerCP-Cy5.5 (3G8) | 20 | BD Biosciences |
| CD56-PE (B159)* | 5 | BD Biosciences |
| CD159a-PE (Z199) | 5 | Beckman Coulter (Brea, CA) |
| CD45-PerCP TruCount (D058-1283) | NA | BD Biosciences |
| CD45-PeCy7 (HI30)* | 2.5 | BD Biosciences |
| CD45-PeCy7 (D058-1283) | 2.5 | BD Biosciences |
| Mouse IgG1 kappa-AF488 or-AF647(MOPC-21) | 2.5 | BioLegend (San Diego CA) |

*used for staining human cells only

In studies outlined in Table 2, cells were stained and analyzed using a validated method developed and performed by Charles River Laboratories (Reno, NV). Monkey blood samples were collected into sodium heparin tubes before and at multiple times after AB79 treatment and specific lymphocyte populations measured by flow cytometric analyses using FACSCanto™ II Flow Cytometer (BD Biosciences). Commercial antibodies and a CD38 antibody (AB19; Table 3); U.S. Pat. No. 8,362,211) were titered to optimal concentrations for staining. Monkey CD38+/−, T cell (CD3+), B cell (CD3−/CD20+), and natural killer (NK) cell (CD3−/CD20−/CD16+) populations were identified and lymphocytes quantified using CD45TruCount™ tubes (BD Biosciences). Approximately 100 µL aliquots of each blood sample were placed into an appropriate well of a 96-well plate and antibodies added at the indicated volume, mixed and incubated for a minimum of 30 minutes at RT in the dark. After incubation, red blood cells were lysed, samples mixed and incubated at RT for an additional 10 minutes in the dark. The plate was centrifuged and the supernatant was decanted. The cell pellet was then resuspended in 1,800 µL of stain buffer, samples mixed, centrifuged and the supernatant decanted. The cell pellet was resuspended in 500 µL of stain buffer with fetal bovine serum and approximately 300 µL of the cell suspension transferred to a 96-well v-bottom plate for analysis. The NK cell percentages, as well as those for the total T cells and B cells were applied to the cell count values obtained with TruCount™ tubes (BD Biosciences; San Jose, CA) and used to determine the absolute cell counts for each cell population. In studies 1-4 CD38+NK, B, and T cell subsets were assessed at baseline with the labeled anti-CD38 antibodies AB79 or AB19. Although AB19 binds to a different epitope the results were very similar and are therefore not presented separately. Processed samples were analyzed immediately.

PK Model Development

During PK model development, one-, two-, and three-compartment model structures were investigated. The two-compartment model was clearly superior to the one-compartment model, as judged by goodness-of-fit (GOF) plots and a decrease in objective function value (OFV). Based on visual inspections of diagnostic plots, the introduction of a third compartment was not necessary to describe the data adequately. The bioavailability (F) was modeled using the logit transformation F=exp (PAR)/(1+exp (PAR)), where PAR designates the model parameter, to ensure that the estimates are bounded between 0 and 1. The non-linear PK at low concentrations was modeled with the quasi steady state (QSS) approximation model of the target mediated drug disposition (TMDD) process (Gibiansky and Gibiansky (2009) Expert Opin. Drug Metab. Toxicol. 5: 803-812).

A schematic representation of the model is provided in FIG. 2C. For the QSS approximation we assume that the steady state concentrations of the free drug C, the target R and the drug target complex RC are established very quickly compared to all other processes. This implies that the binding process is balanced with the dissociation and internalization processes and that the following equation holds in the appropriate units: $K_{ON}*C*R$ ($K_{OFF}+K_{INT}$)*RC, where $K_{ON}$ designates the binding rate constant and $K_{OFF}$ the dissociation rate constant and $K_{INT}$ the internalization rate constant.

The between-subject variability (BSV) was investigated for all parameters and modeled with exponential models of the following type: $PAR_i = TVPAR*e^{ETAPAR_i}$, where $PAR_i$ is the individual and TVPAR the typical parameter estimate and $ETAPAR_i$ is the estimate of the deviation of individual i. The $ETAPAR_i$ values were assumed to follow a normal distribution with mean zero. The residuals were described with a combined additive and proportional error model (Beal and Sheiner (1992) NONMEM User Guides, in University of California CA).

The following parameters were investigated to identify potential covariate effects on the PK of AB79: body weight, sex, dose, route of administration, and study.

PK-PD Model Development

For each of the three cell types PK-PD model development was performed separately. Note that for model development measurements close to the drug administration (<8 hours post dose) were not utilized because they were influenced by a non-specific drug-independent effect potentially due to multiple blood samples taken over short amount of time. The PK model and parameter estimates were fixed. Turnover, transit compartment and direct response models of various forms were tested (Friberg et al. (2002) J. Clin. Oncol. 20: 4713-4721; Mager et al. (2003) Drug Metab. Dispos. 31: 510-518). In the turnover models the drug effect was introduced on the cell elimination rate in form of an Emax type model with or without Hill factors. In our notation, an Emax model is a function $f$ of the drug concentration c of the following form: $f(c)=EMAX*c^H/(c^H+C50^H)$, EMAX denotes the maximal effect, C50 the concentration at which half of the maximal effect is achieved, and H the Hill factor. In the transit compartment model (TCM) the drug effect was introduced and tested on different positions: on the rate of proliferation, on circulating cells and on the third transit compartment. Combinations of these effects and whether the data supports the presence of a feedback mechanism from the circulation to the rate of proliferation were also tested. In addition, Emax type direct response models with and without Hill factors were tested to describe the drug concentration-effect curve.

Random-effect parameters were introduced to estimate the between-subject variability on the baseline cell count, on the cell production rate (KIN), on transit time in the transit compartment model (MTT), on C50 and on EMAX. Individual mean baseline cell levels were provided in the data set (column BL). This was used as typical value in the model. A random effect parameter was added to enable the adjustment of the individual baseline estimate based on all measurements of the individual. The PD residuals were described with a proportional error model.

For model validation during the course of modeling (PK and PK-PD) OFV, standard errors, GOF plots and individual prediction versus data plots were used to assess the models and compare them to alternative ones.

The following software packages were utilized: NONMEM (Version 7.2), KIWI (Version 1.6), Berkeley Madonna (version 8.3.14), PSN (Version 4), and R (Version 3.3.0).

Data Set Preparation

The data sets from the 8 monkey studies were collected, reorganized in a single format and merged into three separate NONMEM readable PK-PD data sets. Each of the three data sets contained individual characteristics of the monkeys (study, ID, group, body weight, sex), the dosing information, the PK and either NK, B, or T cell data. For animals of the control groups only cell counts but no PK data were added to the data sets, assuming implicitly no serum levels of AB79. Time-resolved information about the antidrug immunogenicity status (ADA), namely TITER containing the quantitative measurement result and the 0/1-flag variable ADAF (ADAF=1 if ADA affects the concentration of AB79, ADAF=0 if it does not), was added in separate columns to each observation. ADA titers were measured with different method specifications in the different studies and, therefore, between studies the values are quantitatively not directly comparable. To utilize the ADA information in a consistent manner across all studies we applied the following procedure for each animal separately: ADA titers that increased at time points later than 7 days over the initially measured levels were considered ADA-positive and flagged in the data set (ADAF=1). If a sample at one time point was flagged ADA-positive all samples that were taken after that time point were also flagged ADA-positive in this animal regardless of the measured titer. ADA positive observations were not used for parameter estimation during model development. Note that also PD measurements from sampling time points of ADA affected PK concentrations were flagged with ADAF=1.

For the cell count data, the individual baseline values for each cell type (NK, B, and T cells) were calculated as mean value of all available predose measurements of a given animal. In most studies, this was a single measurement. The baseline value of each animal was then added as an observation at the time of the first dosing event (TIME=0) and as a constant value in column BL to each observation of the respective animal. Based on this baseline value the percent of baseline for each observed cell count was calculated and added to the data set.

Scaling of Monkey PK Parameters

The final PK and PK-PD models were used as starting point to simulate PK and PK-PD profiles for the first in human clinical trial. Although never conclusive, comparative analyses of data from therapeutic monoclonal antibodies have shown that PK parameters derived from studies in monkeys can be scaled to help predict human PK profiles with acceptable accuracy (Han and Zhou (2011) Ther. Deliv. 2: 359-368). The publication indicated that using a fixed exponent of 0.85, human clearances of monoclonal antibodies can be predicted reliably. Consequently, this relationship was applied to scale human clearance parameters (CL, Q), whereas volume parameters (VC, VP) were scaled using a direct relation between body weights (BW):

$$CL_{human} = CL_{animal} \cdot \left(\frac{BW_{human}}{BW_{animal}}\right)^{0.85}$$

$$V_{human} = V_{animal} \cdot \frac{BW_{human}}{BW_{animal}}$$

Results

Pharmacokinetics of AB79

Figure 3:
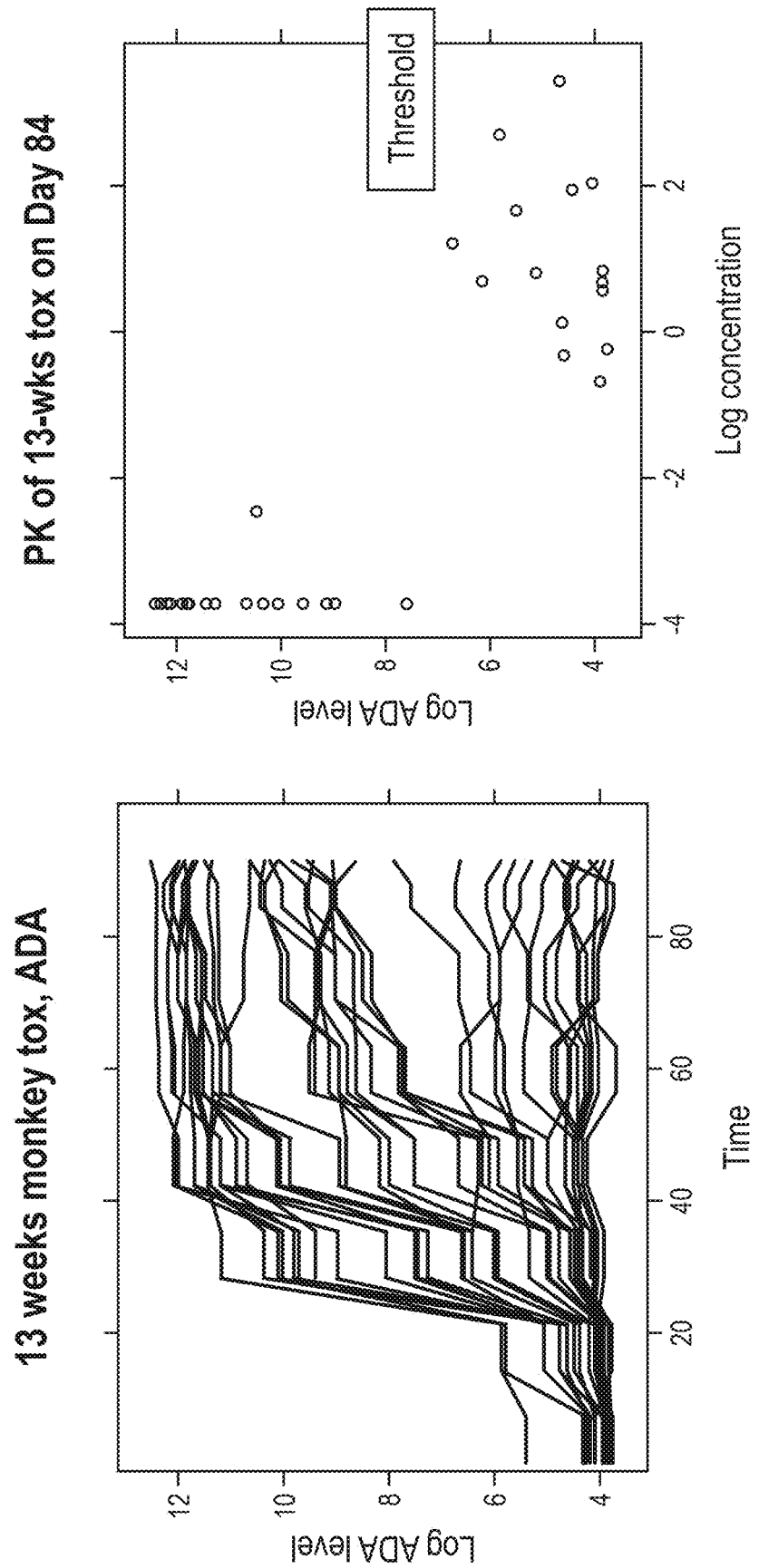
FIG. 3 shows ADA effects and PK in a 13 week cyno toxicology study. The evaluation refers to the final population PK model (FIG. 2, Table 2). Presented are the following goodness-of-fit (GOF) plots stratified by dose and route of administration (Keizer et al. (2013) CPT Pharmacometrics Syst. Pharmacol. 2:e50): (1) Conditional weighted residuals (CWRES) versus time; (2) Observed concentration versus population model prediction; (3) CWRES versus population model prediction; and (4) Observed concentration versus individual model prediction.
Figure 4A:
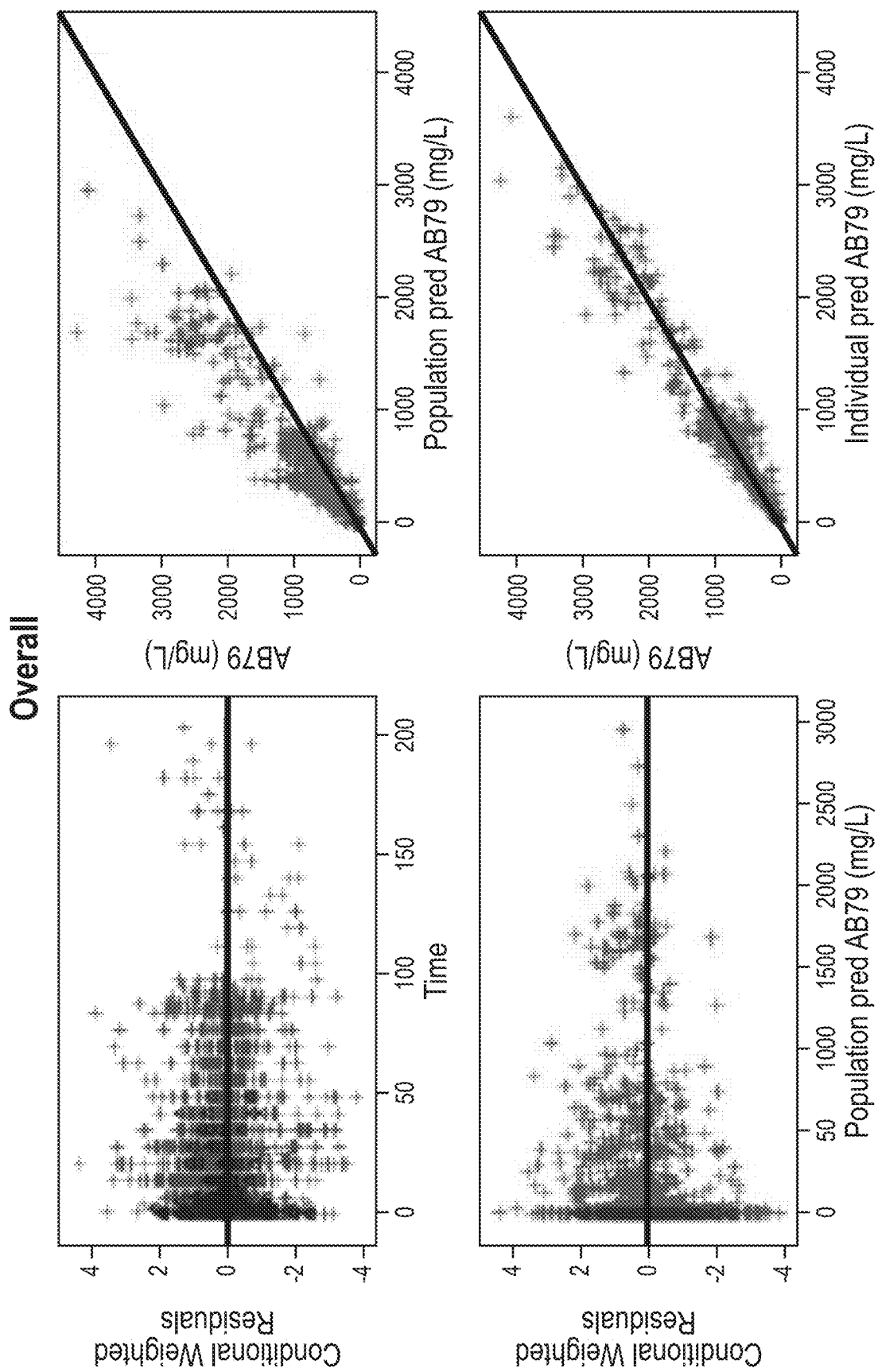
FIG. 4A—over all.
Figure 4B:
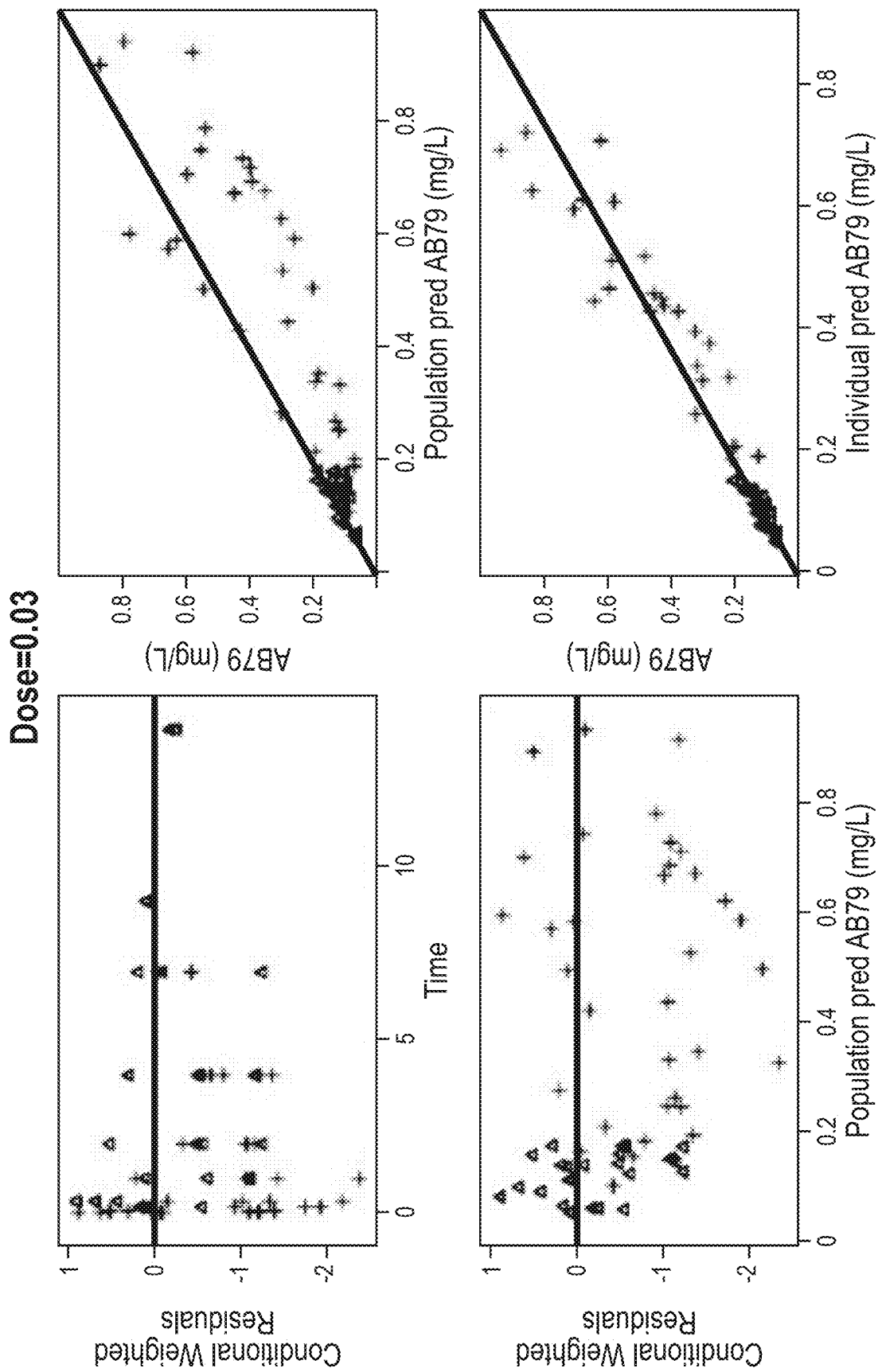
FIG. 4B—dose 0.03 mg/kg.
Figure 4C:
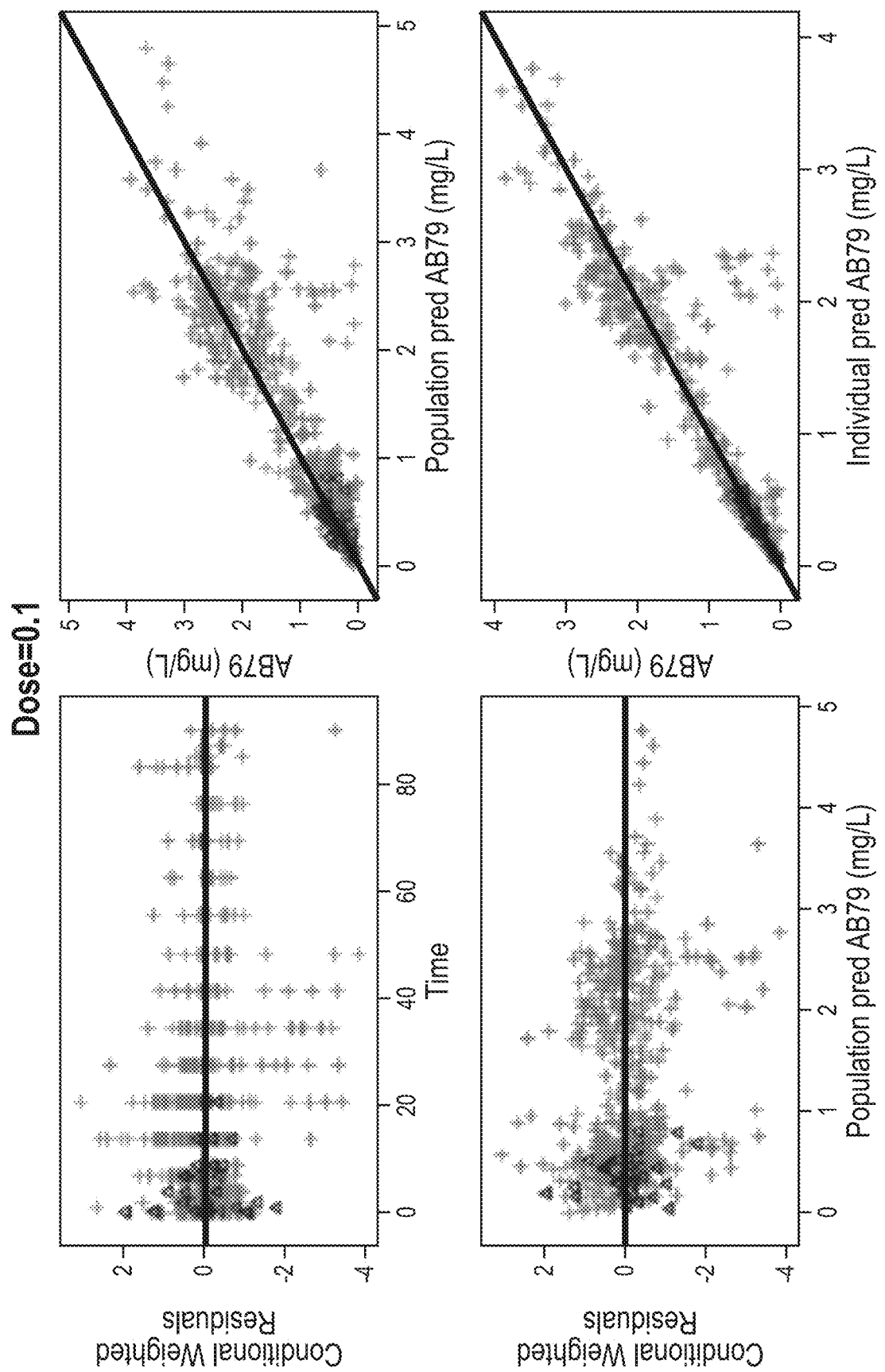
FIG. 4C—dose 0.1 mg/kg.
Figure 4D:
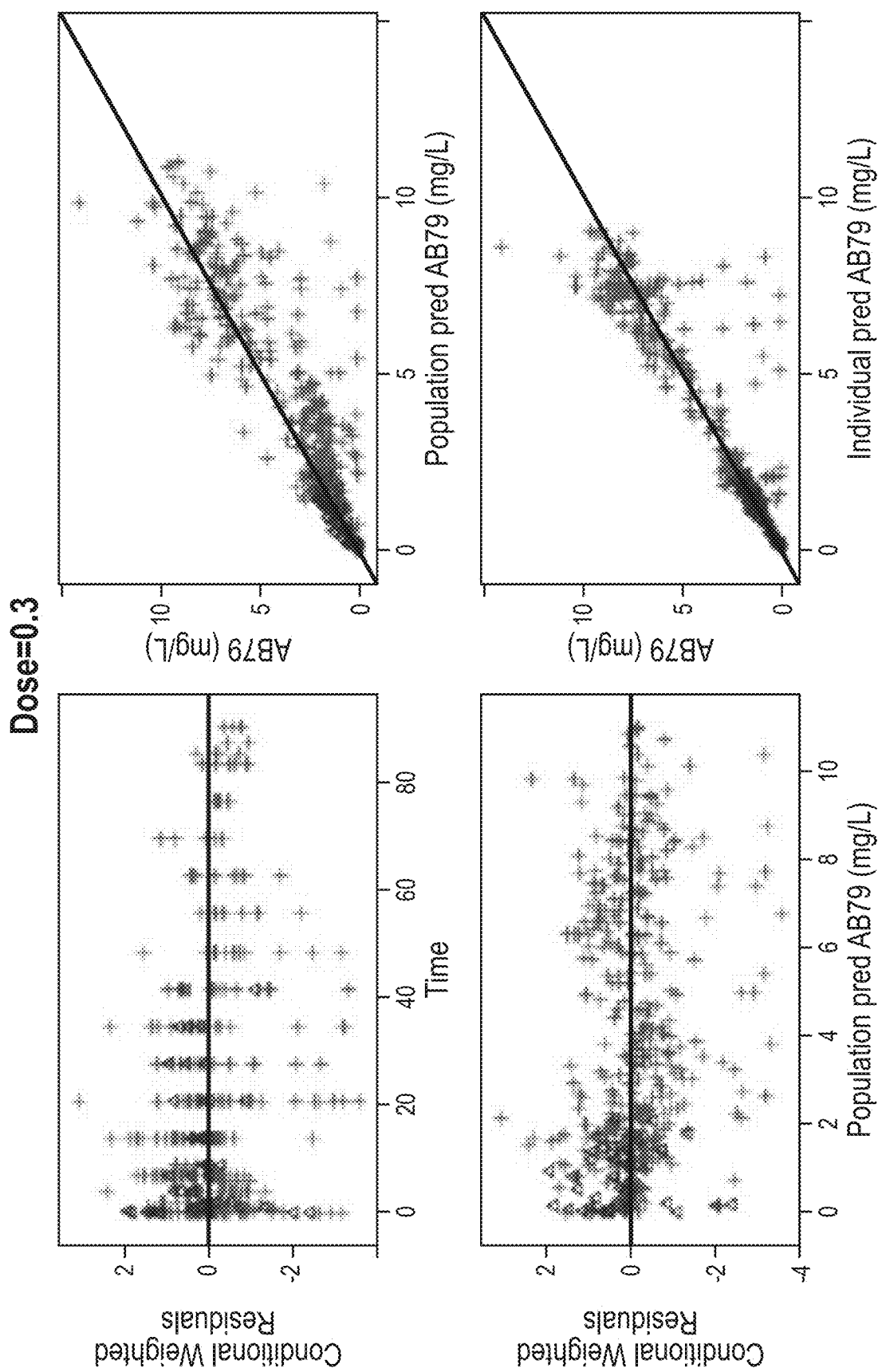
FIG. 4D—dose 0.3 mg/kg.
Figure 4E:
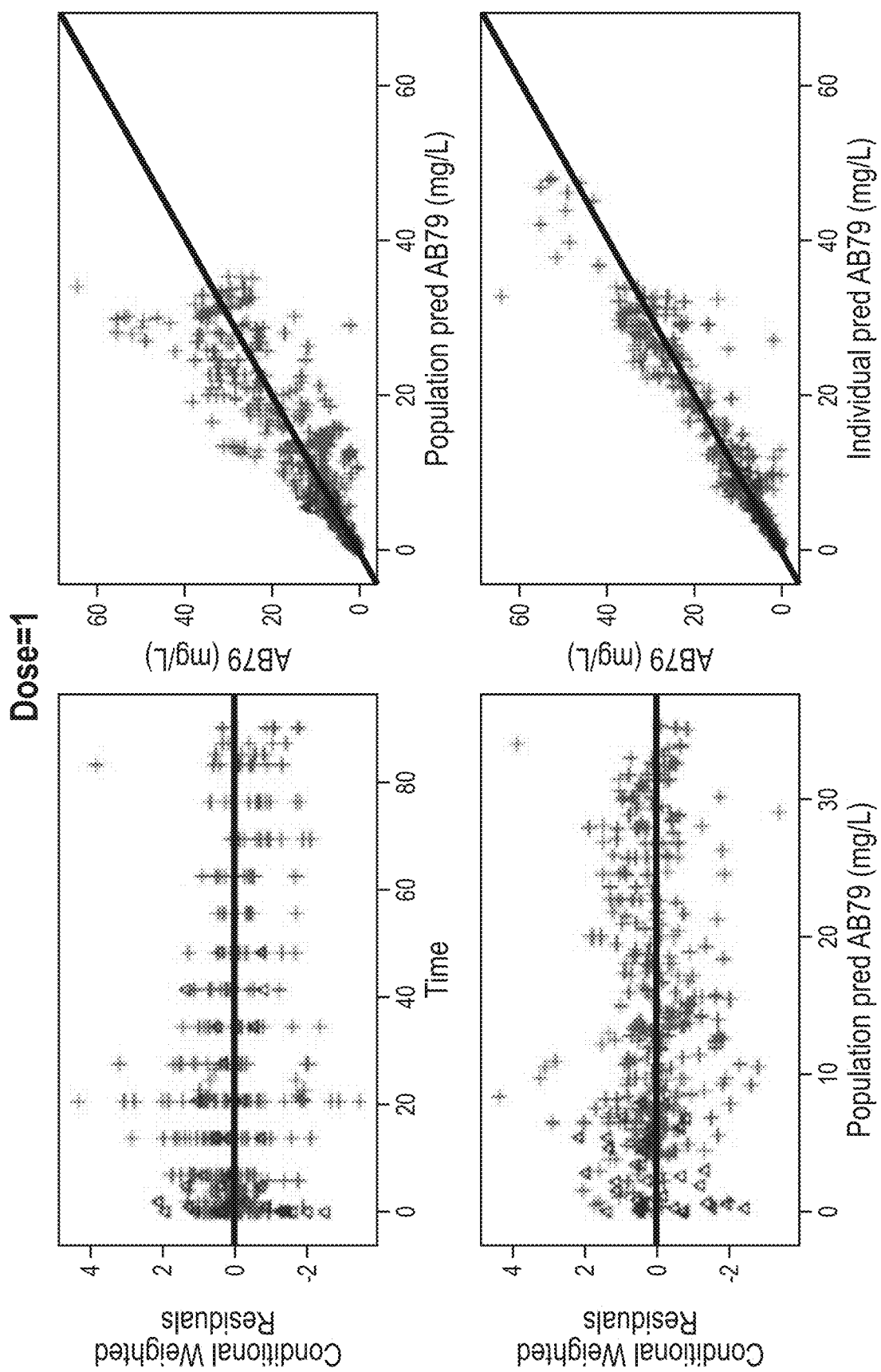
FIG. 4E—dose 1.0 mg/kg.
Figure 4F:
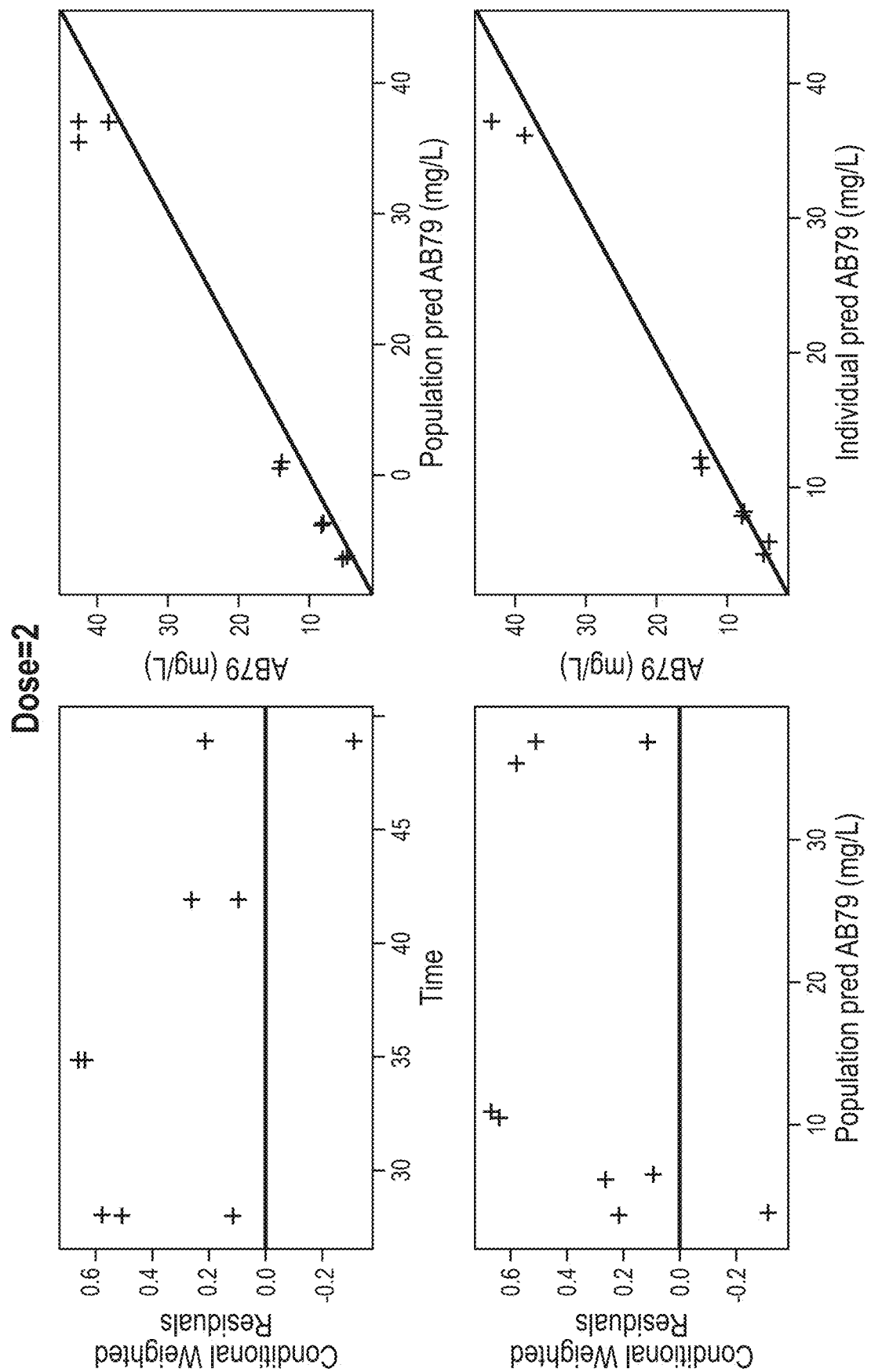
FIG. 4F—dose 2.0 mg/kg.
Figure 4G:
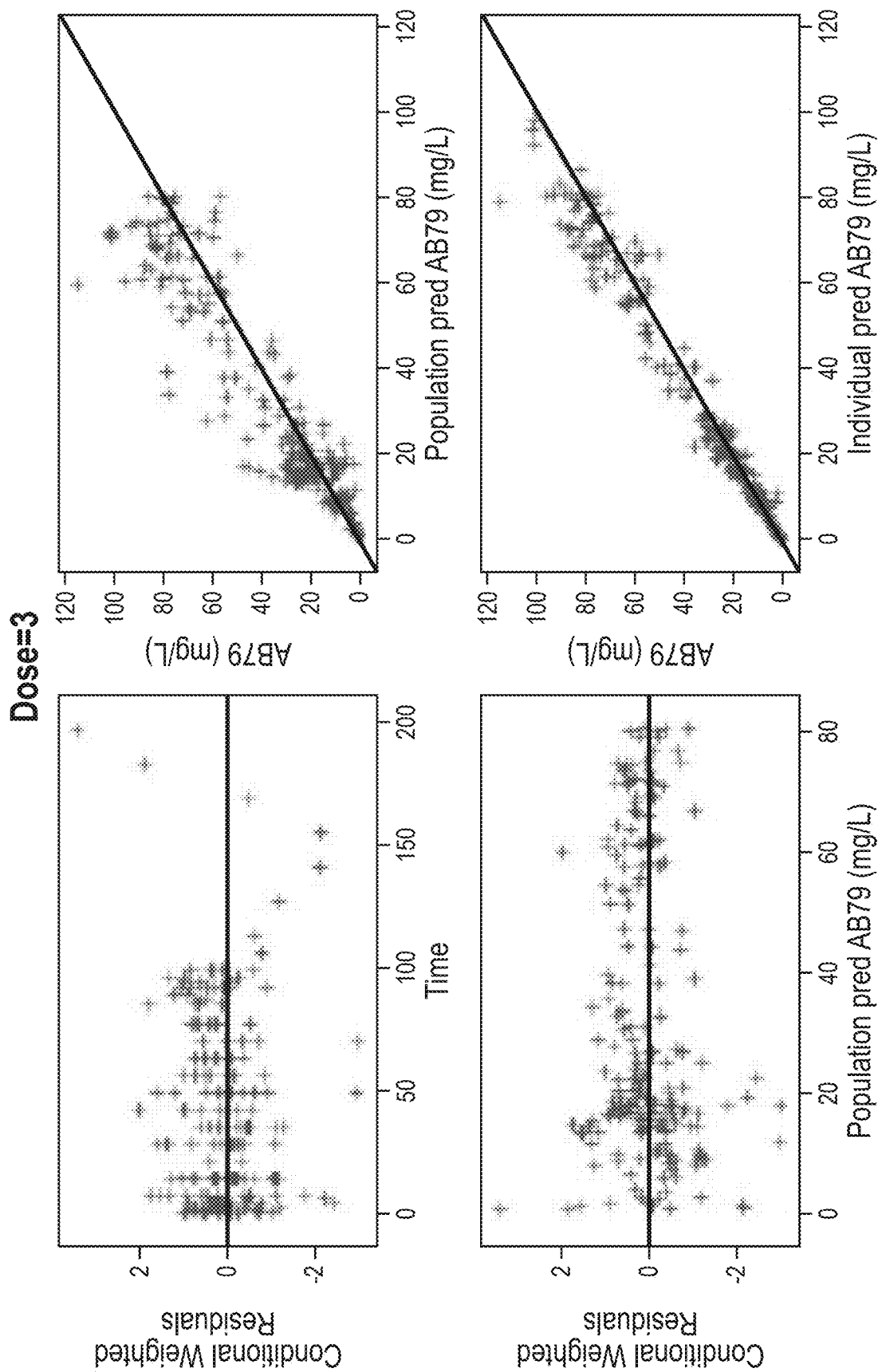
FIG. 4G—dose 3.0 mg/kg.
Figure 4H:
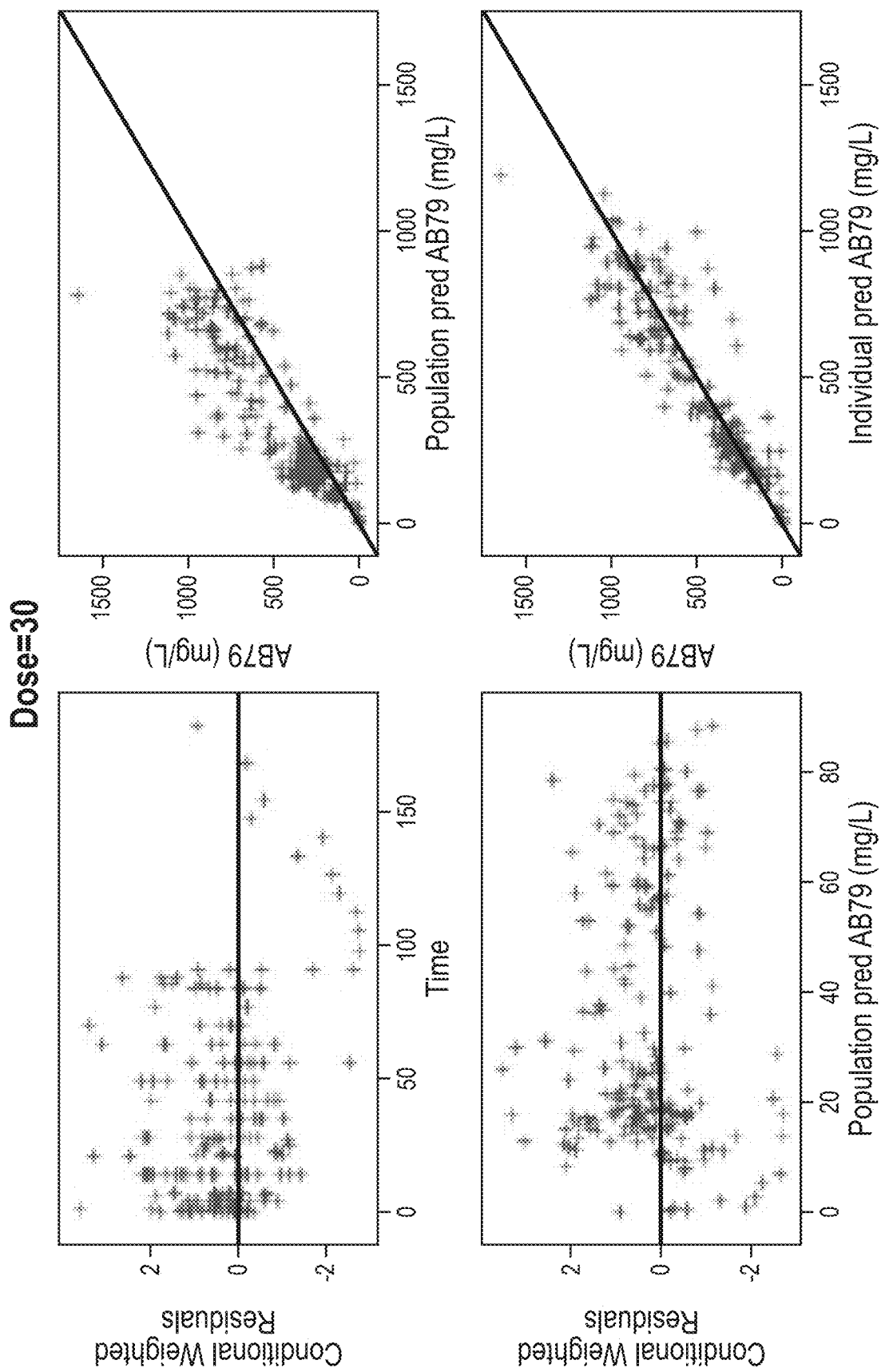
FIG. 4H—dose 30 mg/kg.
Figure 4I:
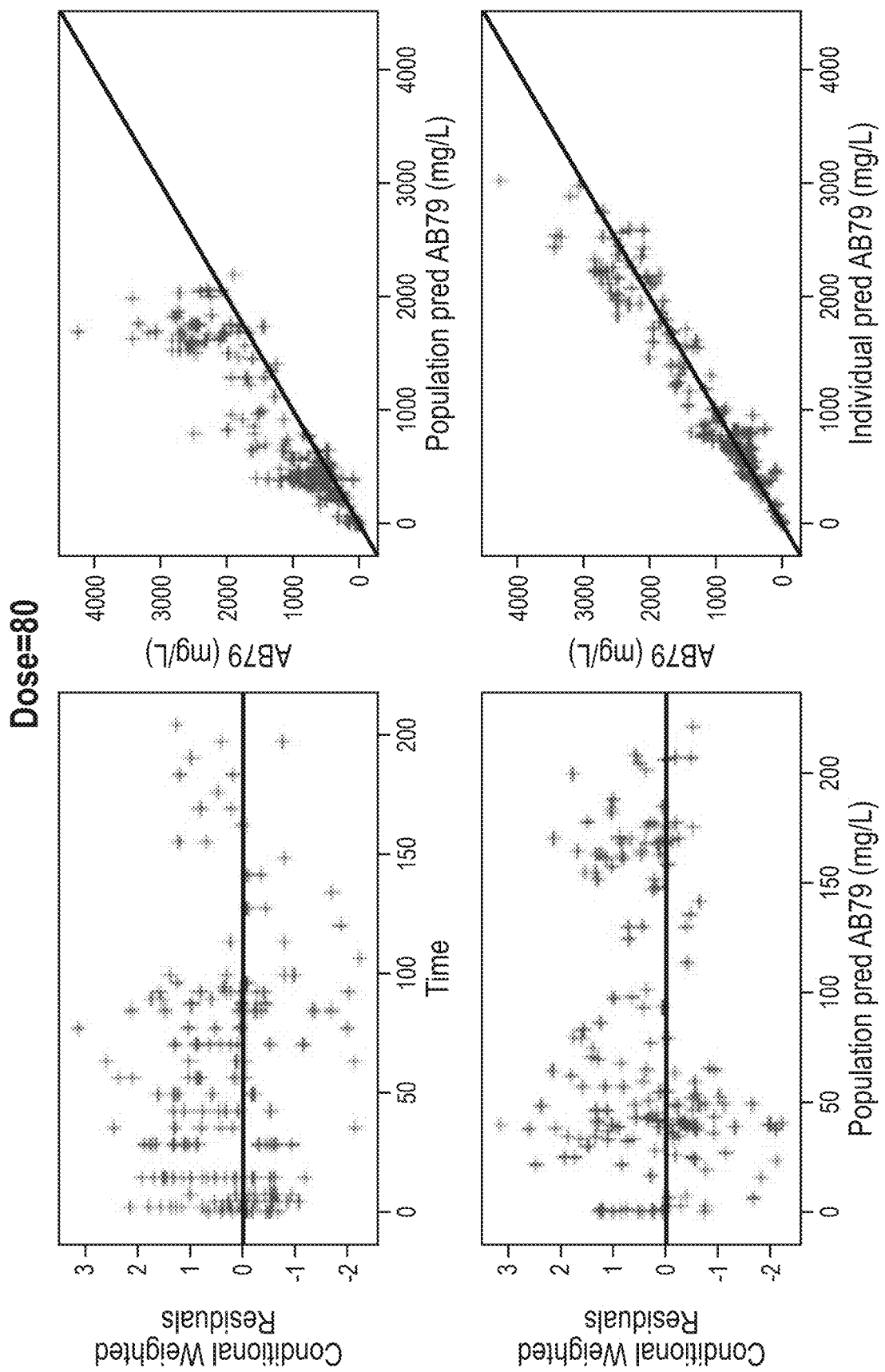
FIG. 4I—dose 80 mg/kg.
Figure 4J:
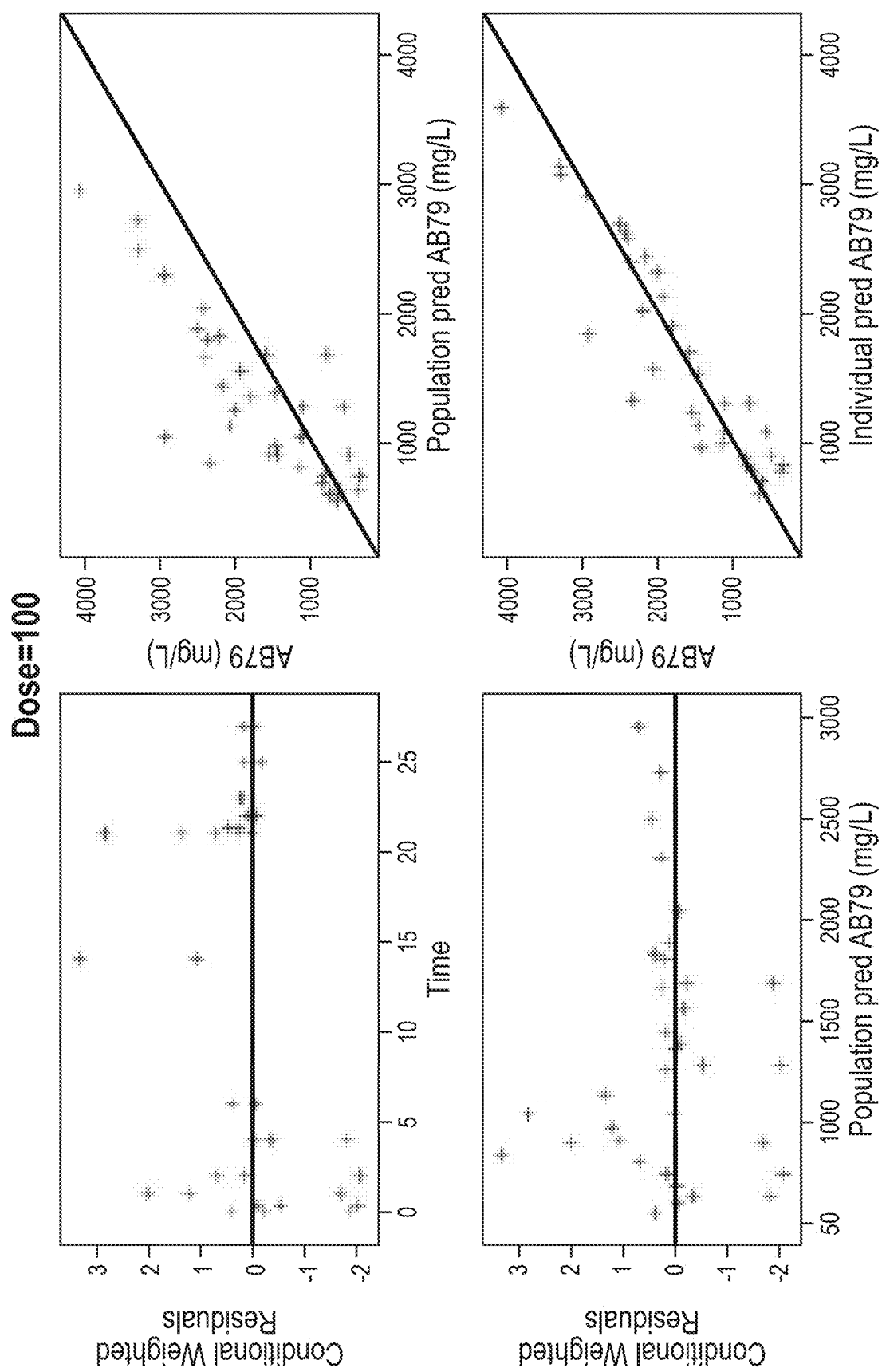
FIG. 4J—dose 100 mg/kg.

The PK data set was pooled from all 8 studies in healthy monkeys excluding the placebo groups (Table 2). In total, the set contained data from 140 animals, 58 of which were male and 82 were female. The body weights of the studied animals ranged from 2.1 to 4.7 kg and the doses ranged from 0.03 to 100 mg per kg body weight (mg/kg). In one group of study 7 and three groups of study 8 doses of 0.03, 0.1, 0.3 and 1 mg/kg were administered SC (15 animals in total). The pooled data set contained 2,199 measurable PK observations greater than LLOQ (FIGS. 2A and 2B). The PK was most densely sampled after the first dose and even in the long-term toxicology studies most animals were terminated before Day 98. Only study 4 included recovery groups and we could only gather PK data from 4 animals, 2 from the 80 mg/kg group and one from each of the 30 mg/kg and 3 mg/kg groups (FIG. 2B). In parallel to AB79 concentrations, ADA was assessed. 229 PK observations were affected by ADA (FIG. 3).

Initially, for each of the monkey studies, PK analyses were performed using standard non-compartmental techniques (NCA). Based on the single dose studies (IV bolus injection or 30 minute IV infusion) the volume of distribution during the terminal phase (Vz) was calculated to range from 64 to 116 mL/kg, the clearance from 6.04 to 14.7 mL/kg/day, and the terminal elimination half-life (T1/2) from 4.75 to 11.2 days. Area under the concentration time curve (AUC) and maximal concentration (Cmax) values were found to increase proportionally with dose over a wide range. Only the PK profiles of the lowest dose groups (<1 mg/kg, FIGS. 2D-2F) provide evidence for non-linearly augmented clearance at concentrations below 0.5 µg/mL likely caused by target-mediated mechanisms (TMDD) (Kamath (2016) Drug Discov. Today Technol. 21-22: 75-83). Based on the data of all monkey studies excluding the two lowest dose groups (dose >0.3 mg/kg) a linear 2-compartment model was constructed. When the PK of the lowest dose groups was simulated and overlaid with the measured concentrations it was evident that the linear model over predicts the concentrations (FIGS. 2D-2F).

The available PK data after single dose SC administration revealed that Cmax was 70-80% lower in the SC versus IV groups of the same dose and that the AUCs were comparable. No differences in PK parameters between male and female monkeys were observed. The results of these initial analyses were used as the starting point for model development.

PK Model Development

Model development started with single IV dose data and then the initial model was gradually extended utilizing more complex data. Similar to other therapeutic antibodies, the PK grossly follows a linear 2-compartment model (Kamath (2016) Drug Discov. Today Technol. 21-22: 75-83). The non-linear elimination component (TMDD) describing the accelerated clearance at low concentrations was modeled with the quasi steady state (QSS) approximation (Gibiansky and Gibiansky (2009) Expert Opin. Drug Metab. Toxicol. 5: 803-812). The assumption that the drug-target association process is much faster than the processes of drug dissociation, distribution and elimination, and of target and drug-target complex elimination leads to the simplified TMDD model (FIG. 2, Table 4). The amount of data at low concentrations was relatively small such that all the parameters were not estimated in a single estimation run of the software program. Therefore, the parameters of the TMDD model were first estimated by focusing on the data of the low single dose studies 7 and 8. The resulting TMDD parameter estimates were then kept fixed during the final estimations on the entire data set (Table 4).

TABLE 4

Population PK Modeling Results, Parameter Estimates And Standard Errors In Percent (% SEM)

| Parameter | Final Parameter Estimate | | Interindividual Variability/Residual Variability | |
|---|---|---|---|---|
| | Typical Value | % SEM | Magnitude | % SEM |
| F | 0.227 | 121 | NE | — |
| $K_A$ (L/day) | 0.399 | 20.5 | 42.1% CV | 53.8 |
| CL (L/day) | 0.0187 | 5.17 | 42.9% CV | 20.1 |
| $V_C$ (L) | 0.141 | 3.23 | 19.8% CV | 22.5 |
| Q (L/day) | 0.127 | 14.7 | NE | — |
| $V_P$ (L) | 0.127 | 6.45 | 39.4% CV | 20.8 |
| $K_{INT}$ (l/day) | 0.1 | FIXED | 49.3% CV | 36.7* |

TABLE 4-continued

Population PK Modeling Results, Parameter Estimates
And Standard Errors In Percent (% SEM)

| Parameter | Final Parameter Estimate | | Interindividual Variability/Residual Variability | |
|---|---|---|---|---|
| | Typical Value | % SEM | Magnitude | % SEM |
| $K_{SS}$ (l/day) | 5.68 | 38.7* | NE | — |
| $K_{SYN}$ (u/L/day)$ | 0.04 | FIXED | NE | — |
| $K_{DEG}$ (l/day) | 0.00452 | 30.1* | NE | — |
| ROUT on $V_C$ | −0.697 | 6.51 | NE | — |
| RV add | 3.17E−04 | 21.2 | 0.0178 SD | — |
| RV prop | 0.0677 | 1.58 | 26.0% CV | — |

Minimum value of the objective function = 5748.412
$ $K_{SYN}$ is the synthesis rate of the receptor CD38. Since actual concentration measurements or information about the in vivo synthesis or degradation rate of CD38 were not available, "u" was used as unit for a certain unknown amount of CD38.
*The estimates and standard errors for the TMDD parameters were gained from a separate run that focused on the data of the low dose groups, and were then fixed for the final estimation of the other PK parameters.
NE: Not Estimated.

Estimates for the absorption parameters KA and F were obtained when the data of the SC groups was added. All SC data came from four lower single dose groups from studies 7 and 8. These lower doses (≤1 mg/kg) covered the clinically relevant range but may limit the generalizability of the parameter estimates for higher doses.

The between subject variability (BSV) for the PK parameters was described with exponential models. Absorption rate ($K_A$), clearance (CL), and peripheral volume of distribution ($V_P$) have an estimated BSV of about 40% and the central volume of distribution ($V_C$) of about 20% (Table 4). Covariate analysis identified an effect of the route of administration on $V_C$. The typical value for $V_C$ was 0.141 L if administered IV and 0.043 L (about 70% smaller) if administered SC. Other significant covariate effects were not identified. Because of the limited amount of data at low concentrations the between subject variability and the individual predictions of the TMDD parameters were only estimated for the internalization rate $K_{INT}$ (BSV: 49%). Model evaluation based on residual errors, OFV, standard errors, GOF plots and individual curve fits corroborated that the final model adequately described the PK of AB79 in healthy monkeys (Table 4, FIGS. 4A-4J).

Pharmacodynamics

Figure 5:
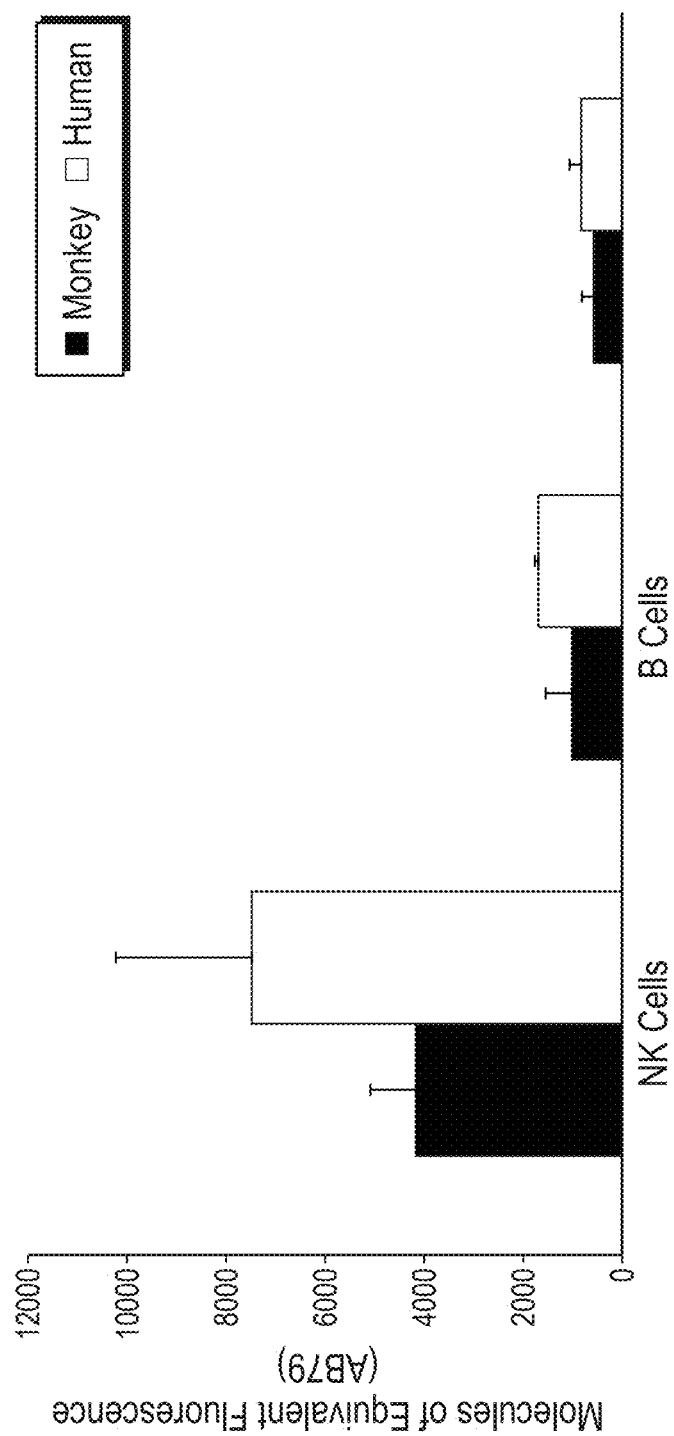
FIG. 5 shows a comparison of CD38 expression on the surface of human and monkey NK, B, and T cells. The flow cytometric measurements were standardized and the signals are reported in molecules of equivalent soluble fluorescence (MOEF). Human and monkey blood lymphocytes bind similar levels of AB79. Direct comparison of CD38 expression levels on monkey NK cells (CD3−, CD159a+), B cells (CD3−, CD20+) and T cells (CD3+) and human NK cells (CD3−, CD16/CD56+), B cells (CD3−, CD19+) and T cells (CD3+) were evaluated by flow cytometry. The median fluorescent intensity (MFI) for an AB79 staining for each cell population was converted into units MOEF using a standard curve generated using Rainbow Beads (Spherotech; Lake Forest, IL). Data shown are from 3 individuals of each species and show the MOEF+SD for each cell type. There are differences in CD38 expression between blood lymphocytes, with a higher level of AB79 binding on NK cells>B cells>T cells. The pattern of AB79 binding is similar in blood cells from monkeys, but the level of AB79 binding/CD38 expression is lower.

The level of AB79 binding on human and monkey blood NK cells, T cells and B cells was compared by flow cytometric analysis. As shown in FIG. 5, monkey lymphocytes had CD38 expression levels, based on AB79 molecules of equivalent fluorescence (MOEF), that were slightly lower compared to their human counterparts but with a similar relationship between cell types, e.g., CD38 expression on NK cells >B Cells >T cells. These data support the use of this non-human primate species as a relevant model to help predict AB79's potential for PD activity in humans.

For the in depth quantitative analyses of the relationships between drug exposure (PK) and the extent and duration of cell depletion (PD) we compiled data sets from PK concentrations, NK cell, B cell and T cell counts of all 8 monkey studies including the placebo treated animals, where available (Table 2). The initial characterization of the data set showed that at baseline, T cells had a median value of 3,732 cells per μL (interquartile range (IQR): 2,881-5,176) and were the most abundant lymphocyte subtype as compared to B cells with 1,279 cells per μL (IQR: 860.8-1,890) and NK cells with 685 cells per μL (IQR: 482.8-970.1). Baseline CD38 expression on these cell populations was assessed in studies 1-4 (Table 2, n=67). 86.7% (SD 11.3) of NK cells expressed CD38 with smaller variability. In contrast, 58.7% (SD 27.0) of B cells and 34.5% (SD 24.5) of T cells expressed CD38 with larger variability.

Figure 6A:
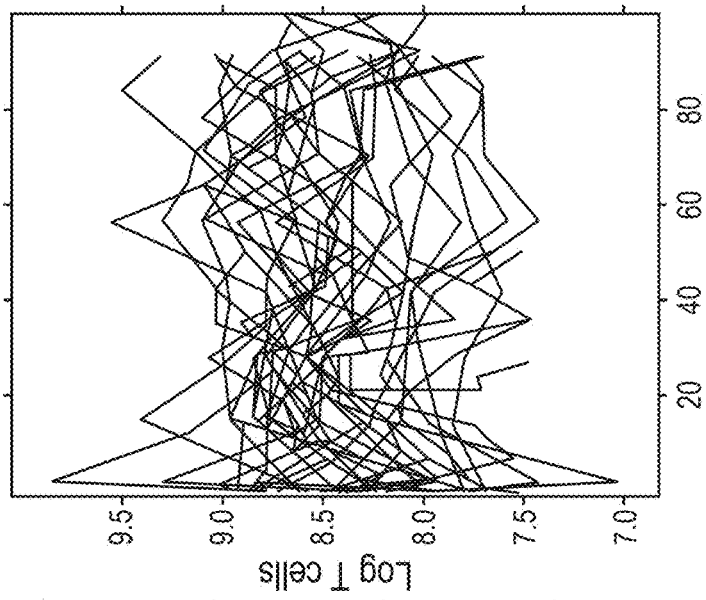
FIG. 6A—NK cells.
Figure 6B:
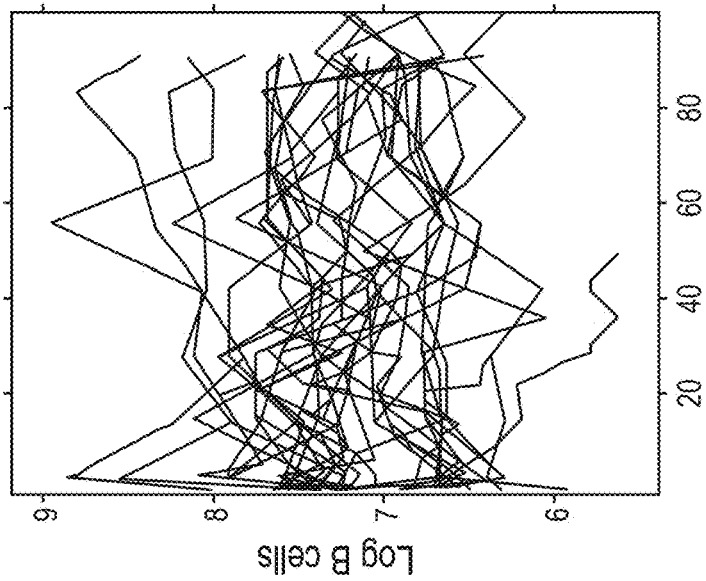
FIG. 6B—B cells.
Figure 6C:
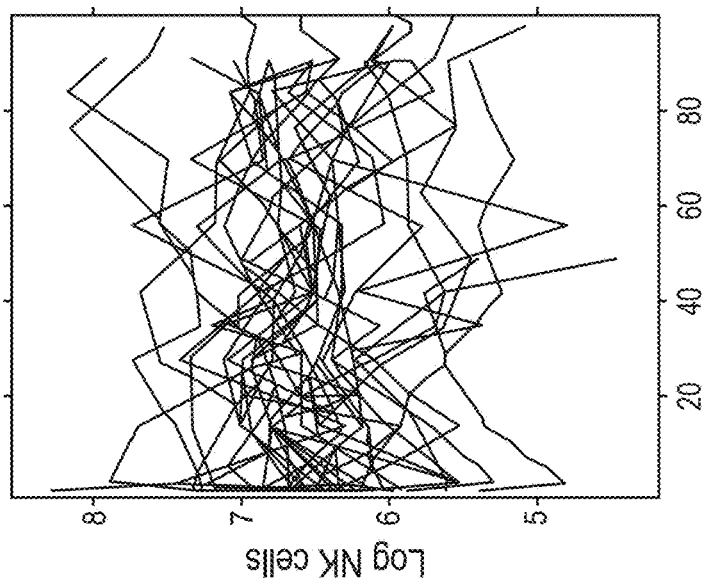
Figure 7A:
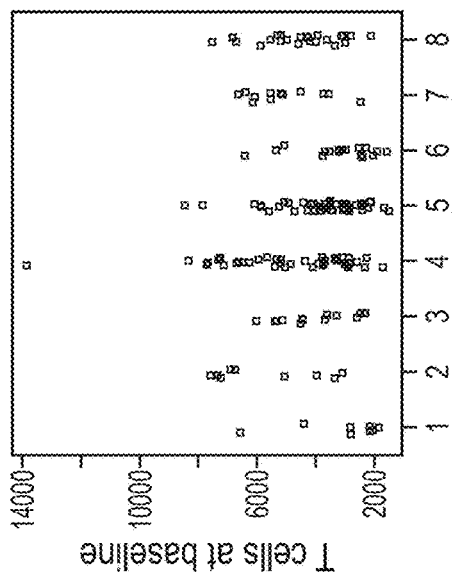
FIG. 7A—NK cells by study.
Figure 7B:
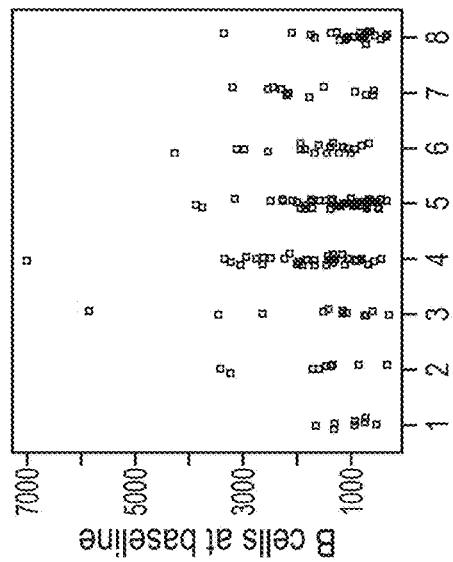
FIG. 7B—B cells by study.
Figure 7C:
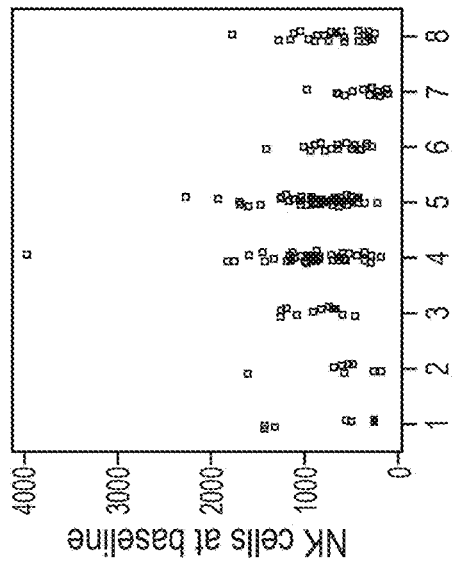
Figure 7D:
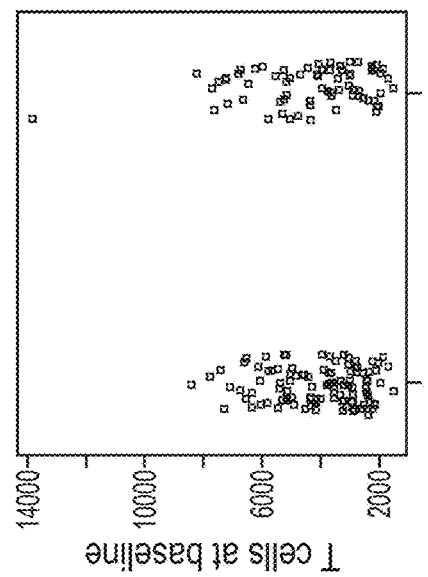
FIG. 7D—NK cells by male/female.
Figure 7E:
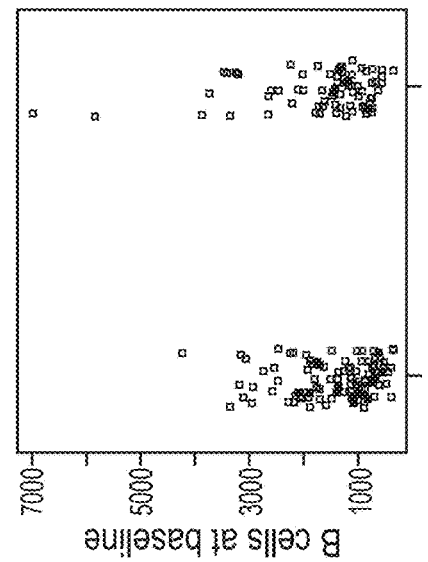
Figure 7F:
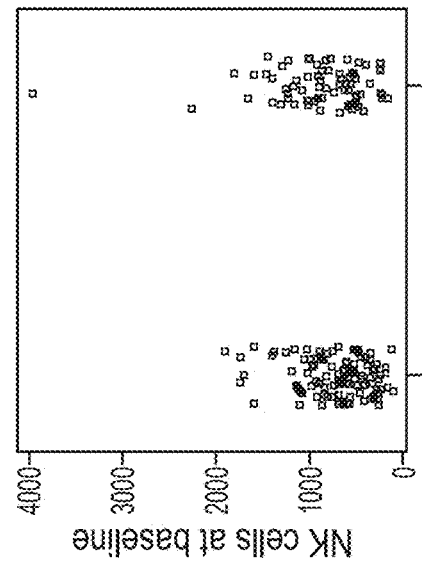

Data from the placebo treated animals showed that the average number of each of the cell types varied over time between individual animals more than one would expect from the variability within one individual (FIG. 6). For example, the average coefficient of variation of B cell counts of the individual placebo curves was 27% but the individual average B cell levels ranged from 436.6 to 4,389. In addition, there were also differences between average baseline lymphocyte numbers from male and female animals and from animals of different studies adding to the variability (FIG. 7). Based on these results each post-treatment cell count was calculated relative to its individual baseline value in percent, rather than the absolute cell numbers at each time point. For example, a value of 33% means that in the sample cell count was 1/3 of the baseline cell count. This provided standardized values that could be compared across the entire data set.

The rapid onset of depletion of AB79 binding cells suggests that the initial blood concentration drives the decrease in lymphocyte counts (FIG. 8). At IV doses of 0.3 mg/kg AB79, the median maximal effect on NK cells was depletion of 93.9% (i.e., 6.1% of baseline cell counts remaining). At 0.1 mg/kg, the peak depletion was 71% (29% of baseline remaining). At doses >0.3 mg/kg, NK cells were nearly completely depleted in the blood compartment (Nadir (range): 1.06% of baseline (0.17, 6.23); FIG. 8A). After a single dose of 0.3 mg/kg it took approximately 7 days for the NK cells to recover to an average of 50% of baseline, albeit the kinetics of the recovery were highly variable between individuals (FIGS. 8B and 8C). In concordance with these results, NK function was also tested in a subset of animals in study 7 (n=3/group; Table 2). This experiment showed a dose-dependent reduction with minimal changes in blood NK activity at 48 hours post-treatment in animals treated with 0.1 mg/kg AB79 (% lysis at 100:1 effector: target ratio ±SD; 44.5% ±23.6% vs. 41.4% ±25.8%) and almost complete loss of NK activity in animals treated with 1.0 mg/kg (% lysis at 100:1 effector: target ratio ±SD; 37.4% ±10.3% vs. 6.8% ±12.5%). NK cell function showed recovery at 57 days, the next time point measured (% lysis at 100:1 effector: target ratio ±SD; 16.0%±11.9%).

Figures 8D, 8E, 8F:
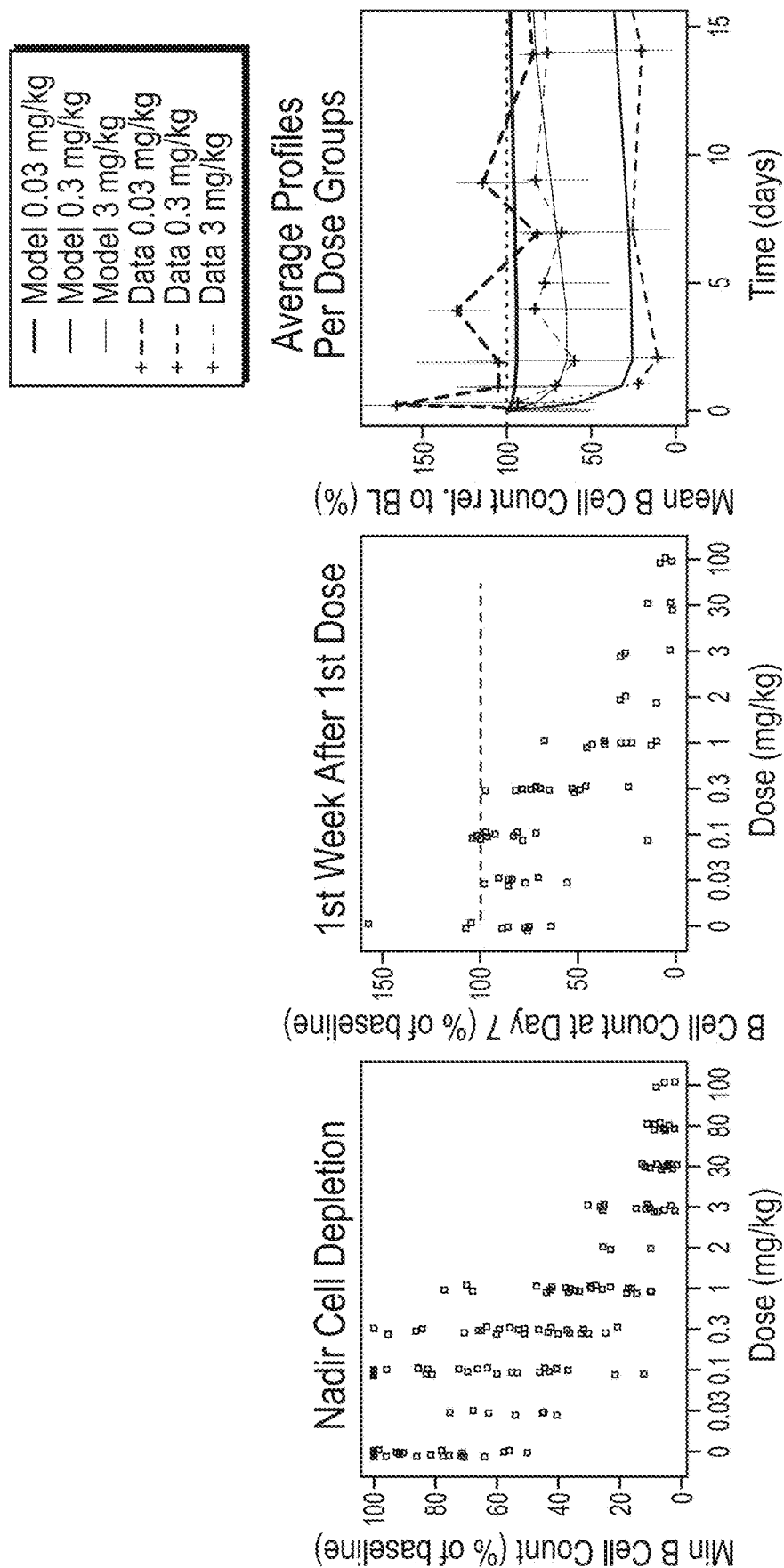
Figures 8G, 8H, 8I:
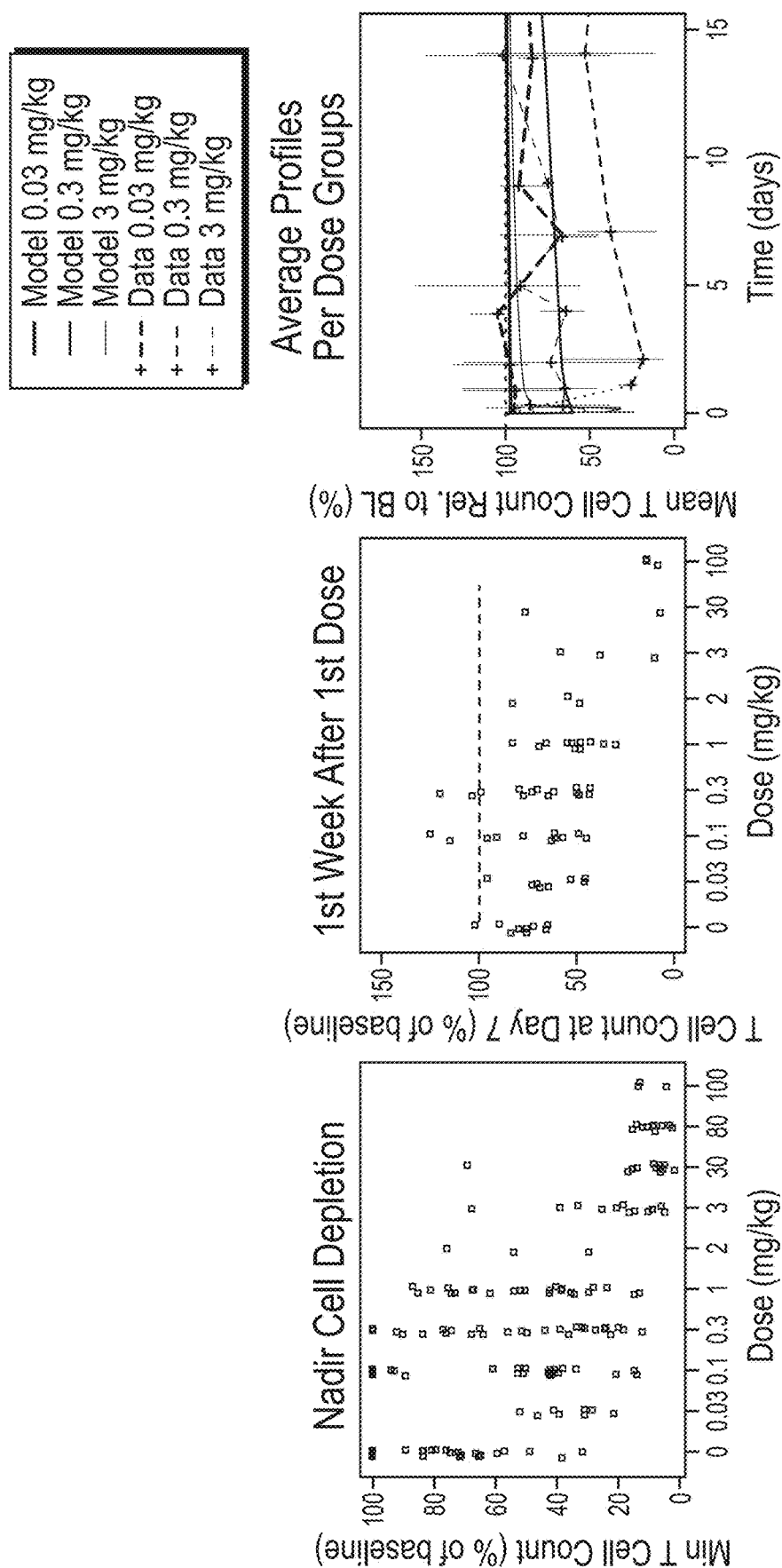

B cells and T cells were depleted to a lesser extent as compared to NK cells, which is consistent with their lower CD38 expression levels (FIG. 5). At 0.3 mg/kg IV AB79, for example, B cells had a median maximal level of depletion to 45% of baseline, and T cells were depleted to 43% of baseline (FIGS. 8D and 8G). At this dose level, a 50% reduction from baseline of B cell counts was not achieved in all animals. Only at the highest doses of ≥30 mg/kg were the B cells almost completely depleted (FIG. 8D). T cells were depleted to an extent similar to B cells but the recovery was faster (FIGS. 8G-8I).

In the two studies 7 and 8, the IV and SC dosing (FIGS. 8C, 8F, and 8I) was compared. There were no obvious differences in cell depletion between the routes of administration. At the lower doses (study 8) a sustained (>24 hours) cell depletion of 50% below baseline values was only seen in the NK cell population and not with T and B cells; although all cells showed specific cell depletion at early time points. The timing of the onset of NK cell depletion appeared similar between dose groups regardless of the route of administration and the duration of depletion was dose-dependent. Cell recovery in all test groups was seen by Day 57.

PK-PD models

Separate PK-PD models were developed to describe the effects of AB79 exposure on NK, B, and T cells. During PK-PD modeling the PK parameters were kept fixed to the estimates of the final PK model and a variety of PD models were tried. The NK cell population in the peripheral blood was adequately described with a turnover model and the depleting drug effect was linked via the PK concentration with an Emax type model to the rate of depletion. In this model the EMAX represents the maximum rate of additional NK cell depletion and the C50 the concentration at which the rate of additional NK cell depletion is half-maximal. The structural PK-PD model for NK cells was of the following form:

$$\frac{dNK}{dt} = K_{IN} - K_{OUT} \cdot NK - NK \cdot \frac{EMAX \cdot c}{C50 + c}$$

In the formula, NK represents the actual NK cell count, $K_{IN}$ the production rate and $K_{OUT}$ the elimination rate when no drug is present. Note that with the given baseline measurement BL $K_{OUT}$ is defined by the equation $K_{OUT}=K_{IN}/BL$. c represents the AB79 concentration in the central compartment. When all parameters were estimated at once the software program did not produce stable results. The individual estimates of KIN, EMAX and C50 were highly correlated. Moreover, due to limited differentiation between the maximal effects of the different doses (see previous section) and the large interindividual variability, accurate estimates of all parameters could not be expected. In a series of estimations, one or two of the three parameters KIN, EMAX and C50 were fixed to different values and estimated the others. A stable run and reasonable goodness of fit with a fixed KIN of 10,000 and an EMAX of 322 was achieved. The typical C50 estimate was 29.0 µg/mL (Table 5). In addition, the sensitivity of the selected KIN and EMAX values was tested by choosing different combinations of higher and lower values. The between subject variability was large with 113% for the NK production rate $K_{IN}$ and with 149% for the C50, which is in accordance with the large individual differences at baseline and between treated animals. The model was evaluated based on residual errors, OFV, standard errors, GOF plots and individual curve fits (Table 5, FIG. 9).

TABLE 5

PD Modeling Results, Parameter Estimates And Standard Errors In Percent (% SEM)

| Parameter | Final Parameter Estimate | | Interindividual Variability/ Residual Variability | |
|---|---|---|---|---|
| | Typical Value | % SEM | Magnitude | % SEM |
| NK Cells | | | | |
| KIN (count/day) | 10000 | FIXED | 113% CV | 19.2 |
| C50 (µg/mL) | 29.0 | 18.8 | 149% CV | 25.1 |
| EMAX | 322 | FIXED | NE | — |
| Baseline (NK cells)* | NE | — | 28.3% CV | 20.8 |
| NK cells residual | 0.291 | 2.42 | 53.9% CV | — |
| B Cells | | | | |
| MTT (day) | 8.48 | 15.4 | 135% CV | 17.4 |
| C50 (µg/mL) | 19.5 | 7.58 | NE | — |
| EMAX | 2.37 | FIXED | NE | — |
| Baseline (B cells)* | NE | — | 24.1% CV | 10.7 |
| B cells residual | 0.136 | 2.20 | 36.9% CV | — |
| T Cells | | | | |
| C50 (µg/mL) | 11.86 | 7.267 | NE | — |
| EMAX | 0.4656 | 6.578 | 69.46% CV | 29.50 |
| Baseline (T cells)* | NE | — | 29.08% CV | 15.50 |
| T cells residual | 0.1343 | 2.406 | 36.65% CV | — |

*For each individual animal the typical baseline value was calculated as average of all predose measurements;
NE: Not Estimated The transit compartment model was superior to direct response or turnover models to describe AB79 induced B cell depletion. Four transit compartments turned out to be adequate and the drug effect was described with an Emax type model on the depletion rate. Similar to the NK cell depletion model, the EMAX represents the maximum rate and the C50 the concentration at which the rate is half-maximal. Thus the structural PK-PD model for the B cells is given by the following five equations:

$$\frac{dTR_1}{dt} = K_{PROL} - K_{TR} \cdot TR_1$$

$$\frac{dTR_i}{dt} = K_{TR} \cdot TR_{i-1} - K_{TR} \cdot TR_i, \text{ for } i = 2, 3, 4$$

$$\frac{dB}{dt} = K_{TR} \cdot TR_4 - K_{CIRC} \cdot B - B \cdot \frac{EMAX \cdot c}{C50 + c}$$

$TR_i$(1i1-4) represent the four transit compartments. $K_{TR}$, $K_{PROL}$ and $K_{CIRC}$ are defined by the following equations $K_{TR}=K_{PROL}=K_{CIRC}=4/MTT$, where MTT is the mean transit time (Friberg et al. (2002) J. Clin. Oncol. 20: 4713-4721). B represents the B cell count in the blood and c the AB79 concentration in the central compartment.

With a fixed EMAX of 2.37 the typical C50 was 19.5 µg/mL and the typical mean transit time (MTT) was 8.48 days (Table 5). The delay of the maximal effect relative to the maximal AB79 concentration was well captured. The model indicates that AB79 primarily affects circulating B cells. No additional effects and no feedback loop on progenitor cells were necessary to describe the available monkey B cell data. Between-subject variability on MTT of 135% and on the baseline B cell levels (BASE) of 24.1% indicates large individual differences between animals.

The drug induced depletion of T cells with a rapid recovery was adequately described with a direct response model: $T(c) \; BL_T*(1-EMAX*c/(c+C50))$, where T represents the actual T cell count, $BL_T$ the T cell count at baseline and c the AB79 concentration in the central compartment. The typical C50 was estimated to be 11.86 µg/mL and the typical EMAX was 0.47, indicating that in this case only about half of the T cells can be depleted by AB79 (Table 5). Note however, that the between subject variability on EMAX was nearly 70%. In this model, different from the NK and B cell depletion models, the C50 represents the concentration at which the depletion of T cells was half-maximal.

Figure 9B:
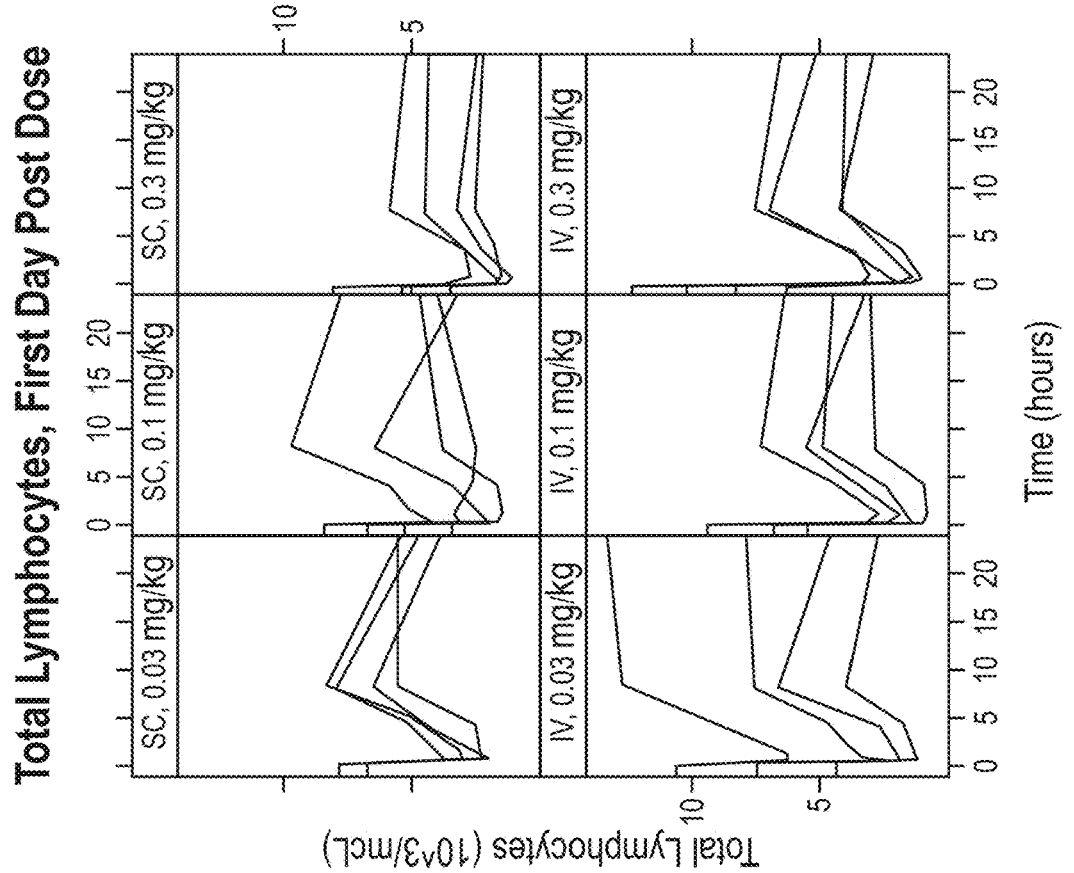
FIG. 9B—AB79 via SC.
Figure 9A:
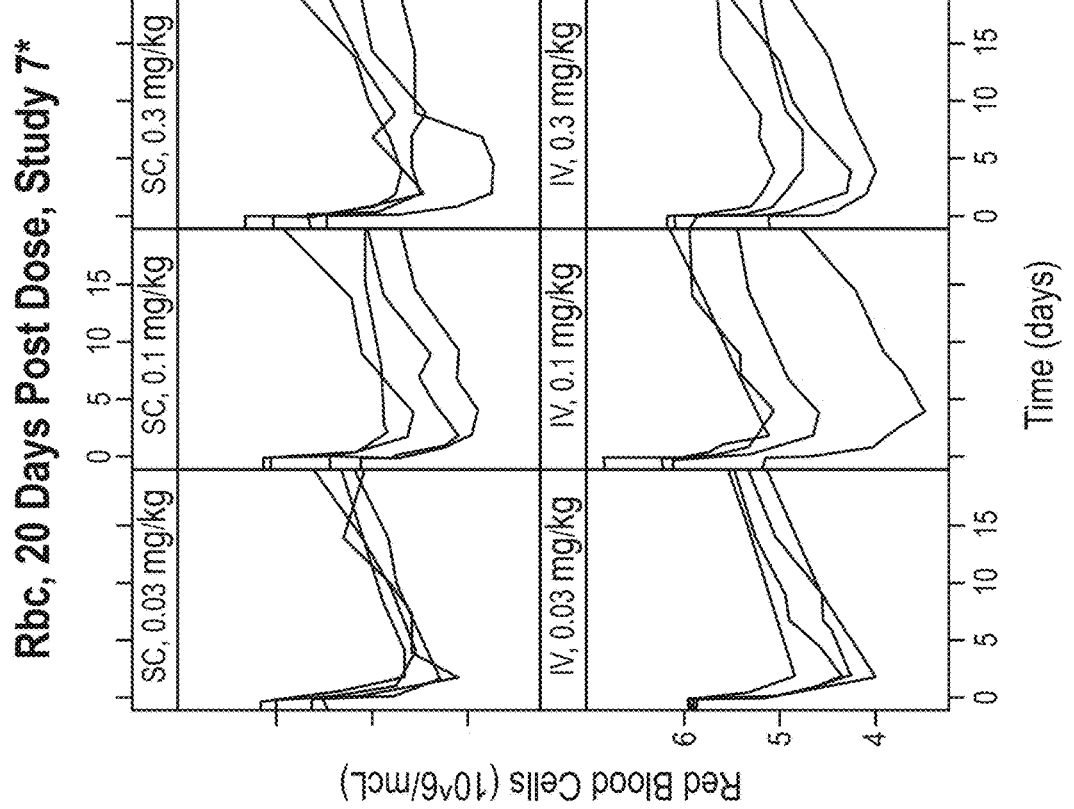
FIG. 9A—AB79 via IV.

As for the NK cells, model evaluation of the final PK-PD models for B and T cells based on residual errors, OFV, standard errors, GOF plots and individual curve fits corroborated that they adequately described the available monkey data (Table 5, FIG. 9).

Simulation Of Human PK And Cell Depletion

The monkey PK and PK-PD models were used as starting point for the model-based simulation of human PK and cell count data to support the design and to justify the selected doses for the first in human (FIH) clinical trial in healthy volunteers. To this end, it was assumed that the model structures including TMDD derived from the monkey data also describe the main features of the human PK and the ensuing lymphocyte depletion. To obtain predictions for the human PK parameters we scaled the estimates of the following monkey PK parameters: central and peripheral volume of distribution ($V_C$, $V_P$), and clearance (CL) and intercompartmental clearance (Q) with a straight-forward approach for monoclonal antibodies (Han and Zhou (2011) Ther. Deliv. 2: 359-368). AB79 is a fully human monoclonal antibody and, therefore, we expect less immunogenicity in humans than that observed in monkeys. Consequently, for modeling and simulation we excluded ADA-positive samples from the data set.

Figure 10:
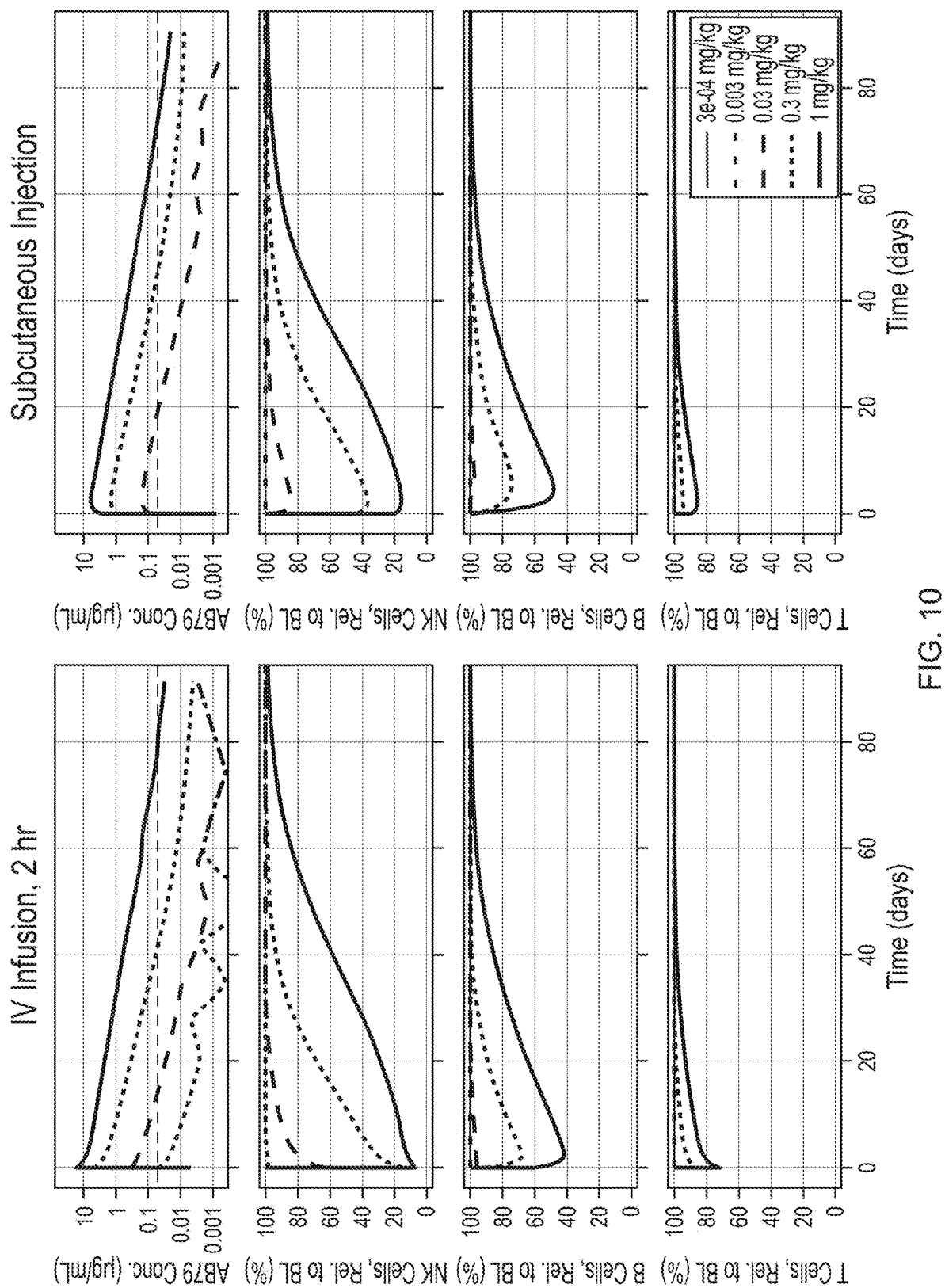
FIG. 10 shows simulated human PK and NK cell, B cell and T cell depletion profiles of AB79. Based on the scaled monkey PK and PK-PD models, 5 single IV and SC dose PK and cell depletion profiles were simulated (from 0.0003 to 1 mg/kg). The left plots show the data after IV administration and the right plots show the data after SC administration. The first row of plots displays the PK profiles. The lower limit of quantification (LLOQ) of 0.05 μg/mL is indicated by a horizontal dashed line. The PK of the lowest dose was completely superimposed by noise and only at doses of 0.03 mg/kg did the PK reach levels above LLOQ.

Using the scaled model, exposure was simulated and NK, B, and T cell depletion profiles for single doses via a 2 hours infusion (IV) or via subcutaneous injection (SC) from 0.0003 to 1.0 mg/kg as planned for the FIH study (FIG. 10). According to the simulations, after an IV dose of 0.0003 mg/kg any observable drug induced effects on lymphocyte counts and not even measurable PK concentrations above LLOQ would not be expected. Due to the variability and due to the limited size of the dose groups it was assumed that the minimal detectable drug effect on NK cell counts would be a reduction of at least 10%. At doses of 0.01 mg/kg IV and 0.03 mg/kg SC, it was predicted that NK cells were to be depleted to less than remaining 90% of baseline.

At an IV dose of 0.3 mg/kg we predicted NK cell depletion to remaining 17% of baseline within 3 hours after the end of infusion and recovery to more than 50% after 11 days (FIG. 10). At the same dose the model predicts that B cells are maximally depleted to 67% of baseline after 2.5 days and T cells are immediately depleted to 86% of baseline. For the subcutaneous administration of the same dose of 0.3 mg/kg, the model predicted that it leads to less and later maximal depletion (nadirs relative to baseline: NK cells 37%, B cells 74%, T cells 94%).

These in vitro and in vivo preclinical studies demonstrate that the monkey is an appropriate animal model to study the pharmacology of AB79. Densely sampled PK and cell count data of NK, B, and T lymphocytes from eight monkey studies with diverse doses and dosing regimen provide a rich data source for a comprehensive and quantitative understanding of the relationships between AB79 dose, exposure, and cell depletion. The generated population PK and PK-PD models adequately describe the observed data and provide a powerful tool to predict exposure and lymphocyte depletion not only for future studies in monkey but also for clinical trials in human subjects.

Figure 11:
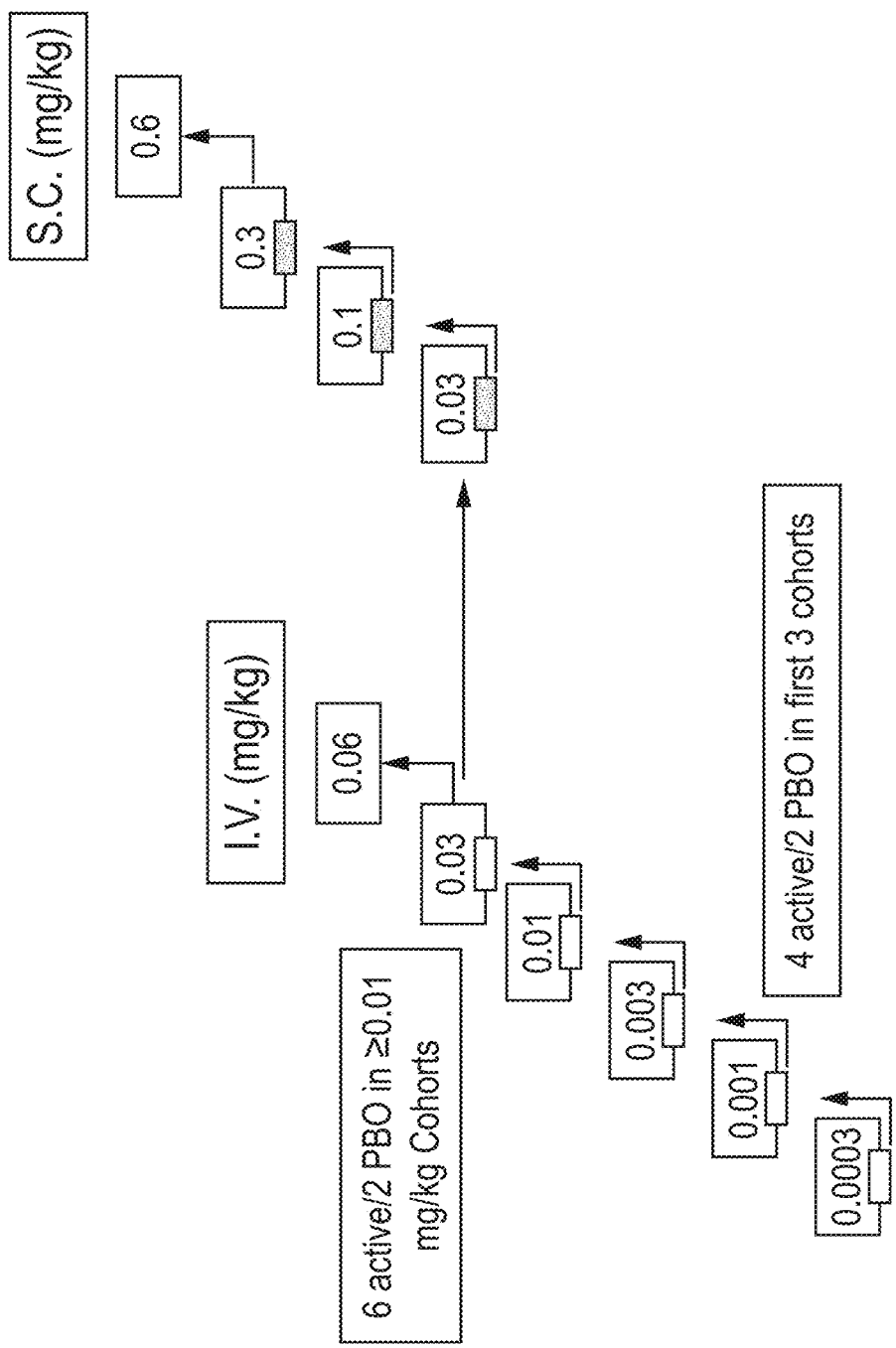
FIG. 11 shows the plan for an AB79 single rising dose toxicity study in healthy volunteers. A total of 6 IV and 4 SC cohorts in 74 subjects were randomized and received a single dose of AB79. Extensive blinded safety, PK, and PD data were reviewed after each cohort before dose escalation. Stopping criteria included depletion of target cells to avoid potential immunosuppression of healthy volunteers. Each subject was followed up for 92 days after dosing.

The first in human (FIH) single rising dose trial in healthy volunteers has been conducted (www.clinicaltrials.gov: NCT02219256) (FIG. 11). The intended pharmacological effect of AB79 is the depletion of activated lymphocytes. A profound and lasting depletion of lymphocytes (enhanced pharmacology), however, can lead to impairments of the immune system, which would not be tolerable for patients or healthy study participants. Therefore, a safe I.V. starting dose of 0.0003 mg/kg was chosen for the FIH trial.

The monkey data suggested that NK cell depletion was determined to be the most sensitive biological effect. The PK-NK simulation results helped to determine the minimal dose level of 0.01 mg/kg IV at which the most sensitive pharmacological effect (NK cell depletion) would be expected to be detectable in humans. The emerging data of the FIH trial revealed that the overall pattern of the dose-dependent and cell type specific depleting effects of AB79 are in accordance with the model-based predictions (manuscript in preparation). AB79 appears to be even more efficient than predicted. For example, at an IV dose of 0.03 mg/kg, NK cells in human subjects were depleted to remaining less than 10% of baseline. The median nadir (lowest depletion point) in monkeys at this dose was 20.0% (FIG. 8).

Three cytolytic anti-CD38 monoclonal antibodies (daratumumab, SAR650984 and MOR202) are in clinical development for multiple myeloma (van de Donk et al. (2016) Immunol. Rev. 270: 95-112). Daratumumab (Darzalex™, given as an intravenous infusion) was recently approved for multiple myeloma in the United States and for non-Hodgkin lymphoma in Europe. Unlike AB79, daratumumab does not cross react with monkey CD38. Therefore, a comparison of our results with AB79 in cynomolgus monkey with daratumumab was not possible. Moreover, multiple myeloma patients have high levels of CD38 positive malignant cells, which could require higher effective antibody concentrations for this cancer indication (de Weers et al. (2011) J. Immunol. 186:1840-1848).

It is however remarkable that daratumumab is approved at a weekly IV dose of 16 mg/kg in multiple myeloma, even though AB79 achieved complete depletion of peripheral NK cells at about. 1 mg/kg and of B cells at about 3 mg/kg (FIG. 8).

Figure 12A:
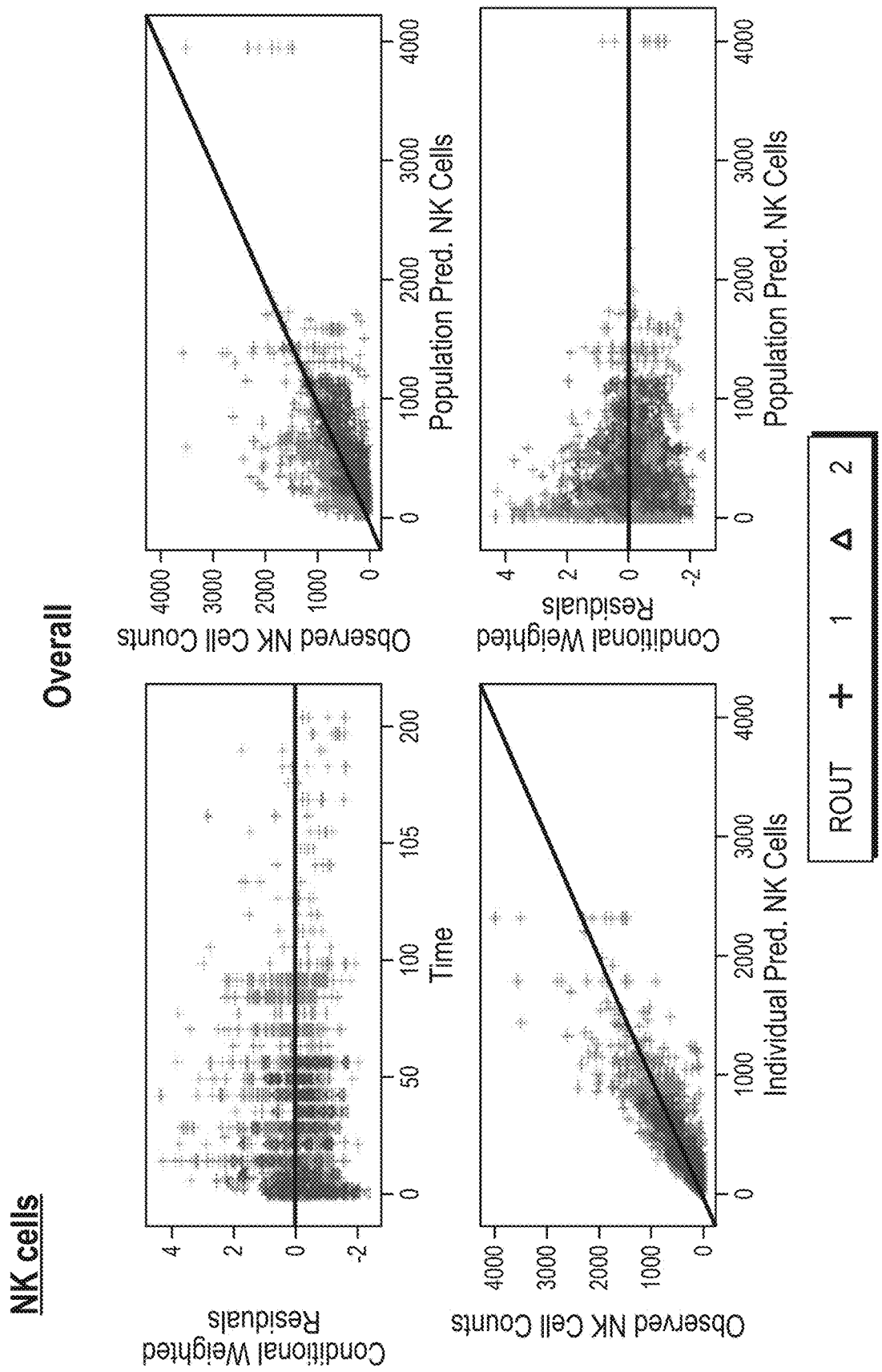
FIG. 12 shows GOF plots for PK-PD models, stratified on route of administration (IV—red; SC—blue) with FIG. 12A—NK cells.
FIG. 12B—B cells.
FIG. 12C—T cells.
Figure 12B:
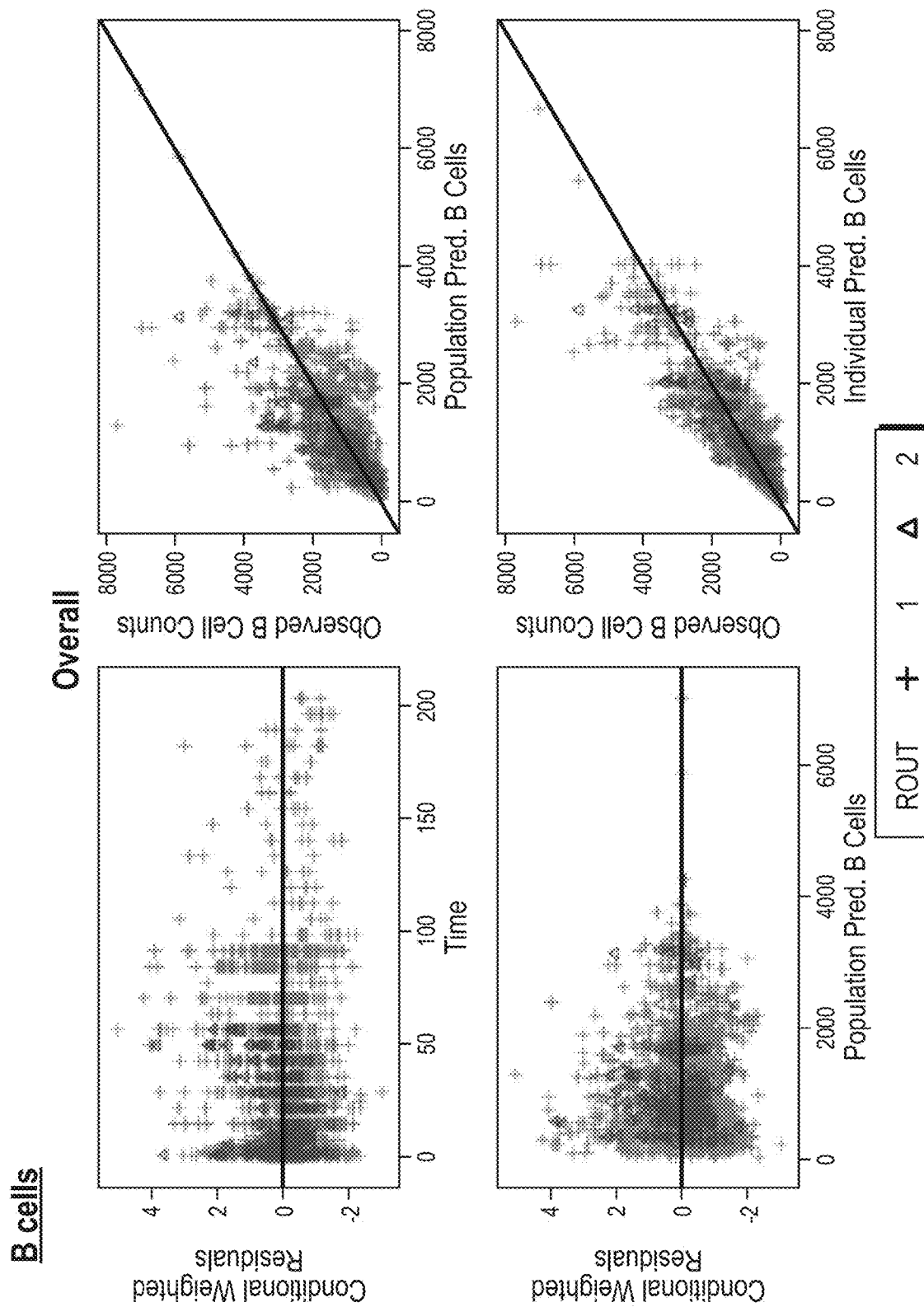
Figure 12C:
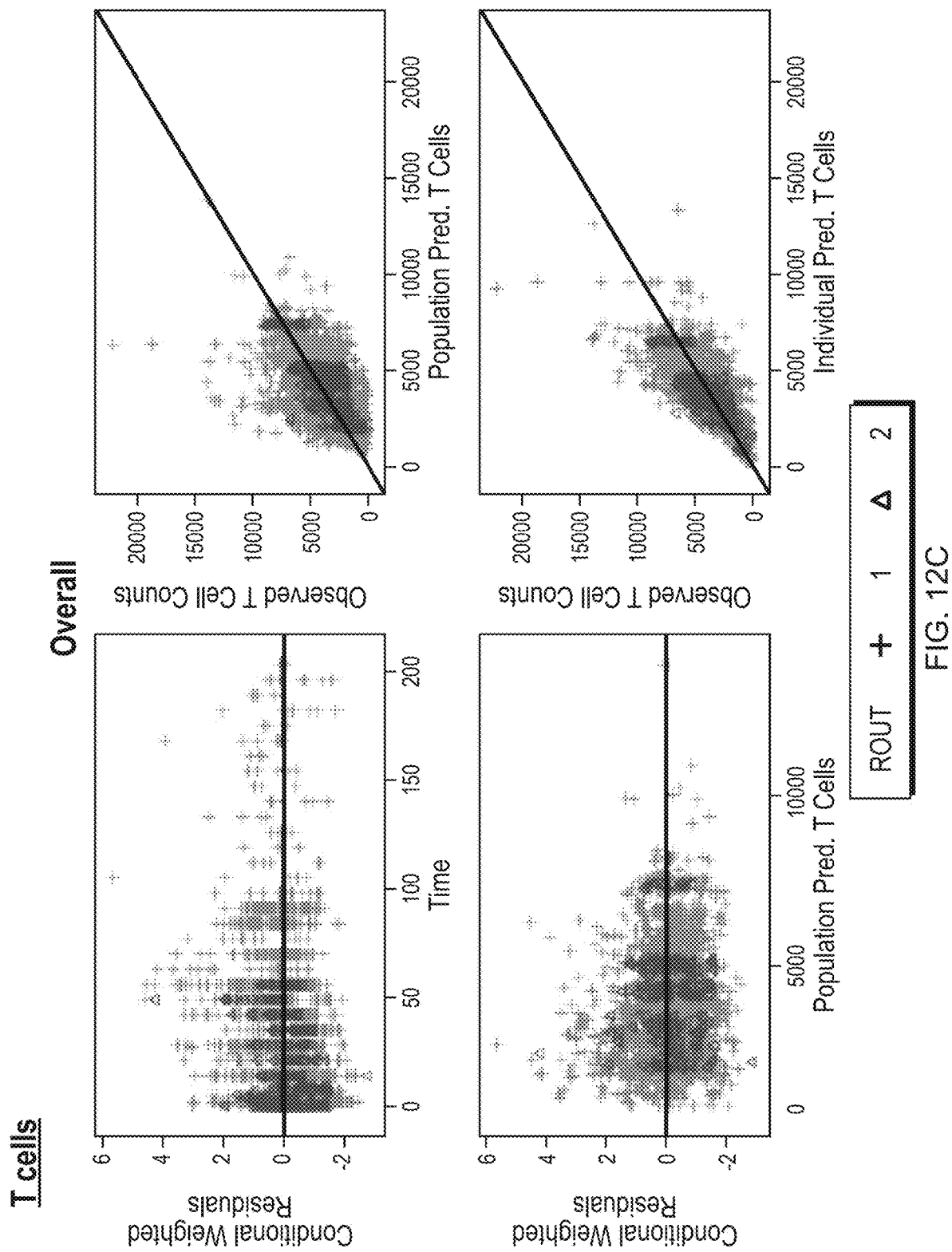

In spite of the rich database from 8 monkey studies, a number of limitations were recognized. AB79 effectively depletes NK cells even at the lowest studied dose of 0.03 mg/kg. At such low doses the PK quickly drops below the quantification limit of the bioanalytical assay, which prevented resolving the exposure-effect relationship at lower doses. Moreover, during preclinical development it was recognized that maximal cell depletion occurs shortly after the maximal drug concentration but the resolution of the early phase of depletion is technically limited by the overall sample number and potentially by non-specific cell depletion due to repeated blood collections (blood draw effect). The blood draw effect was observed as a transient pancytopenia characterized by depletion of cell types that do not bind AB79 (e.g., RBCs) and was not dose-dependent suggesting it was due to loss of blood volume as a result of multiple blood draws rather than any specific effects of AB79 (FIG. 12). Consequently, the power to accurately estimate the model parameters especially for NK cell depletion was limited and the typical values of KIN and EMAX required fixing to achieve stable and adequate estimation results.

The effect of AB79 on tissue plasma cells or plasmablasts could not be measured. However, like plasma cells and plasmablasts, NK cells have high levels of CD38 on their surface and cell depletion efficiency of a specific lymphocyte subset depended, at least in part, on the expression levels of CD38. Therefore, the cytolytic effect of AB79 on plasmablasts and plasma cells may be comparable to the effect on NK cells. At present, the information about long term effects of AB79 treatment in monkeys is limited. Only a small subset of animals in the 13-weeks toxicology studies was investigated in a recovery group over a longer period of time and most of the animals in all dose groups developed ADA (FIG. 3). Moreover, the baseline values and depletion profiles of the different lymphocyte subsets were highly variable between individuals. Therefore, the long term effects of AB79 cannot be investigated in monkey and will have to be studied in humans.

With the emerging human data it will be interesting to compare human and monkey PK and PD data in detail. The construction of a PK model based on human data and a comparison to the monkey model will allow refining the TMDD model of AB79. Data generated in patient studies will provide insights regarding how AB79 mediated depletion of B lineage cells compares between RA and SLE patients and those of multiple myeloma patients and healthy subjects. The investigation of subject or disease related factors that may influence cell depletion efficiency in addition to CD38 expression levels is also important and could lead to a personalization of the treatment. In addition, a thorough head-to-head comparison of AB79 with daratumumab and/or the other CD38 antibodies in vitro and in vivo will reveal valuable information about the pharmacology of anti-CD38 antibodies and their optimal application.

The rich pharmacological data and the PK and PK-PD models enabled characterization of exposure-effect relationships in cynomolgus monkeys. The model-based analyses of NK, B, and T cells supported and quantified the finding that each of the blood lymphocyte subsets are depleted by the antibody at different rates and require different time spans to replete the blood compartment. The models proved to be excellent means for simulations of PK and PD data under different dosing scenarios in preparation of clinical trials.

Example 2: CD38+Cell Depletion By AB79

Table 6 shows that AB79 mediates cell depletion by antibody dependent cellular cytotoxicity (ADCC) and complement dependent cytotoxicity (CDC). Cell lines with increased CD38 expression were more susceptible to ADCC. No ADCC was seen in a human lymphoblast cell line that did not express CD38 (MV-4-11) or with a Chinese hamster ovary cell line transfected with CD157, a molecule closely related to CD38 (data not shown). Unlike other B cell-selective therapies which target CD20 and do not directly deplete plasmablasts, which are $CD20^{low/negative}$, CD38 is expressed at high levels on plasmablasts and plasma cells making these cells a direct target of AB79. In vitro studies with human blood cells and cell lines showed that binding of AB79 to CD38 did not result in PBMC cytokine activation demonstrating that AB79 is not an agonist, as discussed below. Rather, AB79 mediated cell depletion of human B lineage cell lines by ADCC and CDC and in most cases cell lines with increased CD38 expression were more susceptible to cell lysis.

TABLE 6

AB79 Mediates Cell Depletion of Human B Cells Lines by ADCC and CDC.

| Cell Line | CD38 (Receptor #) | ADCC $EC_{50}$ ± SD (nM) | CDC $EC_{50}$ ± SD (nM) |
|---|---|---|---|
| Molp8 | 623,891 | 0.05 ± 0.04 n = 9 | 1.1 ± 1.0 n = 7 |
| Daudi | 417,874 | 0.03 ± 0.04 n = 4 | 1.6 ± 0.4 n = 3 |
| NCI-H929 | 82,341 | 0.14 ± 0.11 n = 6 | nd |
| RPMI-8226 | 98,080 | 0.46 ± 0.53 n = 8 | nd |
| OPM2 | 54,556 | 0.65 ± 0.64 n = 4 | nd |

$EC_{50}$, 50% effective concentration;
nd, not done;
SD, standard deviation.

Figure 13C:
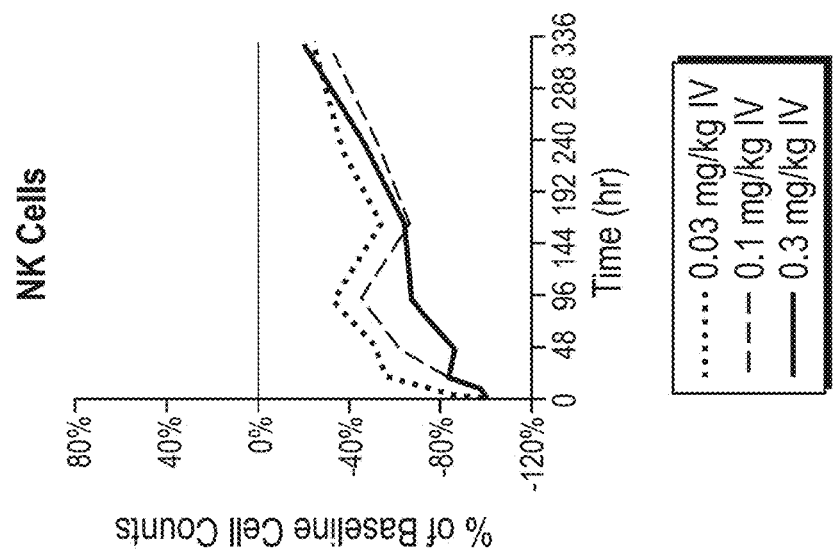
FIG. 13C—NK cells.
Figure 13B:
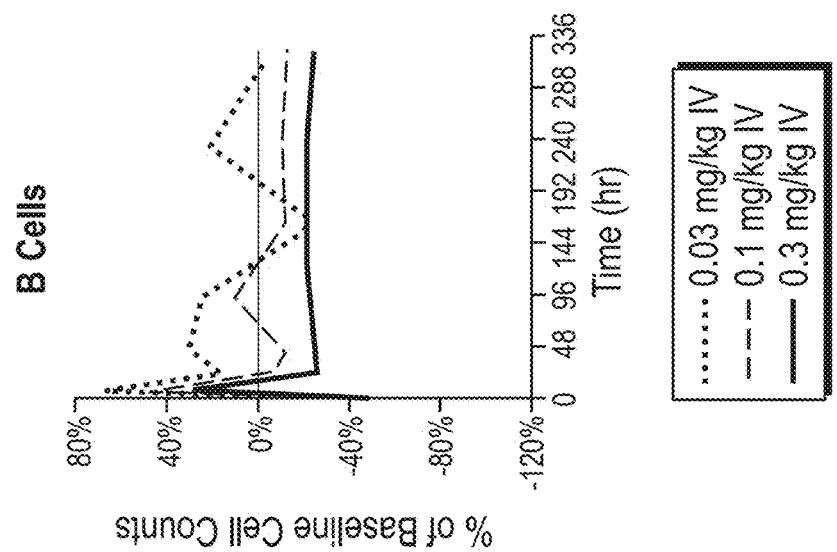
FIG. 13B—B cells.
Figure 13A:
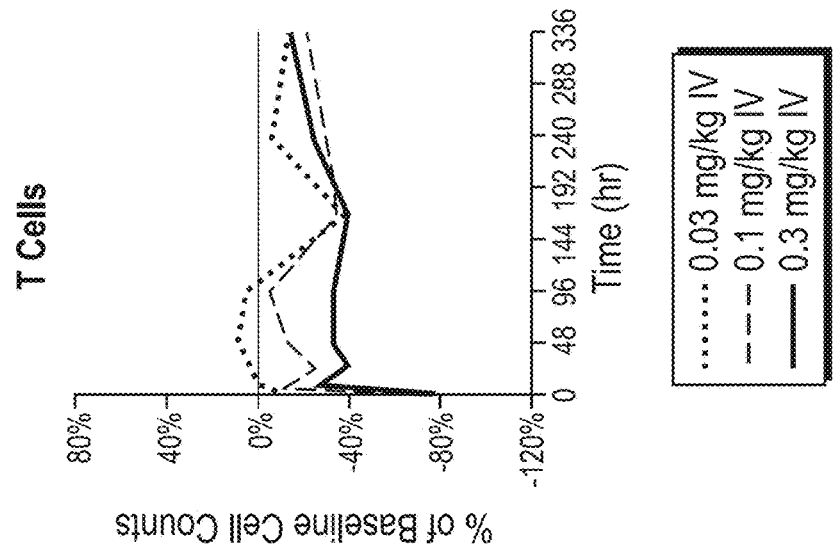
Figure 14:
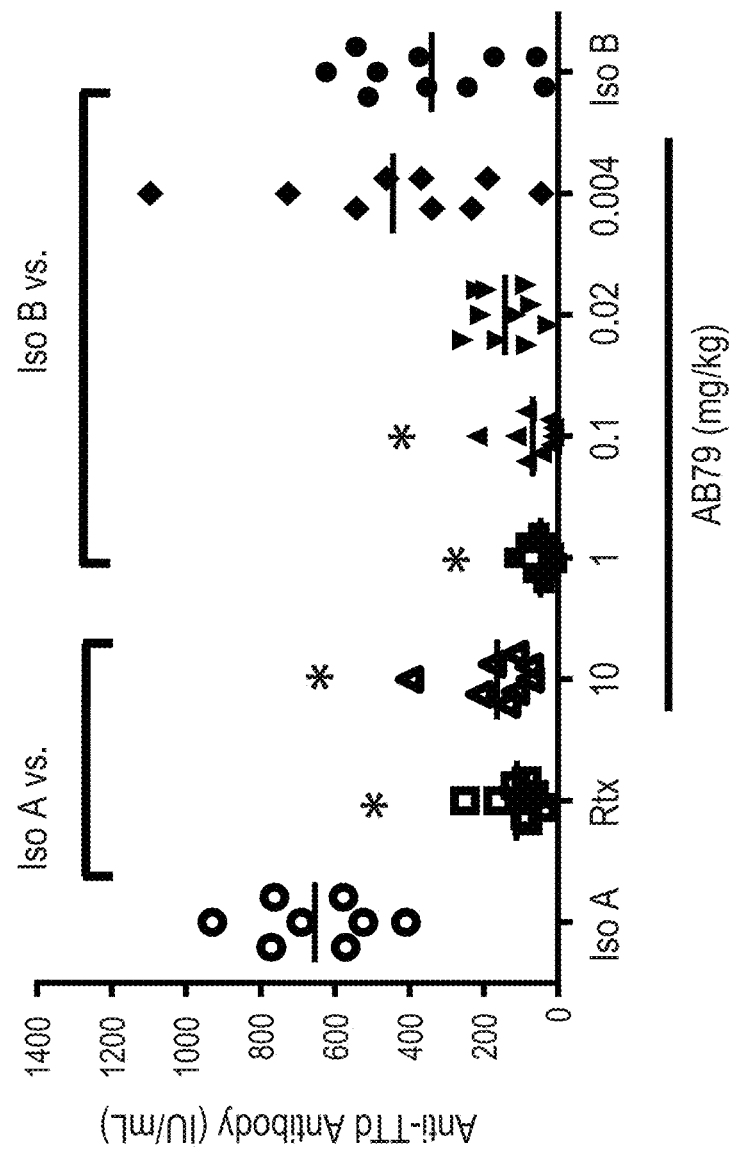
FIG. 14 shows that human tetanus toxoid (TTd) recall responses are reduced by AB79 treatment. CB17/SCID mice were treated with anti-asialo GM1 to eliminate NK cells and then given $25 \times 10^6$ human peripheral blood lymphocytes. After 7-10 days, serum samples were collected for evaluation of human Ig and the level of Ig was the basis for randomization. Mice were given TTd to induce the recall response and treated with the indicated antibodies twice/week for 10 days. Three days after the last treatment serum was collected and analyzed for anti-TTd antibodies. AB79 dose-dependently suppressed the TTd recall response, to a similar extent as Rituxan (Rtx) (Isotype (Iso), Rtx and AB79 all at 10 mg/kg).

This is consistent with findings in healthy cynomolgus monkeys where the efficiency of depletion correlated with level of CD38 expression and AB79 dose level. NK cells, which express high levels of CD38, were depleted to a greater extent than CD20+ B cells and CD3+ T cells, which express less CD38 (FIG. 13). In vivo, AB79 potently suppressed the human B cell recall responses to antigen in a mouse adoptive transfer model (FIG. 14). Together these data support the further investigation of AB79 in autoimmune diseases.

Human PBMCs were treated with AB79 under multiple conditions and inflammatory cytokine release measured. The cynomolgus monkey was used to show the relationship of cell type-specific depletion and AB79 dose because AB79 cross reacts with monkey CD38, which shares 91% protein identity to the human protein. A second animal model, mice adoptively transferred human PBMCs, was used to determine if AB79 could target human antibody producing cells. AB79 Binds CD38 and Mediates ADCC and CDC Receptor number was determined with the FIKIT (DAKO, cat #K0078) using mouse anti-human CD38 antibody (clone HIT2) and was calculated by converting mean fluorescence intensity (MFI) of the stained samples to a calibration curve generated from the MFI of 5 populations of beads bound with a defined number of antibody molecules. Absolute receptor # was calculated by subtracting isotype control (mouse IgG1) MFI from anti-CD38 antibody MFI.

CDC was evaluated by plating cell lines at 10,000 cells/well and adding AB79, control IgG or media. A 5-point dose-response curve (0.001-10 mg/ml) was typically performed. Rabbit complement (2-15 ul; #CL 3441 CedarLane Laboratories), was added to each well except control wells. CytoTox-Glo reagent (Promega, G7571/G7573) was used to detect cytotoxicity by luminescence. Tested groups: cells alone; cells+complement; cells+IgG control+complement; cells+AB79+ complement. % CDC equation: % CDC=100−((RLU (test)/RLU (complement alone))×100).

ADCC was tested by plating 5000 target cells/well (T, cell lines) with 50 ml of AB79, control IgG, Triton X-100 (1%; Sigma Chemical) or media alone and 50 ml of human effector (E) PBMCs at a ratio of between 1:25 to 1:50 T:E cells. A 9-point antibody dose-response curve (0.000001-

100 nM) was typically performed. Experimental lysis=PBMCs+cell line+antibody. Spontaneous lysis=PBMCs+cell line with no antibody. Maximal lysis=cell line+Triton X-100. Cytotoxicity assessed using the CytoTox-Glo™ Cytotoxicity Luminescence assay (Promega).

AB79 Does Not Have Agonist Activity

Figure 15:
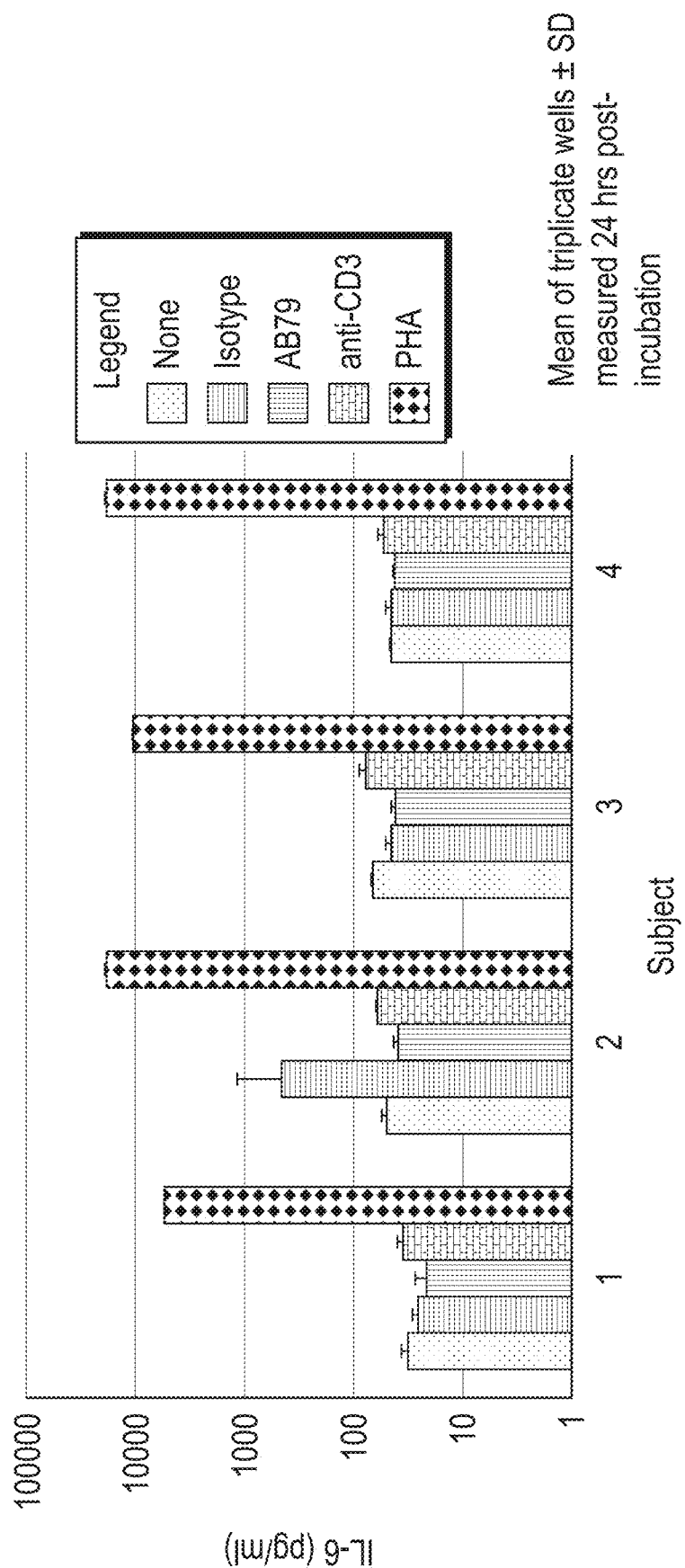
FIG. 15 shows that AB79 does not induce cytokine induction. AB79 did not increase IL-6 levels in PBMCs collected from 4 different subjects after 24-hour incubation as compared to IgG1 isotype control. Positive controls PHA and anti-CD3 increased cytokine levels in all subjects demonstrating that cells had the capacity to make IL-6. Similar results were seen with PBMCs stimulated for 48 hours when IL-2, IL-4, IL-10, GM-CSF, IFNγ and TNFα were tested (data not shown). The bars are as follows for each subject: (i) No Ab; (ii) Isotype control; (iii) AB79; (iv) anti-CD3; (v) PHA. Each value is a mean of triplicate wells ±SD measured 24 hours post-incubation.

The capacity of AB79 treatment to induce cytokine production in human PBMCs was compared to negative IgG1 isotype control and positive controls, PHA, anti-CD3 (clone OKT3) or anti-CD52 (Campath) antibodies (FIGS. 15 and 16).

Soluble AB79 did not increase IL-6 levels (mean±SD) in PBMCs collected from 4 different subjects after a 24 hour incubation as compared to IgG1 isotype control. PHA increased cytokine levels in all subjects demonstrating that the cells had the capacity to make IL-6 (FIG. 15). Similar results were seen with PBMCs stimulated for 48 hours and when IL-2, IL-4, IL-10, GM-CSF, IFNγ and TNFα were tested (data not shown).

Figure 16A:
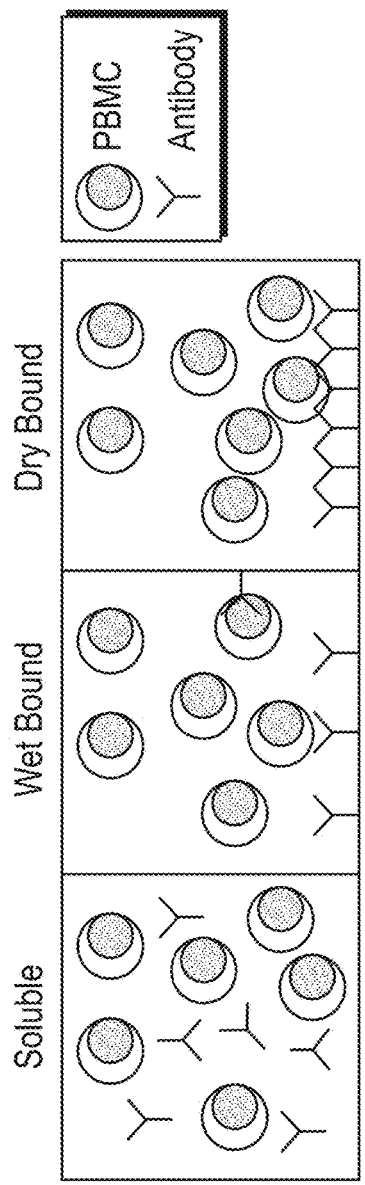
FIG. 16A shows the set up of the dry bound, wet bound and soluble experiment of FIG. 16B (modified from Stebbings et al. (2007) J. Immunol. 179: 3325-3331).
Figure 16B:
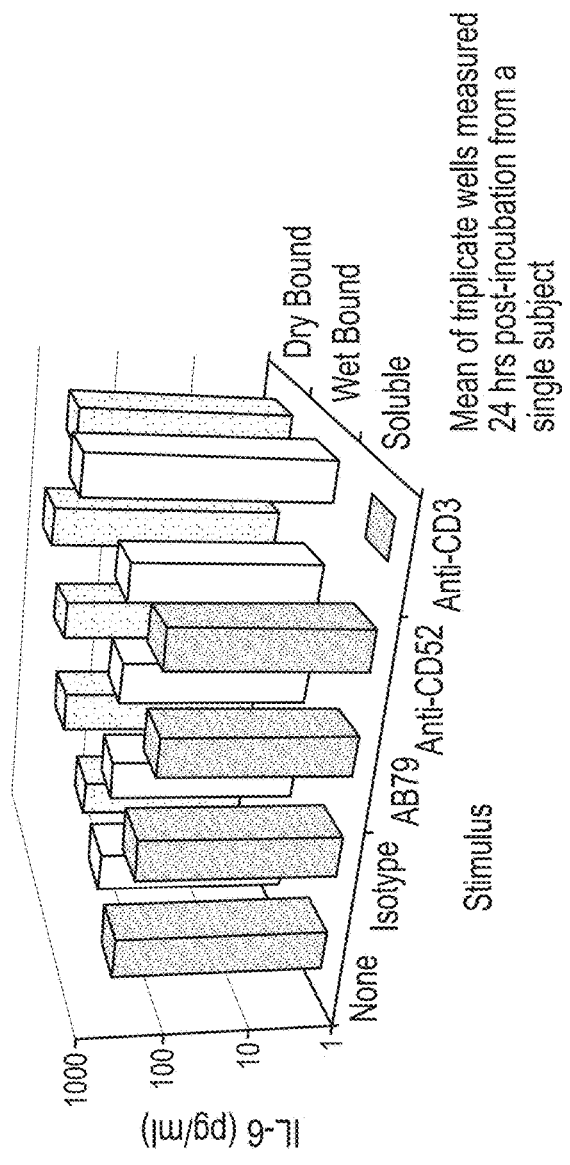
FIG. 16B shows that AB79 does not have agonist activity. AB79 was highly concentrated when it was added to the wells in solution and the liquid allowed to evaporate (Dry Bound) vs. AB79 allowed to bind to wells in solution (Wet Bound) or added directly to PBMCs (Soluble). AB79 did not stimulate IL-6 or IL-2, IL-4, IL-8, IL-10, GM-CSF, IFNγ, or TNFα under any of the conditions tested after 24 hours. IL-8 was constitutively produced by PBMCs and was not altered by any treatment (data not shown). Each measure is a mean of triplicate wells measured 24 hours post-incubation from a single subject.

The method by which an antibody is presented to a cell may contribute to the outcome of antibody: ligand engagement and cell response (Stebbings et al. (2007) J. Immunol. 179: 3325-3331). Stebbings et al. showed that the maximal cell response (cytokine release) to an agonistic antibody occurred when the antibody was highly concentrated and adhered to the well surface such as when antibody was added to a well in solution and the liquid allowed to evaporate (Dry Bound) as compared to antibodies allowed to bind to wells in solution (Wet Bound) or added directly to PBMCs (Soluble) (FIG. 16A). AB79 did not stimulate cytokine production in using any of these approaches (FIG. 16B).

AB79 (100 mg/ml) did not stimulate IL-2, -4, -6, -8, -10, GM-CSF, IFNγ or TNFα under any of the conditions tested after 24 hours. AB79 did not induce IL-10 or GM-CSF, but both were induced by anti-CD3 (not shown, all values except anti-CD3 were below LLOQ). IL-8 was constitutively produced by PBMCs and was not altered by any treatment (data not shown) (Table 7).

TABLE 7

AB79 and Cytokine Stimulation

| Antibody Presentation | None | Isotype | AB79 | Anti-CD52 | PHA | Anti-CD3 |
|---|---|---|---|---|---|---|
| IL-2 | | | | | | |
| Soluble | LLOQ | LLOQ | LLOQ | LLOQ | 14953 ± 3117 | nd |
| Wet Bound | LLOQ | LLOQ | LLOQ | LLOQ | Nd | 395.0 ± 64.8 |
| Dry Bound | LLOQ | LLOQ | LLOQ | LLOQ | Nd | 167.9 ± 90.1 |
| IL-4 | | | | | | |
| Soluble | 7.3 ± 1.4 | 4.1 ± 0.8 | 6.4 ± 3.2 | 6.9 ± 4.0 | 50.4 ± 8.9 | nd |
| Wet Bound | 5.3 ± 0.08 | 3.8 ± 1.5 | 6.4 ± 0.6 | 8.5 ± 3.7 | Nd | 17.8 ± 2.4 |
| Dry Bound | 4.4 ± 1.8 | 7.8 ± 2.7 | 9.1 ± 2.6 | 10.5 ± 2.1 | Nd | 16.2 ± 3.1 |
| IL-6 | | | | | | |
| Soluble | 325.1 ± 65.3 | 236.0 ± 98.9 | 170.5 | 202.0 ± 48.0 | 18880 ± 0 | nd |
| Wet Bound | 216.8 ± 95.1 | 191.2 ± 47.0 | 194.6 ± 66.0 | 207.2 ± 60.2 | Nd | 902.7 ± 114.1 |
| Dry Bound | 165.0 ± 79.4 | 369 ± 143 | 465.8 ± 230 | 811.1 ± 473.7 | Nd | 500 ± 17 |

TABLE 7-continued

AB79 and Cytokine Stimulation

| Antibody Presentation | None | Isotype | AB79 | Anti-CD52 | PHA | Anti-CD3 |
|---|---|---|---|---|---|---|
| IFNγ | | | | | | |
| Soluble | 1190.2 ± 117.5 | 857.1 ± 311.7 | 770.1 ± 203.6 | 1116.9 ± 330.8 | 15857 ± 4614.8 | nd |
| Wet Bound | 1052.8 ± 385.8 | 657.2 ± 222.6 | 993.4 ± 198.1 | 1138.9 ± 339.1 | Nd | 5674.6 ± 564.7 |
| Dry Bound | 768.1 ± 110.0 | 1583.1 ± 418.6 | 1927.6 ± 517.6 | 1827.0 ± 281.5 | Nd | 3513.2 ± 708.3 |
| TNFα | | | | | | |
| Soluble | 28.71 ± 8.1 | 11.6 ± 7.1 | 59.6 ± 90.1 | 79.9 ± 18.2 | 9270.0 ± 0 | nd |
| Wet Bound | 16.5 ± 3.4 | 16.1 ± 3.9 | 14.8 ± 8.8 | 166.1 ± 21.7 | Nd | 2123.3 ± 239.7 |
| Dry Bound | 16.2 ± 7.4 | 919.2 ± 77.4 | 745.1 ± 141 | 984.4 ± 317.0 | Nd | 2231.6 ± 687 |

A Multiplex cytokine assay was used according to manufacturer's instructions (Bio-Plex ProTM Human Cytokine Standard 8-Plex) to measure IL-2, -4, -6, -8, -10, GM-CSF, IFNγ and TNFα concentrations.
Abbreviations:
LLOQ Lower Limit of Quantification;
nd, not done;
PHA, phytohemagglutinin;
PBMC, peripheral blood mononuclear cell.

AB79 Depletes CD38+Cells

AB79 binds CD38 with high affinity and mediates CDC and ADCC. AB79 is not an agonist and did not induce cytokine release from human PBMCs. AB79 bound CD38 from both human and cynomolgus monkey. Lymphocytes from both species had similar cell-specific patterns of CD38 expression with NK cells>B cells>T cells based on Median Fluorescent Intensity of AB79 staining. Treatment with AB79 depleted monkey lymphocytes in a reversible, cell-specific and dose-dependent manner. AB79 effectively blocked human antibody recall response in a mouse adoptive transfer model.

Example 3: Evaluation Of AB79 Binding To Human And Cynomolgus Monkey Red Blood Cells And Platelets AB79, a fully human, high affinity, non-agonist, IgG1 monoclonal Ab directed to human CD38, was evaluated to determine its binding to human or cynomolgus monkey (cyno) red blood cells (RBC) or platelets. Thirty blood samples from healthy human volunteers and thirty whole blood samples from healthy cynos were evaluated for AB79 binding, in comparison to an isotype matched control monoclonal antibody, Palivizumab, of irrelevant specificity that does not bind to RBC or platelets.

Methods

Blood samples from 30 normal human subjects (15 male and 15 female) for platelets, 25 male and 5 female for RBCs) and 30 cynos of Chinese origin (15 male and 15 female) were purchased from Bioreclamation, (Long Island, NY). Whole blood was collected in sodium citrate tubes and shipped overnight at ambient temperature.

For the evaluation of AB79 binding to platelets, 50 μL of whole blood was stained with a cyno cross reactive anti-human CD61 FITC mAb (BD Biosciences Cat #555753) to identify platelets in combination with Alexa Fluor 647 (AF647) conjugated AB79 or an isotype matched control, AF647 conjugated Palivizumab (MedImmune cat #60574-

4113-1), a humanized monoclonal antibody which is specific against an epitope in the A antigenic site of the F protein of respiratory syncytial virus (RSV), an antigen not present on RBC or platelets. RBC lysis was performed post staining and samples analyzed using a BD Canto flow cytometer. CD61+ platelets were gated on for analysis.

For the evaluation of AB79 binding to RBCs, 50 µl of whole blood was stained with AF647 conjugated AB79 or isotype matched control, AF647 conjugated Palivizumab. In some experiments, a cyno cross reactive anti-human CD45 PERCP (BD Biosciences Cat #552724) was used to stain lymphocytes in order to provide evidence of AB79 binding to a subset of lymphocytes as observed in previous studies. The samples were analyzed using a BD Canto flow cytometer. Data were expressed as mean fluorescence intensity (MFI) of AB79 or isotype control.

Results and Discussion

Figure 17:
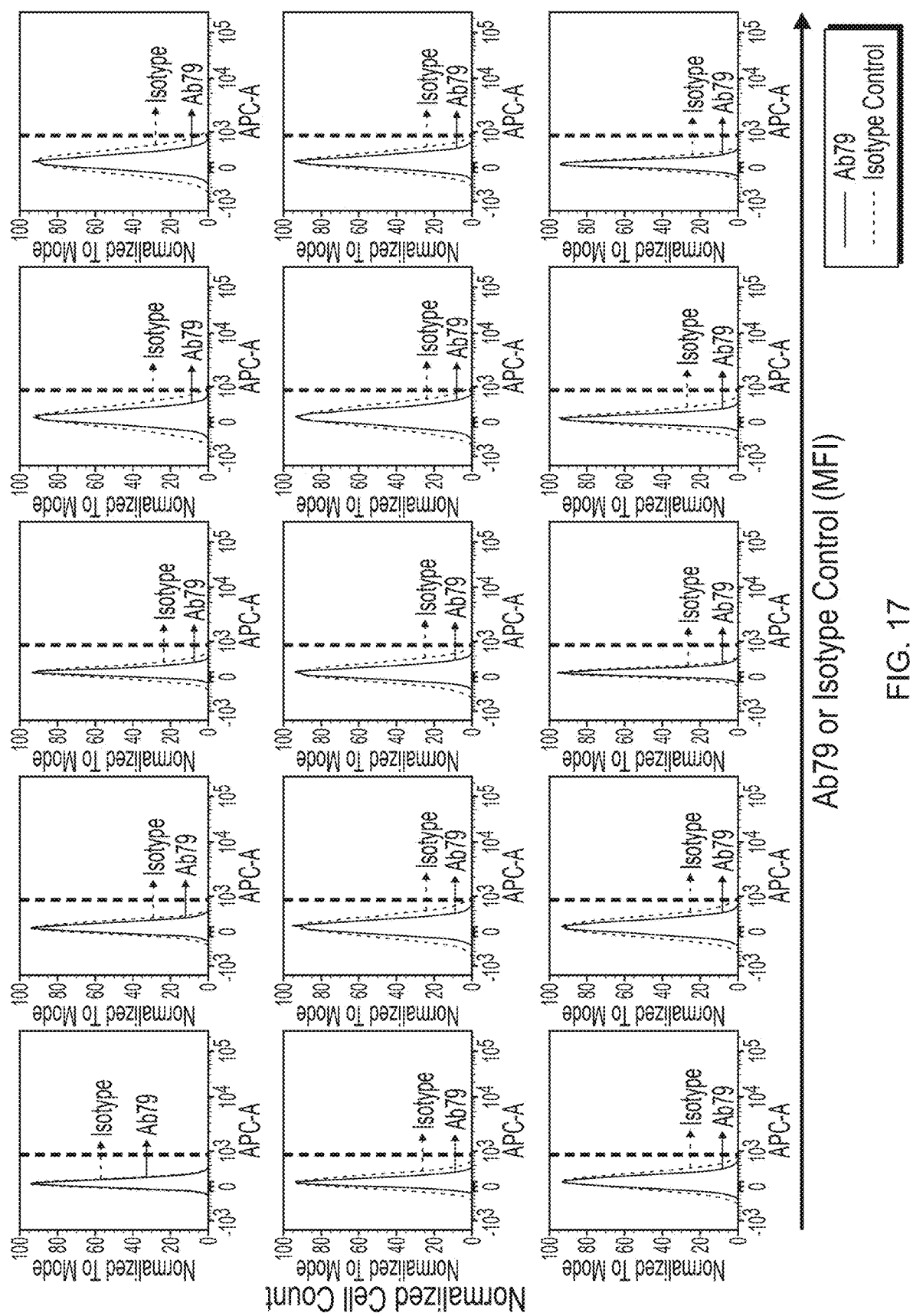
FIG. 17 shows an evaluation of AB79 binding to human RBCs. No binding of AB79 (solid histogram) or isotype control (hatched histogram) to RBC in the whole blood of thirty human volunteers was observed in this study. Representative data from 15 of 30 human volunteers is shown.
Figure 18:
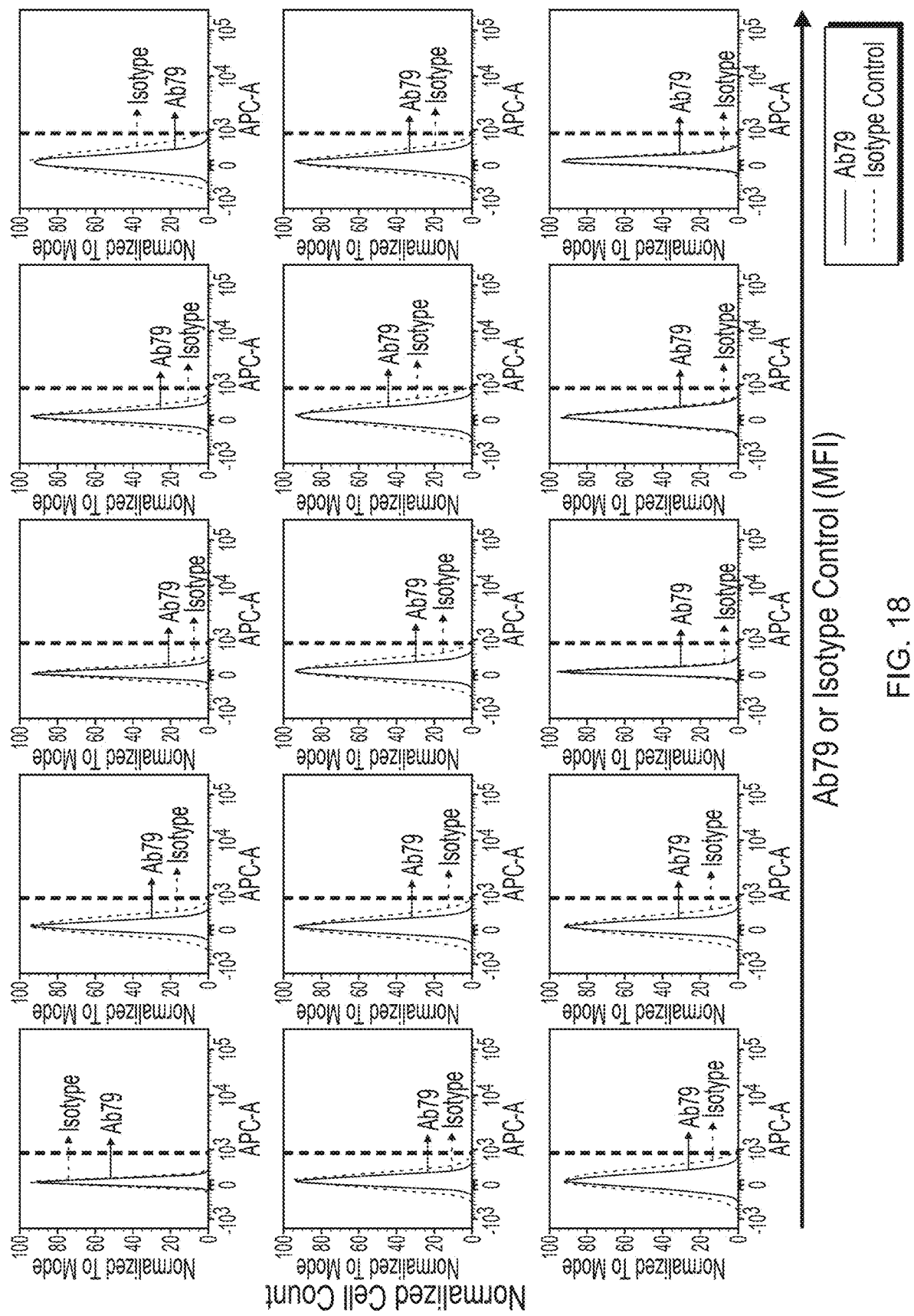
FIG. 18 shows an evaluation of AB79 binding to cynomolgus monkey RBCs. No binding of AB79 (solid histogram) or isotype control (hatched histogram) to RBC in the whole blood of thirty cynomolgus monkeys was observed in this study. Representative data from 15 of 30 cynos is shown.

The ability of AB79 to bind to RBCs from thirty healthy human volunteers and thirty healthy cynos was evaluated using flow cytometry. Staining of RBCs with AB79 was not above the level of staining seen with the isotype control antibody in any of the human blood samples (FIG. 17 and Table 8) or the cyno blood samples (FIG. 18 and Table 8). No detectable binding was observed in either species and no difference in the ratio of MFI for AB79/isotype control was observed between humans and cynos.

TABLE 8

Ratio of RBC AB79/Isotype Control Mean Fluorescence Values

| Donor # | Human | Cyno |
|---|---|---|
| 1 | 1.047 | 1.025 |
| 2 | 1.018 | 0.904 |
| 3 | 1.006 | 0.912 |
| 4 | 0.867 | 0.878 |
| 5 | 0.800 | 0.805 |
| 6 | 0.937 | 0.980 |
| 7 | 0.900 | 0.893 |
| 8 | 0.920 | 0.861 |
| 9 | 0.896 | 0.839 |
| 10 | 0.958 | 0.868 |
| 11 | 0.896 | 0.863 |
| 12 | 0.950 | 0.866 |
| 13 | 1.016 | 1.027 |
| 14 | 0.946 | 0.989 |
| 15 | 0.985 | 0.969 |
| 16 | 0.829 | 0.990 |
| 11 | 0.861 | 0.985 |
| 18 | 0.903 | 1.022 |
| 19 | 0.914 | 0.915 |
| 20 | 0.914 | 0.911 |
| 21 | 0.813 | 0.882 |
| 22 | 0.859 | 0.888 |
| 23 | 0.947 | 0.960 |
| 24 | 0.917 | 0.940 |
| 25 | 0.976 | 0.948 |
| 26 | 0.933 | 0.931 |
| 27 | 0.889 | 0.967 |
| 28 | 0.938 | 0.949 |
| 29 | 0.976 | 0.941 |
| 30 | 0.934 | 0.951 |
| Mean | 0.928 | 0.929 |
| StDev | 0.056 | 0.057 |

Figure 19:
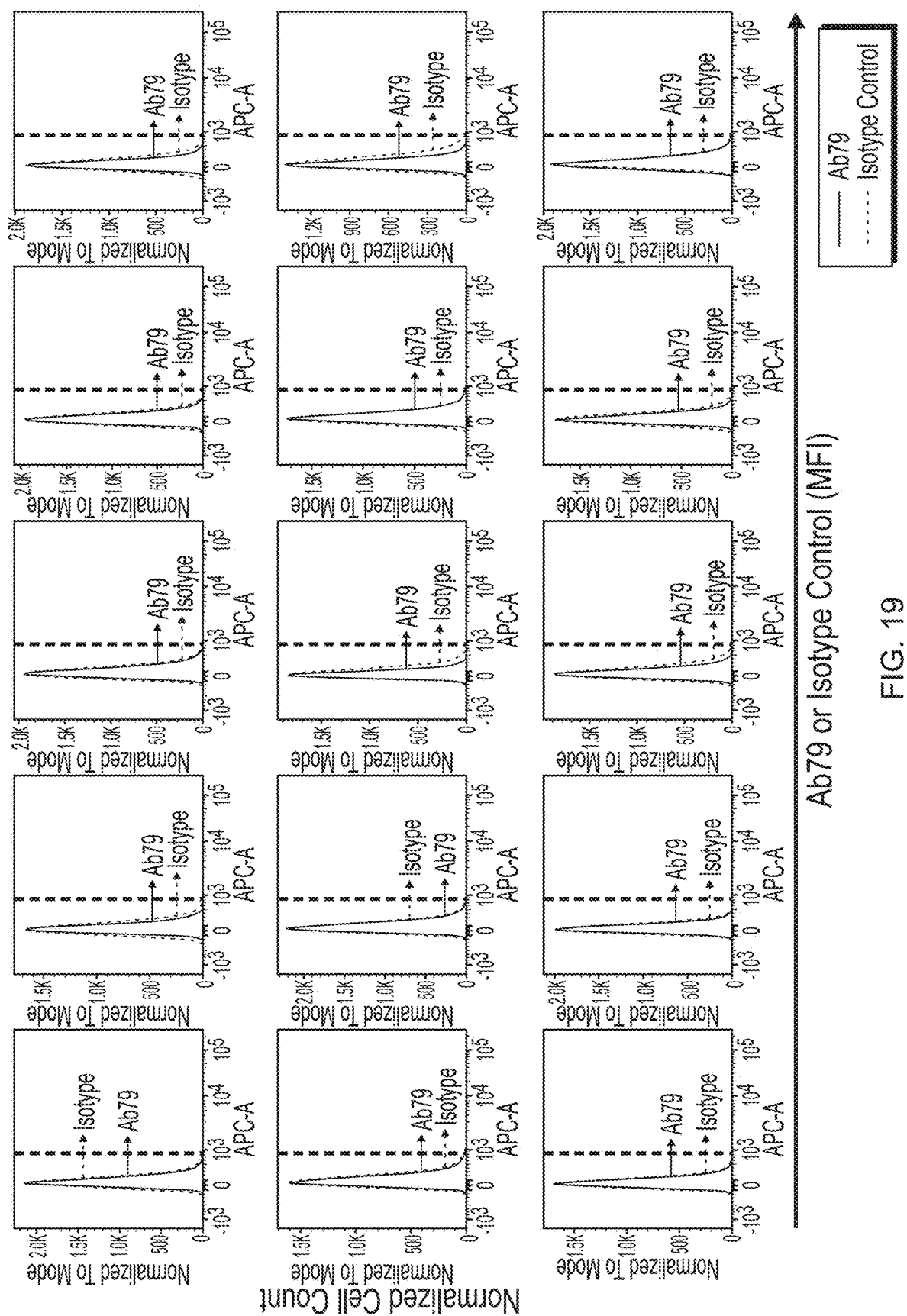
FIG. 19 shows an evaluation of AB79 binding to human platelets. No binding of AB79 (solid histogram) or isotype control (hatched histogram) to CD61+ gated platelets in the whole blood of thirty human volunteers was observed in this study. Representative data from 15 of 30 human volunteers is shown.
Figure 20:
FIG. 20 shows an evaluation of AB79 binding to cynomolgus monkey platelets. No binding of AB79 (solid histogram) or isotype control (hatched histogram) to CD61+ gated platelets in the whole blood of thirty cynomolgus monkeys was observed in this study. Representative data from 15 of 30 cynos is shown.

The ability of AB79 to bind to CD61+ platelets from thirty healthy human volunteers and thirty healthy cynos (donors 1-15 were male; donors 16-30 were female) was evaluated using flow cytometry. AB79 staining of platelets was not above the level of staining observed with the isotype control in any of the human (FIG. 19 and Table 9) or the cyno blood samples (FIG. 20 and Table 9). No detectable binding was observed in either species and no difference in the ratio of MFI for AB79/isotype control was observed between humans and cynos.

TABLE 9

Ratio of Platelet AB79/Isotype Control Mean Fluorescence Values

| Donor # | Human | Cyno |
|---|---|---|
| 1 | 1.46 | 0.96 |
| 2 | 1.10 | 0.88 |
| 3 | 1.76 | 0.90 |
| 4 | 1.16 | 0.88 |
| 5 | 1.21 | 1.28 |
| 6 | 1.53 | 1.19 |
| 7 | 2.14 | 0.85 |
| 8 | 1.14 | 0.78 |
| 9 | 1.14 | 0.97 |
| 10 | 0.53 | 1.37 |
| 11 | 0.38 | 0.63 |
| 12 | 0.60 | 0.98 |
| 13 | 1.06 | 0.71 |
| 14 | 1.33 | 0.93 |
| 15 | 0.78 | 1.06 |
| 16 | 1.06 | 1.03 |
| 17 | 0.95 | 0.83 |
| 18 | 1.25 | 0.80 |
| 19 | 1.09 | 1.55 |
| 20 | 0.89 | 1.28 |
| 21 | 0.95 | 1.61 |
| 22 | 1.24 | 1.24 |
| 23 | 0.36 | 0.99 |
| 24 | 1.34 | 1.40 |
| 25 | 0.53 | 1.04 |
| 26 | 0.91 | 1.29 |
| 27 | 0.85 | 1.14 |
| 28 | 0.68 | 1.05 |
| 29 | 1.03 | 1.46 |
| 30 | 1.13 | 2.28 |
| Mean | 1.05 | 1.11 |
| StDev | 0.39 | 0.33 |

Figure 21:
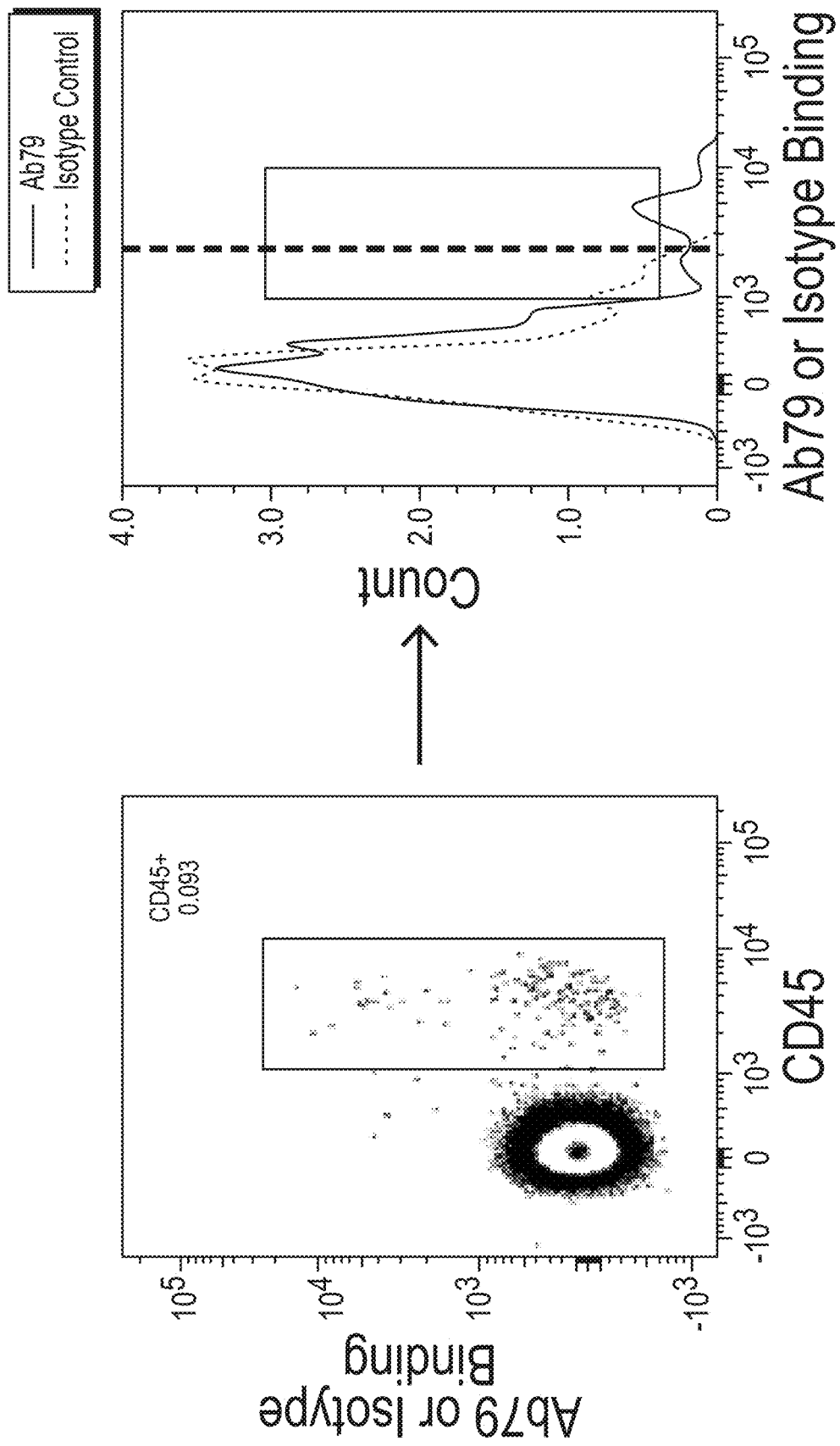
FIG. 21 shows an evaluation of AB79 binding to cynomolgus monkey CD45+ lymphocytes. Binding of AB79 to CD45+ lymphocytes in unlysed cynomolgus monkey whole blood. CD45+ lymphocytes are gated on and then the binding of AB79 (solid histogram) or isotype control (hatched histogram) binding was evaluated. AB79 binding was detected on a subset of the lymphocytes as illustrated in the fraction of cells to the right of the vertical dashed line. Little to no binding of the isotype control to lymphocytes is observed.

As a positive control for AB79 staining, AB79 staining was measured in a portion of the blood samples. Because of the high predominance of RBCs in blood, 200,000 events were acquired and a small population of CD45+ lymphocytes were gated on for further evaluation. No binding was observed for isotype control; however, AB79 bound to a small population of CD45+ lymphocytes (FIG. 21). This confirmed AB79 was capable of staining blood cells under conditions where no detectable binding of AB79 was observed to RBC or platelets.

Example 4: Evaluation of AB79 Binding To Human And Cynomolgus Monkey Red Blood Cells And Platelets Using a Higher Sensitivity Flow Cytometry Assay A higher sensitivity flow cytometry assay was developed to further evaluate whether AB79 binds to human or cynomolgus monkey (cyno) RBCs in case the previous assay may not have been sensitive enough to detect a low level of CD38 expression on RBCs. Blood samples from 4 healthy human volunteers were incubated with fluorescently labeled AB79 or fluorescently labeled daratumumab, another anti-CD38 antibody that is known to bind to CD38 on RBCs. Each sample was preincubated with its respective unlabeled drug product to block CD38 binding with the fluorescently labeled drug products, serving as the negative control for the assay. Antibodies against CD45 and CD235a were added to the samples to identify RBC positive cells and then subsequently analyzed on a flow cytometer. Fluorescently labeled daratumumab was used as the positive control. The results indicated that AB79 and daratumumab bind to RBCs from healthy human donors.

Methods

Blood samples from four healthy human donors (Millennium's blood donor program) were collected in accordance with company protocol. Briefly, peripheral blood samples for RBC binding determination were collected into sodium heparin tubes and for lymphocyte staining, peripheral blood samples were collected into BD Vacutainer® CPT™ tubes (BD Biosciences, Franklin Lakes, NJ, USA). A separate tube was used to collect peripheral blood mononuclear cells (PBMCs) to confirm binding of fluorescently labeled AB79 and fluorescently labeled daratumumab to CD38+ lymphocytes. For both the RBC binding and lymphocyte staining experiments, peripheral blood samples were stored at RT and processed within 2 hours of collection to maintain viability of the cells. For RBC binding, peripheral blood samples were first diluted 1:10,000 in stain buffer (BD Biosciences, Franklin Lakes, NJ, USA) to dilute out the high number of RBCs present in the sample. Because the normal range of RBCs in healthy human blood samples is approximately 5 million cells per microliter, samples need to be substantially diluted in order to have an acceptable number of RμBCs to stain for flow cytometric analysis. Samples were then transferred to a V-bottom 96-well plate and incubated overnight at 4° C. on a gentle shaker with unlabeled 25 μL/well AB79 (500 μg/mL), unlabeled daratumumab (500 μg/mL), or BD buffer only (no drug). A plate shaker was used to prevent settling of the RBCs during the incubation period. Peripheral blood samples were preincubated with the unlabeled drug products in order to block CD38 antigenic sites on the surface of RBCs, which served as the negative control for the assay. After this incubation period, clinically relevant concentrations of biotin-streptavidin-BV421 daratumumab (0, 0.1, 1, 10, and 100 μg/mL) or biotin-streptavidin-BV421 AB79 (0, 0.1, 1, 10, and 100 μg/mL) were added to the samples for 3 hours at RT on a gentle shaker. Samples were then washed several times with BD buffer and stained with cell surface markers CD45 and CD235a for RBC identification (RBCs are CD45– CD235a+) and streptavidin-BV421 to bind the biotinylated antibodies. By using biotin-streptavidin, the low level of CD38 expression on RBCs could be amplified. BV421 fluorescent dye was selected because it is one of the brightest fluorophores commercially available and uses the violet laser on the flow cytometer, thereby minimizing the amount of spectral overlap with the other channels/markers in the panel. Together, this signal amplification approach provides an opportunity to detect molecules on the cell surface that would otherwise fall within the instrument noise. Samples were subsequently washed and acquired on a BD FACSCanto™ II (BD Biosciences, Franklin Lakes, NJ, USA). Target cell acquisition was set at 10,000 CD235a+ events. For lymphocyte binding, peripheral blood from the same healthy donors collected into CPT tubes was centrifuged and peripheral blood mononuclear cells (PBMCs) were isolated using standard techniques. Cells were washed, stained, and processed as described for the RBC experiments.

Figure 22:
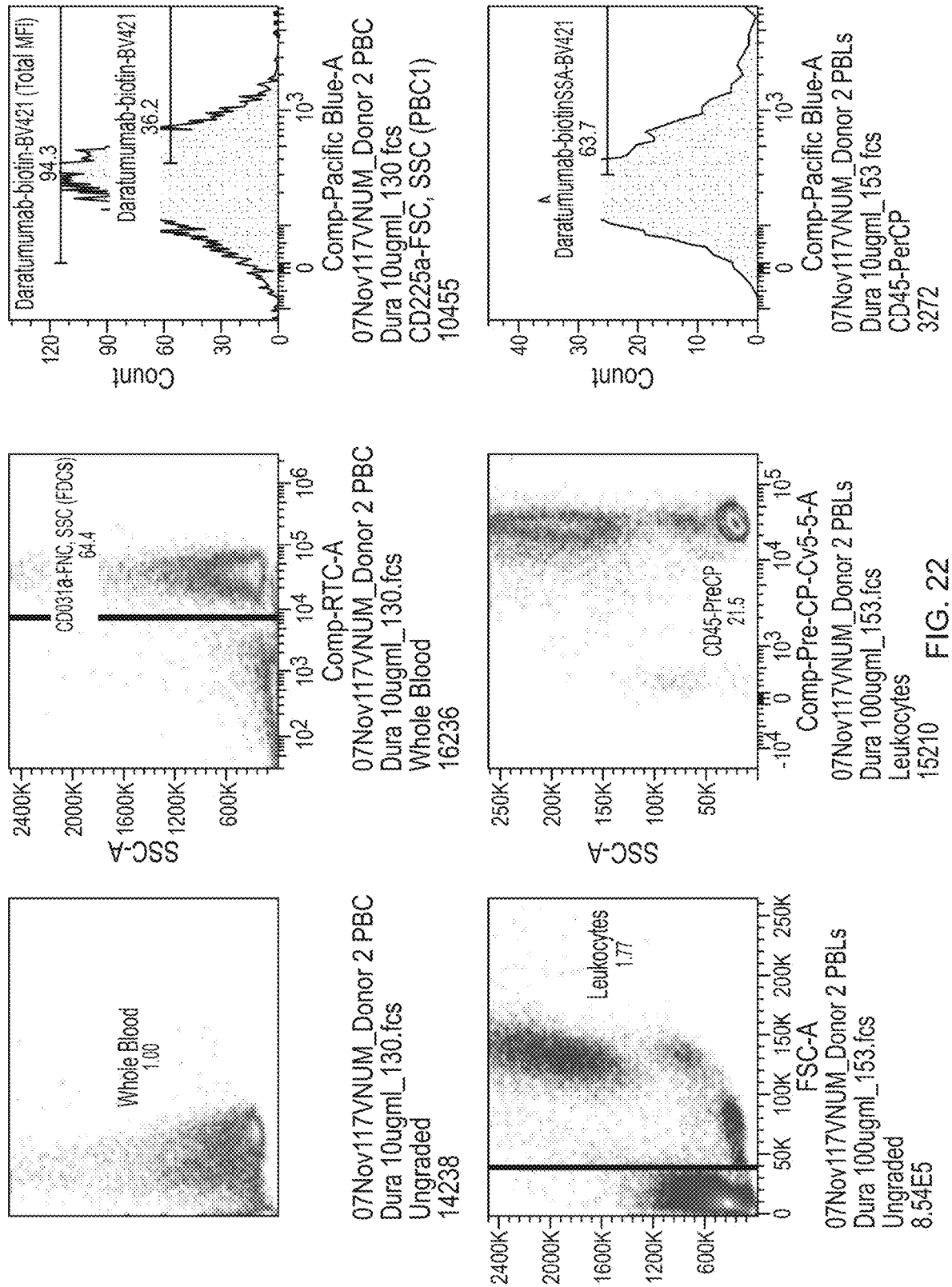
FIG. 22 shows the gating heriarchy for (A) RBC identification and (B) lymphocyte identification of human RBCs.

To prepare biotinylated antibodies, AB79 (21.4 mg/mL, Takeda California, USA) and daratumumab (20 mg/mL, Janssen Biotech, Horsham, PA, USA) were purified concurrently on the same day using a commercial protein A column kit (Abcam, Cambridge, UK) to remove substances that could potentially interfere with the biotinylation procedure. The protein concentrations of the purified products were determined by A280/260 and equal protein amounts of each antibody were conjugated to biotin using a Lightning Link Rapid Biotin Conjugation kit (Innova Biosciences, Cambridge, UK). At the end of the procedure, the protein concentrations were measured again using A280/260. Both antibodies were conjugated to commercial polystyrene microspheres that have antibody binding capacity to any antibody isotype or to inert beads (negative beads). After mixing the beads with biotin-strepavidin-BV421 AB79 or biotin-strepavidin-BV421 daratumumab, the two components mixed together provide a distinct high-signal positive control with an appropriate negative population that can be used to estimate the median fluorescence (MFI) of each test antibody by flow cytometry. Samples were acquired on a BD Biosciences FACSCANTO™ II instrument using a BD Biosciences FACSDiva™ (BD Biosciences, Franklin Lakes, NJ, USA). Raw data files were transferred onto a secure server and then analyzed offline using FlowJo® Version 10 (FlowJo, LLC; Ashland, OR, USA). For RBC identification, CD235a+cells were first gated. Then, the geometric MFI and percent positive biotin-strepavidin-BV421 AB79 and biotin-strepavidin-BV421 daratumumab events were determined for the gated cells and plotted as a histogram (FIG. 22). This was compared with the isotype control (samples preincubated with unlabeled AB79 or unlabeled daratumumab and then incubated with their respective biotin-strepavidin-BV421 labeled drug products). For lymphocyte identification, debris was first excluded using forward versus side scatter (FSC-A vs. SSC-A). CD45 positive population was then gated and the MFI and percent positive of biotin-strepavidin-BV421 AB79 and biotin-strepavidin-BV421 daratumumab was determined for the gated cells and plotted as a histogram (FIG. 22). This was compared with the isotype control (samples preincubated with unlabeled AB79 or unlabeled daratumumab and then incubated with their respective biotin-strepavidin-BV421 drug products).

TABLE 10

AB79 and Daratumumab Red Blood Cell Binding Summary (Geometric Median Fluorescence)

| Conc. (μg/mL) | Donor 1 | Donor 2 | Donor 3 | Donor 4 | Mean | SD |
|---|---|---|---|---|---|---|
| AB79 Biotin-Streptavidin-BV421 | | | | | | |
| 0 | 138 | 155 | 202 | 284 | 195 | 65.37 |
| 0.1 | 175 | 201 | 207 | 355 | 235 | 81.53 |
| 1 | 193 | 224 | 282 | 392 | 273 | 87.64 |
| 10 | 196 | 205 | 557 | 521 | 370 | 196.02 |
| 100 | 143 | 139 | 533 | 445 | 315 | 204.11 |
| Cold AB79 and AB79 Biotin-Streptavidin-BV421 | | | | | | |
| 0 | 139 | 143 | 220 | ND | 167 | 45.65 |
| 0.1 | 133 | 137 | 198 | ND | 156 | 36.43 |
| 1 | 132 | 142 | 223 | ND | 166 | 49.90 |
| 10 | 136 | 148 | 421 | ND | 235 | 161.19 |
| 100 | 133 | 140 | 447 | ND | 240 | 179.30 |
| Daratumumab Biotin-Streptavidin-BV421 | | | | | | |
| 0 | 150 | 158 | 182 | 274 | 191 | 56.98 |
| 0.1 | 227 | 297 | 215 | 411 | 288 | 89.92 |
| 1 | 304 | 394 | 387 | 527 | 403 | 92.22 |
| 10 | 317 | 352 | 556 | 599 | 456 | 142.11 |
| 100 | 162 | 190 | 643 | 493 | 372 | 234.74 |
| Cold Daratumumab and Daratumumab Biotin-Streptavidin-BV421 | | | | | | |
| 0 | 143 | 164 | 180 | ND | 162 | 18.56 |
| 0.1 | 133 | 146 | 191 | ND | 157 | 30.44 |

TABLE 10-continued

AB79 and Daratumumab Red Blood Cell Binding Summary
(Geometric Median Fluorescence)

| Conc. (μg/mL) | Donor 1 | Donor 2 | Donor 3 | Donor 4 | Mean | SD |
|---|---|---|---|---|---|---|
| 1 | 135 | 147 | 216 | ND | 166 | 43.71 |
| 10 | 155 | 170 | 431 | ND | 252 | 155.20 |
| 100 | 133 | 142 | ND | ND | 138 | 6.36 |

ND = not determined;
SD = standard deviation

Results and Discussion

Figure 23:
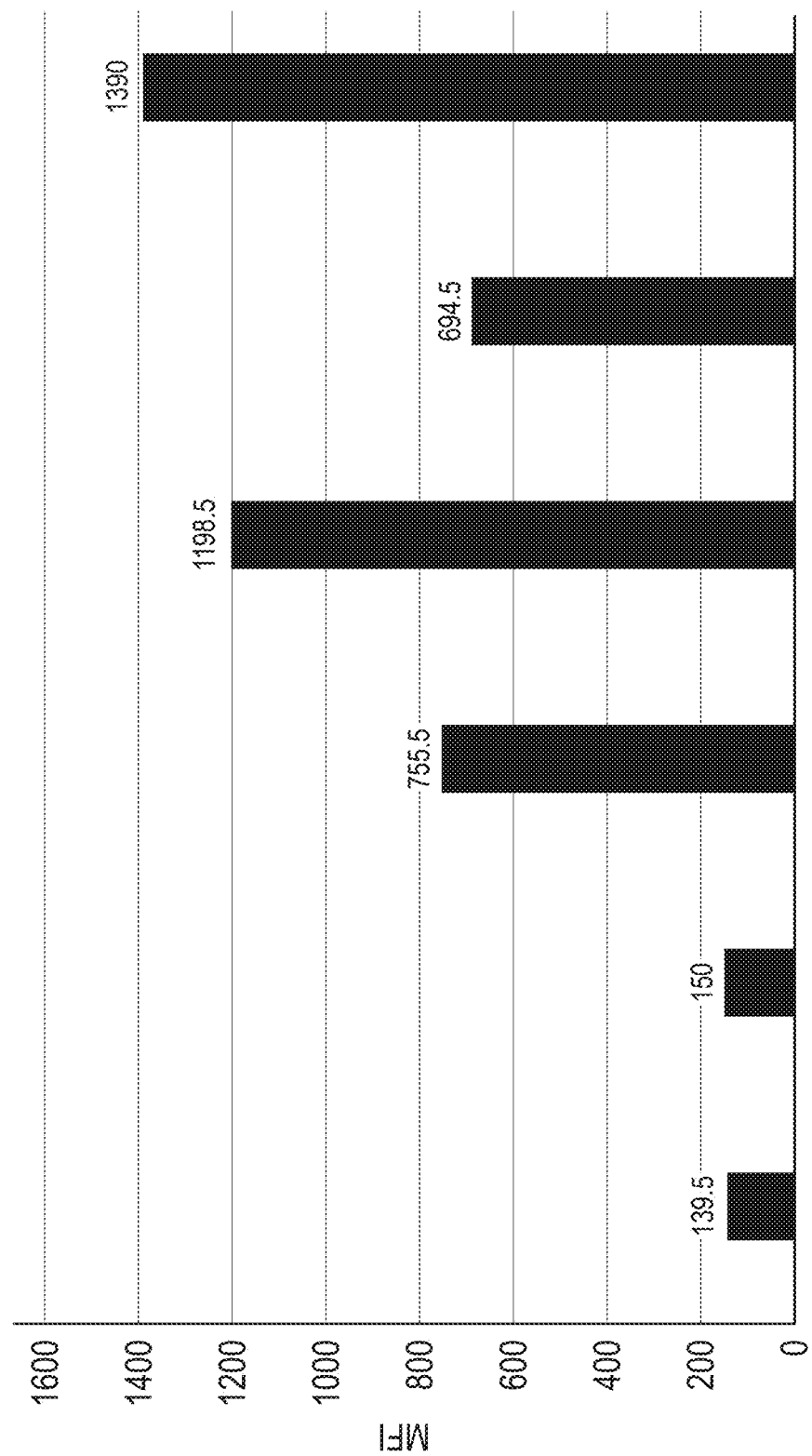
FIG. 23 shows antibody binding capacity for biotin-streptavidin-BV421 AB79 and biotin-streptavidin-BV421 daratumumab. The bars represent (i) negative beads, (ii) Sav-Bv421 only negative control, (iii) AB79-biotin/Sav-BV421 (5 µg/ml), (iv) daratumumab-biotin/Sav-BV421 (5 µg/ml), (v) AB79-biotin/Sav-BV421 (10 µg/ml), (vi) daratumumab-biotin/Sav-BV421 (10 µg/ml). MFI=median fluorescence, Sav=streptavidin. A photomultiplier tube (PMT) voltage of 275 was used.

The amount of biotin on AB79 and daratumumab was determined using a high-sensitivity flow cytometry assay. As the results show in FIG. 23, biotin-strepavidin-BV421 daratumumab binds 1.6-to 2.0-fold more antibody-bound beads than biotin-strepavidin-BV421 AB79. Therefore, biotin-strepavidin-BV421 daratumumab is a "brighter" antibody compared to biotin-strepavidin-BV421 AB79. Consequently, comparisons of MFI intensity should be calibrated for this difference in labeling.

Figure 24:
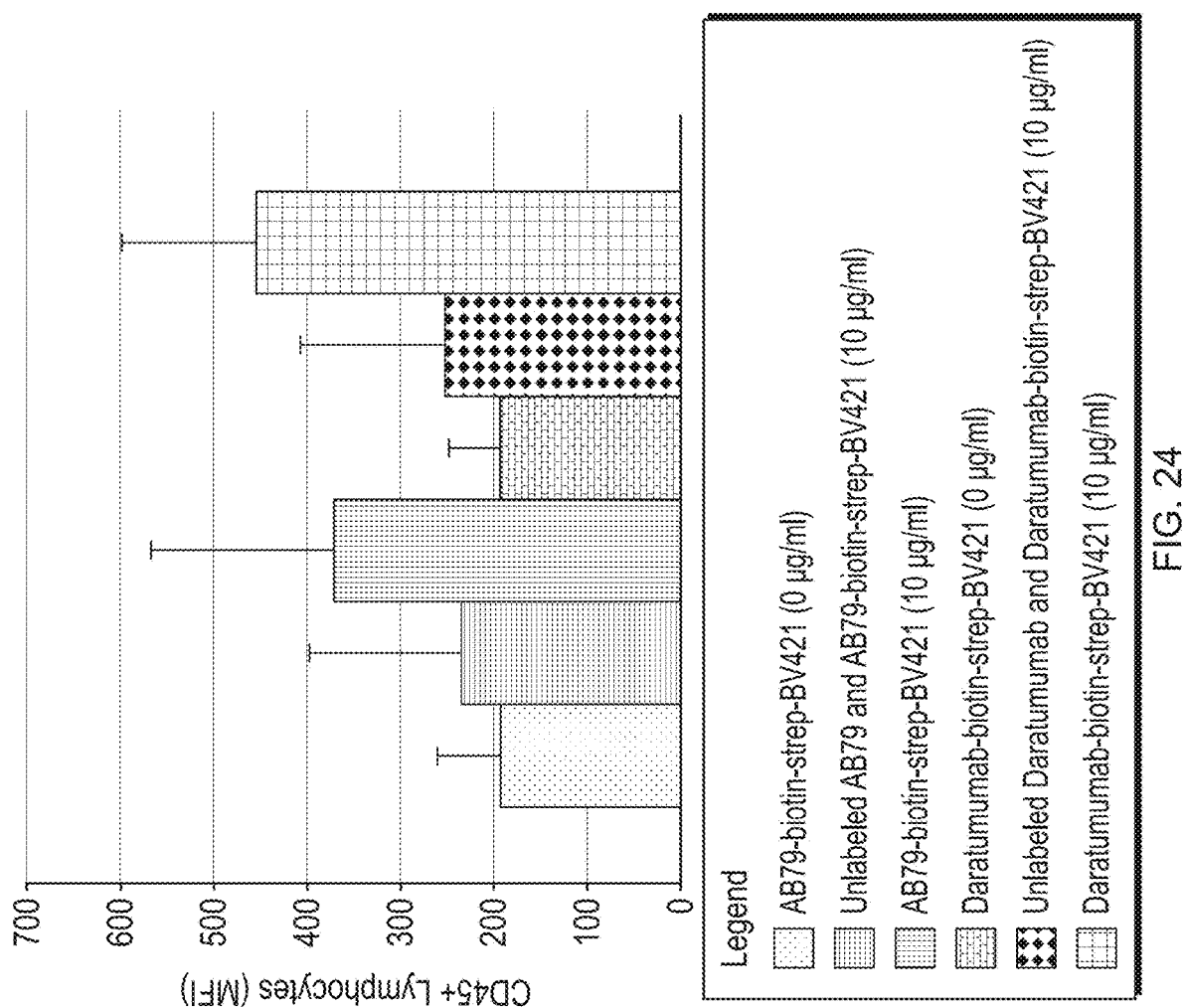
FIG. 24 shows biotin-streptavidin-BV421 AB79 and biotin-streptavidin-BV421 daratumumab binding to CD38+ lymphocytes. The bars represent (i) AB79-biotin-strep-BV421 (0 µg/ml), (ii) unlabeled AB79 and AB79-biotin-strep-BV421 (10 µg/ml), (iii) AB79-biotin-strep-BV421 (10 µg/ml), (iv) daratumumab-biotin-strep-BV421 (0 µg/ml), (v) unlabeled daratumumab and daratumumab-biotin-strep-BV421 (10 µg/ml), (vi) daratumumab-biotin-strep-BV421 (10 µg/ml). The vertical lines represent the standard deviation; n=4 donors (3 donors for unlabeled conditions). MFI=median fluorescence.

Confirming the specificity of the biotin-labeled drug products was an important step in ensuring the observed results are a result of specific binding to the target protein. Competition assays were a common way to test for antibody specificity. A flow cytometric assay was used for this competition assessment. Briefly, peripheral blood samples from healthy volunteers were preincubated with unlabeled AB79 or unlabeled daratumumab, and then subsequently stained with biotinylated AB79 or biotinylated daratumumab, respectively. Samples preincubated with the unlabeled drug product were expected to block the binding of the biotinylated drug products. As demonstrated in FIG. 24, biotinylated AB79 and biotinylated daratumumab could be blocked to peripheral blood lymphocytes using the unlabeled drug products.

Figure 25:
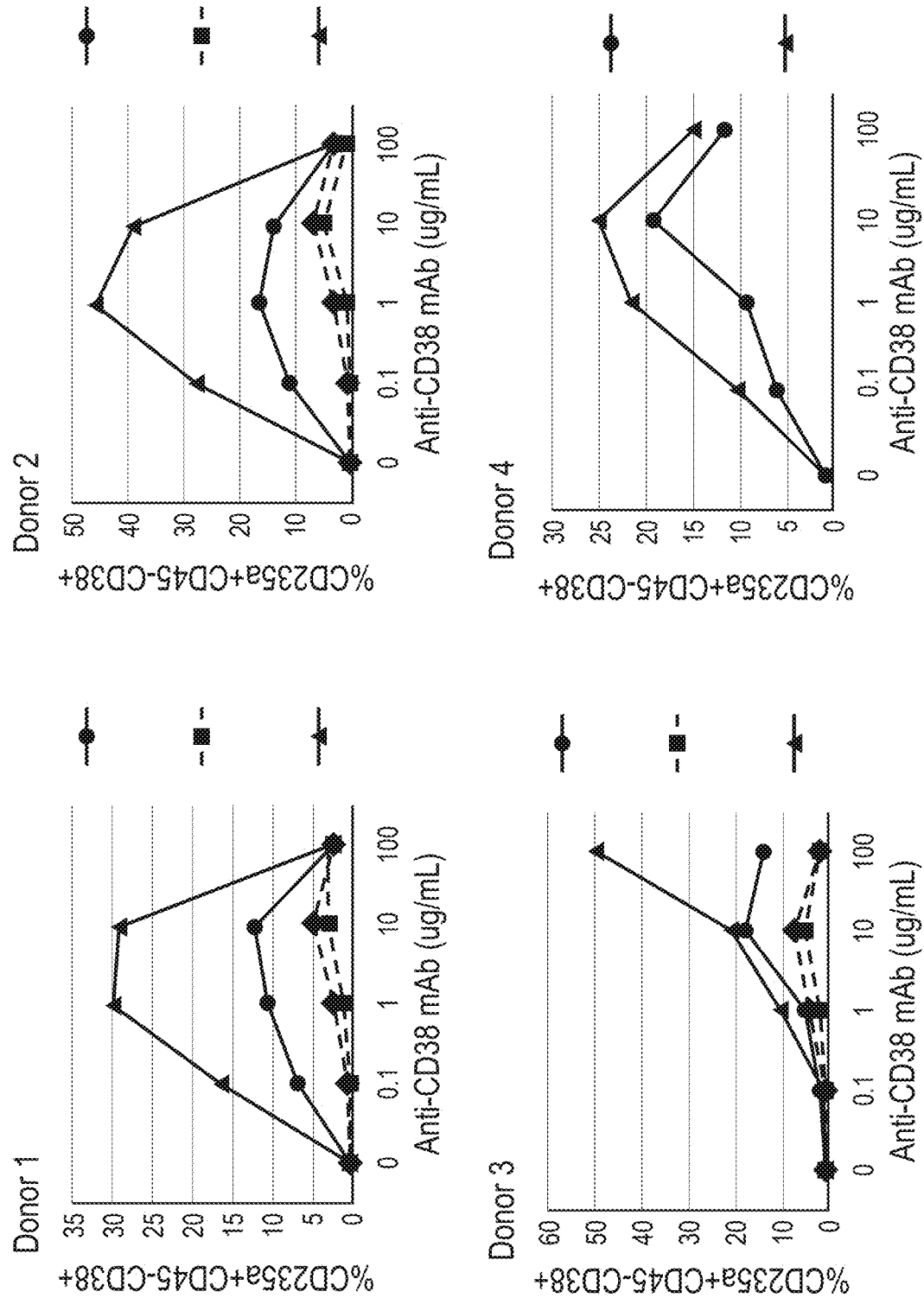
FIG. 25 shows AB79 and daratumumab binding to human RBCs (individual donor % positive results). Peripheral blood from four healthy volunteers incubated with biotin-streptavidin-BV421 AB79 (0, 0.1, 10, 100 µg/ml) or biotin-streptavidin-BV421 daratumumab (0,0.1, 1, 10, 100 µg/ml) for 3 hours at RT on a gentle shaker in the presence or absence of unlabeled AB79 (500 µg/ml) or unlabeled daratumumab (500 µg/ml). Key: ▬■▬ AB79-biotin-strep-BV421; ▬■▬ cold AB79 and AB79-biotin-strep-BV421; ▬■▬ daratumumab-biotin-strep-BV421; ▬■▬ cold daratumumab and daratumumab-biotin-streptavidin BV421.
Figure 26:
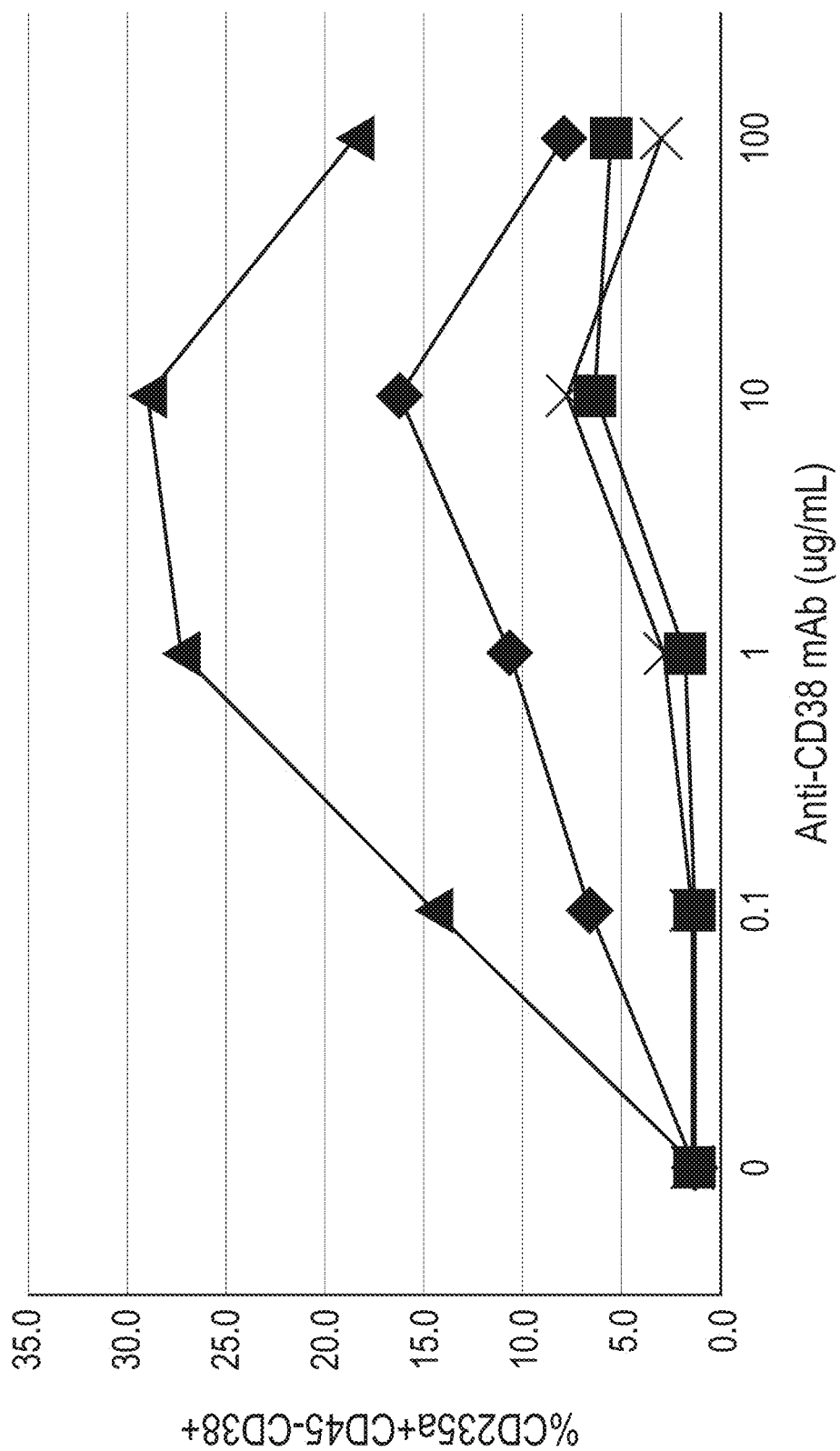
FIG. 26 shows AB79 and daratumumab binding to human RBCs (summary % positive data). Peripheral blood from four healthy volunteers incubated with biotin-streptavidin-BV421 AB79 (0, 0.1, 10, 100 µg/ml) or biotin-streptavidin-BV421 daratumumab (0,0.1, 1, 10, 100 µg/ml) for 3 hours at RT on a gentle shaker in the presence or absence of unlabeled AB79 (500 µg/ml) or unlabeled daratumumab (500 µg/ml). Key: ▬■▬ AB79-biotin-strep-BV421; ▬■▬ cold AB79 and AB79-biotin-strep-BV421; ▬■▬ daratumumab-biotin-strep-BV421; ▬■▬ cold daratumumab and daratumumab-biotin-strep-BV421.

The percentage of biotin-strepavidin-BV421 AB79 and biotin-strepavidin-BV421 daratumumab binding to RBCs was determined using a total of four peripheral blood samples from healthy volunteers. As shown in FIGS. 25 and 26, AB79 bound CD38 expressing RBCs in a dose-dependent manner in all four donors tested. Peak RBC binding levels differed among healthy volunteers and were observed between 1 and 10 μg/mL for both drug products. At 10 and 100 μg/mL of either biotin-strepavidin-BV421 AB79 or biotin-streptavidin-BV421 daratumumab, RBC levels were lower in 3 of the 4 donors tested. There are several factors that may explain the decreased level of drug binding to CD38 including increase in RBC hemolysis or flipping of the catalytic domain from the outside of the cell to the inside of the cell (Yoshiga et al. (2008) Int. J. Mol. Med. 22:369-374). In addition, daratumumab reduced CD38 expression levels, at least in part, through trogocytosis (Cole et al. (2018) Arthritis Res. Ther. 20(1):85); CD38 complexes and accompanying cell membrane were actively transferred from multiple myeloma cells to monocytes and granulocytes (Kraan et al. (1999) Rheumatology (Oxford) 38(11):1074-1080). One donor (Donor 3) had RBC levels that increased with increasing amounts of drug, perhaps as a result of having more surface RBC CD38 expression. Additional experiments would need to be conducted to better understand the decline in drug binding at the highest concentration tested.

Figure 27:
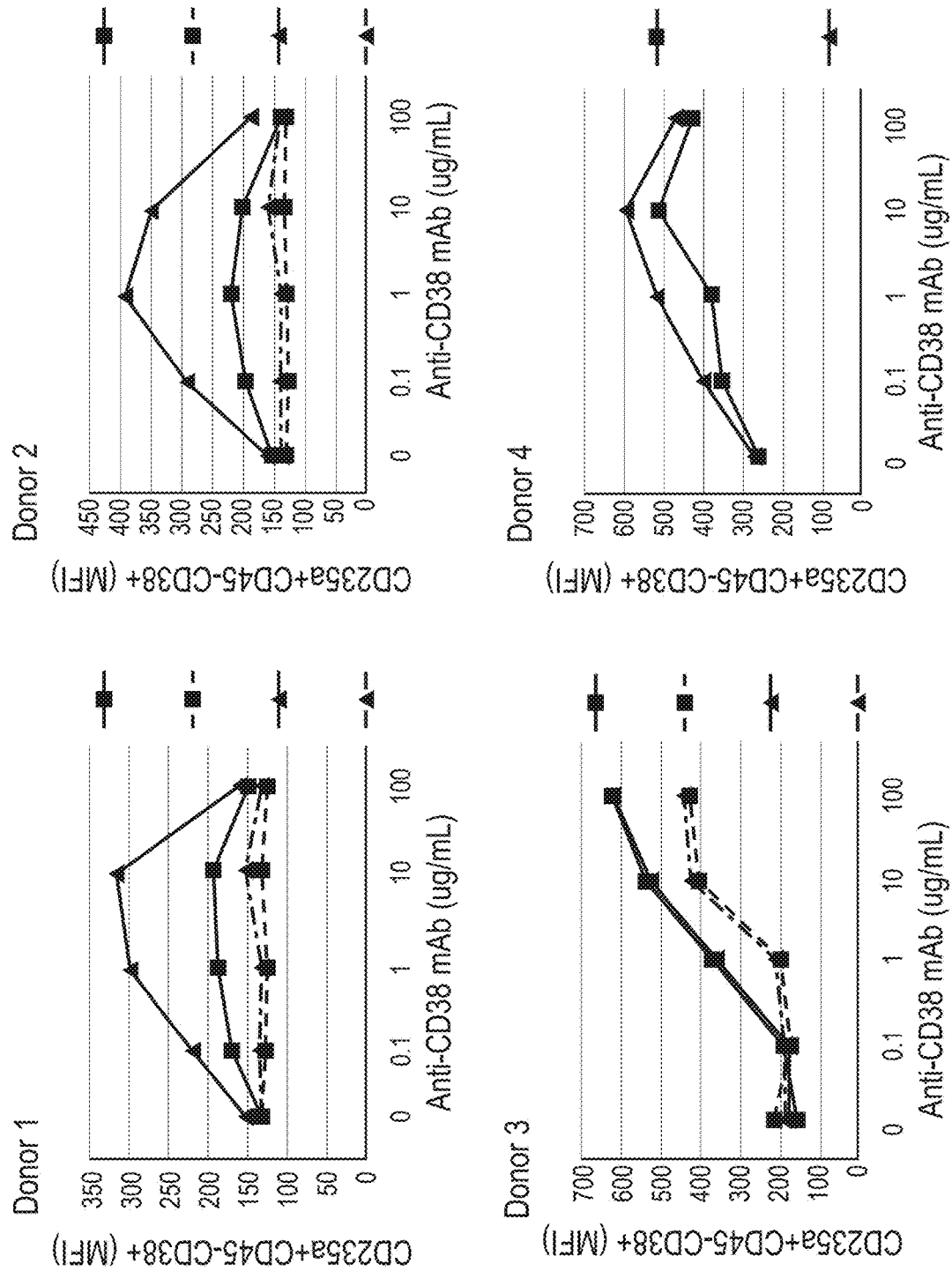
FIG. 27 shows AB79 and daratumumab binding to human RBCs (individual donor median fluorescence). Peripheral blood from four healthy volunteers incubated with biotin-streptavidin-BV421 AB79 (0, 0.1, 10, 100 µg/ml) or biotin-streptavidin-BV421 daratumumab (0,0.1, 1, 10, 100 µg/ml) for 3 hours at RT on a gentle shaker in the presence or absence of unlabeled AB79 (500 µg/ml) or unlabeled daratumumab (500 µg/ml). Key: ▬■▬ AB79-biotin-strep-BV421; ▬■▬ cold AB79 and AB79-biotin-strep-BV421; ▬■▬ daratumumab-biotin-strep-BV421; ▬■▬ cold daratumumab and daratumumab-biotin-strep-BV421.
Figure 28:
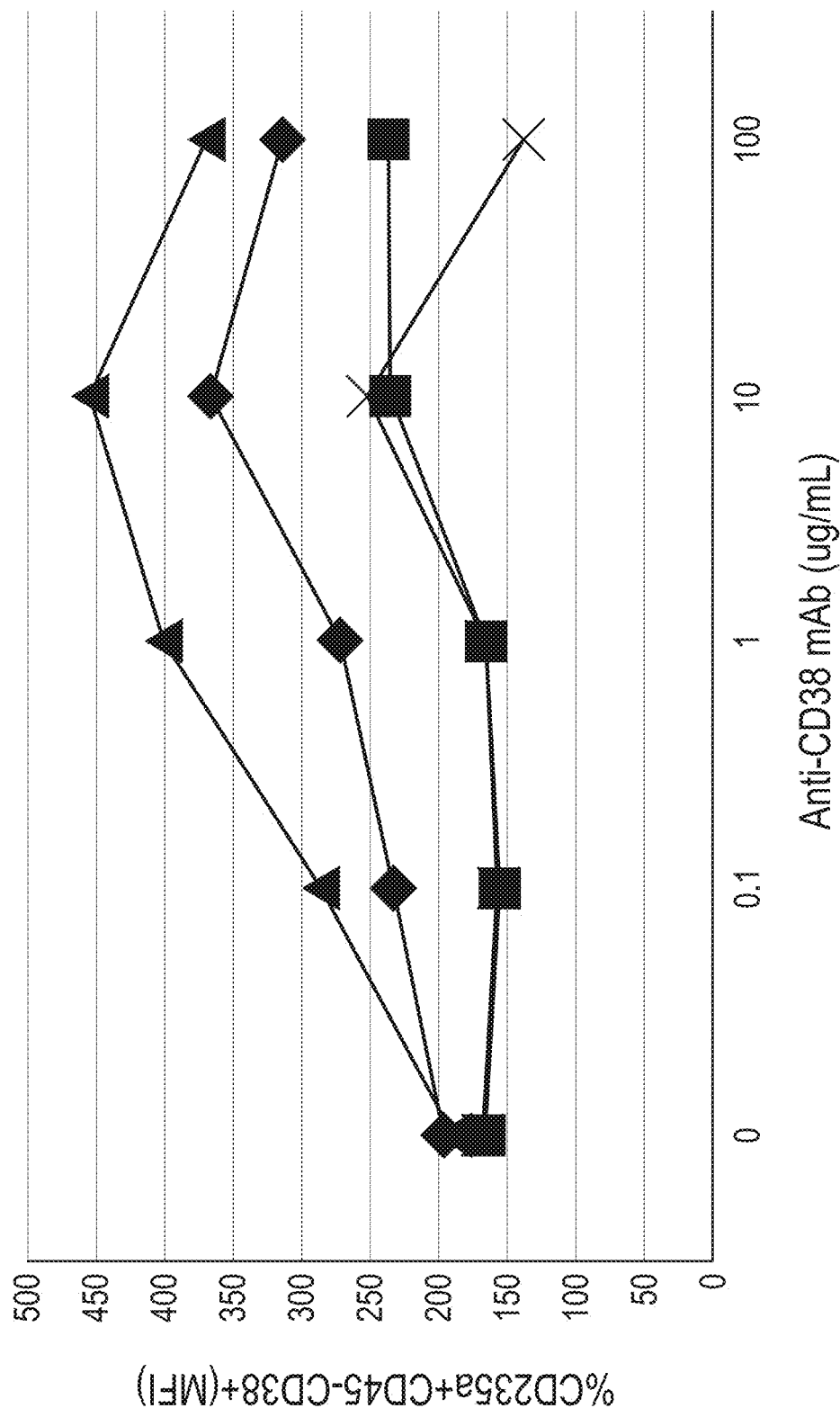
FIG. 28 shows AB79 and daratumumab binding to human RBCs (summary median fluorescence). Peripheral blood from four healthy volunteers incubated with biotin-streptavidin-BV421 AB79 (0, 0.1, 10, 100 µg/ml) or biotin-streptavidin-BV421 daratumumab (0,0.1, 1, 10, 100 µg/ml) for 3 hours at RT on a gentle shaker in the presence or absence of unlabeled AB79 (500 µg/ml) or unlabeled daratumumab (500 µg/ml). Key: ▬▬▬ AB79-biotin-strep-BV-421; ▬▬▬ cold AB79 and AB79-biotin-strep-BV-421; ▬▬▬ daratumumab-biotin-strep-BV421; ▬▬▬ cold daratumumab and daratumumab-biotin-strep-BV421.

The RBC binding profiles of AB79 and daratumumab were compared. As depicted in Table 10 and FIGS. 27 and 28, there appeared to be a difference in the magnitude of RBC binding (i.e., MFI) between the drug products in 3 of 4 donors tested; however, this difference may be attributed to the differential biotin levels on each of the antibodies, with daratumumab having 1.6-to 2.0-fold more biotin then AB79. An alternate analysis, which controls for a potential difference in the fluorescent labeling of antibodies, is to compare the concentration versus binding profile of each antibody and a useful metric is the concentration at which the maximum binding occurs (i.e., maximum specific binding of antigen (Bmax)). The Bmax is identical for both antibodies in 3 of 4 donors (e.g., 1 μg/mL for Donor 1). Collectively these data indicate that both antibodies bind with similar affinities, within the current resolution limit of the assay, which is a factor of 10. In conclusion, both AB79 and daratumumab bound to RBCs in this assay with affinities that were within 10-fold of one another; a 10-fold or greater difference in binding affinity of these antibodies for RBCs did not exist within this assay system.

Example 5: Evaluation of AB79 Hemolysis of Human or Monkey RBCs In Vitro

Fresh whole blood from normal healthy human volunteers and cynomolgus monkey (cyno), five (n=5) individuals per species, was evaluated for in vitro hemolysis in response to in vitro treatment with AB79 (27.3 mg/mL; Takeda California, USA), human IgG1 isotype control (7.14 mg/mL Bio X Cell), and daratumumab (20 mg/mL; Janssen Biotech, Horsham, PA, USA). A dose response for the test articles of interest was examined at 0, 0.03, 0.08, 0.25, 0.74, 2.2, 6.6, and 20 g/ml. A semi-log dilution of saponin was evaluated starting at a top 1% saponin solution was used as a technical positive control for blood responsiveness. Treatment was performed for 1 hour at 37° C., 5% $CO_2$ for acute hemolysis measurement. Absorbance was measured at 540 nm wavelength using a spectrophotometer and percent hemolysis was calculated as follows:

$$\text{Hemolytic Index} = \frac{\text{O.D. test sample} - \text{mean O.D. negative control}}{\text{O.D. 100\% hemolysis control} - \text{mean O.D. negative control}} \times 100$$

The hemolytic index is graded as follows (Hemolytic Index=Hemolytic Grade): 0-2=non-hemolytic; 2-5=slightly hemolytic, >5=hemolytic.

Figure 29:
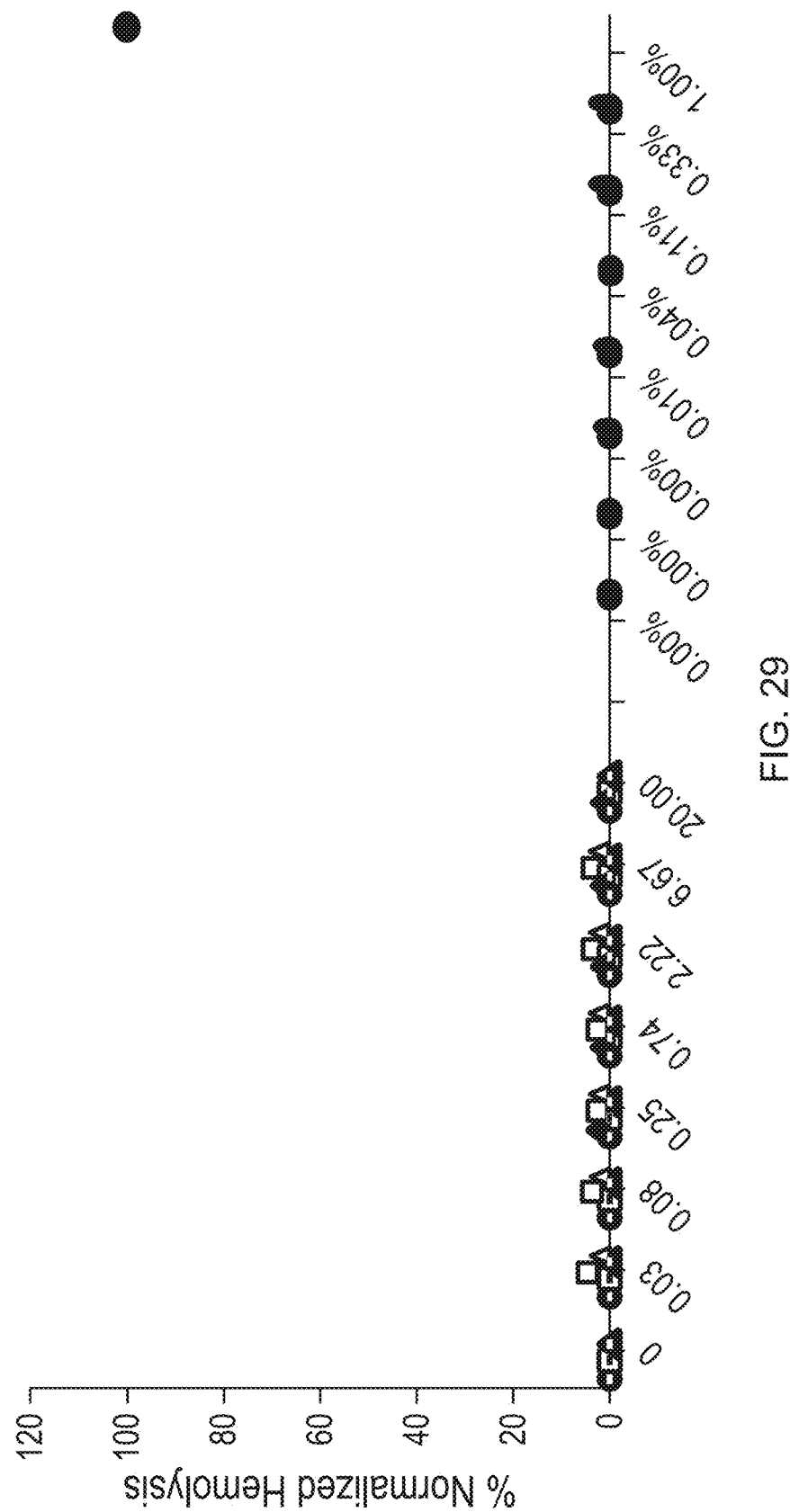
FIG. 29 shows the hemolysis (% normalized) of human red blood cells by: ○ human IgG1 isotype control, ▢ daratumumab, △ AB79, and ● saponin control in µg/ml. Each symbol represents the average of 3 replicates of human (n=5 donors).
Figure 30:
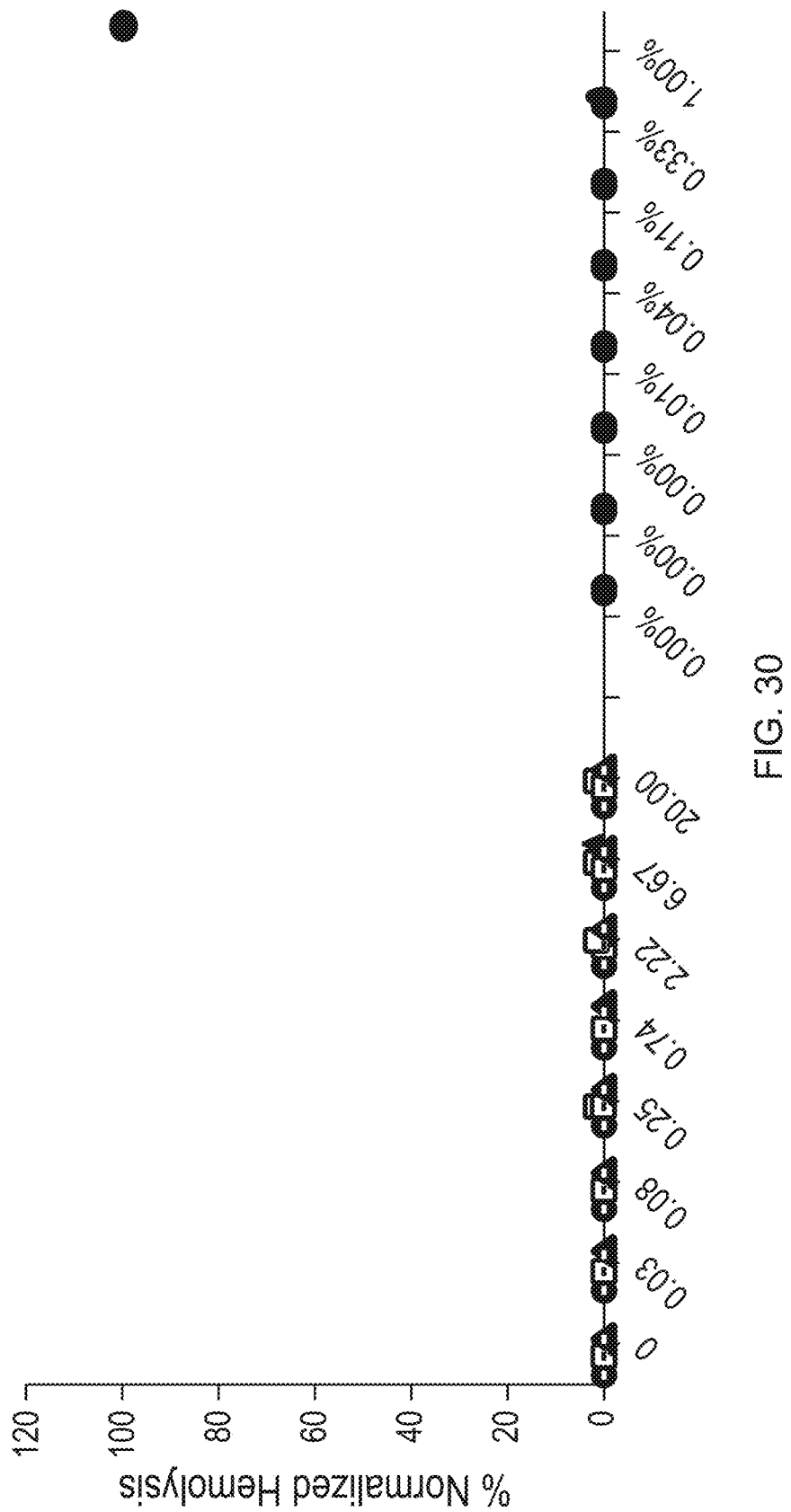
FIG. 30 shows the hemolysis (% normalized) of cynomolgus monkey red blood cells by: ○ human IgG1 isotype control, ▢ daratumumab, △ AB79, and ● saponin control in µg/ml. Each symbol represents the average of 3 replicates of cyno (n=5 donors).

Results: RBCs of all individuals of each species, human and cyno, exhibited in vitro acute hemolysis in response to a 1% saponin solution titration with a hemolytic index of greater than 5. AB79, daratumumab and human IgG1 isotype control did not induce detectable hemolysis in any red blood samples across the species evaluated with a non-hemolytic index of zero (FIGS. 29 and 30).

Example 6: Evaluation of AB79 in a Cynomolgus Monkey Collagen-induced Arthritic Model Expression of the ectoenzyme CD38 is increased on lymphocytes in response to an antigenic challenge and it is hypothesized that targeting these activated lymphocytes could ameliorate pathologic activities in autoimmune diseases. The cynomolgus monkey is an appropriate model for assessing potential effects of targeting CD38 in humans because this species exhibits similar CD38 expression profiles and the human anti-CD38 antibody AB79 binds to monkey CD38 with an affinity ($EC_{50}=4.5$ nM) that enables pharmacologic intervention. The potential activity of AB79 was therefore investigated in a monkey collagen-induced arthritis (CIA) model of autoimmune disease. Prophylactic administration of AB79 (3 mg/kg i.v. weekly) was well-tolerated and prevented the development of arthritis, in contrast to vehicle-treated control animals which exhibited progressive disease with radiographic damage and worsening clinical scores over the course of the study. Therapeutic treatment of arthritic monkeys with AB79 (3 mg/kg i.v. weekly) was also well tolerated and reduced disease progression and symptoms. Arthritis scores and joint swelling were significantly lower than the vehicle control and this was accompanied by decreases in blood levels of CRP, ALP, NK, B and T cells. Histopathology, morphometry and radiology revealed significantly less joint damage in animals exposed prophylactically to AB79 treatment as compared to vehicle-treated animals and significantly ($p<0.05$) less damage in animals treated therapeutically with AB79 or dexamethasone (0.1 mg/kg p.o. daily), illustrating potential disease modifying activity. In conclusion, these data indicate that depletion of CD38-expressing cells could be a therapeutic alternative for treating autoimmune diseases without the deleterious effects of steroids.

Methods and Materials

Antibodies

AB79 was available in-house. Fluorochrome-conjugated anti-mouse IgG was purchased from Jackson Immunoresearch Laboratories (West Grove, PA). Pharmlyse buffer was obtained from BD Biosciences (San Jose, CA). Fluorochrome-conjugated antibodies to monkey proteins were purchased from various sources: CD20 from BD Biosciences (San Jose, CA); mouse antibody to CD3 from eBioscience (San Diego, CA); mouse antibody to CD16 from Miltenyi Biotech (Auburn, CA); mouse antibodies to CD4 and CD8 from R&D Systems. Unconjugated antibodies to AB79 and a humanized control antibody with a different antigen specificity but the same Fc IgG1 were available in-house, in addition to Alexa Fluor 647-conjugated AB79. Primary antibodies for the monkey tissue cross-reactivity investigation were a rabbit anti-AB79 (generated in-house) and a negative control human IgG1 (Millipore Bioscience Research Reagents, Temecula, CA).

Immunohistochemistry of Tissues

The expression profile of the CD38 antigen was compared across 15 different tissue types collected from healthy human and cynomolgus monkey donors using immunohistochemistry. The suitability of each tissue for detecting CD38 was verified using a positive-control antibody against the related transmembrane receptor CD31 (Dako North America, Inc.). Sections (5 m) were cut from fresh-frozen tissue samples embedded in OCT Compound (Sakura Finetek USA, Inc., Torrance, CA) and fixed in acetone for 10 minutes at RT. Just before staining, slides were fixed for 10 seconds in 10% neutral buffered formalin. Acetone/formalin-fixed cryosections were rinsed twice in phosphate-buffered saline (PBS) and incubated for 20 minutes with a protein block (PBS; 0.5% casein; 5% human gamma globulins; 0.02% goat IgG; 1 mg/ml heat-aggregated human IgG) designed to reduce nonspecific binding. Unconjugated AB79 or a negative control human IgG1 (Millipore Bioscience Research Reagents) were applied to sections at 5 or 25 g/ml and incubated at RT for 1 hour. The slides were then rinsed twice with PBS and an indirect immunoperoxidase procedure was performed to detect these primary reagents. The secondary antibody, rabbit anti-AB79, was then applied at 5 g/ml for 30 minutes and rinsed twice with PBS. Endogenous peroxidase was blocked by incubating the slides for 5 minutes with the peroxidase solution provided in the Dako EnVision+Kit and then rinsing twice with PBS. The slides were then treated for 30 minutes with the peroxidase-labeled goat anti-rabbit IgG polymer supplied in the Dako EnVision+Kit, rinsed twice with PBS, and treated for 8 minutes with the substrate-chromogen (DAB+) solution supplied in the Dako EnVision+Kit. All slides were rinsed with tap water, counterstained with hematoxylin, washed, "blued" in saturated lithium carbonate, washed, dehydrated through alcohols, cleared in xylene, and cover-slipped according to standard methods. Staining intensity was graded semi-quantitatively by a blinded American College of Veterinary Pathologists (ACVP)-certified anatomic pathologist.

AB79 Binding to Recombinant CD38

Chinese hamster ovary K1 (CHO-K1) cells stably expressing either human, mouse or monkey CD38 were generated to study cell surface binding of anti-CD38 antibodies. CHO-K1 cells (Lonza, USA) were transfected with full-length cDNA clones of human, mouse or cynomolgus monkey CD38 (Origene Technologies, Rockville, MD). After selection, the pools were sorted by flow cytometry and the highest human, mouse or cynomolgus monkey CD38 expressing clones (top 15% mean fluorescence intensity (MFI)) were utilized for binding studies. 200,000 cells per well were plated in a 96 well round bottom plate and stained with 66.7 nM of directly conjugated Alexa Fluor® 488 to Abs in 50 μl of FACS buffer (1% BSA in PBS) on ice for 30 minutes to 1 hour. Cells were washed 3 to 4 times in a final volume of 200 to 250 μl of FACS buffer. The final cell pellet was resuspended in 100 μl of FACS buffer containing 1% paraformaldehyde. Samples were evaluated on the FACS Canto II HTS (BD Biosciences) and analyzed using Flojo software (Tree Star, USA).

Flow Cytometry of Cell Lines and Whole Blood

For the staining of cell lines, cells were resuspended at $2 \times 10^6$/ml in FACS buffer (5% fetal bovine serum and 0.05% sodium azide in D-PBS (Dulbecco's phosphate buffers saline without calcium and magnesium) (VWR, West Chester, PA) and 200 μl samples were stained with the appropriate monoclonal antibodies at 4° C. for 30 minutes. Samples were washed with FACS buffer and analyzed by flow cytometry (FACSCalibur, BD). For the staining of whole blood, 200 l samples from monkeys were stained with the appropriate monoclonal antibody at 4° C. for 30 minutes. Red blood cells were lysed with BD FACS lysing solution, and samples then washed with FACS buffer and analyzed by flow cytometry. In all cases, antibodies were used at saturating concentrations and, in many cases, up to four antibodies were used per sample.

AB79 Activity in Whole Blood From Cynomolgus Monkeys

Cynomolgus monkey whole blood was obtained from Charles River Laboratories (Wilmington, MA, USA). For binding assays, anticoagulated cynomolgus monkey peripheral whole blood (100 μl) was incubated with increasing concentrations of AB79 antibody (43-690 nM) for 30 minutes at RT. Binding of AB79 to the cells was assayed using a PE-labeled goat anti-human IgG Fc antibody (Thermo Fisher Scientific). Following binding of the antibodies, red blood cells (RBC) were lysed using fixative-free high yield lyse (Thermo Fisher Scientific). The cells were then washed twice with magnetic-activated cell sorting (MACS) buffer containing 0.5% BSA (Miltenyi Biotec). Cell staining data was collected by flow cytometry (Attune NxT Acoustic Focusing Cytometer) and analyzed using FlowJo software.

For cytolysis assays, 90 μL of the whole blood was plated into each well of a 96-well U-bottom plate. Immediately after plating, the whole blood was treated with 0.69, 2.06, 6.17, 18.52, 55.56, 166.67 and 500 nM of AB79 or PBS control for 6, 24 and 48 hours. At each time point, control and testing molecule treated whole blood in the 96-well U-bottom plate was transferred to a deep-well plate for RBC lysis. After lysis, cells were resuspended in stain buffer with CD16-BV605, CD56-PE and CD38-FITC antibodies for surface marker staining. Cells were protected against light and incubated at 4° C. for 20 minutes. After incubation, cells were centrifuged at 350 g at RT for 5 minutes and washed with 1× Annexin V binding buffer. The cells were resuspended in 1× Annexin V binding buffer containing Annexin V Alexa Fluor 647 at RT for 15 minutes. The stained cells were analyzed using a BD FACSCelesta flow cytometer and the data were recorded with BD FACSDiva software, Version 8.0.1. The NK cell viability at each testing concentration and IC50 values of AB79 NK cell depletion at each time point were graphed and fitted with GraphPad Prism 7.04.

Dose-Range Finding Studies in Healthy Monkeys

In a series of investigations, healthy, purpose-bred, experimentally naive cynomolgus monkeys received vehicle control, 0.03, 0.1, 0.3 and 1 mg/kg of AB79 weekly or at 3, 30 or 80 mg/kg bi-weekly via a 20-minute intravenous infusion (Charles River Laboratories). In all investigations, the animals were evaluated for changes in clinical signs (twice daily cage side observations, postdose observations, weekly detailed examinations, food consumption, and weekly body weight). Blood samples were collected pre- and postdose in all investigations for evaluation of pharmacokinetics, pharmacodynamics, and primate antihuman antibodies (PAHA). Investigations were conducted in cynomolgus monkeys in accordance with the testing facility SOP (Charles River Laboratories), which adheres to the regulations outlined in the USDA Animal Welfare Act (9 CFR, Parts 1, 2, and 3) and the conditions specified in the Guide for the Care and Use of Laboratory Animals (ILAR publication, 1996, National Academy Press).

Bioanalytical Procedure for Determination Of AB79 Serum Concentrations

The concentration of AB79 in cynomolgus monkey serum was measured using an enzyme linked immunosorbent assay (ELISA) method. This method is an indirect ELISA utilizing a 96-well microtiter format. The plate was coated with a mouse anti-idiotypic antibody against AB79. Blanks, standards, and quality control (QC) samples containing AB79 at various concentrations as well as monkey serum samples were added to the coated microtiter plate and incubated for 55-65 minutes at RT. After washing the microtiter plate, the detection antibody (peroxidase conjugated affinipure mouse anti-human IgG) was added, and the plate incubated for an additional 55-65 minutes. The plate was washed again, and tetramethylbenzidine (TMB) was added to the wells to generate a chromophore, and the development of color was stopped by the addition of a stopping solution (2N sulfuric acid). The absorbance at 450 nm was measured, and the AB79 concentrations were calculated using a 4-parameter logistic weighted (1/y2) standard calibration curve.

Bioanalytical Procedure for Determination Of Anti-AB79 Antibodies

Anti-AB79 antibody screening of cynomolgus monkey serum was measured using an enhanced chemiluminescence (ECL) method. The design of this qualitative ECL method is such that undiluted cynomolgus monkey serum samples were incubated with 300 mM acetic acid. Acid-dissociated samples were incubated in a mixture of biotinylated AB79, AB79 labeled with SULFO-TAG and 1.5M Trizma base to neutralize the acid and form an immune complex. This complex was then added to a streptavidin-coated MSD plate and allowed to bind. After washing, the complex was detected by the addition of MSD read buffer T to the plate and subsequent excitation of the SULFO-TAG™ via an electrochemical reaction of Ru(bpy)3 to generate luminescence, which was read using the MSD Sector 6000. The quantity of luminescence correlates with the level of cynomolgus monkey anti-AB79 antibodies present in the serum of individual samples. The minimum required dilution (MRD) of cynomolgus monkey serum for this assay was set at 1/30. For graphical representation, all animals were plotted individually as a function of antibody titer and Enrollment day (FIG. 31). Serum samples with values at or below the plate-specific cut-point were plotted using a nominal titer value to facilitate plotting.

Monkey Collagen-Induced Arthritis Model

Ethically responsible use of nonhuman primates was ensured by modeling the pharmacodynamic responses of cynomolgus monkeys to AB79 and then extrapolating the minimum number of animals required per treatment group to yield statistically significant differences in PD responses. Thirty-four naïve female cynomolgus monkeys, ranging from 3-4 years old, 2.5-3.3 kg, were obtained from Biomedical Research (GZ) Ltd (SNBL China). Upon receipt, a health inspection was performed on each animal by the contract research organization (PharmaLegacy Laboratories, Inc., China). The animals were housed one per cage, and acclimated for a minimum of 14 days prior to the commencement of the experimental procedures. The animal room was maintained at a temperature of 20-29° C. with a relative humidity of 40-70%, and a 12-hour light/dark cycle. Animals were trained for receiving intravenous infusions or oral gavage before study initiation. Monkeys had ad libitum access to vegetables, fruit, chow (Shanghai Shilin Biologic Science & Technology Co. Ltd., China) and water according to a conventional protocol. Cages were stratified within the racks to reduce the effect of any environmental influences on the study. This experimental design, all study protocols, and experimental procedures were reviewed and approved by the host Ethics Committee (PharmaLegacy Laboratories Inc), in accordance with Chinese law on animal experimentation.

Monkeys were selected for the study based on pre-screening criteria. One naïve animal was not administered collagen and maintained as a negative control for disease induction. The remaining animals were administered bovine type II collagen (Sichuan, China) dissolved in 0.01N acetic acid (SPGC Sinopharm Chemical Reagent Co., Ltd; Shanghai, China) to a final concentration of 4 mg/mL (Mihara M., et al., Clin Immunol. 2001; 98(3):319-26; Uchiyama Y., et al., Biol Pharm Bull. 2008; 31(6):1159-63; Uchiyama Y, Koike N, Mihara M. Anemia in monkey collagen-induced arthritis is correlated with serum IL-6, but not TNFa. Rheumatol Int 2008 28:879-883; Kato A., et al., Experimental and Molecular Pathology 2008 84:262-270), on Day 0 and Day 21 subcutaneously (Mihara et al. (2001) Clin. Immunol. 98(3):319-26; Uchiyama et al. (2008) Biol. Pharm. Bull. 31(6):1159-63; Uchiyama et al. (2008) Rheumatol. Int. 28:879-883; Kato et al. (2008) Experimental Mol. Path. 84:262-270). Collagen was emulsified with an equal volume of Complete Freund's adjuvant (CFA) (Sigma-Aldrich; St. Louis, USA). The animals were pre-sedated with ketamine (4 mg/kg i.m. and additional anesthesia was applied if needed, as 1.5-5% isoflurane (Inhalation anesthesia machine, Matrix vip3000 isoflurane) to effect with a 0.8-1.5 liter flow rate of oxygen. Any ulcerative skin lesions developing at the immunization sites were treated with iodine each time that an animal was sedated, to prevent infection.

Figure 31B:
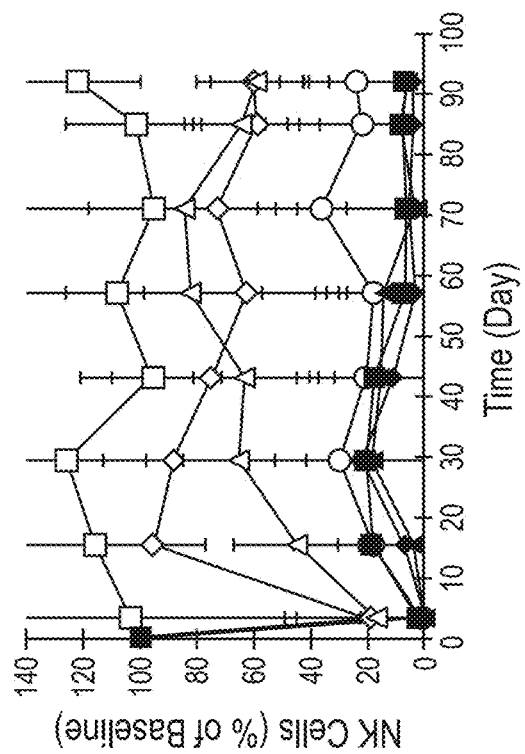
FIG. 31 shows (A) the mean concentration of AB79 in serum from monkeys infused IV with AB79 and the percent change from pre-dose baseline in mean absolute cell counts of (B) CD20-/CD3-/CD16+ NK cells; (C) CD3-/CD20+ B cells; and (D) CD3+ T cells in peripheral blood of monkeys after IV infusion of AB79. Vehicle control (open squares), 0.1 mg/kg (open diamonds), 0.3 mg/kg (open triangles), 1.0 mg/kg (ope circles), 3.0 mg/kg (closed squares), 30.0 mg/kg (closed diamonds) and 80.0 mg/kg (closed triangles) of AB79. Cohorts denoted with open symbols (n=7 animals) were dosed weekly and closed symbols (n=5 animals) biweekly for 3 months. Error bars denote the standard deviation.
Figure 31D:
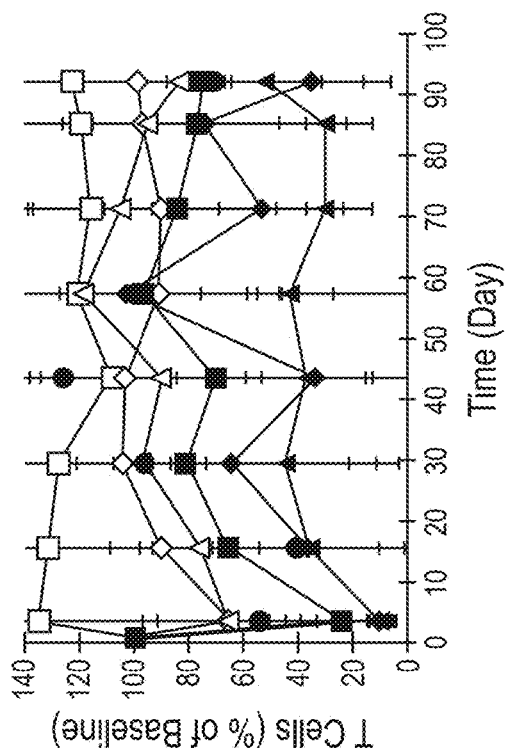
Figure 31A:
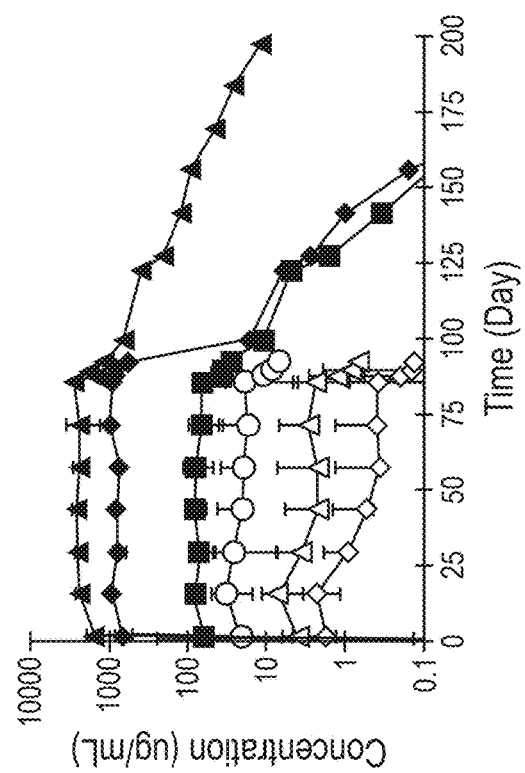

Seven animals receiving collagen were assigned to the prophylactic AB79 group on Day 0 (FIG. 31A). The prophylactic AB79 animals received weekly infusions of 3 mg/kg AB79 starting from Day 7, with the last dose administered on Day 56, for a total of 8 doses (FIG. 31A). Animals in this group were sacrificed on Day 63. The remaining immunized animals were treated as one group and received a weekly 30-minute intravenous infusion of vehicle (saline) starting from Day 7 until an animal reached or exceeded ≥15% of the maximum Clinical Arthritis Score (CIA). At this point the animal was enrolled into the vehicle control group, the therapeutic AB79 group or the therapeutic dexamethasone group and enrollment continued on a rolling basis due to the time differences in disease onset (FIG. 31A). For animals enrolled in the vehicle control group, weekly infusions of vehicle were performed for 5 weeks (FIG. 31A). Animals in this group were sacrificed 7 days after the last dose. For animals enrolled in the therapeutic AB79 group, infusions were performed weekly for 5 weeks (FIG. 31A). Animals in this group were sacrificed 7 days after the last dose. Animals enrolled in the therapeutic dexamethasone group received daily oral gavage for 5 weeks (FIG. 31A) and were sacrificed 1 day after the last dose. Animals were observed daily for signs of ill health and general reaction to treatments. All exceptions to normal healthy appearance and behavior were recorded and detailed in standard clinical observations forms.

Assessment of Arthritic Activity

Body weight of monkeys was measured once during acclimation period (5 days prior to the start of the experiment), on the day prior to each cycle of disease induction, and then once weekly through the end of the study. The number of animals in a group with joint swelling was recorded on Day 0 and Day 21, and then daily through the end of study. The number of proximal interphalangeal (PIP) joints (each hand and foot, respectively) with joint swelling was recorded for each animal on Day 0, Day 21, and then once weekly through the end of the study. The longitudinal and transverse axes of PIP joints of the fore and hind limbs (without thumb) were measured with calipers on Day 0, Day 21, and then once weekly after disease onset through the end of study for all PIPs with arthritis. Mean oval area of 16 PIP joints was calculated and adopted as individual data. The oval area of each PIP was calculated using the following formula: Oval area=longitudinal axis×transverse axis×3.14×¼. Percent oval area change and joint swelling was calculated using the following formula: % change of oval area= (mean oval area on Day X/mean oval area on the day of 1st sensitization)×100. Joint swelling=(mean oval area on Day X—mean oval area on the day of 1st sensitization).

Clinical Arthritis Score

The severity of arthritis of each limb in monkeys were scored on Day 0 and Day 21, and then once weekly through the end of the study according to these criteria: (0) Normal; (1) Mild arthritis, subtle but definite; (2) Moderate swelling; (3) Severe arthritis with significant swelling and/or noticeable joint deformity. The following joints of each paw were examined and scored: 15 joints in total including 5 metacarpophalangeal (MCP) joints, 4 PIP (proximal interphalangeal) joints; 4 DIP (distal interphalangeal) joints, 1 first digit interphalangeal joint; each wrist or ankle was scored as a single compound joint. The knee/elbow of each limb was also evaluated for disease severity. The arthritic score of each animal was the total score of each individual joint with a maximum score of 192 (16X3×4) (16: total number of joints plus the knee/elbow for each limb; 3: maximum score for each individual joint; 4: number of limbs per monkey).

Blood Collection and Analysis

Blood samples were used for CBC, blood chemistry and serum preparation for antibody, PK, and ADA measurements, and were collected from animals at the time points indicated below. Animals from the vehicle control group and the prophylactic AB79 group: During Week 1 and 5, blood was collected twice, once prior to dosing, and once the following day. During Weeks 2, 3, 4, 6, 7 and 8, blood samples were collected just before AB79 administration. During Week 9, blood samples were collected when animals were terminated. All other animals had weekly blood collections up until the time that the disease reached the threshold of 15% of maximum arthritis score. After assignment to the vehicle group, the therapeutic AB79 group, or the therapeutic dexamethasone group, blood samples were collected weekly just prior to dosing and at termination. In addition, samples were collected the day after the first dose of drug and the day after the fifth dose. For the vehicle control, prophylactic AB79, therapeutic AB79 and dexamethasone groups, blood samples for flow cytometry were collected before the first dose (on the day of infusion), on the day following the first dose, before the second dose (on the day of dosing), before the fifth dose (on the day of dosing) and on the day of termination. For the therapeutic AB79 group, blood samples for flow cytometry were collected before the first dose of drug, on the day following first dose, before the 8th dose, before the 29th dose and on the day of termination.

Radiographic Examination

Examinations were performed for each joint (DIP, PIP, $1^{st}$ IP and MCP—sites typically involved in human RA) on the hands and feet of live, anesthetized animals at study termination. Radiographic grading was carried out in a blinded fashion, based on a 0-4 grading system: (0) Normal; (1) Minor deformity in articular cartilage layers, and/or subchondral bone regions; (2) Severe deformity in articular cartilage layers and subchondral bone regions, a small amount of osteophytes present at periosteal surfaces and joint margins that are fuzzy but still visible; (3) The same types of changes observed in grade 2 but advanced further and a large amount of osteophytes present at periosteal surfaces, the joint cavity is indistinguishable or invisible; (4) The same type of changes as in grade 3 but advanced further, the joint cavity becomes undetectable, bones appeared sclerotic or ankylosing, major disfiguration occurs.

Histopathology and Histomorphometry Of Tissue From Arthritic Monkeys

Animals were euthanized by exsanguination under anesthesia at the end of the study. The paws, spleen, colon and lymph nodes (mesenteric and inguinal) were collected and fixed in neutral buffered formalin. PIP joints and DIP joints were decalcified with 15% EDTA, dehydrated and embedded in paraffin: (8 blocks/paw×4 paws×22 animals=704 blocks). Frontal coronal sections of the joints were obtained using a rotary microtome. Histopathology scoring was performed using toluidine blue stained sections (32×22 animals=704 slides) by a bone histopathologist in a blinded manner. The histology sections were qualitatively assessed for the following histopathology features: cell infiltration, pannus, cartilage lesion, and bone resorption. Quantitative histomorphometry was performed using Osteomeasure software (OsteoMetrics, Inc., Atlanta, GA) interfaced with a Nikon Eclipse E400 light/fluorescent microscope and video subsystem. Histomorphometric measurements of the articular area and surface were performed blinded, by a bone histopathologist, using toluidine blue stained slides (704 slides).

Statistical Analysis

Data are presented as Mean±Standard Error of the Mean (SEM). Statistical analyses were conducted with GraphPad Prism on each parameter among naïve, model, and reference drug (dexamethasone) and test article groups. $p<0.05$ was considered significantly different.

Results

Expression Profile of CD38 In Cynomolgus Monkey

To determine if the cynomolgus monkey could be an adequate model for assessing the potential effects of targeting CD38 in humans, the expression profile of the CD38 antigen was compared across 15 different types of tissues collected from healthy human and cynomolgus monkey donors. Immunohistochemistry revealed that AB79 bound to mononuclear leukocytes in colon, stomach, small intestine, bone marrow, and lymph node, as well as some endothelium in the lamina propria of colon, stomach, and small intestine in both species (Table 11).

TABLE 11

Comparison of Expression Profiles of CD38 in Human and Monkey Tissues

| | Human | | | | | Monkey | | | | |
|---|---|---|---|---|---|---|---|---|---|---|
| | Anti-CD38 mAb | | Human IgG1 Control | | | Anti-CD38 mAb | | Human IgG1 Control | | |
| | \multicolumn{10}{c}{Tissue} | | | | | | | | | |
| | 5 µg/mL | 25 µg/mL | 5 µg/mL | 25 µg/mL | AB79 Comments | 5 µg/mL | 25 µg/mL | 5 µg/mL | 25 µg/mL | AB79 Comments |
| Bone marrow | 3, C/M | 2+, M | Neg | Neg | Bone marrow cells, possibly leukocytes | 1+, C/M | 1+, M | Neg | Neg | Few bone marrow cells, possibly leukocytes |
| Heart | Neg | Neg | Neg | Neg | | Neg | Neg | Neg | Neg | |
| Colon | 3+, C/M | 4+, C/M | Neg | Neg | Leukocytes, including lymphocytes, in lamina propria; some endothelium | 2+, C/M | Neg | Neg | Neg | Cells in lamina propria, possibly lymphocytes, some endothelium |
| Stomach | Neg | Neg | Neg | Neg | Leukocytes, including lymphocytes, in lamina propria; some endothelium | 1+, C/M | 1+, C | Neg | Neg | Spindle cells in lamina propria, apparently endothelium |
| Small intestine | 4+, C/M | 4+, C/M | Neg | Neg | Leukocytes, including lymphocytes, in lamina propria; some endothelium | 2+, C/M | 1+, C/M | Neg | Neg | Cells in lamina propria, possibly lymphocytes, some endothelium |
| Renal glomerulus | Neg | Neg | Neg | Neg | in lamina propria; some endothelium | Neg | Neg | Neg | Neg | |
| Renal tubule | Neg | Neg | Neg | Neg | | Neg | Neg | Neg | Neg | |
| Liver | Neg | Neg | Neg | Neg | | Neg | Neg | Neg | Neg | |
| Lymph node | 3+, C/M | 4+, C/M | Neg | Neg | Cells in medullary cords and sinuses; possibly plasma cells; few in cortex | 4+, M | 3+, C | Neg | Neg | Cells in medullary cords and sinuses, fewer in cortex |
| Lung | 3+, C/M | 3+, C/M | Neg | Neg | Interstitial and peribronchiolar cells | Neg | Neg | Neg | Neg | |
| Pancreas | Neg | Neg | Neg | Neg | | Neg | Neg | Neg | Neg | |
| Prostate | 3+, C | 3+, C | Neg | Neg | Acinar epithelium; some interstitial leukocytes | Neg | Neg | Neg | Neg | |
| Skin | Neg | Neg | Neg | Neg | | Neg | Neg | Neg | Neg | |
| Uterus—cervix | 2+, C/M | 1+, C/M | Neg | Neg | Submucosal leukocytes, probably lymphocytes | Neg | Neg | Neg | Neg | |
| Uterus—endometrium | Neg | Neg | Neg | Neg | | Neg | Neg | Neg | Neg | |

Staining Intensity:
1+ = minimal,
2+ = mid,
3+ = moderate,
4+ = marked,
Neg = Negative,
M = Missing.
Staining Frequency of a particular cell type:
Very Rare (VR: <25% of cells);
Rare (R:25-50% of cells);
Occasional (O: >50-75% of cells);
Frequent (F: 76-100% of cells).
Staining pattern include cell type or tissue element (specifics of that cell type (e.g., epithelium) or tissue element (e.g., basement membrane) and subcellular or extracellular (membrane, cytoplasm, cytoplasmic filaments, basement membrane).

Conversely, in humans but not monkeys AB79 also bound to mononuclear leukocytes in liver, lung, prostate, and uterus (cervix), and to prostate acinar epithelium. AB379-binding was not observed in heart, kidney, pancreas, skin, and endometrium of the uterus of either species. AB79 staining was generally moderate to marked (3+ to 4+) in intensity in human tissues and minimal to mild (1+ to 2+) in intensity in cynomolgus monkey tissues (Table 11), which could reflect the difference in affinities of AB79 for human versus monkey CD38 and/or to differences in the magnitude of expression of CD38. The staining pattern was primarily cytoplasmic and cell membranes were stained in some cells (Table 11). Overall, it was concluded that the monkey was an adequate model species to assess the potential pharmacologic effect(s) of targeting CD38 in a model of autoimmune disease.

AB79 Binds to CD38 Expressed By Cynomolgus Monkeys

The amino acid sequence of the human CD38 protein exhibits 91% amino acid identity with its cynomolgus monkey orthologue, 59% with that of mouse and rat and 54% with that of rabbit. A comparison of the binding epitope of AB79 in human CD38 with the corresponding sequence in monkey CD38 revealed a single amino acid substitution of a lysine with a glutamate at position 274. To determine if AB79 could be utilized for assessing the potential effects of targeting CD38 in monkeys, monkey CD38 was expressed in Chinese hamster ovary (CHO) cells and AB79 bound to monkey CD38 with a half-maximal effective concentration ($EC_{50}$) of 4.5 nM (FIG. 32A). This value is approximately 10-fold less than the binding affinity of AB79 for human CD38 expressed by CHO cells (KD=0.7 nM), indicating that AB79 binds monkey CD38 less potently in cynomolgus monkeys than in human counterparts. AB79 also bound to monkey B, NK and T cells in whole blood and NK cells exhibited with a higher mean fluorescent intensity than B cells and T cells (FIG. 32B) indicating that monkey NK cells express a higher density of CD38 per cell. After incubation with monkey whole blood in vitro, AB79 cytolysed NK cells in a dose-dependent manner (FIG. 32C), exhibiting a mean $EC_{50}$ of 29.6 nM, which was approximately 30-fold less potent than cytolysis of NK cells from human peripheral blood by AB79 (data not shown). Collectively these data indicate that cynomolgus monkeys may be less sensitive to the pharmacologic effects of AB79 than humans. Nonetheless, this cross-reactivity profile, as well as similarity in the expression profiles of CD38 suggest that the cynomolgus monkey is a suitable model species for investigating the potential pharmacologic effect(s) of AB79 in vivo.

Pharmacologic Effects Of AB79 In Healthy Monkeys

To characterize the pharmacologic effects of AB79 in vivo, healthy cynomolgus monkeys were infused IV with AB79 at 0.03, 0.1, 0.3 and 1 mg/kg weekly and at 3, 30 and 80 mg/kg bi-weekly for 3 months and a subset of animals were monitored for 3 months after the last dose (FIG. 31A). Peak AB79 concentrations generally occurred at the end of the infusion and were generally dose proportional (Table 12).

TABLE 12

Mean Serum Pharmacokinetic Parameters of AB79 After an Intravenous Infusion into Female Cynomolgus Monkeys

| Dose (mg/kg) | Dose schedule | Sample Timing | $C_{max}$ (μg/mL) | $AUC_{366}$ (hr*μg/mL) | $T_{1/2}$ (hr) |
|---|---|---|---|---|---|
| 0.1 | Weekly | Week 1 | 1.77 | 104 | NC |
| | | Week 13 | 2.49 | 218 | NC |
| 0.3 | Weekly | Week 1 | 4.32 | 327 | NC |
| | | Week 13 | 7.78 | 665 | NC |
| 1.0 | Weekly | Week 1 | 21.1 | 1630 | NC |
| | | Week 13 | 28.6 | 2700 | NC |
| 3 | Biweekly | Week 1 | 62.1 | 7600 | NC |
| | | Week 13 | 90.1 | 18,400 | 237 |
| 30 | Biweekly | Week 1 | 680 | 92,800 | NC |
| | | Week 13 | 962 | 228,000 | NC |
| 80 | Biweekly | Week 1 | 1630 | 220,000 | NC |
| | | Week 13 | 3140 | 456,000 | 415 |

Exposure generally increased in a dose-proportional manner at steady state in animals which did not exhibit anti-AB79 antibodies and accumulated 1.7 to 2.4-fold by week 13 (Table 12), which is consistent with decreased clearance due to target-mediated drug disposition of AB79. The half-life after the last dose of animals in the 3 and 80 mg/kg cohorts which did not exhibit anti-AB79 antibodies was 237 and 415 hours, respectively (Table 12). No gender differences in PK characteristics were observed.

The NK cell population expressed CD38 with a uniformly high density (FIG. 32B) and were reduced in peripheral blood after the first infusion of AB79 with a $ED_{50}$ of 0.3 mg/kg (FIG. 31B), a corresponding $C_{max}$ of 7.63 μg/mL and an overall mean exposure of 665 hr*μg/mL at week 13 (Table 12). In contrast, the B cell population expressed CD38 heterogeneously, with a lower median density NK cells (FIG. 32B), and were reduced in peripheral blood after the initial infusion of AB79 with an $ED_{50}$ of 1.0 mg/kg (FIG. 31C), a $C_{max}$ of 21.1 μg/mL and an overall mean exposure of 2700 hr*μg/mL at week 13 (Table 12). The T cell population also expressed CD38 heterogenously with an even lower median density than that of B cells (data not shown) and was reduced in peripheral blood after the first infusion of AB79 with an $ED_{50}$ of 30 mg/kg (FIG. 31D), a $C_{max}$ of 62.1 μg/mL and an overall mean exposure of 18400 hr*μg/mL at week 13 (Table 12). Collectively, these dose-range finding data indicated than a weekly dose of 3 mg/kg would sustain the total NK, B and T cell populations by greater than 80, 60 and 20% from baseline levels in peripheral blood, respectively.

Profile Of AB79 In Collagen-Induced Arthritis

Figure 33:
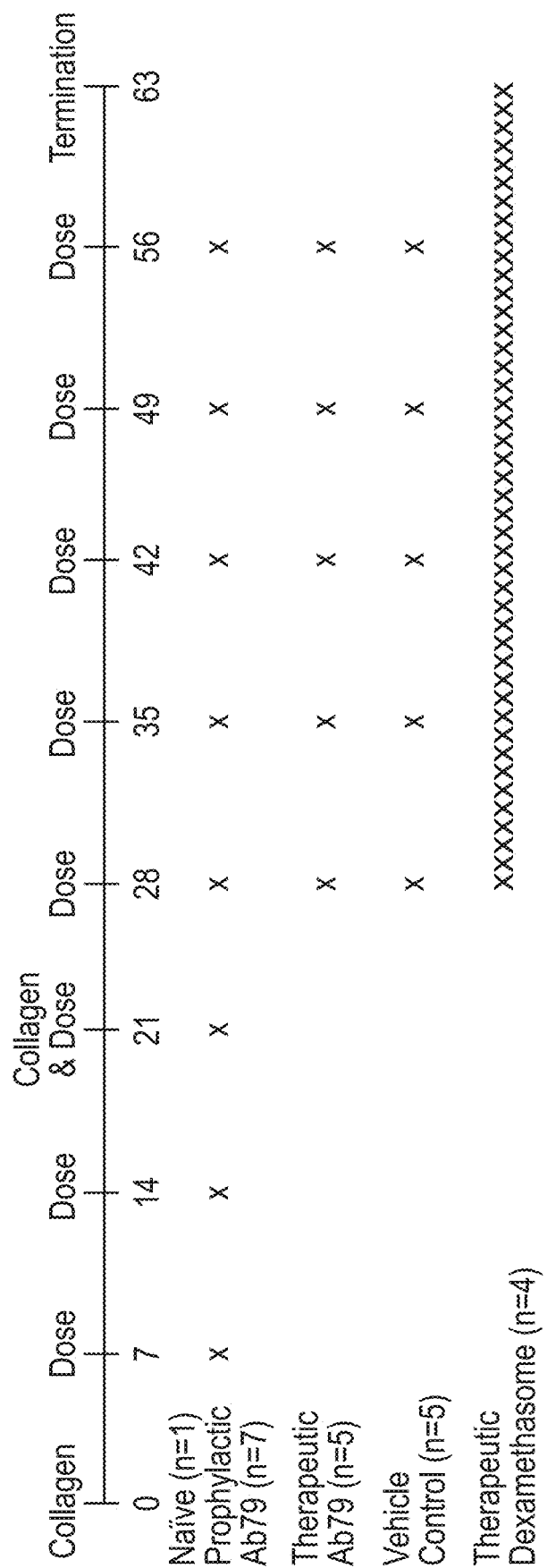
FIG. 33 shows the schedule of dosing strategy for Example 7.

Potential efficacy of AB79 was investigated with a CIA model in cynomolgus monkeys, a species whose immune system, joints and skeletal anatomy is similar enough to human counterparts to enable using clinical indices. To induce arthritis, monkeys were treated intradermally on Day 0 and Day 21 with type II collagen (FIG. 33) and the emergence of anti-collagen antibodies confirmed successful immunization of each animal (data not shown). One group of animals was treated on Day 7 with a 3 mg/kg prophylactic AB79 treatment regimen that continued for 8 weeks. In the 3 therapeutic groups, monkeys which had overt disease were randomized and administered a vehicle control, 3 mg/kg TAK 079, or 0.1 mg/kg dexamethasone. Therapeutic treatment continued for 5 weeks after initiation of treatment (FIG. 33).

Figure 34B:
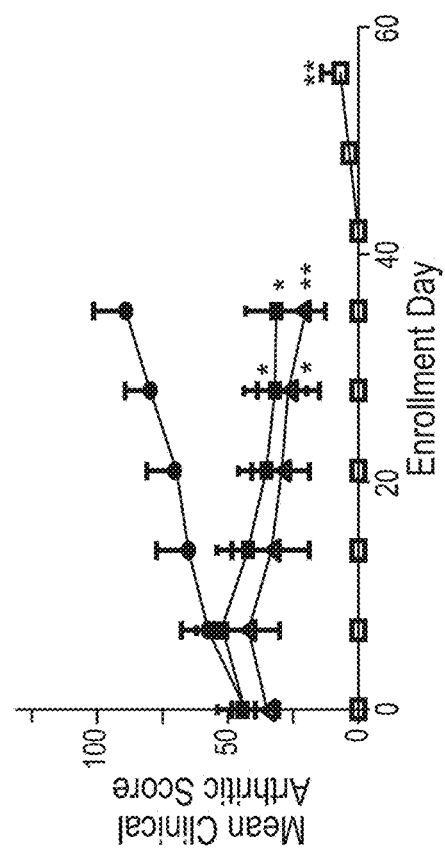
FIG. 34 shows the (A) body weight measurements normalized for percent change from the time of enrollment: A non-arthritic control animal (open circles); untreated arthritic animals (closed circles); animals treated prophylactically with AB79 (open squares); animals treated therapeutically with AB79 (closed squares); animals treated therapeutically with dexamethasone (open triangles; (B) Mean Clinical Arthritis score from 16 joints: Untreated arthritic animals (closed circles); animals treated prophylactically with AB79 (open squares); animals treated therapeutically with AB79 (closed squares); animals treated therapeutically with dexamethasone (open triangles); (C) The number of PIP joints with joint swelling; and (D) The mean oval area of 16 PIP joints calculated and reported as the Mean Joint Swelling for each animal. Radiographic examination was performed following X-ray imaging for every joint of (E) DIP and (F) MCP. Data are the mean±standard error for each group. * $p<0.05$ ** $p<0.01$ as compared to the untreated group (One-ANOVA\Dunn's Multiple Comparison Test).
Figure 34D:
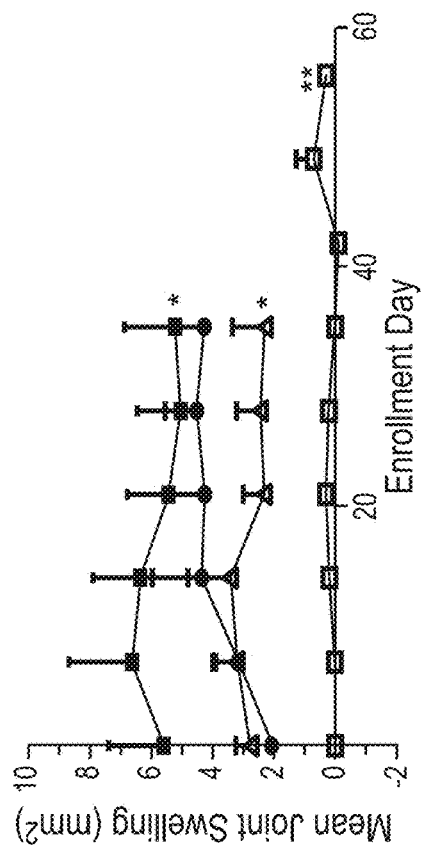
Figure 34A:
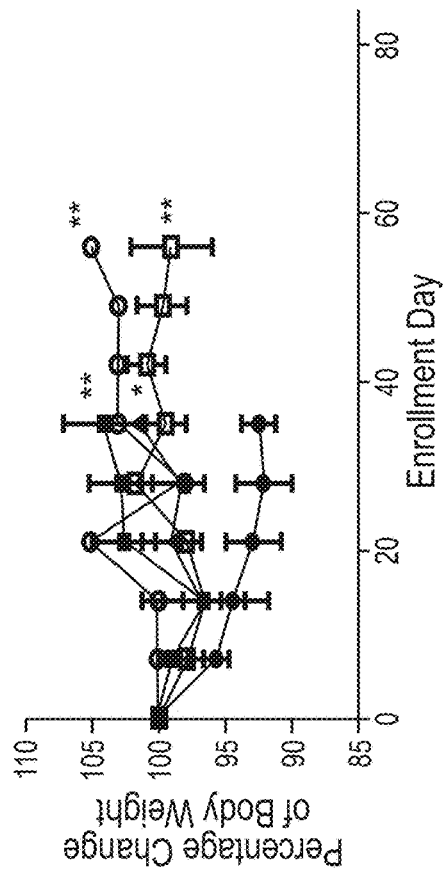
Figure 34C:
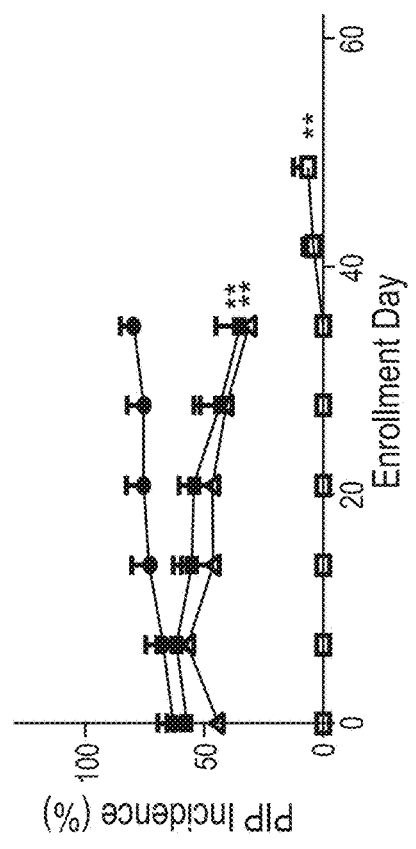
Figure 34F:
Figure 34E:
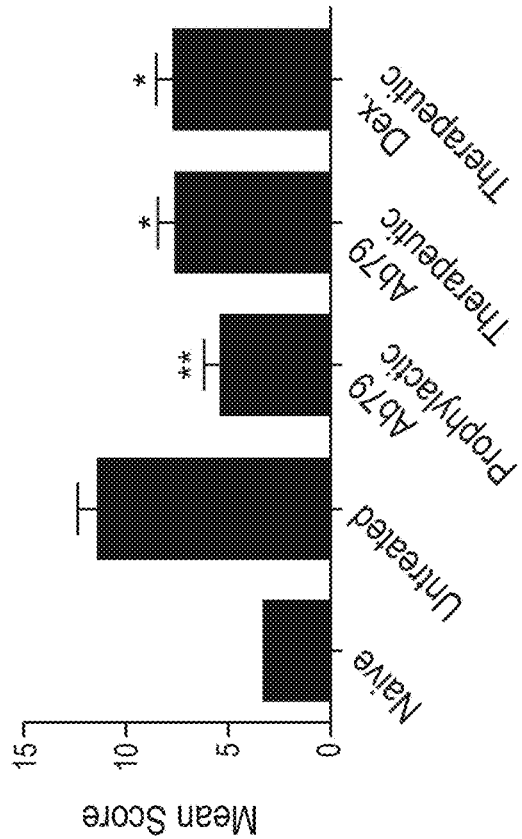
Figure 35A:
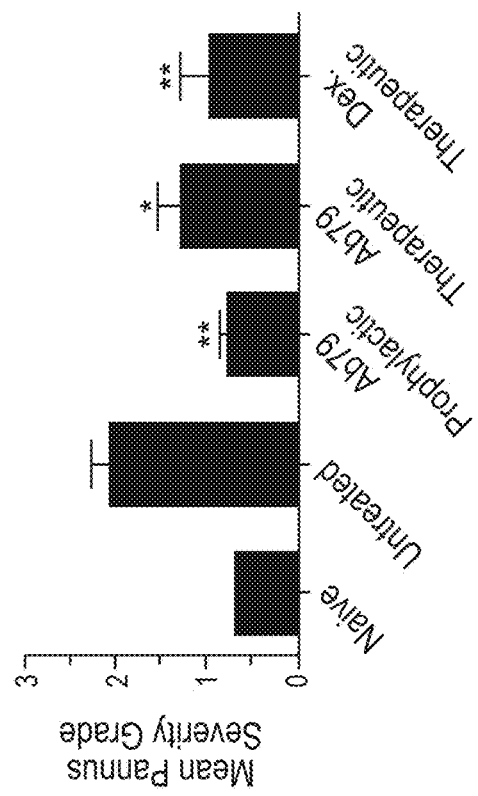
FIG. 35 shows prophylactic exposure to AB79 resulted in composite scores which were significantly less ($p<0.01$) than the vehicle control value and comparable in magnitude to animals not immunized with collagen (FIG. 35A). AB79 had a similar effect on each component; scores were significantly less ($p<0.01$) than the vehicle control value for pannus (FIG. 35B); infiltrating leukocytes (FIG. 35C); cartilage lesions (FIG. 35B); bone resorption (FIG. 35E); and osteophyte formation (FIG. 35F).
Figure 35B:
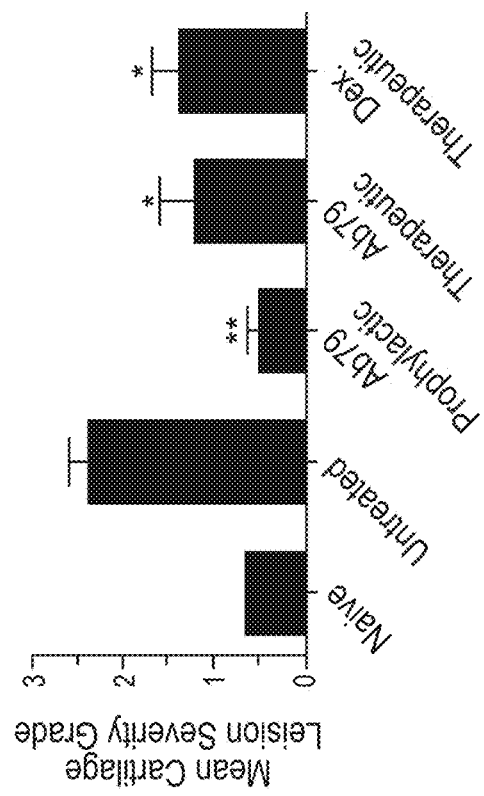
Figure 35C:
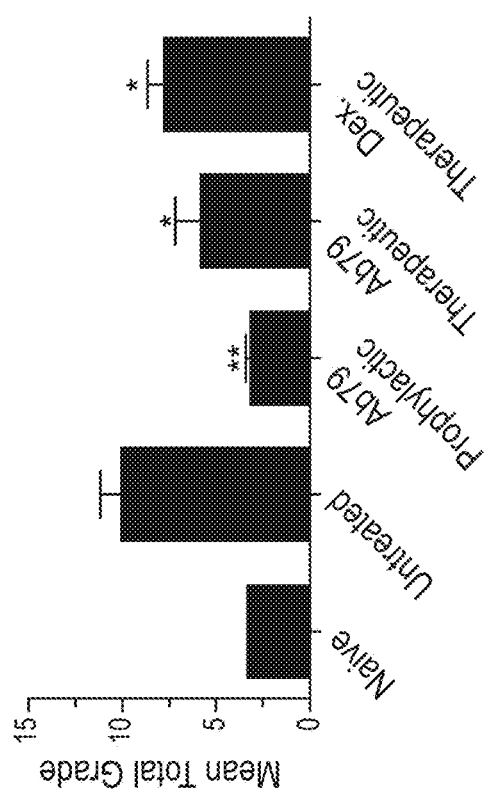
Figure 35D:
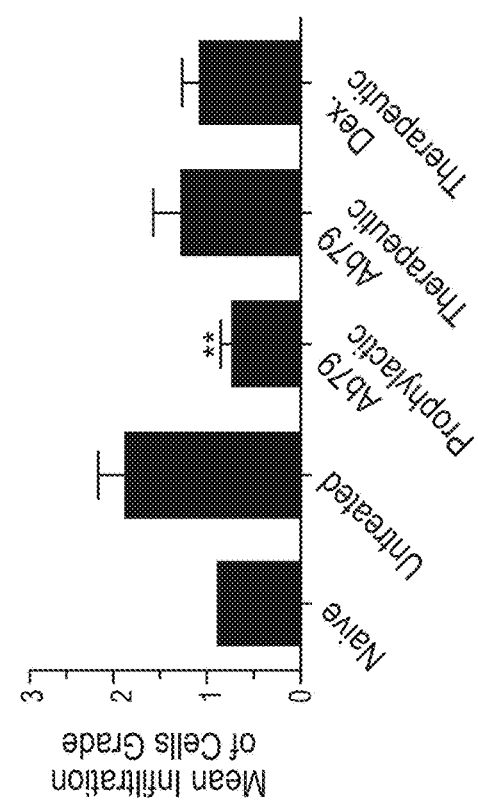
Figure 35F:
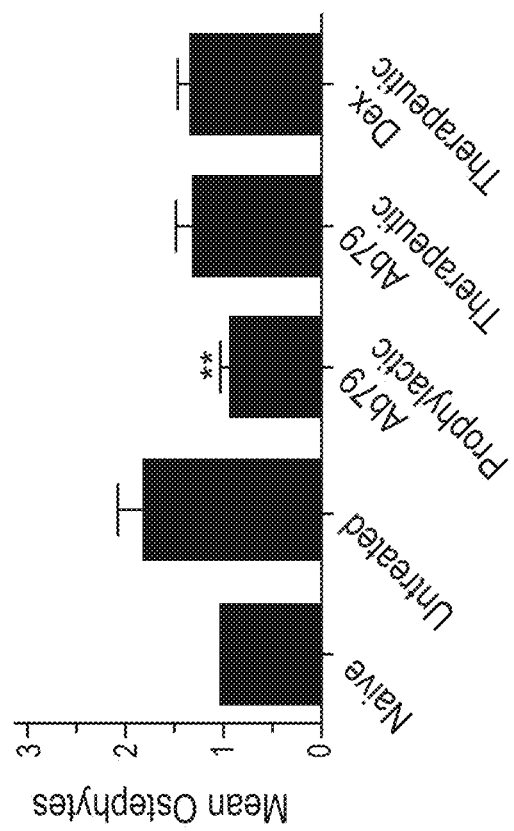
Figure 35E:
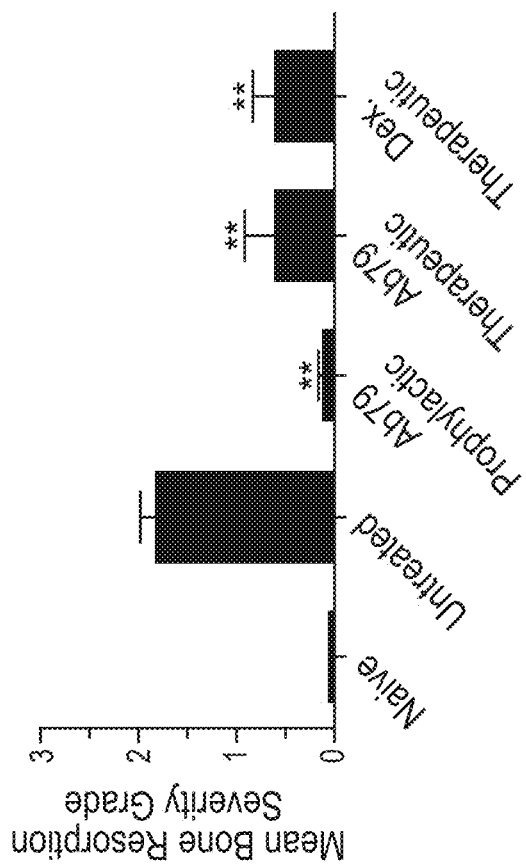

AB79 was well tolerated in both the prophylactic and therapeutic regimens. The healthy control monkey gained body weight over time, whereas the collagen-immunized monkeys in the other four groups started to lose body weight from day 7 (FIG. 34A), indicating a systemic impact associated with the development of arthritis. Based on the percentage change in body weight against baseline body weight upon enrollment, the animals in the prophylactic AB79 group, the therapeutic AB79 group, and the therapeutic dexamethasone group were found to re-gain their body weight beginning 14 days after the start of treatment, suggesting a therapeutic benefit from both AB79 and the dexamethasone positive control treatment. Weight gain approached near-normal levels in the AB79- and dexamethasone-treated monkeys compared with a healthy, untreated control; arthritic animals treated with vehicle lost weight (FIG. 34A). The severity of arthritis was assessed using the Clinical Arthritis Score which is a global assessment of disease activity that considers every measurable joint in the animal over the course of the study using a 192-point scoring system. Vehicle-treated animals exhibited progressive disease, with increasing clinical scores over the course of the study (FIG. 34B). Prophylactic exposure to AB79 prevented the development of arthritis significantly ($p<0.01$) as compared to the vehicle control. Similarly, therapeutic treatment with AB79 or dexamethasone inhibited the development of arthritis significantly ($p<0.05$) as compared to vehicle control and reduced arthritis scores from the pretreatment baselines (FIG. 34B). Similar effects were observed in the subset of PIP joints both with respect to the number of inflamed PIP joints (FIG. 34C) and the overall mean swelling of all PIP joints (FIG. 34D). To obtain a comprehensive assessment of the arthritic joints and the potential for AB79 to have 'disease modification' activity in human arthritis, radiographic examination was performed for every IP and MCP joint. Prophylactic exposure to AB79 prevented damage in PIP (data not shown), DIP (FIG. 34E) and MCP (FIG. 34F) joints significantly ($p<0.01$) as compared to vehicle control. Similarly, therapeutic exposure to AB79 or dexamethasone resulted in significantly ($p<0.05$) less damage in PIP (data not shown), DIP (FIG. 34E) and MCP (FIG. 34F) joints than in vehicle control animals. To characterize components of the progressive arthritis, DIP and PIP joints were analyzed histologically with respect to cell infiltration, pannus severity, cartilage damage, bone resorption and osteophyte formation. Prophylactic exposure to AB79 resulted in composite scores which were significantly less ($p<0.01$) than the vehicle control value and comparable in magnitude to animals not immunized with collagen (FIG. 35A). AB79 had a similar effect on each component; scores were significantly less ($p<0.01$) than the vehicle control value for pannus (FIG. 35B), infiltrating leukocytes (FIG. 35C), cartilage lesions (FIG. 35D), bone resorption (FIG. 35E) and osteophyte formation (FIG. 35F). Similar differences of lesser magnitude were also observed for therapeutic treatment with AB79 or dexamethasone (FIGS. 35A-E), although not all differences reached statistical significance.

Figure 36B:
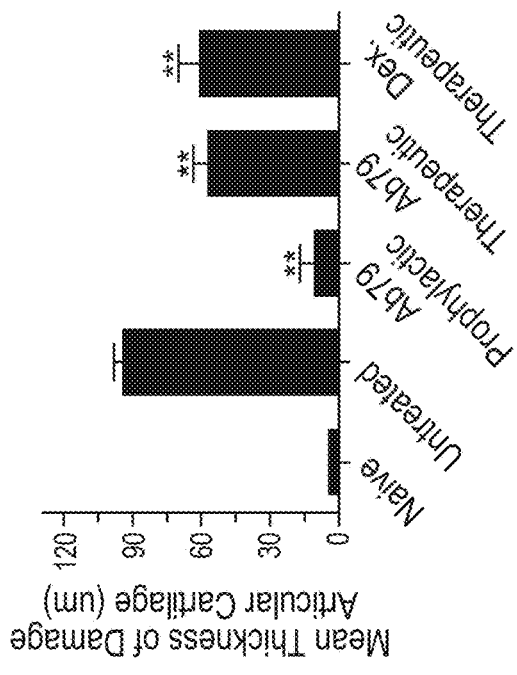
FIG. 36 shows quantitative histomorphometry of the articular area and surface of DIP joints performed blinded by a bone histopathologist using toluidine blue stained slides (32×22 animals=704 slides). The individual results from each animal were plotted as the mean±standard error for each group. Statistical analysis was conducted as specified on the chart above. (A) total articular cartilage area; (B) thickness of damaged articular cartilage; (C) percent of damaged articular surface; and (D) osteophyte area. Data are the mean±standard error for each group. * $p<0.05$ ** $p<0.01$ as compared to the untreated group (One-ANOVA\Dunn's Multiple Comparison Test).
Figure 36D:
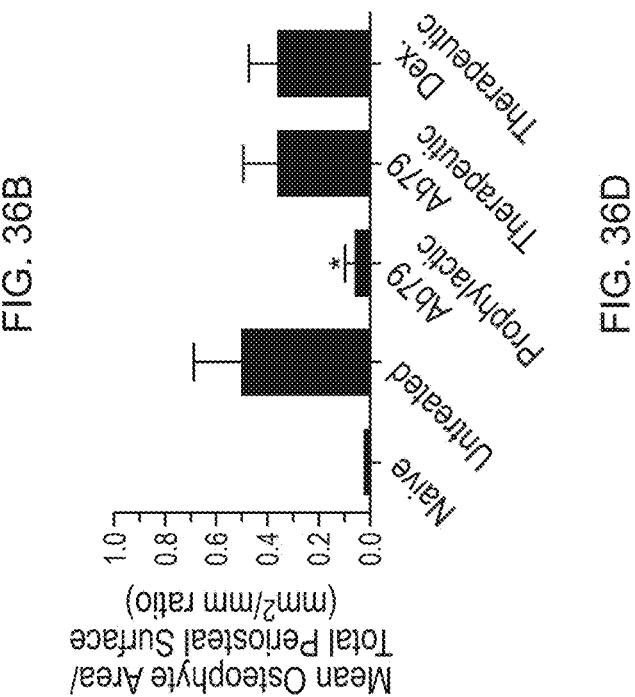
Figure 36A:
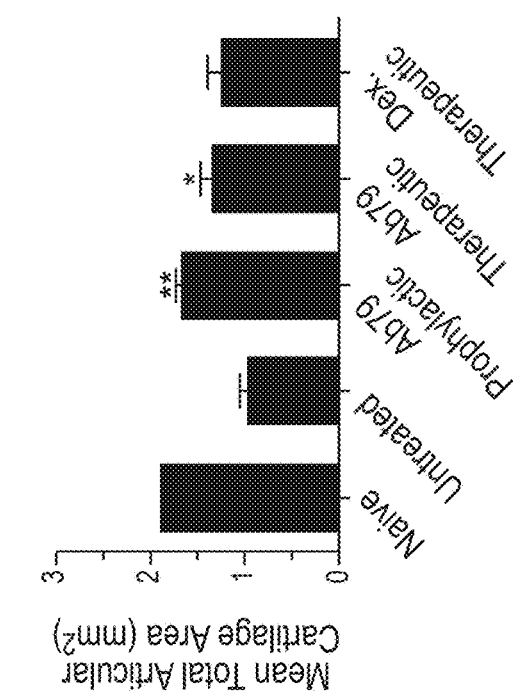
Figure 36C:
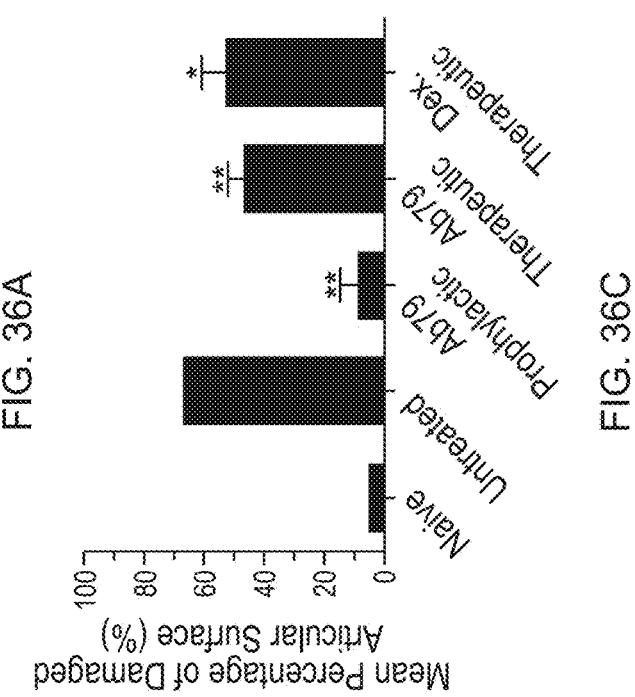

Quantitative histomorphometry was performed on all DIP and PIP joints in blind studies by a board-certified, veterinary pathologist, including articular cartilage area (FIG. 36A), thickness of damage articular cartilage (FIG. 36B), percentage of damaged articular surface (FIG. 36C) and osteophyte area versus total periosteal surface (FIG. 36D). All the parameters illustrated that prophylactic exposure to AB79 prevented the development of articular damage significantly. Therapeutic treatment with AB79 reduced the severity of disease, although some histomorphometric measures didn't achieve statistical significance. The therapeutic effects of AB79 were similar to dexamethasone administered therapeutically.

Figure 37B:
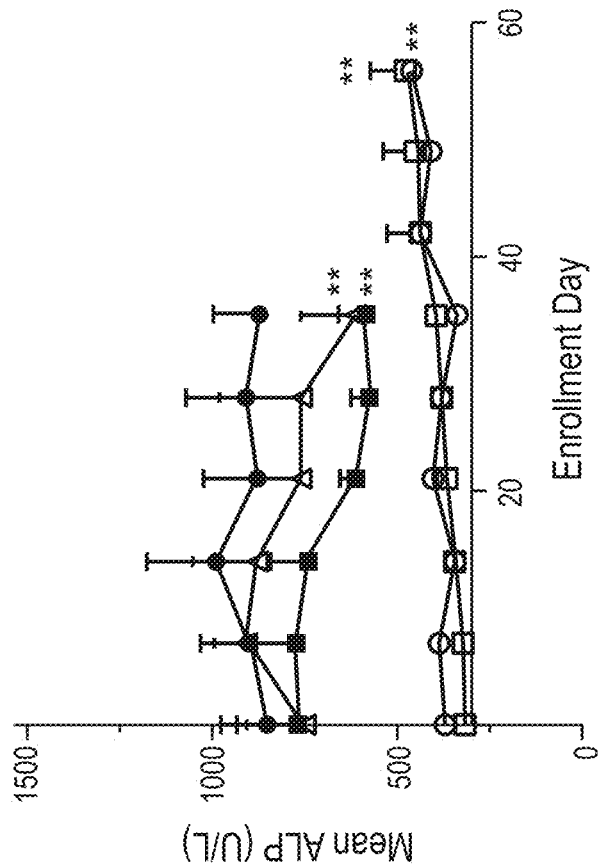
FIG. 37 shows serum chemistry levels of (A) CRP and (B) ALP over time. A non-arthritic control animal (open circles); untreated arthritic animals (closed circles); animals treated prophylactically with AB79 (open squares); animals treated therapeutically with AB79 (closed squares); animals treated therapeutically with dexamethasone (open triangles). Data are the mean±standard error for each group. * $p<0.05$ ** $p<0.01$ as compared to the untreated group (One-ANOVA\Dunn's Multiple Comparison Test).
Figure 37A:
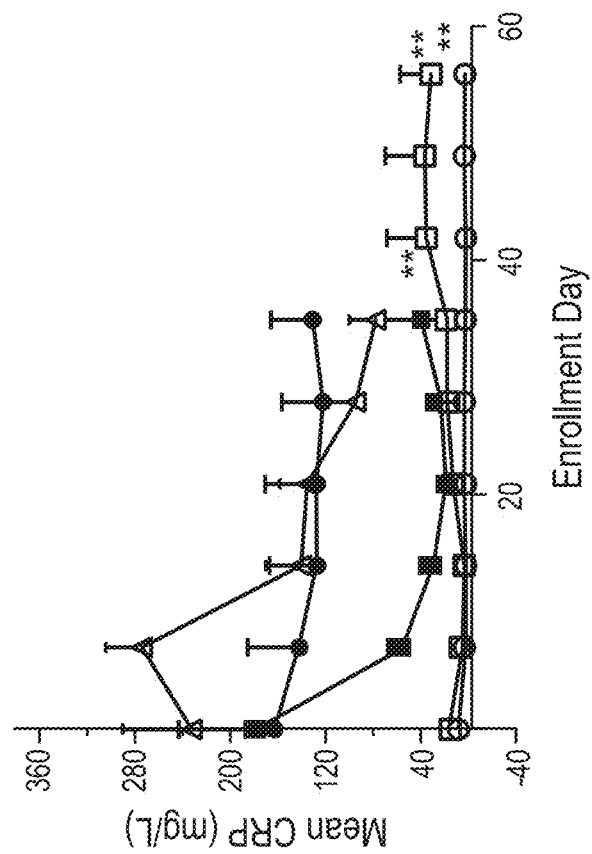

Levels of C-reactive protein (CRP) (FIG. 37A), alkaline phosphatase (ALP) (FIG. 37B) and albumin (ALB) (data not shown) correlated with disease severity. Prophylactic treatment with AB79 prevented the inflammation-associated increases in CRP (FIG. 37A) and ALP (FIG. 37B) observed in the vehicle control animal. Therapeutic treatment with AB79 caused a rapid decrease in CRP and ALP, whereas prolonged treatment with dexamethasone was required to reduce CRP and ALP levels (FIGS. 37A and 37B, respectively). No evidence of liver damage was found in serum chemistry parameters (e.g., increased ALT or AST), which suggests that the increased ALP was due to the development of bone disease in animals with CIA, and that the reduced ALP was due to reduced bone damage in AB79-exposed animals. Serum chemistry values for creatinine, blood urea nitrogen, glucose, and total protein varied over time but showed no consistent correlation with arthritis severity or treatment regimen (data not shown).

Figure 38A:
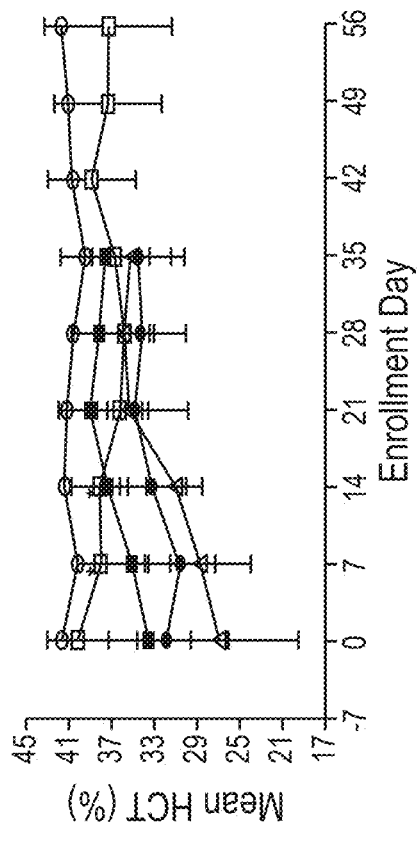
FIG. 38 shows levels of (A) red blood cells; (B) hematocrit; (C) reticulocytes, (D) platelets, (E) neutrophils, and (F) lymphocytes in animals over time: A non-arthritic control animal (open circles); untreated arthritic animals (closed circles); animals treated prophylactically with AB79 (open squares); animals treated therapeutically with AB79 (closed squares); animals treated therapeutically with dexamethasone (open triangles). Data are the mean±standard error for each group. * $p<0.05$ ** $p<0.01$ as compared to the untreated group (One-ANOVA\Dunn's Multiple Comparison Test).
Figure 38B:
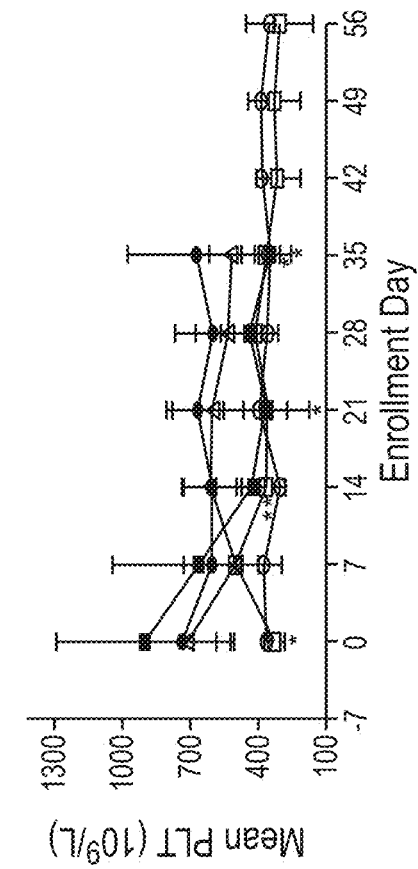
Figure 38C:
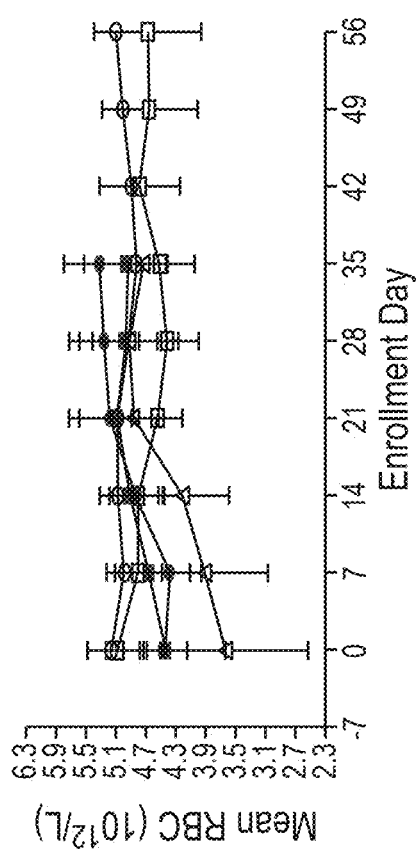
Figure 38D:
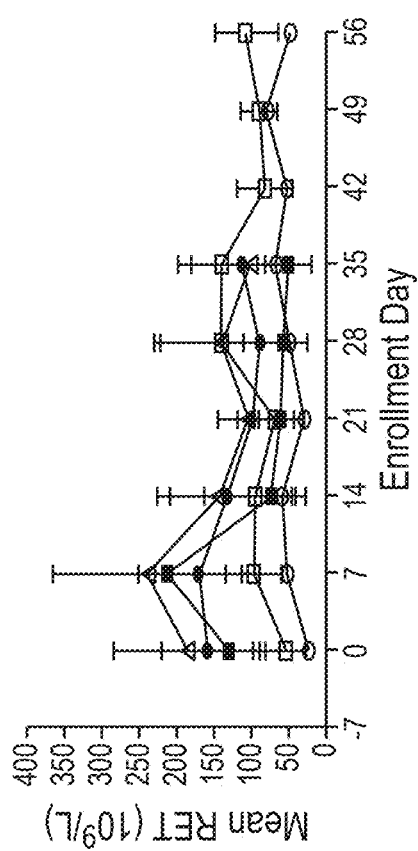
Figure 38F:
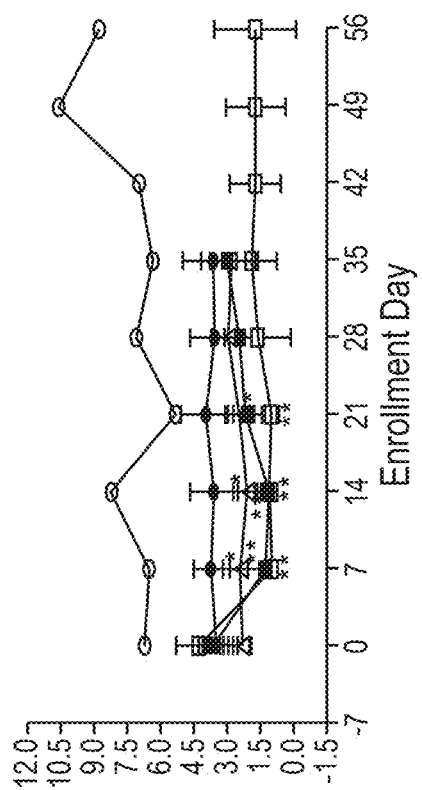
Figure 38E:
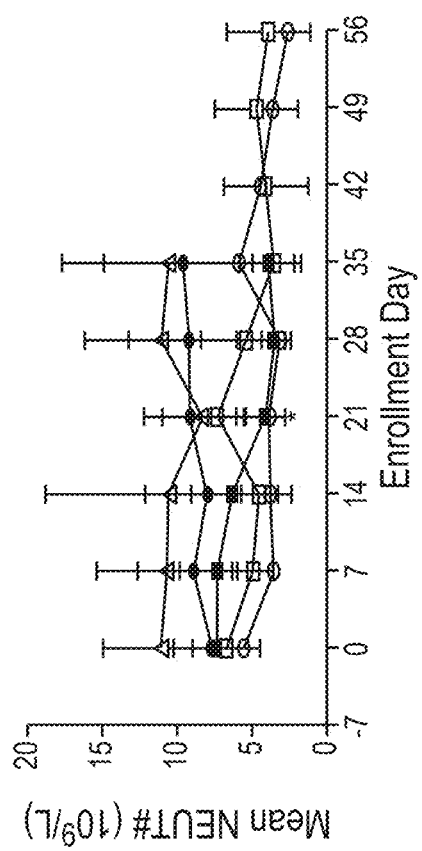

Hematology, complete blood count and differential analysis was conducted during the study and key parameters were reported. No change was observed in levels of RBCs after exposure to AB79 or dexamethasone (FIG. 38A). Furthermore, the hematocrit count was decreased after development of arthritis and increased back toward the naïve control levels after treatment with either AB79 or dexamethasone (FIG. 38B). Reticulocytes were elevated after development of arthritis and both AB79 and dexamethasone treatment reduced the reticulocyte count toward the normal level found in the naïve control (FIG. 38C). Both platelet and neutrophil levels were elevated with arthritis and AB79 treatment reduced both platelet and neutrophil levels toward the naïve control, whereas dexamethasone had no effect (FIGS. 38D and 38E, respectively). In contrast, total lymphocyte levels were decreased with disease relative to the naïve control and treatment with AB79, as expected, further reduced lymphocyte levels, whereas treatment with dexamethasone had no effect (FIG. 38F).

Figure 39A:
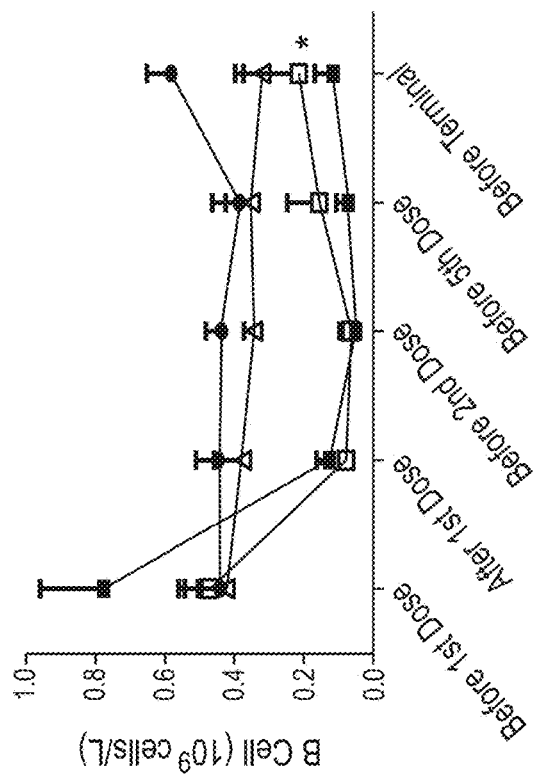
FIG. 39 shows levels of (A) NK cells; (B) B cells; (C) T cells and; (D) monocytes in peripheral blood over time: A non-arthritic control animal (open circles); untreated arthritic animals (closed circles); animals treated prophylactically with AB79 (open squares); animals treated therapeutically with AB79 (closed squares); animals treated therapeutically with dexamethasone (open triangles). Data are the mean±standard error for each group. * $p<0.05$ ** $p<0.01$ as compared to the untreated group (One-ANOVA\Dunn's Multiple Comparison Test).
Figure 39B:
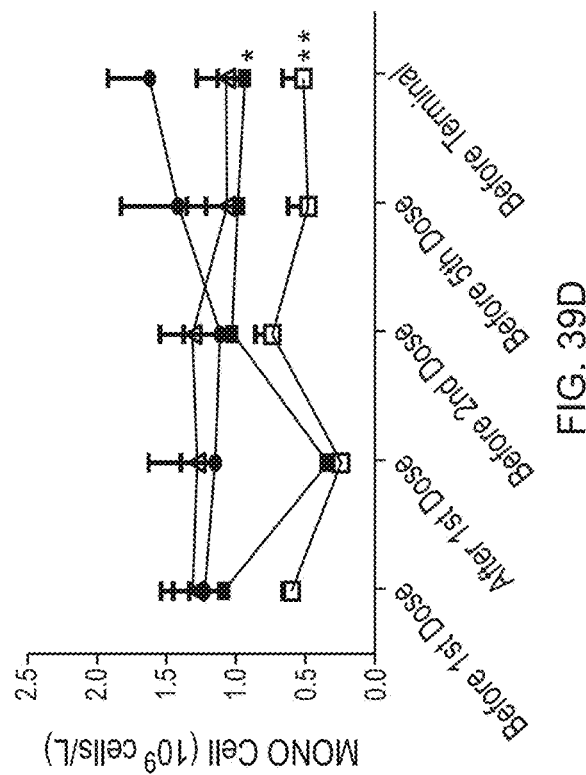
Figure 39C:
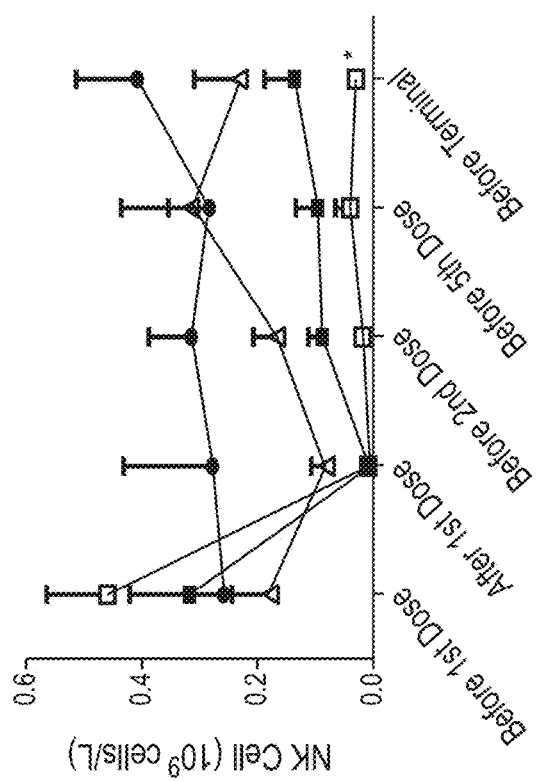
Figure 39D:
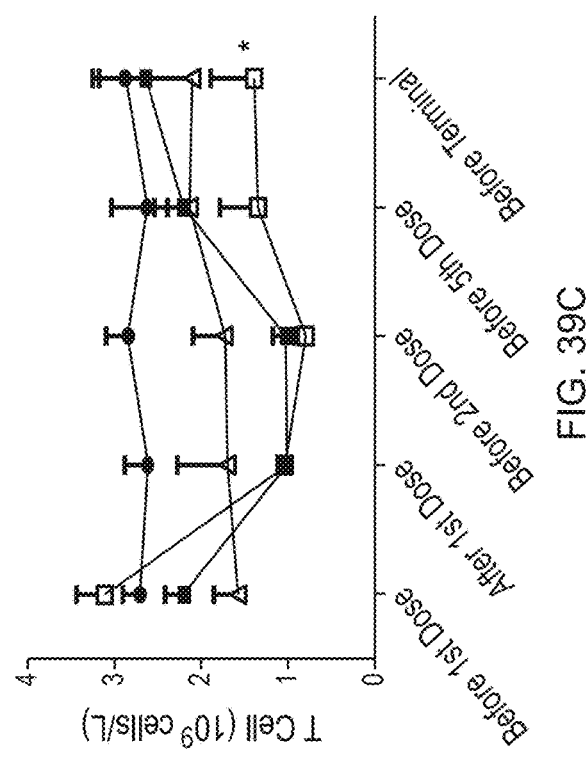
Figure 40A:
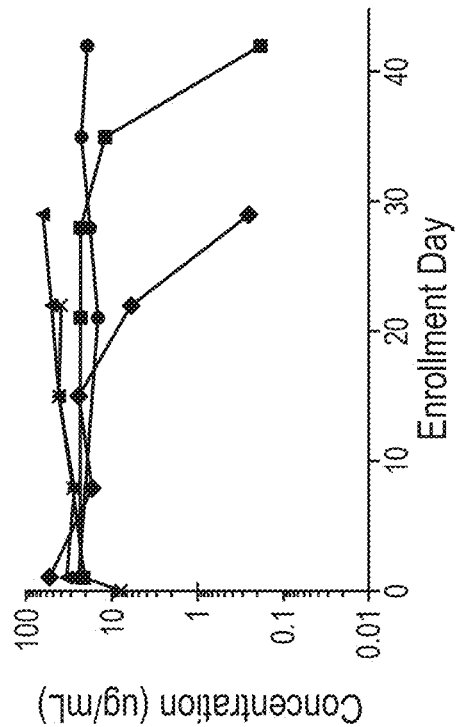
FIG. 40 shows serum concentrations of AB79 in individual monkeys when administered (A) prophylactically or (B) therapeutically. Serum concentrations of anti-AB79 antibodies in individual monkeys when administered (C) prophylactically or (D) therapeutically.
Figure 40B:
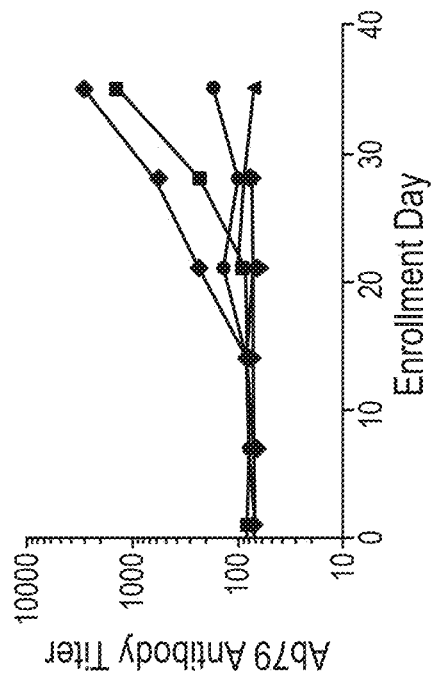
Figure 40C:
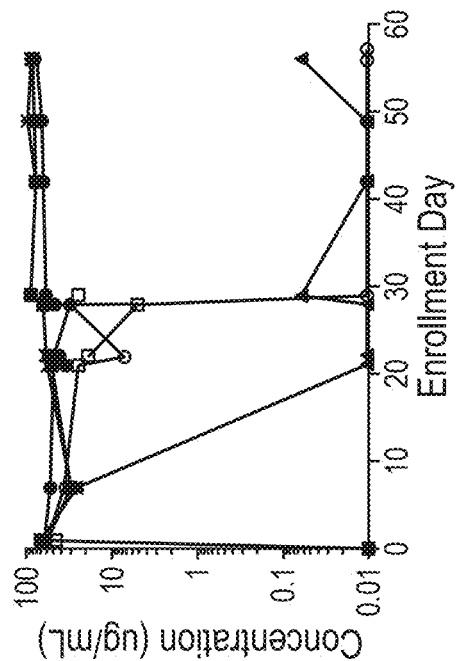
Figure 40D:
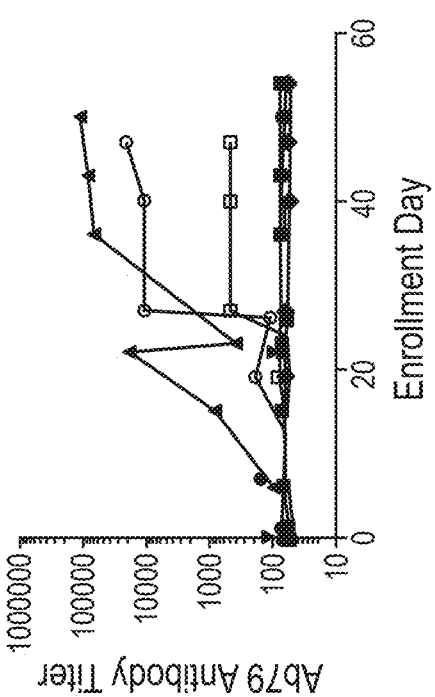

Among subsets of lymphocytes in peripheral blood, NK cells were reduced >95% below baseline levels (FIG. 39A) within 24 hours of exposure to AB79, whereas baseline levels of B cells (FIG. 39B), T cells (FIG. 39C), and monocytes (FIG. 39D) were reduced by a maximum of 60%, 55% and 50%, respectively. NK and B cell reductions were sustained throughout dosing, whereas T-cell and monocyte reductions were transient and only observed after the first infusion. A similar reduction pattern was seen in each cell population after AB79 prophylactic treatment, except this group of animals had lower monocyte levels before treatment, and the monocyte levels did not change in response to treatment. No differences were seen in B, NK, T cells, or monocyte counts between vehicle and dexamethasone-treated animals (FIGS. 39A, 29D, and 29F, respectively). Serum bioanalysis was conducted to measure concentrations of AB79 and anti-AB79 antibodies. Substantial exposure was achieved in each animal dosed prophylactically (FIG. 40A) or therapeutically (FIG. 40B) with the $C_{max}$ ranging from 24-97 µg/mL. All animals exposed to AB79 exhibited trough concentrations that exceeded the $EC_{50}$ for CD38 saturation (FIG. 32A) and NK cell lysis (FIG. 32C) in vitro. Anti-AB79 antibodies were detected in 4 of 7 animals in the prophylactic group (FIG. 40C) from 14-30 days after initial dosing and until the end of the study. Two animals exhibited high titers which corresponded with low concentrations of AB79 in these animals by Day 31 (FIG. 40A) indicating that these anti-AB79 antibodies may be affecting clearance. Anti-AB79 antibodies were also detected in 4 of 5 animals in the therapeutic group (FIG. 40D) from 21 days after initial dosing until the end of the study and two animals also exhibited high titers which corresponded with low concentrations of AB79 in these animals by the end of the study (FIG. 40B). Nonetheless, all animals were included in data analyses because most target cells remained reduced from baseline levels throughout the duration of the study (FIGS. 39E and 39F), the exception being T cells after the second therapeutic dose (FIG. 39G).

DISCUSSION

A deficiency of CD38 in mice was reported to result in attenuated forms of CIA, illustrating a nonredundant function(s) of this molecule in a model of autoimmune disease, however the role of CD38 cells in primate models has not been investigated. In addition, numerous studies have indicated that the overall level of CD38 expression on peripheral blood cells correlates positively with disease activity in human RA and SLE patients (Cole S., et al., *Arthritis Res Ther.* 2018 May 2;20(1):85; Kraan M. C., et al., Rheumatology (Oxford). 1999 November; 38(11):1074-80; Vital E. M., et al., *Arthritis Rheum.* 2011 October;63(10):3038-47; or Banchereau R., et al., Cell. 2016 Apr. 21; 165(3):551-65). The anti-CD38 mAb AB79 depleted plasma cells in blood or bone marrow samples from patients with RA or SLE in vitro (Smithson et al. (2017) J. Immunol. 198 (1 Supplement) 224.20; Cole et al. (2018) Arthrit. Res. Ther. 20(1):85; Wang et al. (2016) Arthrit. Rheumatol. 68(suppl 10). 2016 ACR/ARHP Annual Meeting, 1085; Mihara M., et al., Clin Immunol. 2001; 98(3):319-26; and Uchiyama Y., et al., Biol Pharm Bull. 2008; 31(6):1159-63). In contrast to other anti-CD38 mAbs in development (e.g., daratumumab, isatuximab and MOR202), AB79 binds to CD38 expressed by cynomolgus monkeys, and provided the unique opportunity to determine if reducing the level of cells expressing CD38 would prevent and/or ameliorate inflammation and tissue damage in a non-human primate model of autoimmunity. AB79 is a high affinity monoclonal antibody that effectively mediates CD38+ cell depletion (Smithson, G., et al., *J Immunol* May 1, 2017, 198 (1 Supplement) 224.20). Integrative analysis reveals CD38 as a therapeutic target for plasma cell-rich pre-disease and established rheumatoid arthritis and systemic lupus erythematosus (Cole S., et al., *Arthritis Res Ther.* 2018 May 2;20(1):85).

Figure 31C:
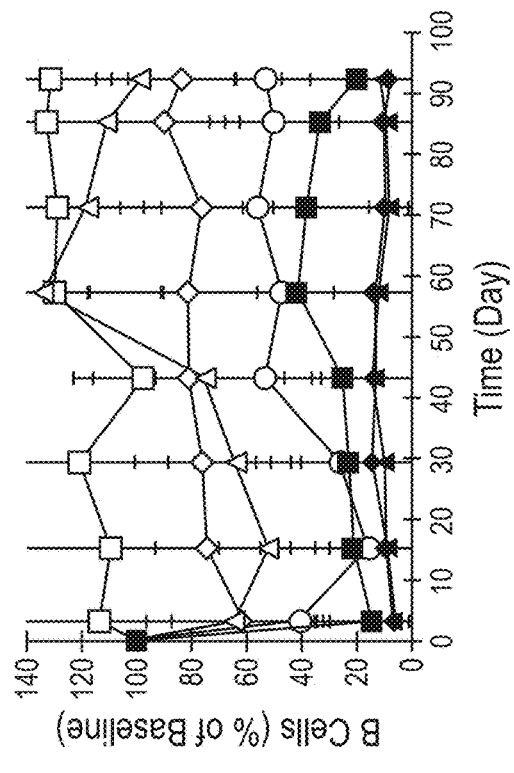

The cynomolgus monkey was determined to be a suitable model for assessing potential effects of AB79 in an autoimmune disease because the CIA in these monkeys features a symmetrical small joint polyarthritis that resembles human RA (Mihara et al. (2001) Clin. Immunol. 98(3):319-26; Uchiyama et al. (2008) Biol. Pharm. Bull. 31(6):1159-63; Uchiyama et al. (2008) Rheumatol. Int. 28:879-883; Kato et al. (2008) Experimental Mol. Path. 84:262-270, the expression profiles for CD38 are similar between these species (Table 11), and AB79 bound to monkey CD38 with an affinity that was 10-fold less than that of human CD38 (FIG. 32). We concluded that a weekly AB79 dose of 3 mg/kg would be adequate for assessing the potential role of CD38 in CIA because dose-range studies in healthy monkeys indicated that a weekly dose of 3 mg/kg of AB79 would reduce the total NK, B and T cell populations by more than 80, 60 and 20% from baseline levels in peripheral blood, respectively (FIGS. 31B, 31C and 31D). Similar reductions NK, B and T cells were achieved in the CIA model for prophylactic dosing (FIGS. 37E, 37F and 37G) despite the emergence of anti-AB79 antibodies in some animals (FIGS. 39C and 39D). The decrease in concentration of AB79 over time in 3 animals exposed prophylactically (FIG. 39A) indicate that these antibodies may have increased clearance, however B, NK and T cells had not recovered to baseline levels by study termination (FIGS. 37E, 37F and 37G), indicating that exposures to AB79 were sufficient to maintain PD effects throughout the investigation. These animals were therefore included in all analyses. This was also generally true for therapeutic treatment with AB79. NK and B cells had not recovered to baseline levels by study termination (FIGS. 37E, 37F and 37G), indicating that exposures to AB79 were sufficient to maintain PD effects throughout the investigation. In contrast, T cell counts had recovered to baseline levels by study termination (FIG. 37G), suggesting that anti-AB79 antibodies could partially confound interpretation of the therapeutic data (i.e., underestimate the contribution of CD38-expressing T cells in monkey CIA).

Prophylactic administration of AB79 prevented arthritis development, as illustrated consistently across all assessments, whereas therapeutic treatment with AB79 inhibited the development of arthritis and articular damage (FIGS. 34, 35, and 36). Histologic assessment of joints demonstrated that AB79 exerted relatively broad effects, preventing pannus formation (FIG. 35B), infiltration (FIG. 35C), cartilage lesions (FIG. 35D), bone erosion (FIG. 35E) and osteophyte formation (FIG. 35F). It is noteworthy that therapeutic treatment with AB79 and dexamethasone also inhibited these progressive histologic changes, albeit to a lesser magnitude than prophylactic administration. The arthritis scores decreased over time with therapeutic treatment (FIGS. 34B, 34C and 34D) indicating potential reversal of damage. Collectively, these data demonstrated consistent disease-modifying effects with exposure to AB79 prophylactically and therapeutically.

The effect of these therapeutic AB79 and dexamethasone treatments appear comparable to one another for the regimes investigated. Therapeutic use of steroids, such as dexamethasone, is highly effective in treating human autoimmune diseases, including RA and SLE, however deleterious side-effects (e.g., osteoporosis, hypertension, diabetes, weight gain, cataracts, glaucoma, thinning of the skin and bruising) restrict chronic use of these therapeutics. The potential for targeted CD38 cell depletion to provide comparable efficacy in human autoimmune diseases without the deleterious side-effects of steroids warrants future clinical investigation.

The prophylactic and therapeutic effects of AB79 were associated with sustained reductions in the blood level of total lymphocytes (FIG. 38F), NK, B and T cells (FIGS. 37C-37E), a transient reduction in monocytes (FIG. 37F), and no changes in red blood cells (FIG. 38A), platelets (FIG. 38D) and neutrophils (FIG. 38E). These pharmacodynamic data illustrate that differences exist in the sensitivity of cells expressing CD38 to reduction by AB79. Reduction generally correlated with the density of CD38 expression by the cell; the NK cell population uniformly expressed the highest median density of CD38 of all the cell types examined (FIG. 32B) and was most sensitive to AB79 (FIGS. 31B and 37C). The highest density of CD38 expressed on B cells was approximately 3-fold lower than on NK cells (FIG. 32B) and the B cell population was less sensitive to AB79 than NK cells (FIGS. 31C and 37C). CD38 is generally expressed at lower median densities on T cells than on B cells (FIG. 32B), and T cells were less sensitive to reduction by AB79 than B and NK cells (FIGS. 31D and 37D). Cells that express low densities of CD38 (e.g., red blood cells) or do not express CD38 (e.g., neutrophils) were not affected by AB79 (FIGS. 37A, 37D, and 37E). An exception are monocytes, which express CD38 uniformly at intermediate densities and were only transiently reduced by AB79 (FIG. 37F). The kinetics of the transient reduction in monocytes is distinct from the sustained reduction observed for B, T and NK cells and indicates distinct mechanisms. A direct cytolysis of NK cells by AB79 was observed in vitro (FIG. 32C) and a sustained reduction in NK, B, and T cells occurs after a single dose of AB79 in vivo (data not shown), which indicates that CDC and/or ADCC mediate these B, T and NK cell reductions in vivo. In contrast, monocytes were not cytolysed in vitro (data not shown) and do not exhibit sustained reduction in vivo (FIG. 37F), which indicates an alternate mechanism (e.g., margination) mediates transient reductions in vivo. Resistance of human monocytes to cytolysis by AB79 has also been observed in healthy subjects (unpublished) and described for daratumumab in multiple myeloma patients (Nijhof et al. (2016) Blood 128(7):959-70). The expression of inhibitors of CDC and ADCC by human monocytes did not correlate significantly with resistance to cytolysis by daratumumab and it remains unknown why monocytes are relatively insensitive to daratumumab and AB79.

While for the reduction in NK cells observed with AB79 is qualitatively consistent with NK cell reduction by daratumumab in refractory myeloma patients, quantitative differences exist. The IV infusion dose (0.3 mg/kg), the maximal concentration ($C_{max}$=4.32 µg/mL) and exposure ($AUC_{366}$=327 µg·hr/mL) of AB79 required to maintain peripheral blood NK cells at 50% below baseline levels in monkeys (FIG. 31B), was approximately 80-, 116- and 297-fold lower than the corresponding IV infusion dose (24 mg/kg), the maximal concentration ($C_{max}$ ~573 µg/mL) and exposure ($AUC_{inf}$ ~97175 µg·hr/mL) required for comparable reductions of NK cells by daratumumab in refractory myeloma patients (Casneuf et al. (2017) Blood Adv. 1(23): 2105-2114; Clemens et al. (2017) Clin. Pharmacokinet. 56(8):915-924. It is noteworthy that AB79 binds to monkey lymphocytes with an affinity (KD=4 nM) that is similar to daratumumab binding to cells expressing human CD38 (KD=4 nM) (Center For Drug Evaluation And Research Application Number: 761036orig1s00 Pharmacology Review(s)), however it's unknown whether these differences result from a potential difference between the species, disease states and/or potencies of the respective antibodies. A more definitive comparison nonetheless requires pharmacokinetic and dynamic data for AB79 in refractory myeloma patients because daratumumab does not cross-react with CD38 from mouse, rat, rabbit, pig, cynomolgus and rhesus monkeys (1 Apr. 2016 EMA/278085/2016 Committee for Medicinal Products for Human Use (CHMP) Assessment report Darzalex International non-proprietary name: daratumumab Procedure No. EMEA/H/C/004077/0000).

In conclusion, a reduction in cells expressing CD38 with the cytolytic antibody AB79 prevented the development of CIA in monkeys when administered prophylactically and reversed disease progression when administered therapeutically. A previous study utilizing blood and bone marrow samples from SLE patients demonstrated that AB79 depleted 80% of short- and long-lived plasma cells and reduced autoantibodies (e.g., VH4-34 9G4+, anti-Ro, and anti-dsDNA) in vitro (Wang et al. (2016) Arthritis Rheumatol. 68(suppl 10). 2016 ACR/ARHP Annual Meeting, 1085). These collective data suggest that this therapeutic strategy may be effective in treating human RA, SLE as well as other autoimmune diseases.

Example 7: Evaluation of AB79 in Healthy Human Volunteers

This investigation characterised the safety, tolerability, pharmacokinetics, and pharmacodynamics of AB79 by a a randomised, double-blind, placebo-controlled study of a single intravenous (IV) infusion or subcutaneous (SC) injection of AB79 at escalating doses in healthy subjects.
Results AB79 was well tolerated. All adverse events (AEs) were mild or moderate and there were no withdrawals due to AEs or infusion or injection site reactions over the tested IV and SC doses up to 0.06 and 0.6 mg $kg^{-1}$, respectively. At higher doses, transient increases in cytokine levels, mostly following IV administration, coincided with reduction in CD38-expressing cells; clinical symptoms primarily included mild pyrexia, headache, and postural hypotension. No remarkable findings for laboratory tests, electrocardiograms, vital signs, or physical examinations were reported related to AB79 treatment. AB79 reduced plasmablasts and natural killer (NK) cell levels at similar doses, with a 50% of maximum effective dose of approximately 0.003 and 0.1 mg $kg^{-1}$ for IV and SC administration, respectively. Reductions in immunoglobulin (Ig)M and IgA occurred without comparable changes in IgG. Total white blood cell, granulocyte, lymphocyte, red blood cell, and platelet counts remained within normal ranges for all dose levels.

CONCLUSIONS

AB79 reduced the plasmablasts and NK cell levels in peripheral blood of healthy subjects when administered IV or SC and was overall safe and well tolerated. SC dosing was better tolerated with more durable target cell depletion than IV dosing. This plasmacytolytic profile could be useful for treating disorders caused by plasma or NK cells, malignant counterparts (e.g., multiple myeloma and NK cell leukemia), and pathogenic immunoglobulins.
Study Design and Objectives This was a first in human (FIH) Phase 1, randomised, double-blind, placebo-controlled, single-dose study of AB79 in healthy adult subjects. The primary study objective was to assess the safety and tolerability of single escalating doses of AB79 after IV infusion or SC injection. Secondary objectives were to assess the PK and PD on blood cell populations and immunogenicity. A total of 74 subjects were enrolled in this study. After two screening visits, separated by a minimum of five days within a 28-day window before randomisation, subjects were admitted at Day-2 prior to dosing for baseline assessments. AB79 was administered on Day 1 via a 2 hour-IV infusion at sequential ascending doses of 0.0003, 0.001, 0.003, 0.01, 0.03, or 0.06 mg $kg^{-1}$ in six cohorts, or via SC injection at doses of 0.03, 0.1, 0.3, or 0.6 mg $kg^{-1}$ in another four cohorts. Dose selection was based on a PK/PD model derived from a series of studies in cynomolgus monkeys (Roepcke et al. (2018) Pharmacol Res Perspect. 6(3):e00402). At each dose level, six to eight subjects were randomised to AB79 (n=4 to 6) or matching placebo (n=2).

Sentinel dosing was used for each cohort with an initial two subjects receiving either AB79 or placebo (1:1). The 24-hour post-dose safety and tolerability data from these two subjects was reviewed before the remaining subjects in each cohort were dosed. Participants were confined to an inpatient Clinical Pharmacology Unit (CPU) until Day 8 followed up by weekly or bi-weekly follow up visits, with the last planned clinic visit on Day 78 for general safety assessment and PK, PD, and immunogenicity analysis. A final follow-up phone call occurred at Day 92.

Dose escalation was based predominantly on AE severity as graded using the Common Terminology Criteria for Adverse Events grading criteria. Dose escalation was to be stopped if at least two subjects in one cohort experiencing cytokine release syndrome (CRS) leading to moderate clinical syndromes or moderate to severe administration reactions. Given that AB79 is a lymphocyte cell-depleting antibody, no further dose escalation was allowed if clinically relevant reductions in total or subtypes of lymphocyte counts (nominally >50% reduction from the subject's lowest pre-dose value and below the lower limit of normal reference ranges (NRRs)) were observed and were maintained for ≥29 days. The investigator and sponsor reviewed all blinded safety data for all participants at each dose level prior to proceeding to the next higher dose.

The study was conducted in accordance with Good Clinical Practice guidelines at the Parexel International Phase 1 CPU located in Northwick Park Hospital, Harrow, UK. The protocol was reviewed and approved (approval number 16/LO/2067) by a local independent ethics committee, the London-Brent Research Ethics Committee (London, UK). All subjects signed the Informed Consent Form before initiation of any study procedures.

Study Participants

Eligible participants were healthy, males or females (without child-bearing potential) between the ages of 18 to 55 years, weighing 50 to 100 kg and with a body mass index (BMI) 18.5 to 30 kg m$^{-2}$.

The flow cytometry-based counts of CD45+ lymphocytes, T cells, CD4+ T cells and B cells were required to be above the lower limit of NRRs and NK cell counts within the upper 50th percentile of the NRR given that CD38 is highly expressed on NK cells. NRRs were defined by Takeda who performed the flow cytometry analyses.

Participants were excluded if they met the exclusion criteria defined in the protocol, such as known immunodeficiency, elevated infection risk, history of malignancy, or taking another investigational drug prior to the study that could impact the effect of the investigational drug.

To measure serum AB79 concentrations, serial blood samples were collected prior to the dosing and up to 168 hours post-dose, and additional blood samples were collected at intermediate timepoints post-dose or at early termination (ET). Serum AB79 concentrations were determined using an enzyme-linked immunosorbent assay validated at ICON (Whitesboro, NY).

To assess the PD response of AB79, peripheral blood samples were collected at the screening visits, Days-1, 1, 2 (SC only), 3 (SC only), 4 (IV only), 5 (SC only), 6, 8, 15, 22, 29, 50, and 78 post-dose or at ET. The primary and secondary PD endpoints were the plasmablasts and NK cell counts measured in blood, respectively. Additional assessments included total white blood cell count and differential, total T cells, CD4 and CD8 T cell subsets, B cell, monocyte, and granulocyte counts. Lymphocyte subsets, monocytes and plasmablasts were measured by flow cytometry at Covance (Brussels, Belgium). An electrochemiluminescent assay was validated for the detection of anti-AB79 antibodies in human serum at ICON.

Routine safety parameters such as AEs, clinical laboratory parameters, physical examinations, electrocardiograms (ECGs), and vital signs were monitored at screening, before dosing, and throughout the confinement period and follow-up visits.

Infusion reactions have been reported in clinical studies of other anti-CD38 antibodies administered to MM patients after IV infusion (Voorhees et al. (2015) Blood 126:1829). Although ex vivo experiments showed no evidence of agonist activity by AB79 in human blood cells, and infusion of AB79 did not induce observable findings suggestive of infusion reaction in nonclinical studies in monkeys, signs of infusion reaction or CRS (headache, fever, chills, hypotension, nausea, and vomiting) were closely monitored. Inflammatory-mediators including serum C-reactive protein (CRP) and tumor necrosis factor (TNF) a and interleukins 1 (IL-1) and 6 (IL-6) levels were evaluated at various timepoints on Days 1 and 2, and Day 4 (SC cohorts only). Decreasing the rate of infusion and/or oral prophylactic pre-medications with paracetamol (acetaminophen) and antihistamines (anti-H1 and anti-H2) were allowed to minimize side effects, if needed.

For the SC cohorts, signs of injection site reactions (ISR) such as injection site pain, burning, redness, itching, swelling, or induration were monitored.

Summary statistics and data analysis were conducted using SAS version 9.2 and R version 3.5.1. PK parameters were calculated using noncompartmental analysis. PD variables were assessed and compared between active dose groups and between each AB79 dose level and placebo.

Results

Seventy-four subjects were enrolled and received a single dose of AB79 (n=54) or placebo (n=20). Six IV cohorts receiving AB79 at doses of 0.0003, 0.001, 0.003, 0.01, 0.03, or 0.06 mg kg$^{-1}$ or matching placebo and four SC cohorts receiving AB79 at doses of 0.03, 0.1, 0.3, or 0.6 mg kg$^{-1}$ or matching placebo were monitored for 92 days; all completed the study. Participants were all men except for one woman in the SC placebo group. The study population consisted of Caucasian (n=51), Asian (n=13), African (n=4), and multiracial (n=6) ethnicities. The mean age (34.4 years, with range 19 to 55 years) and BMI (24 to 25 kg m$^{-2}$) were similar between IV cohorts and SC cohorts, and between AB79 and placebo-treated groups.

All doses of AB79 were well tolerated in this study. The AEs were mild to moderate in intensity with most AEs being mild and well balanced between placebo and AB79 treated groups (Table 13). There were no serious AEs (SAEs) or deaths, and no AEs led to either study or visit discontinuation. No remarkable findings for laboratory tests, ECGs, vital signs, or physical examinations were reported that were related to AB79 treatment.

TABLE 13

Total TEAEs and AEs Reported in Two or More Subjects in Any Treatment Group

| | IV Infusion | | | | | | |
|---|---|---|---|---|---|---|---|
| | Pooled | AB79 (mg kg$^{-1}$) Number of Subjects (%) | | | | | |
| | Placebo (n = 12) | 0.0003 (n = 4) | 0.001 (n = 4) | 0.003 (n = 4) | 0.01 (n = 6) | 0.03 (n = 6) | 0.06 (n = 6) |
| Subjects with any TEAEs | 11 (91.7) | 3 (75.0) | 3 (75.0) | 3 (75.0) | 6 (100.0) | 6 (100.0) | 6 (100.0) |
| Pyrexia | 0 | 0 | 0 | 0 | 1 (16.7) | 1 (16.7) | 3 (50.0) |
| Chills | 0 | 0 | 0 | 0 | 0 | 0 | 2 (33.3) |
| Nasopharyngitis | 2 (16.7) | 0 | 1 (25.0) | 0 | 0 | 0 | 2 (33.3) |

TABLE 13-continued

Total TEAEs and AEs Reported in Two or More Subjects in Any Treatment Group

| Headache | 4 (33.3) | 0 | 0 | 1 (25.0) | 2 (33.3) | 3 (50.0) | 5 (83.3) |
|---|---|---|---|---|---|---|---|
| Dizziness postural | 0 | 0 | 0 | 0 | 0 | 1 (16.7) | 5 (83.3) |
| Somnolence | 0 | 0 | 0 | 0 | 0 | 1 (16.7) | 2 (33.3) |

SC Injection

| | Pooled Placebo (n = 8) | AB79 (mg kg$^{-1}$) Number of Subjects (%) | | | |
|---|---|---|---|---|---|
| | | 0.03 (n = 6) | 0.1 (n = 6) | 0.3 (n = 6) | 0.6 (n = 6) |
| Subjects with any TEAEs | 6 (75.0) | 6 (100.0) | 6 (100.0) | 5 (83.3) | 5 (83.3) |
| Injection site erythema | 1 (12.5) | 5 (83.3) | 0 | 1 (16.7) | 1 (16.7) |
| Injection site pain | 0 | 3 (50.0) | 3 (50.0) | 0 | 0 |
| Feeling hot | 0 | 0 | 1 (16.7) | 1 (16.7) | 2 (33.3) |
| Nasopharyngitis | 1 (12.5) | 2 (33.3) | 3 (50.0) | 1 (16.7) | 3 (50.0) |
| Headache | 2 (25.0) | 2 (33.3) | 1 (16.7) | 1 (16.7) | 3 (50.0) |
| Oropharyngeal pain | 1 (12.5) | 0 | 2 (33.3) | 0 | 1 (16.7) |

A TEAE was defined as an AE that occurs or gets worse after receiving the first dose of study drug and within 94 days after the last dose of study drug. Subjects with one or more AEs within a treatment group and level of MedDRA term were counted only once in that level. Percentages are based on the number of subjects in the safety set per treatment. MedDRA (Version 18.0) was used for coding AEs.
AE, adverse event;
IV, intravenous;
MedDRA, Medical Dictionary for Regulatory Activities;
SC, subcutaneous;
TEAE, treatment-emergent adverse event.

As shown in Table 13, most of the AEs were sporadic with no trend of dose relationship, except for headache, dizziness, and chills, which were seen more frequently at the higher IV AB79 dose groups consistent with higher incidence of CRS. These effects (Table 14) were mostly observed in subjects receiving the higher doses (one subject and six subjects in the 0.03 and 0.06 mgkg$^{-1}$ IV, respectively; one subject and two subjects in the 0.3 and 0.6 mg kg$^{-1}$ SC, respectively). These subjects exhibited reductions in plasmablasts and NK cells, suggesting that these symptoms result from depletion of cells expressing CD38.

TABLE 14

Number and Percentage of Subjects With Clinical CRS

IV Infusion

| | Pooled Placebo (n = 12) | AB79 (mg kg$^{-1}$) Number of Subjects (%) | | | | | |
|---|---|---|---|---|---|---|---|
| | | 0.0003 (n = 4) | 0.001 (n = 4) | 0.003 (n = 4) | 0.01 (n = 6) | 0.03 (n = 6) | 0.06 (n = 6) |
| CRS | 0 | 0 | 0 | 0 | 0 | 1 (16.7) | 6 (100) |
| Severity | | | | | | Mild | All mild |

TABLE 14-continued

Number and Percentage of Subjects With Clinical CRS

SC Injection

| | Pooled Placebo (n = 8) | AB79 (mg kg$^{-1}$) Number of Subjects (%) | | | |
|---|---|---|---|---|---|
| | | 0.03 (n = 6) | 0.1 (n = 6) | 0.3 (n = 6) | 0.6 (n = 6) |
| CRS | 0 | 0 | 0 | 1 (16.7) | 2 (33.3) |
| Severity | | | | Mild | All mild |

Only mild, transient ISR were observed after SC injections, the majority of which resolved within 7 days. These reactions exhibited an inverse dose-effect relationship, as five of six subjects treated with lowest SC dose and only one subject in each of the two highest dose cohorts had reactions.

Serum concentrations of AB79 at all PK sampling timepoints from IV Cohorts 1 (0.0003 mg kg$^{-1}$) through 4 (0.01 mg kg$^{-1}$) were below the lower limit of quantification (LLOQ) of the detection assay (i.e., 10 ngmL$^{-1}$), presumably due to low doses and in the absence of anti-drug antibodies (data not shown). Following IV infusion of 0.03 and 0.06 mg kg$^{-1}$ AB79, the maximum observed serum concentration ($C_{max}$) was 21.4 and 100.4 ng mL$^{-1}$, respectively, and occurred 5 minutes after the end of infusion (Table 15 and FIG. 41). Subsequently, the serum concentrations decreased rapidly to below the LLOQ within 1 or 4 hours after end of infusion, respectively, and exposures could not be calculated accurately. $C_{max}$ appeared to increase approximately five-fold over a two-fold dose increase from 0.03 to 0.06 mg kg$^{-1}$. Due to the limited AB79 serum concentrations (at one to three timepoints per subject) available from IV 0.03 and 0.06 mg kg$^{-1}$ cohorts, PK parameters other than time to maximum serum concentration ($t_{max}$) and $C_{max}$ could not be estimated reliably.

TABLE 15

Summary PK Parameters of AB79 Following a Single 2-Hour IV Infusion of AB79 at 0.03 and 0.06 mg kg$^{-1}$ or a Single SC Injection of AB79 at 0.6 mg kg$^{-1}$ to Healthy Subjects

| Route | Dose | $t_{max}$ (h) n n = 6 | $C_{max}$ (ng mL$^{-1}$) n = 6 | AUC$_{last}$ (ng day$^{-1}$ mL$^{-1}$) n = 6 |
|---|---|---|---|---|
| IV | 0.03 mg kg$^{-1}$ | 6  2.09 (2.07, 2.67) | 21.4 (39) | NA |
|    | 0.06 mg kg$^{-1}$ | 6  2.09 (2.07, 2.13) | 100.4 (52) | NA |
| SC | 0.6 mg kg$^{-1}$ | 6  23.87 (7.98, 96.02)$^a$ | 23.0 (67) | 90.4 (92) |

$^a$n =5.

Values represent mean (% CV), except for $t_{max}$ where median (min, max) are presented.
AUC$_{last}$, area under the serum concentration-time curve from time 0 to time of the last quantifiable concentration;
$C_{max}$, maximum observed serum concentration;
CV, coefficient of variance;
IV, intravenous;
NA, not applicable;
PK, pharmacokinetics;
SC, subcutaneous;
$t_{max}$, time to maximum serum concentration.

Figure 41:
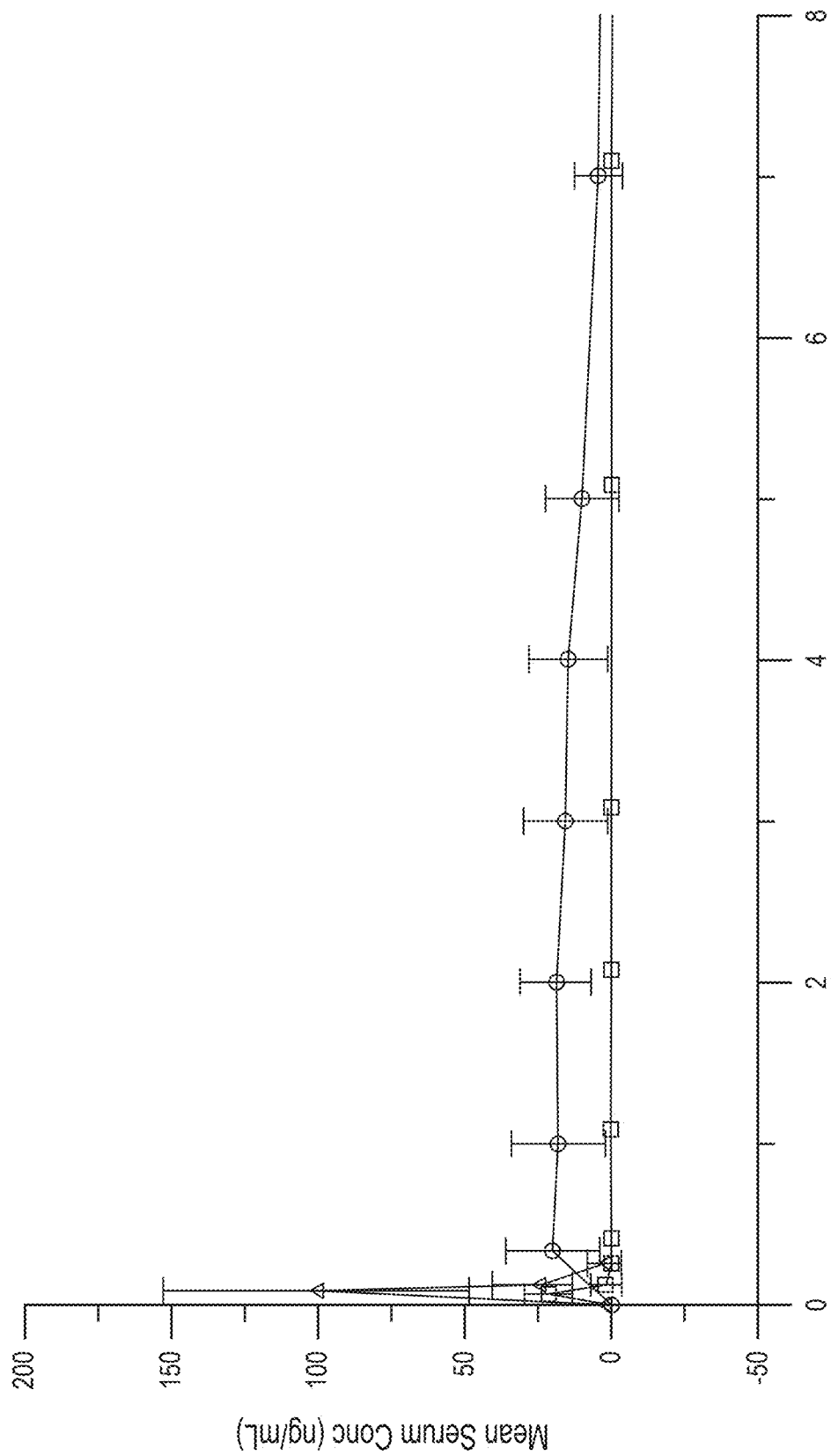
FIG. 41 shows the mean serum concentration-time profiles of AB79 following a single 2-hour IV infusion of AB79 at 0.03 (squares) and 0.06 (triangles) mg or a single SC injection of AB79 at 0.6 mg kg$^{-1}$ (circles) to healthy subjects. Error bars represent standard deviation (n=6). IV, intravenous; SC, subcutaneous.

Serum concentrations of AB79 from all subjects in SC Cohorts 1 (0.03 mg kg$^{-1}$) through 3 (0.3 mg kg$^{-1}$) were below the LLOQ of the detection assay at all timepoints. Following a single 0.6 mg kg$^{-1}$ AB79 SC injection, five subjects in this cohort exhibited a median $t_{max}$ at approximately 24 hours after injection. Mean $C_{max}$ of all six subjects (including one subject with serum concentrations below LLOQ) in this cohort was 23.0 ng mL$^{-1}$, which was approximately 23% of the $C_{max}$ value following a 2-hour IV fusion at 0.06 mg kg$^{-1}$ (one-tenth of the SC dose in this cohort). Serum concentrations of AB79 decreased gradually to below the LLOQ by 3 to 14 days after injection (FIG. 41). One subject in the 0.6 mg kg$^{-1}$ SC cohort did not exhibit detectable level of AB79 throughout the PK sampling period. Compared with the PK parameters from the IV cohorts, higher inter-subject variability was observed following a SC injection at 0.6 mg kg$^{-1}$. Individual $t_{max}$ ranged between approximately 8 to 96 hours (0.33 to 4 days) after injection for the five subjects with measurable concentrations in this cohort.

Figure 42A:
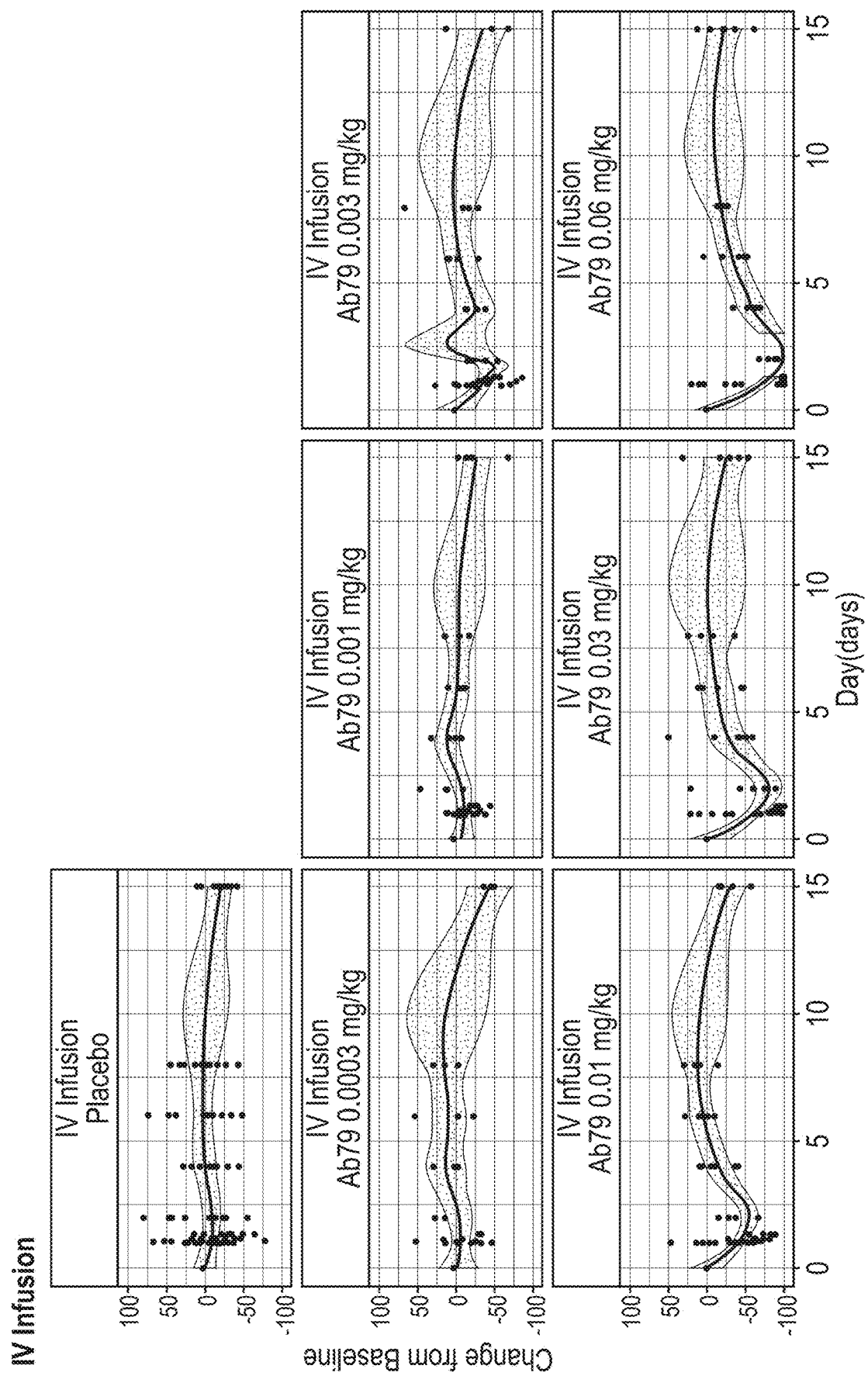
FIG. 42A-42B shows levels of NK cells in peripheral blood of healthy subjects after a single IV or SC administration of AB79. IV, intravenous; SC, subcutaneous.
Figure 42B:
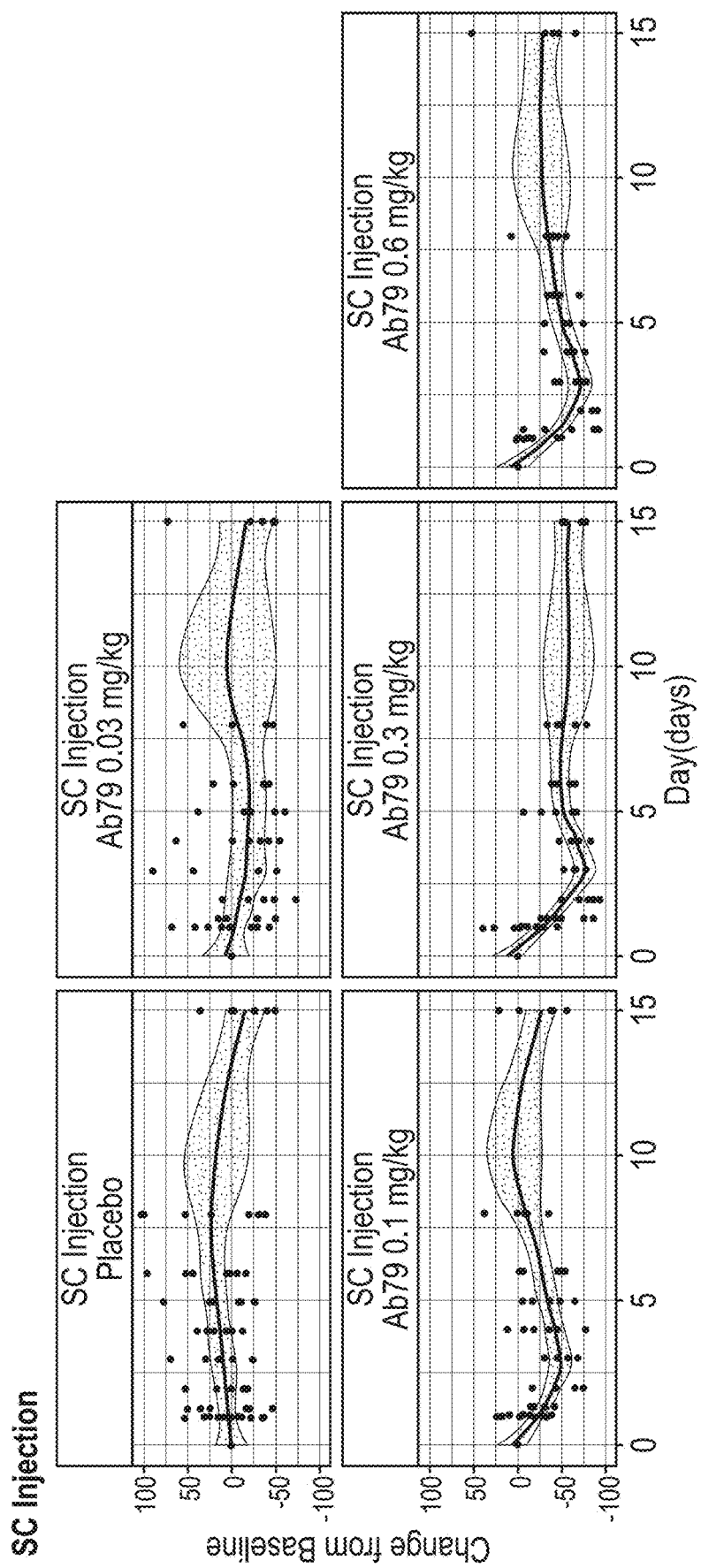
Figure 43:
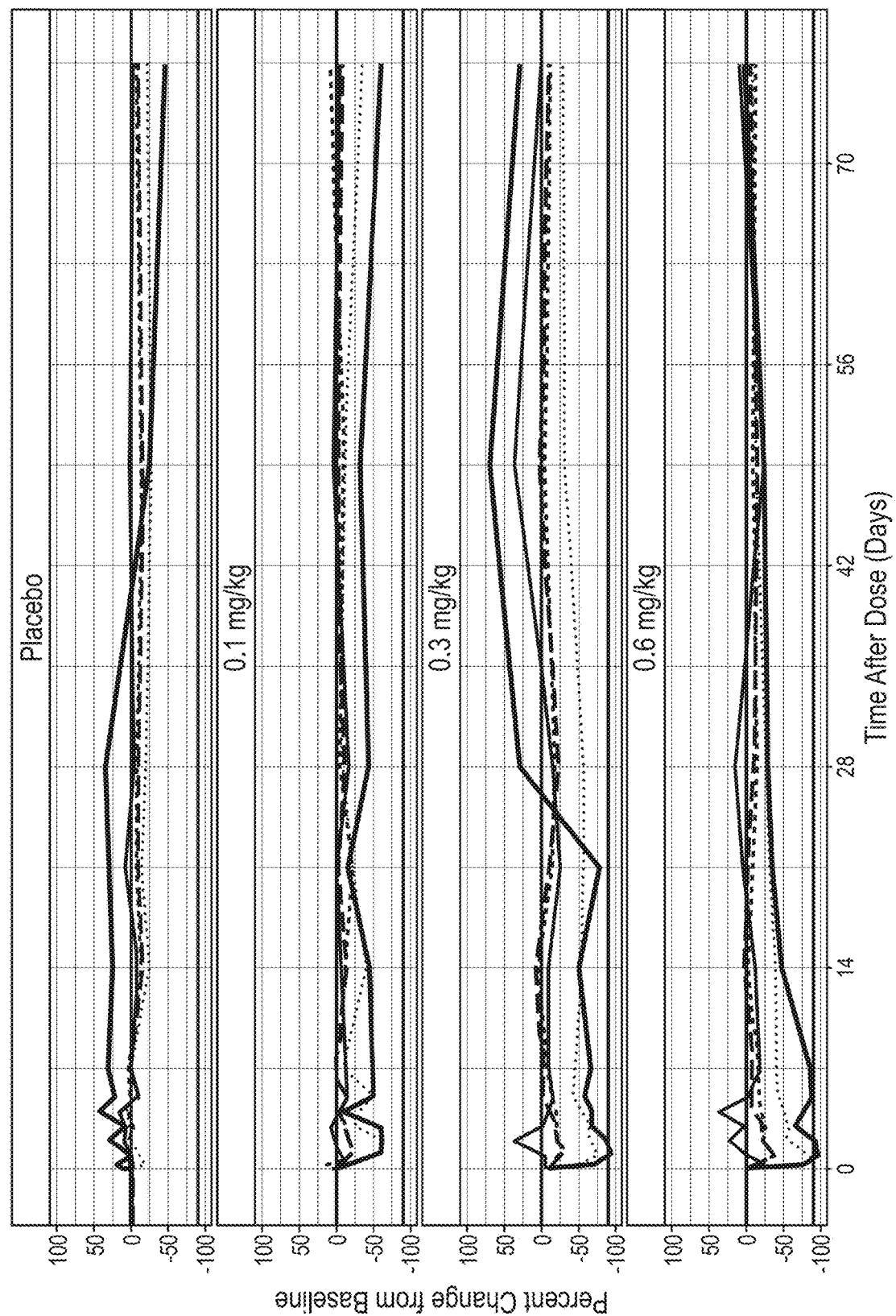
FIG. 43 shows levels of plasmablasts, monocytes, B, T, and NK cells in peripheral blood from healthy subjects after a single injection of placebo control, 0.1, 0.3, or 0.6 mg kg$^{-1}$ of AB79 SC. ▬▬▬ Absolute monocytes (cells/µL), ⋯⋯ NK cells (cells/µL), ▬ ▬ Total T cells (cells/µL), ▬ ▬ B cells (cells/µL), ▬▬▬ plasmablast cells (cells/µL). The centered curves represent the median. NK, natural killer (cell); SC, subcutaneous.

In the cohorts administered AB79 by IV infusion, dose-dependent reductions in NK cells were observed at doses ≥0.003 mg kg$^{-1}$, with ≥90% reduction occurring in all subjects receiving a 0.06 mg kg$^{-1}$ infusion (FIG. 42). An effective concentration at 50% of maximum response (EC$_{50}$) occurred below the LLOQ of the PK assay (i.e., 10 ng mL$^{-1}$), nonetheless a 75% of maximum effective concentration (EC$_{75}$) for reduction in NK cells by IV administration of AB79 was 21.4 ng mL$^{-1}$ (Table 15). While the level of NK cells was consistently reduced from baseline by the end of the infusion, the duration of recovery to baseline levels (<−20%) was variable and generally related to dose; recovery to baseline levels for the 0.003, 0.01, 0.03, and 0.06 mg kg$^{-1}$ doses required a mean of 4, 4, 6, and 8 days, respectively (FIG. 43). No clinically meaningful reductions were observed for total lymphocytes, B and T cells, helper T cells and cytotoxic T cells, granulocytes, red blood cells, or platelets with an IV administration of AB79 (data not shown).

In the cohorts treated with AB79 by SC injection, a dose-dependent reduction in NK cells (FIG. 42) and plasmablasts (FIG. 43) were observed at doses ≥0.1 mg kg$^{-1}$ with ≥90% reduction in plasmablasts within all subjects receiving a 0.6 mg kg$^{-1}$ injection. A 75% reduction in NK cells occurred at 0.6 mg kg$^{-1}$ (data not shown) with a $C_{max}$ of 23.0 ng mL$^{-1}$ (Table 15). The levels of plasmablasts and NK cells were reduced from baseline within 8 hours after injection and exhibited a $t_{max}$ of 48 hours. The duration of recovery to baseline levels was variable; recovery to baseline (i.e., within −20% of baseline levels) for the 0.1, 0.3, and 0.6 mg kg$^{-1}$ doses required a mean of 4, 78, and 50 days, respectively (data not shown). There were minimal or no reductions observed for total lymphocytes, B and T cells, cytotoxic T cells, helper T cells, monocytes (FIG. 43) and granulocytes, red blood cells and platelets (data not shown).

Figure 44:
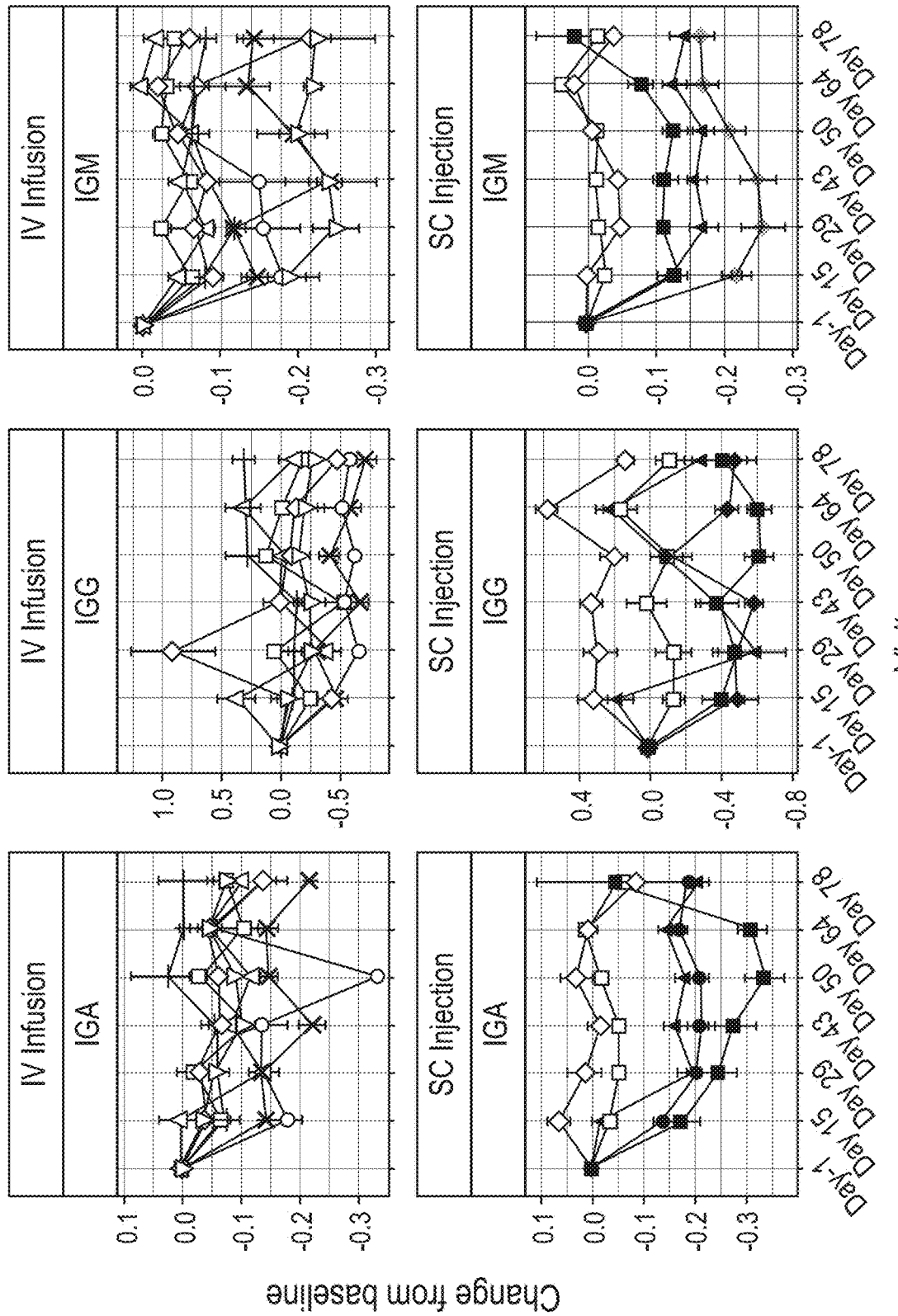
FIG. 44 shows the change from baseline levels of total IgA, IgG, and IgM in serum from healthy subjects after a single administration of placebo or 0.003 to 0.06 mg kg$^{-1}$ of AB79 IV, placebo, or 0.03 to 0.6 mg kg$^{-1}$ of AB79 SC. Symbols represent the mean value for the cohort and error bars represent the standard error of the mean. ▫ placebo, ◇ AB79 0.0003 mg/kg △ AB79 0.001 mg/kg ✳ AB79 0.003 mg/kg × AB79 0.01 mg/kg ◊ AB79 0.03 mg/kg ▽ AB79 0.06 mg/kg ✷ AB79 0.1 mg/kg ◆ AB79 0.3 mg/kg ▲ AB79 0.6 mg/kg. Ig, immunoglobulin; IV, intravenous; SC, subcutaneous.

While the levels of total Igs remained within NRRs, total IgM levels were reduced in cohorts administered 0.03 and 0.06 mg kg$^{-1}$ of AB79 IV and were significantly (P<0.05) lower than a time-matched placebo control cohort on days 15-64 (FIG. 44, upper panels). Significant (P<0.01) reductions in total IgM levels were also observed on days 15-64 for AB79 administered at 0.3 and 0.6 mg kg$^{-1}$ SC (FIG. 44, lower panels). IgM levels exhibited a trend toward recovery to baseline on day 78. A significant effect on levels of IgA and IgG was not observed for AB79 administered IV or SC (data not shown).

Of the 54 subjects who received AB79, one subject in the 0.03 mg kg$^{-1}$ SC cohort exhibited a persistent (i.e., Days 15, 29, and 78), higher titer (i.e., 160, 1280, and 320) of anti-AB79 antibody (data not shown). The serum concentrations of AB79 in this subject were below LLOQ over the entire study period, as were the AB79 levels in the anti-drug antibody (ADA)-negative subjects in the same cohort, therefore the potential impact of ADA on the PK of AB79 could not be determined. Need to also mention that ADA did not coincide with AEs.

One therapeutic strategy for treating SLE and RA is to reduce the level of CD38+ lymphocytes, based on several reports that show an association between CD38+ lymphocyte level and disease activity (Cole et al. (2018) Arthritis Res. Ther. 20(1):85; Kraan et al. (1999) Rheumatology (Oxford) 38(11):1074-1080; Vital et al. (2011) Arthritis Rheum. 63(10):3038-3047; Banchereau et al. (2016) Cell 165(3):551-565; and Grammer et al. (2003) J. Clin. Invest. 112(10):1506-1520). This could be achieved with AB79 because it specifically binds to CD38 and depletes cells (Smithson et al. (2017) J. Immunol. 198(1 Suppl):224.20). The addition of AB9 to blood or bone marrow samples from patients with SLE or RA reduced PC populations and decreased production of autoantigen-specific antibodies (Wang et al. (2016 ACR/ARHP Annual Meeting abstract 1085) Arthritis Rheum. 68(suppl 10). AB79 also reduced lymphocytes expressing high levels of CD38 in monkeys (Roepcke et al. (2018) Pharmacol Res Perspect. 6(3): e00402), prevented the development of CIA when administered prophylactically, and inhibited arthritis progression when administered therapeutically (Smithson et al. (2017) J. Immunol. 198(1 Suppl):127.17). Therefore, the purpose of this investigation was to characterise the safety, tolerability, PK, and PD of single IV infusion and SC injection of AB79 in healthy subjects and determine if a clinical study in patients is warranted.

This is the first characterisation of tolerability, PK, and PD of a cytolytic CD38 antibody administered to healthy subjects. All doses of AB79 were well tolerated in this study. AEs were mild to moderate in intensity with the majority being mild (Table 13). There were no SAEs or deaths, and no AEs led to either study or visit discontinuation. No remarkable findings for laboratory tests, ECGs, vital signs, or physical examinations were reported that were related to AB79 treatment. While infusion-related reactions were not observed in this study, CRS was observed in seven subjects in the AB79 IV infusion group and three subjects in the AB79 SC group (Table 14). Cases of CRS coincided with reductions in plasmablasts and NK cells (FIGS. 42 and 43), moderate increases in cytokines (e.g., TNF-α, IL-1β and IL-6; data not shown), and C-reactive protein in blood (data not shown). These data are consistent with studies in monkeys illustrating that cell depletion coincided with an elevation in serum levels of TNF-α (Roepcke et al. (2018) Pharmacol Res Perspect. 6(3):e00402). As compared to IV treatment groups, the SC treatment cohorts experienced a lower incidence of CRS and had minimal cytokine level increases, at comparable concentrations of AB79 in peripheral blood (e.g., 0.03 mg kg$^{-1}$ IV versus 0.6 mg kg$^{-1}$ SC). These results are consistent with the lower incidence of infusion reactions for SC versus IV administration of daratumumab in refractory myeloma patients. Different formulations are utilised for IV versus SC administration of daratumumab, whereas the same formulation was employed for IV versus SC administration of AB79 to healthy subjects. The data for AB79 indicate that lower rates of CRS are primarily attributable to a SC route of administration, as opposed to differences in formulation.

Nonclinical assessment of AB79 in monkeys suggested area under the serum concentration-time curve increased greater than dose proportionally after a single IV and SC administration of AB79 (Roepcke et al. (2018) Pharmacol Res Perspect. 6(3):e00402). Due to the limited amount of serum concentration data in healthy subjects, a formal assessment on the dose proportionality or SC bioavailability of AB79 could not be conducted. However, $C_{max}$ following IV infusion appeared to increase greater than dose proportionally (i.e., approximately five-fold increase over a two-fold increase in dose from 0.03 to 0.06 mg kg$^{-1}$), consistent with a similar trend observed in monkeys with AB79 and with those published for other monoclonal antibodies with target-mediated elimination. Dose-normalized $C_{max}$ following a SC injection was substantially lower than that following a 2-hour IV infusion. After $C_{max}$ was reached, serum concentrations decreased much more slowly following a SC injection and were maintained above LLOQ much longer compared with an IV infusion.

The PD response of healthy subjects to AB79 IV is the most potent example of NK cell depletion by an anti-CD38 monoclonal antibody described to date. AB79 at 0.06 mg kg$^{-1}$ generated a mean $C_{max}$ of 100.4 ng mL$^{-1}$ and reduced peripheral blood NK cells in each healthy subject at least 90% lower than their baseline levels (FIG. 42). This extent of NK cell reduction was not achieved in relapsed/refractory MM patients IV infused with daratumumab up to 24 mg kg$^{-1}$ and with a mean $C_{max}$ of up to 573 μg mL$^{-1}$ (Clemens et al. (2017) Clin. Pharmacokinet. 56(8):915-924; Xu et al. (2017) Clin. Pharmacol. Ther. 101(6):721-724). It is unknown whether this difference in potencies results from differences in the study populations and/or properties of the respective antibodies. While healthy subjects and myeloma patients have a similar number of NK cells and these cells express a similar density of CD38 (Krejcik et al. (2016) Blood 128(3):384-394), myeloma patients have higher levels of other CD38+ target cells (i.e., myeloma cells) which could contribute to a difference in the potency of NK cell depletion between these populations. A more definitive analysis requires PK and PD data for AB79 in a similar population of relapsed/refractory myeloma patients.

An attribute of higher potency is that a smaller quantity and volume of therapeutic is required to elicit comparable PD effects. The effectiveness of treating patients with an IV infusion of anti-CD38 mAb could be improved upon by administering as a low volume SC injection because it could be administered within a minute, in contrast to the 2 to 4 hours typically required for receiving an IV infusion, and in chronic therapy could potentially be self-administered by the patient at home safely with convenience and pharmacoeconomic advantages. This is the first demonstration of cell reduction after SC injection of a cytolytic anti-CD38 antibody into human subjects, which showed that SC injection has better tolerability than IV infusion. It is also the first report that a 1 mL SC injection of 0.1 to 0.6 mg kg$^{-1}$ of an anti-CD38 antibody elicits maximal PD activity (e.g., >90% reduction of plasmablasts) in peripheral blood. AB79 reduced plasmablasts and NK cells in a dose-dependent manner at IV doses ≥0.1 mg kg$^{-1}$ (FIGS. 42 and 43). The corresponding $EC_{90}$ for plasmablast reduction was approximately 23.0 ng mL$^{-1}$, whereas it was 100.4 ng mL$^{-1}$ for NK cell reduction (Table 15). This potential difference in sensitivity may be related to the level of CD38 expression expressed by these populations; plasmablasts express approximately a five-fold higher density of CD38 than NK cells (Krejcik et al. (2016) Blood 128(3):384-394). It is unknown whether this difference exists within SLE, RA, and/or MM patients because data describing the level of plasmablasts and NK cells in these patient populations have not been reported to date. If comparable activity is observed in patients, then the efficiency of a low-volume SC injection could potentially provide therapy to patients without access to an infusion facility, and lower overall health care expenditures.

Circulating monocytes, B and T cells express lower levels of CD38 in healthy subjects and these cell types were not reduced to the same extent as plasmablasts and NK cells by AB79. These data are consistent for those described for cynomolgus monkeys after an initial dose of AB79, as well as after chronic exposure for 3 months; NK cells uniformly expressed high levels of CD38 and were more sensitive to AB79 than B and T lymphocytes, which express CD38 heterogeneously and generally at lower levels than NK cells (Roepcke et al. (2018) Pharmacol Res Perspect. 6(3): e00402). These data are also consistent with those described for relapsed/refractory myeloma patients chronically exposed to daratumumab; monocytes were unaffected and subpopulations of CD38+B and T cells are reduced in peripheral blood (Krejcik et al. (2016) Blood 128(3):384-39).

Ig is predominantly produced by PCs residing in lymphoid tissues (e.g. bone marrow, lymph nodes, spleen, etc.). A similar effect has been described in SLE patients exposed to multiple doses of the proteasome inhibitor bortezomib; there were significant decreases in serum levels of total IgM (34%), IgA (34%), and IgG (15%) which corresponded with reductions in blood plasmablasts (54%), bone marrow PCs (50%), and disease activity scores (Alexander et al. (2015) Ann. Rheum. Dis. 74(7):1474-1478). Collectively, these data indicate that AB79 may be effective at lowering Ig levels and potentially, that IgM, and IgA could be selectively reduced relative to IgG. This profile could provide therapeutic utility in IgM, IgA, and IgG nephropathies, while minimising suppression of other components of the immune system.

In conclusion, a single dose of AB79 administered IV or SC was well tolerated by healthy subjects. AB79 depleted plasmablasts and NK cells and reduced levels of serum IgM and IgA. This plasmacytolytic activity could be beneficial for treatment of a variety of hematologic malignancies and/or immunologic disorders involving dysregulated PCs, pathogenic antibodies, Igs, and/or NK cells.

INCORPORATION BY REFERENCE

The contents of all cited references (including literature references, patents, patent applications, and websites) that may be cited throughout this application are hereby expressly incorporated by reference in their entirety for any purpose, as are the references cited therein, to the same extent as if each individual reference was specifically and individually indicated to be incorporated by reference in its entirety for any purposes.

EQUIVALENTS

The disclosure may be embodied in other specific forms without departing from the spirit or essential characteristics thereof. The foregoing embodiments are therefore to be considered in all respects illustrative rather than limiting of the disclosure. Scope of the disclosure is thus indicated by the appended claims rather than by the foregoing description, and all changes that come within the meaning and range of equivalency of the claims are therefore intended to be embraced herein. Modifications for carrying out the invention that are obvious to persons of skill in the art are intended to be within the scope of the appended claims.

---

We claim:

1. A method for treating a disease in a human subject for which antibody binding to CD38 is indicated, the method comprising subcutaneously administering to the subject a unit dosage form of an isolated human anti-CD38 antibody, wherein the anti-CD38 antibody comprises a variable heavy (VH) chain region comprising a CDR1 having the amino acid sequence of SEQ ID NO:3, a CDR2 having the amino acid sequence of SEQ ID NO:4, and a CDR3 having the amino acid sequence of SEQ ID NO:5; and a variable light (VL) chain region comprising a CDR1 having the amino acid sequence of SEQ ID NO:6, a CDR2 having the amino acid sequence of SEQ ID NO:7 and a CDR3 having the amino acid sequence of SEQ ID NO:8, wherein the unit dosage form is in a volume of 1 mL or less, wherein the antibody is administered in a dosage of 0.3 milligram per kilogram body weight, wherein the disease is an autoimmune disease.

2. The method of claim 1, wherein the VH chain region has the amino acid sequence of SEQ ID NO:9 and the VL chain region has the amino acid sequence of SEQ ID NO:10.

3. The method of claim 1, wherein the anti-CD38 antibody comprises a heavy chain amino acid sequence of SEQ ID NO:11 and a light chain amino acid sequence of SEQ ID NO:12.

4. The method of claim 1, wherein the unit dosage form is in a volume of 1 mL.

5. The method of claim 1, wherein administering the anti-CD38 antibody does not cause hemolytic anemia or thrombocytopenia.

6. The method of claim 1, wherein administering the anti-CD38 antibody results in less than 10%, less than 20%, less than 30%, less than 40%, or less than 50% incidence of grade 3 or 4 of one or more treatment-emergent adverse events (TEAEs) selected from the group consisting of anemia, hemolytic anemia, thrombocytopenia, fatigue, infusion-related reactions (IRRs), leukopenia, and lymphopenia.

7. The method of claim 1, wherein administering the anti-CD38 antibody results in less than 10%, less than 20%, less than 30%, less than 40%, or less than 50% depletion of RBCs.

8. The method of claim 1, wherein administering the anti-CD38 antibody results in less than 10%, less than 20%, less than 30%, less than 40%, or less than 50% depletion of platelets.

9. The method of claim 1, wherein the disease is selected from the group consisting of autoimmune thrombocytopenia, immune mediated thrombocytopenia, idiopathic thrombocytopenia purpura, systemic lupus erythematosus (SLE), rheumatoid arthritis (RA), inflammatory bowel disease (IBD), ulcerative colitis (UC), myasthenia gravis (MG), neuromyelitis optica (NMO), immune thrombocytopenic purpura (ITP), thrombotic thrombocytopenic purpura (TTP), anti-phospholipid syndrome (APS), pemphigus vulgaris (PV), pemphigus foliaceus (PF), anti-NMDAR encephalitis (NMDR), autoimmune hemolytic anemia (AIHA), Grave's disease, membranous nephropathy, Sjogren's syndrome (SS), ANCA vasculitis, epidermolysis bullosa acquisita (EBA), bullous pemphigoid (BP), Hashimoto's thyroiditis, scleroderma, IgG4-related disease, and graft-v-host disease.

10. The method of claim 1, wherein the human anti-CD38 antibody is administered in the form of a pharmaceutically acceptable composition.

11. A unit dosage form comprising an isolated antibody that comprises a heavy chain variable region comprising SEQ ID NO:9 and a light chain variable region comprising SEQ ID NO:10, wherein the isolated antibody binds to CD38, wherein the unit dosage form is formulated for subcutaneous administration of the antibody in the treatment of a disease at a dosage of 0.3 milligram per kilogram body weight, wherein the unit dosage form is in a volume of 1 mL or less, wherein the disease is an autoimmune disease.

12. The unit dosage form of claim 11, wherein isolated antibody comprises a heavy chain comprising SEQ ID NO:11 and a light chain comprising SEQ ID NO:12.

13. The unit dosage form of claim 11, wherein the unit dosage form is in a volume of 1 mL.

14. The unit dosage form of claim 11, wherein administering the anti-CD38 antibody does not cause hemolytic anemia or thrombocytopenia.

15. The unit dosage form of claim 11, wherein administering the anti-CD38 antibody results in less than 10%, less than 20%, less than 30%, less than 40%, or less than 50% incidence of grade 3 or 4 of one or more treatment-emergent adverse events (TEAEs) selected from the group consisting of anemia, hemolytic anemia, thrombocytopenia, fatigue, infusion-related reactions (IRRs), leukopenia, and lymphopenia.

16. The unit dosage form of claim 11, wherein administering the anti-CD38 antibody results in less than 10%, less than 20%, less than 30%, less than 40%, or less than 50% depletion of RBCs.

17. The unit dosage form of claim 11, wherein administering the anti-CD38 antibody results in less than 10%, less than 20%, less than 30%, less than 40%, or less than 50% depletion of platelets.

18. The method of claim 1, wherein subcutaneously administering the unit dosage form to the subject results in minimal or no reductions in total lymphocytes, B cells, T cells, cytotoxic T cells, helper T cells, monocytes, granulocytes, and platelets.

19. The unit dosage form of claim 11, wherein subcutaneously administering the unit dosage form to the subject results in minimal or no reductions in total lymphocytes, B cells, T cells, cytotoxic T cells, helper T cells, monocytes, granulocytes, and platelets.

20. The unit dosage form of claim 11, wherein the disease is selected from the group consisting of autoimmune thrombocytopenia, immune mediated thrombocytopenia, idiopathic thrombocytopenia purpura, systemic lupus erythematosus (SLE), rheumatoid arthritis (RA), inflammatory bowel disease (IBD), ulcerative colitis (UC), myasthenia gravis (MG), neuromyelitis optica (NMO), immune thrombocytopenic purpura (ITP), thrombotic thrombocytopenic purpura (TTP), anti-phospholipid syndrome (APS), pemphigus vulgaris (PV), pemphigus foliaceus (PF), anti-NMDAR encephalitis (NMDR), autoimmune hemolytic anemia (AIHA), Grave's disease, membranous nephropathy, Sjogren's syndrome (SS), ANCA vasculitis, epidermolysis bullosa acquisita (EBA), bullous pemphigoid (BP), Hashimoto's thyroiditis, scleroderma, IgG4-related disease, and graft-v-host disease.

21. The unit dosage form of claim 11, wherein the disease is immune thrombocytopenic purpura (ITP).

22. The unit dosage form of claim 11, wherein the disease is rheumatoid arthritis (RA).

23. The unit dosage form of claim 11, wherein the disease is systemic lupus erythematosus (SLE).

24. The method of claim 1, wherein the disease is immune thrombocytopenic purpura (ITP).

25. The method of claim 1, wherein the disease is rheumatoid arthritis (RA).

26. The method of claim 1, wherein the disease is systemic lupus erythematosus (SLE).

27. A method for treating immune thrombocytopenic purpura (ITP) in a human subject, the method comprising subcutaneously administering to the subject a unit dosage form of an isolated human anti-CD38 antibody, wherein the anti-CD38 antibody comprises a heavy chain variable region comprising SEQ ID NO:9 and a light chain variable region comprising SEQ ID NO:10, wherein the unit dosage form is in a volume of 1 mL, wherein the antibody is administered in a dosage of 0.3 milligram per kilogram body weight.

\* \* \* \* \*